United States Patent
Beausoleil et al.

(10) Patent No.: US 10,745,429 B2
(45) Date of Patent: Aug. 18, 2020

(54) PHOSPHOLIDINES THAT ARE BCL FAMILY ANTAGONISTS FOR USE IN CLINICAL MANAGEMENT OF CONDITIONS CAUSED OR MEDIATED BY SENESCENT CELLS AND FOR TREATING CANCER

(71) Applicant: Unity Biotechnology, Inc., Brisbane, CA (US)

(72) Inventors: Anne-Marie Beausoleil, Brisbane, CA (US); Ryan Hudson, Brisbane, CA (US)

(73) Assignee: Unity Biotechnology, Inc., Brisbane, CA (US)

( * ) Notice: Subject to any disclaimer, the term of this patent is extended or adjusted under 35 U.S.C. 154(b) by 0 days.

(21) Appl. No.: 16/425,276

(22) Filed: May 29, 2019

(65) Prior Publication Data

US 2019/0330250 A1 Oct. 31, 2019

Related U.S. Application Data

(63) Continuation of application No. PCT/US2019/030028, filed on Apr. 30, 2019.

(60) Provisional application No. 62/664,891, filed on Apr. 30, 2018, provisional application No. 62/664,863, filed on Apr. 30, 2018, provisional application No. 62/664,860, filed on Apr. 30, 2018, provisional application No. 62/664,850, filed on Apr. 30, 2018.

(51) Int. Cl.
| | |
|---|---|
| C07F 9/653 | (2006.01) |
| C07F 9/6533 | (2006.01) |
| C07F 9/6584 | (2006.01) |
| A61P 35/00 | (2006.01) |
| A61P 3/10 | (2006.01) |
| A61P 19/02 | (2006.01) |

(52) U.S. Cl.
CPC .......... *C07F 9/65844* (2013.01); *A61P 3/10* (2018.01); *A61P 19/02* (2018.01); *A61P 35/00* (2018.01); *C07F 9/65846* (2013.01)

(58) Field of Classification Search
CPC .................. C07F 9/65844; C07F 9/65846
See application file for complete search history.

(56) References Cited

U.S. PATENT DOCUMENTS

| | | | |
|---|---|---|---|
| 5,807,846 | A | 9/1998 | Roark et al. |
| 8,563,735 | B2 | 10/2013 | Bruncko et al. |
| 9,248,140 | B2 | 2/2016 | Diebold et al. |
| 9,849,128 | B2 | 12/2017 | Laberge et al. |
| 9,901,080 | B2 | 2/2018 | Campisi et al. |
| 9,968,076 | B2 | 5/2018 | Kirkland et al. |
| 10,010,546 | B2 | 7/2018 | Laberge et al. |
| 10,195,213 | B2 | 2/2019 | David |
| 2016/0122758 | A1 | 5/2016 | Krizhanovsky et al. |
| 2017/0056421 | A1 | 5/2017 | Zhou et al. |
| 2017/0216286 | A1 | 8/2017 | Kirkland et al. |
| 2017/0266211 | A1 | 9/2017 | Nathaniel et al. |
| 2018/0000816 | A1 | 1/2018 | David et al. |

FOREIGN PATENT DOCUMENTS

| | | |
|---|---|---|
| CN | 105646587 | 8/2016 |
| WO | WO 2012103059 | 8/2012 |
| WO | WO 2014113413 | 7/2014 |
| WO | WO2016095878 | 6/2016 |

(Continued)

OTHER PUBLICATIONS

Das et al. JACS, vol. 99, No. 5, p. 1354-1359. (Year: 1977).*
Ashkenazi et al., (2017) "From basic apoptosis discoveries to advanced selective BCL-2 family inhibitors," Nature Reviews, 16: 273-284.
Baar et al. (2017) "Targeted Apoptosis of Senescent Cells Restores Tissue Homeostasis in Response to Chemotoxicity and Aging," Cell, 169(1): 132-147.

(Continued)

*Primary Examiner* — Emily A Bernhardt
(74) *Attorney, Agent, or Firm* — Rudy J. Ng; Bozicevic, Field & Francis LLP

(57) ABSTRACT

This disclosure provides compounds with Bcl inhibitory activity based on a new chemical scaffold, as shown in Formula (I).

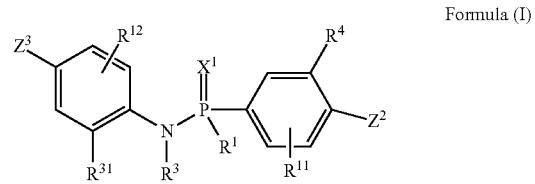

Formula (I)

The phospholidine compounds can include a P-phenyl phospholidine moiety which is substituted with an N-aryl or N-heteroaryl group. The P-phenyl phospholidine moiety can be optionally substituted at phosphorus with thio (=S) instead of oxo (=O). A second heteroatom attached to phosphorus can be cyclically linked to the N-substituted nitrogen atom of the phospholidine that is attached to the phosphorus to provide, together with the phosphorus atom through which they are connected, a heterocyclic ring. By incorporating such a cyclic constraint between two phosphorus substituents of the core linking moiety a favorable binding conformation can be promoted in the compounds. Selected compounds promote apoptosis in senescent cells, and can be developed for treating senescent-related conditions, such as osteoarthritis, ophthalmic disease, pulmonary disease, and atherosclerosis. Selected compounds promote apoptosis in cancer cells, and can be developed as chemotherapeutic agents.

15 Claims, 14 Drawing Sheets

(56) References Cited

FOREIGN PATENT DOCUMENTS

| | | |
|---|---|---|
| WO | WO 2016127135 | 8/2016 |
| WO | WO 2019033122 | 2/2019 |

OTHER PUBLICATIONS

Bai et al., (2014) "BM-1197: A Novel and Specific Bcl-2/Bcl-xL Inhibitor Inducing Complete and Long-Lasting Tumor Regression In Vivo," Plos ONE, 9(6): 1-13.

Bajwa et al. (2012) "Inhibitors of the anti-apoptotic Bcl-2 proteins: a patent review," Expert Opin Ther Pat., 22(1): 37-55.

Baker et al. (2016) "Naturally occurring p16Ink4a-positive cells shorten healthy lifespan," Nature, 530 (7589): 184-189.

Bentrude et al. (1988) "Conformations of Saturated Six-Membered Ring Phosphorus Heterocycles. 2-Aryl-1,3, 2×5-oxazaphosphorinanes," J. Am. Chem. Soc.,110, 7119-7127.

Blagosklonny et al. (2013) "Selective anti-cancer agents as anti-aging drugs," Cancer Biology & Therapy, 14(12): 1092-1097.

Braun et al., (2012) "Cellular Senescence Limits Regenerative Capacity and Allograft Survival," J. Am Soc Nephrol., 23(9): 1467-1473.

Campisi & Robert (2014) "Cell senescence, role in aging and age-related diseases," Interdiscip Top Gerontol, 39: 45-61.

Childs et al., (2017) "Senescent cells: an emerging target for diseases of aging," Nat Rev Drug Discov., 16(10): 718-735.

Durust et al., (2014) Synthesis of Some 1,3,5,2-oxadiazaphosphol-2-oxides, 3H-1,2,3,5-oxathiadiazol-2-oxides, and 1,3,2-oxazaphospholidin-2-Oxides (Sulfides), Phosphorus, Sulfur, and Silicon and the Related Elements, 189: 215-225.

Jeon et al., (2017) "Local clearance of senescent cells attenuates the development of post-traumatic osteoarthritis and creates a pro-regenerative environment," Nature Medicine, 1-9.

Kirkland & Tchkonia (2015) "Clinical Strategies and Animal Models for Developing Senolytic Agents," Exp Gerontol., 68: 19-25.

Wang et al., (2016) "Organocatalytic Enantioselective Synthesis of P-Stereogenic Chiral Oxazaphospholidines," Eur. J. Org. Chem. 2024-2028.

Wendt (2012) "The Discovery of Navitoclax, a Bcl-2 Family Inhibitor," Top Med Chem, 8: 231-258.

Yap et al., (2016) "Expanding the Cancer Arsenal with Targeted Therapies Disarmament of the Antiapoptotic Bcl-2 Proteins by small Molecules," J. Med. Chem A-R 18 pages.

Yosef et al., (2015) "Directed elimination of senescent cells by inhibition of BCL-W and BCL-XL," Nature Communications, 1-11.

Zhou et al. (2012) "Design of Bcl-2 and Bcl-xL Inhibitors with Subnanomolar Binding Affinities Based upon a New Scaffold," J. Med. Chem. 55: 4664-4682.

Zhu et al., (2017) "New agents that target senescent cells: the flavone, fisetin, and the BCL-XL inhibitors, A1331852 and A1155463," Aging, 9: 1-9.

Cheng et al., (2011) "Synthesis of Hybrid Dendritic Molecules with Diazaphospholidine Oxide Grafted at the Surface of Octavinylsilsesquioxane (OVS)", Organic & Biomolecular Chemistry 9(4):1189-1200.

Database (2016) WPI Week 201657 Thomson Scientific, London, GB; AN 2016-38006T XP002792548, & CN 105 646 587 A Univ Yunnan Traditional Chinese Medicine. p. 1-2.

Deng and Chen (2004) "A Convenient Synthesis of Phosphorines and Phospholidins by Lawesson's Reagant and Microwave Irradiation", Chemical Monthly 135(9): 1113-1119.

\* cited by examiner

FIG. 3A

| Compound ID | Bcl-2 IC$_{50}$ (nM) | Bcl-XL IC$_{50}$ (nM) | Bcl-w IC$_{50}$ (nM) | irradiated HRMEC pEC$_{50}$ |
|---|---|---|---|---|
| AMB-1314 | 1.65 | 0.796 | | 7.13 |
| AMB-1428 | 49.9 | 1.46 | >1000 | |
| AMB-1429 | 4.39 | 1.42 | 72.9 | 6.78 |
| AMB-1432 | 27.28 | 1.00 | | 5.53 |
| AMB-1433 | 6.71 | 1.21 | | 6.25 |
| AMB-1447 | 4.21 | 0.23 | | 6.56 |
| AMB-1448 | 3.88 | 0.32 | | 5.72 |
| AMB-1464 | 73.54 | 0.48 | | 7.04 |
| AMB-1465 | 556.00 | 2.04 | | 6.00 |
| AMB-1466 | 176.40 | 0.73 | | 6.02 |
| AMB-1481 | 5.07 | 0.20 | | |
| AMB-1482 | 1.01 | 0.39 | | 7.67 |
| AMB-1483 | 3.59 | 0.24 | | 6.74 |
| AMB-1484 | 0.62 | 0.21 | | 7.93 |
| AMB-1485 | 4.14 | 0.28 | | 6.54 |
| AMB-1487 | 0.71 | 1.03 | | |
| AMB-1488 | 47.47 | 3.21 | | 6.84 |
| AMB-1491 | 37.45 | 2.09 | | 6.93 |
| AMB-1498 | 12.56 | 8.62 | | 8.30 |
| AMB-1499 | 2.20 | 1.23 | | 7.76 |
| AMB-1501 | 59.5 | 2.7 | 169 | 6.54 |
| AMB-1502 | 180 | 2.56 | | 6.05 |
| AMB-1509 | 3.38 | 1.95 | 5.21 | 7.99 |
| AMB-1511 | 8.01 | 0.799 | | 6.60 |
| AMB-1512 | ND | 1.06 | | 6.44 |
| AMB-1513 | 55.7 | 0.434 | | 5.65 |
| AMB-1514 | 23.4 | 0.389 | 199 | 6.64 |
| AMB-1515 | 2.6 | 1.34 | | 7.85 |
| AMB-1516 | 96.5 | 1.42 | | 5.29 |
| AMB-1517 | 1.27 | 0.433 | | 7.14 |
| AMB-1518 | ND | 0.446 | | 5.82 |
| AMB-1519 | 22.7 | 0.649 | | 6.57 |
| AMB-1521 | 1.8 | 0.519 | | 7.66 |

FIG. 3A (cont'd)

| Compound ID | Bcl-2 IC$_{50}$ (nM) | Bcl-XL IC$_{50}$ (nM) | Bcl-w IC$_{50}$ (nM) | irradiated HRMEC pEC$_{50}$ |
|---|---|---|---|---|
| AMB-1522 | 0.736 | 0.39 | | 7.39 |
| AMB-1523 | 1.46 | 0.668 | | 7.63 |
| AMB-1524 | 6.76 | 0.267 | | 6.47 |
| AMB-1752 | 8.48 | 0.78 | | 6.88 |
| AMB-1754 | 0.413 | 0.192 | 3.060 | 7.33 |
| AMB-1791 | 5.41 | 0.09 | | 6.43 |
| AMB-1792 | 0.12 | 0.06 | | 7.69 |
| AMB-1802 | 0.750 | 0.138 | | 7.54 |
| AMB-1826 | 0.098 | 0.029 | | 6.06 |
| AMB-1828 | 8.087 | 3.172 | | 7.34 |
| AMB-1856 | 82.040 | 0.905 | | 6.29 |
| AMB-1877 | 4.152 | 1.602 | | 6.40 |
| AMB-1935 | 22.780 | 1.276 | | |
| AMB-1936 | 1.306 | 0.698 | 4.59 | 6.64 |
| AMB-1939 | 576.900 | 1.365 | | 6.65 |
| AMB-1941 | 9.846 | 0.609 | 26.4 | 7.38 |
| AMB-1942 | 301.100 | 0.567 | | 6.42 |
| AMB-1943 | 8.747 | 0.701 | 27.2 | 7.30 |
| AMB-1971 | 43.13 | 0.71 | | 5.55 |
| AMB-1972 | 1.88 | 0.70 | | 7.05 |
| AMB-1973 | 20.45 | 0.22 | | 4.63 |
| AMB-1974 | 3.59 | 0.53 | 1.43 | 6.53 |
| AMB-1976 | 2.27 | 0.57 | | 5.61 |
| AMB-1977 | 21.30 | 0.08 | | 5.91 |
| AMB-1978 | 0.47 | 0.05 | | 7.56 |
| AMB-1980 | 29.24 | 0.29 | | 6.34 |
| AMB-1981 | 1.42 | 0.20 | | 7.24 |
| AMB-1982 | 2.63 | 0.28 | | 6.05 |
| AMB-1995 | 1.51 | 0.50 | | 7.10 |
| AMB-1996 | 33.29 | 0.47 | | 5.65 |
| AMB-1997 | 1.38 | 0.29 | | 7.12 |

FIG. 3A (cont'd)

| Compound ID | Bcl-2 IC$_{50}$ (nM) | Bcl-XL IC$_{50}$ (nM) | Bcl-w IC$_{50}$ (nM) | irradiated HRMEC pEC$_{50}$ |
|---|---|---|---|---|
| AMB-1998 | 29.58 | 0.57 | | 5.06 |
| AMB-1999 | 1.27 | 0.41 | | 6.17 |
| AMB-2000 | 26.00 | 0.59 | | 4.85 |
| AMB-2001 | 1.76 | 0.44 | | 6.01 |
| AMB-2002 | 1.52 | 0.34 | | 6.43 |
| AMB-2012 | 45.7 | 1.95 | n.a. | |
| AMB-2013 | 76.6 | 0.771 | 1034 | |
| AMB-2015 | 21.1 | 2.86 | 436 | |
| AMB-2018 | 47.5 | 1.13 | n.a. | |
| AMB-2019 | 4.47 | 0.074 | 259 | |
| AMB-2024 | 0.0147 | 0.0112 | 260 | |
| AMB-2025 | 0.0632 | 0.0361 | 203 | |
| AMB-2026 | 0.178 | 0.036 | 3.61 | |
| AMB-2033 | 37.5 | 0.764 | n.a. | |
| AMB-2034 | 0.585 | 0.206 | 111 | 4.79 |
| AMB-2057 | 50.1 | 0.856 | 654 | |
| AMB-2058 | 66 | 1.39 | 1110 | |
| AMB-2059 | 2.16 | 1.37 | 8.44 | |
| AMB-2249 | 1.91 | 1.08 | 1.01 | |
| AMB-2250 | 705 | 1.32 | 513 | |
| AMB-2251 | 3.02 | 1.61 | 1.58 | |
| AMB-2252 | 52.2 | 1.25 | 642 | |
| AMB-2269 | 0.854 | 0.396 | 1.32 | |
| AMB-2270 | 23.2 | 0.791 | 390 | |
| AMB-2479 | 31.6 | 1.39 | 89.1 | |
| AMB-2481 | 41.2 | 0.739 | 827 | |
| AMB-2482 | 1.70 | 0.852 | 2.61 | |
| AMB-2483 | 1.62 | 0.710 | 2.81 | |
| AMB-2484 | 97.6 | 0.658 | 604 | |
| AMB-2491 | 44.0 | 1.22 | 409 | |
| AMB-2492 | 1.85 | 1.49 | 4.67 | |
| AMB-2495 | 35.6 | 0.472 | 532 | |

FIG. 3A (cont'd)

| Compound ID | Bcl-2 IC$_{50}$ (nM) | Bcl-XL IC$_{50}$ (nM) | Bcl-w IC$_{50}$ (nM) | irradiated HRMEC pEC$_{50}$ |
|---|---|---|---|---|
| AMB-2504 | 220 | 1.09 | n.a. | |
| AMB-2505 | 52.4 | 0.825 | 873 | |
| AMB-2578 | 150 | 7.91 | 332 | |
| AMB-2579 | >1000 | 10.7 | n.a. | |
| AMB-2584 | 266 | 1.82 | 363 | |
| AMB-2585 | 8.06 | 2.54 | 8.92 | |
| AMB-2586 | 9.63 | 3.62 | 9.39 | |
| AMB-2587 | 397 | 1.30 | 594 | |

FIG. 3B

| Compound ID | biochemical Bcl-2 IC$_{50}$ (nM) | biochemical Bcl-XL IC$_{50}$ (nM) | Irradiated IMR90 EC$_{50}$ (µM) | IMR90 EC$_{50}$ (µM) |
|---|---|---|---|---|
| AMB-0007 | 1.65 | 0.796 | 0.079 | 0.806 |

FIG. 4

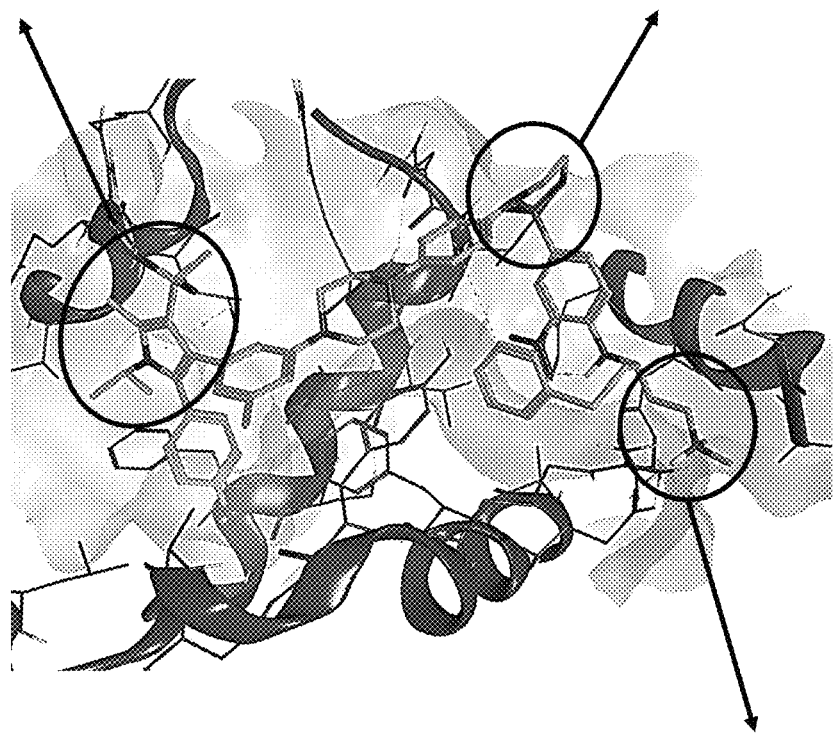

Methyl sulfone or carboxylic acid pyrrole moiety interacts with Arg residue – not many substituents tolerated at this position.

Core region interacts with Gly residue – not many substituents tolerated at this position.

Vector pointing towards solvent exposed region – multiple substituents tolerated at this position. Region may be utilized to manipulate physicochemical properties.

PHOSPHOLIDINES THAT ARE BCL FAMILY ANTAGONISTS FOR USE IN CLINICAL MANAGEMENT OF CONDITIONS CAUSED OR MEDIATED BY SENESCENT CELLS AND FOR TREATING CANCER

RELATED APPLICATIONS

This application is a continuation of international patent application PCT/US2019/030028, filed Apr. 30, 2019 (pending), which claims priority to U.S. provisional patent application No. 62/664,850 (acyl benzylamines), 62/664,891 (phosphonamidates), 62/664,860 (phospholidines), and 62/664,863 (acyl phosphonamidates), all filed Apr. 30, 2018. All the aforelisted priority applications are hereby incorporated herein by reference in their entirety for all purposes.

FIELD OF THE INVENTION

The technology disclosed and claimed below relates generally to the field of senescent cells and their role in age-related conditions. In particular, this disclosure provides new scaffolds for chemical structures that inhibit Bcl protein activity.

SUMMARY

The invention provided here creates a new paradigm for the treatment of senescence related conditions. The disclosure that follows outlines a strategy for selectively eliminating senescent cells, and provides effective compounds, pharmaceutical compositions, development strategies, and treatment protocols, and describes many of the ensuing benefits.

A new family of Bcl inhibitors has been developed based on a new chemical scaffold. Some of the Bcl inhibitors in this family are particularly effective senolytic agents. Contacting senescent cells in vitro or in vivo with the compounds and compositions of this disclosure selectively modulates or eliminates such cells. The inhibitors can be used for administration to a target tissue in a subject having an age-related condition, thereby selectively eliminating senescent cells in or around the tissue and relieving one or more symptoms or signs if the conditions. Selected compounds from the family can be formulated and marketed as chemotherapeutic agents.

The invention is put forth in the description that follows, in the figures, and in the appended claims.

DRAWINGS

FIGS. 3A and 3B are tables of data showing the ability of exemplary phospholidine compounds to inhibit Bcl activity and to remove senescent cells.

FIG. 4 is taken from a three-dimensional model in which the Bcl inhibitors described in this disclosure are fit into the crystal structure of Bcl family proteins. The annotations can be used as a guide to the reader for developing additional compounds that fall within the formulas shown above, that would retain Bcl inhibition activity and senolytic activity.

Figure 5A:
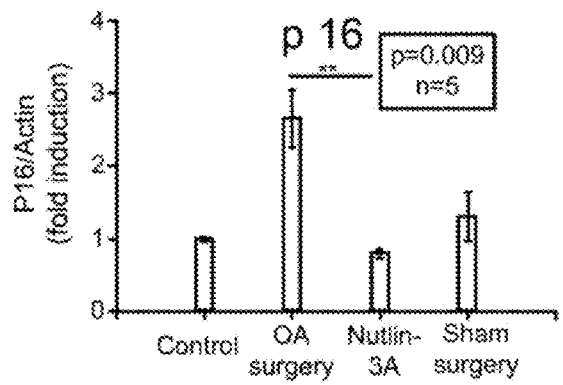
Figure 5B:
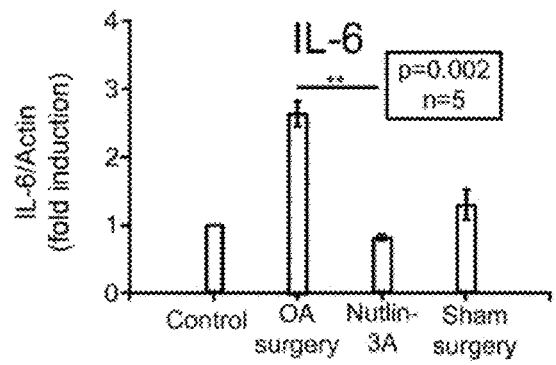
Figure 5C:
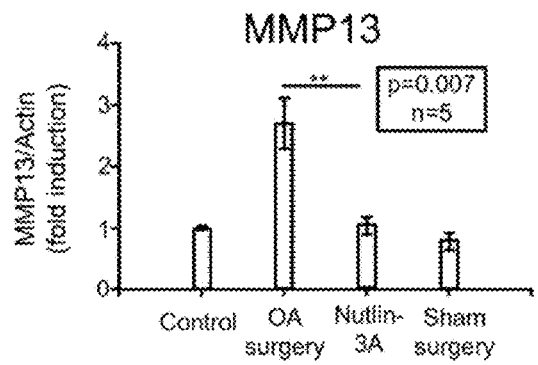

FIGS. 5A, 5B, and 5C show expression of senescent cell markers p16, IL-6, and MMP13 respectively in an osteoarthritis model. The senescence phenotype can be ameliorated by a senolytic agent.

Figure 6A:
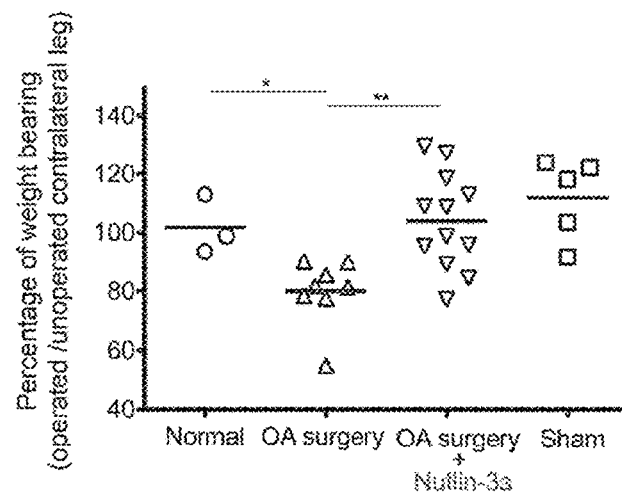
Figures 6B, 6C, 6D:
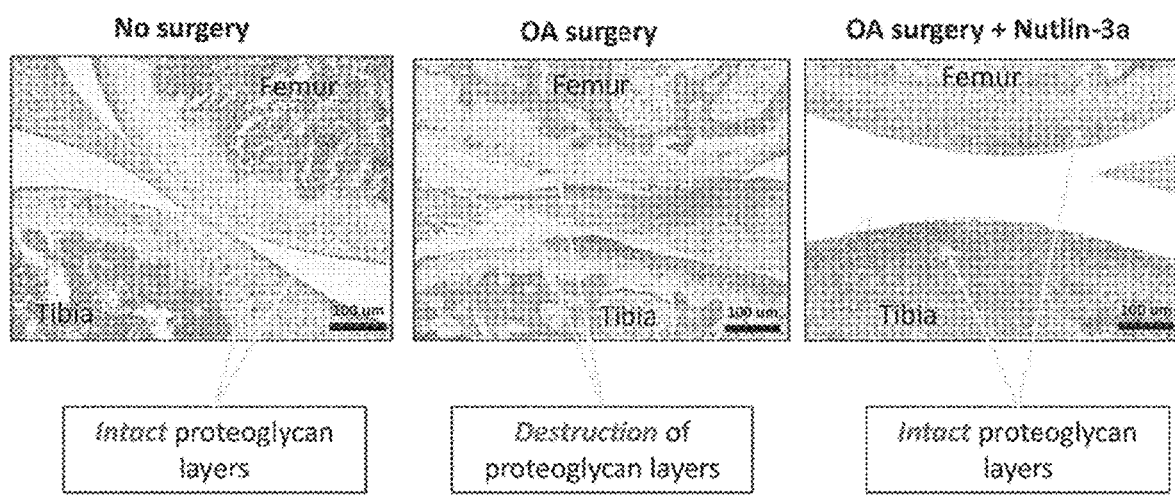

FIG. 6A shows that an effective senolytic agent restores symmetrical weight bearing to treated mice in the osteoarthritis model. FIGS. 6B, 6C, and 6D are images showing histopathology of the joints in these mice. Treatment with the agent helps prevent or reverses destruction of the proteoglycan layer.

Figure 7A:
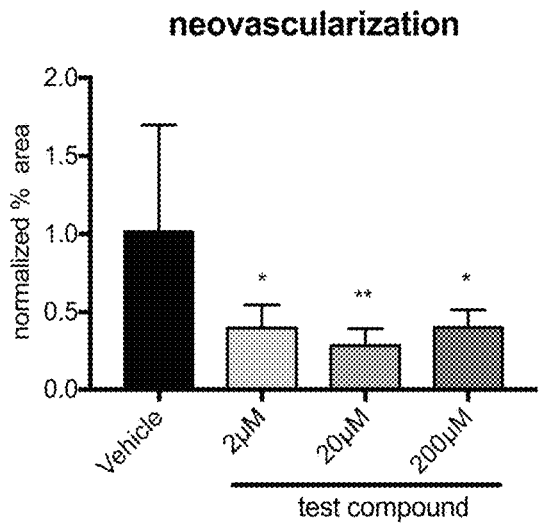
Figure 7B:
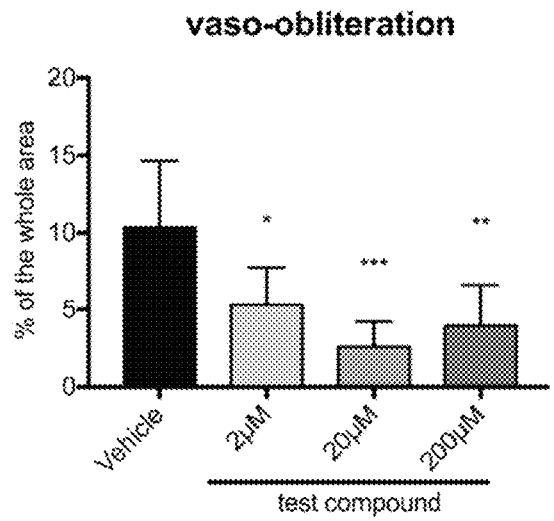
Figure 7C:
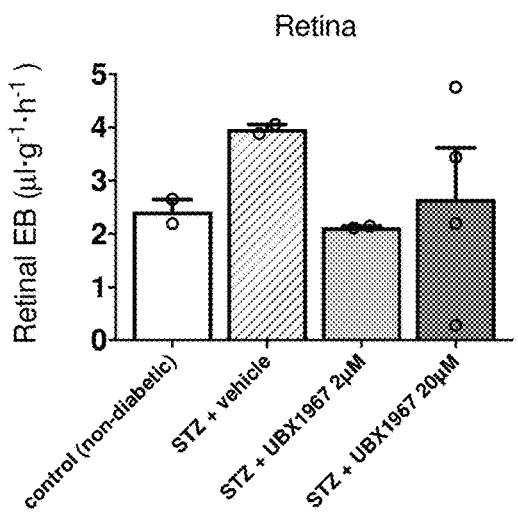
Figure 7D:
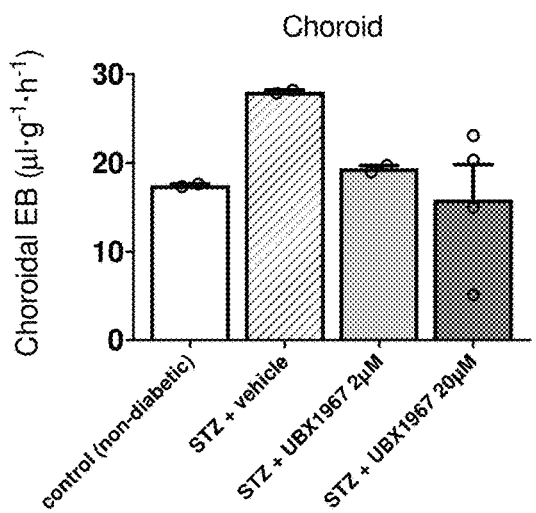

FIGS. 7A and 7B show reversal of both neovascularization and vaso-obliteration in the mouse oxygen-induced retinopathy (OIR) model when intravitreally administered with a senolytic agent. FIGS. 7C and 7D are taken from the streptozotocin (STZ) model for diabetic retinopathy. STZ-induced vascular leakage is attenuated with the intravitreal administration of a senolytic agent.

Figure 8:
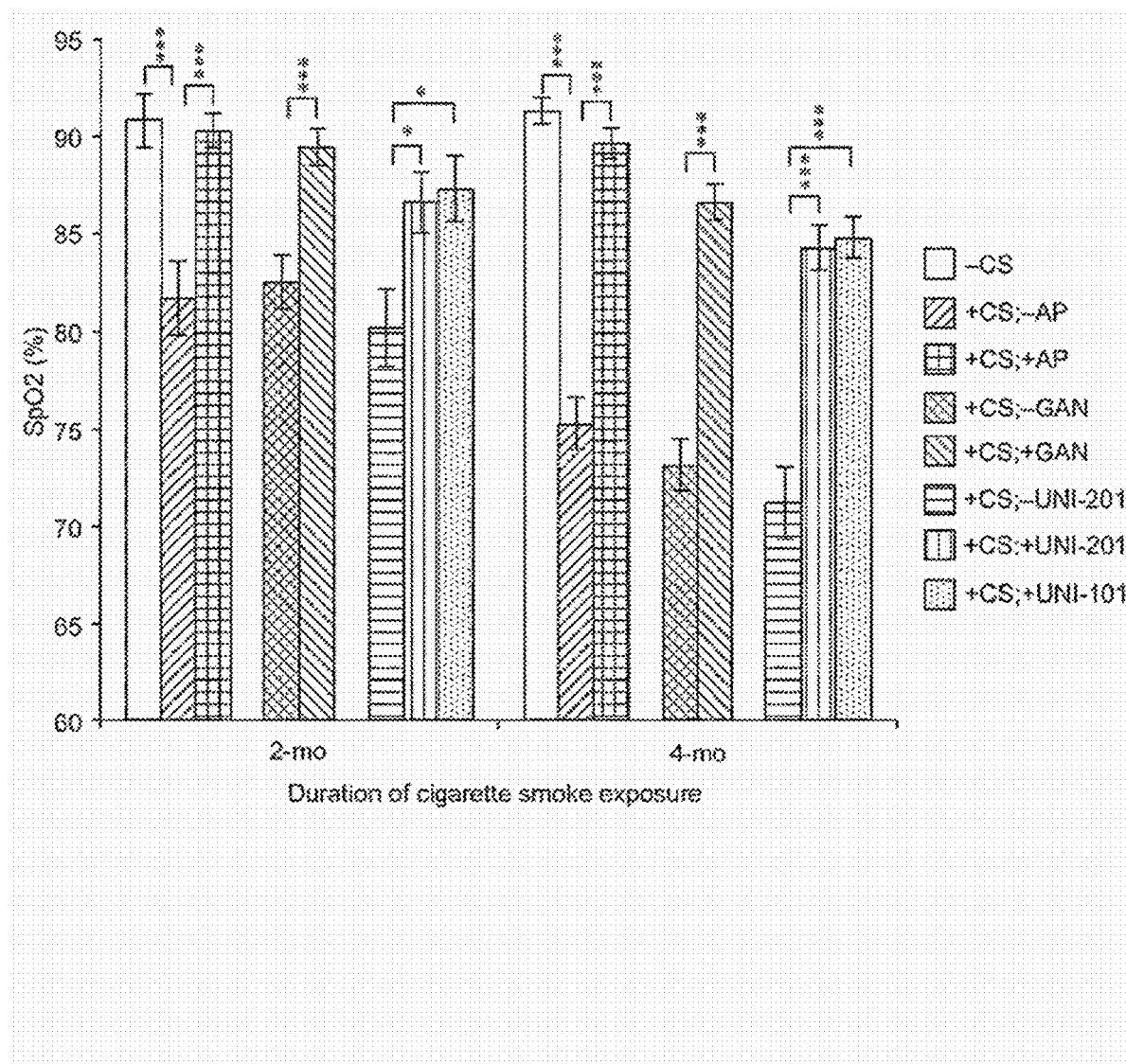

FIG. 8 shows that removing senescent cells helps restore oxygen saturation ($SPO_2$) in a mouse model for cigarette smoke (CS) induced COPD (chronic obstructive pulmonary disease).

Figure 9:
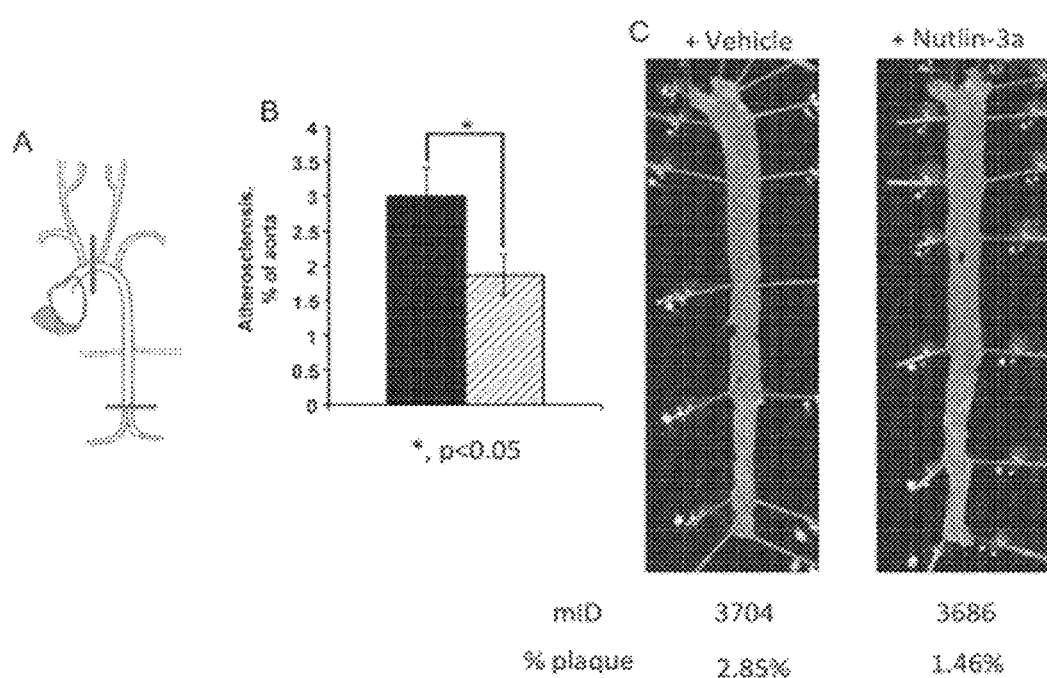

FIG. 9 shows data taken from a mouse model for atherosclerosis, in which inbred mice lacking the LDL receptor were fed a high-fat diet. The right panel shows staining for plaques in the aorta. The middle panel shows quantitatively that the surface area of the aorta covered with plaques was reduced by treatment with a senolytic agent.

DETAILED DESCRIPTION

Senescent cells are characterized as cells that no longer have replicative capacity, but remain in the tissue of origin, eliciting a senescence-associated secretory phenotype (SASP). It is a premise of this disclosure that many age-related conditions are mediated by senescent cells, and that selective removal of the cells from tissues at or around the condition can be used clinically for the treatment of such conditions.

The technology described and claimed below represents the first description of a new class of Bcl inhibitors that can be used to selectively eliminate senescent cells from a target tissue for purposes of treatment of age-related conditions.

Inhibition of Bcl Protein Activity

The Bcl protein family (TC #1.A.21) includes evolutionarily-conserved proteins that share Bcl-2 homology (BH) domains. Bcl proteins are most notable for their ability to up- or down-regulate apoptosis, a form of programmed cell death, at the mitochondrion. The following explanation is provided to assist the user in understanding some of the scientific underpinnings of the compounds of this disclosure These concepts are not needed to practice the invention, nor do they limit the use of the compounds and methods described here in any manner beyond that which is expressly stated or required.

In the context of this disclosure, the Bcl proteins of particular interest are those that downregulate apoptosis. Anti-apoptotic Bcl proteins contain BH1 and BH2 domains, some of them contain an additional N-terminal BH4 domain (Bcl-2, Bcl-x(L) and Bcl-w (Bcl-2L2), Inhibiting these proteins increases the rate or susceptibility of cells to apoptosis. Thus, an inhibitor of such proteins can be used to help eliminate cells in which the proteins are expressed.

In the mid-2000s, Abbott Laboratories developed a novel inhibitor of Bcl-2, Bcl-xL and Bcl-w, known as ABT-737 (Navitoclax). This compound is part of a group of BH3 mimetic small molecule inhibitors (SMI) that target these Bcl-2 family proteins, but not A1 or Mcl-1. ABT-737 is superior to previous BCL-2 inhibitors given its higher affinity for Bcl-2, Bcl-xL and Bcl-w. In vitro studies showed that primary cells from patients with B-cell malignancies are sensitive to ABT-737. In human patients, ABT-737 is effective against some types of cancer cells, but is subject to dose-limiting thrombocytopenia.

US 2016/0339019 A1 (Laberge et al.) describes treatment of certain age-related conditions using MDM2 inhibitors, Bcl inhibitors, and Akt inhibitors. US 20170266211 A1 (David et al.) describes the use of particular Bcl inhibitors for treatment of age-related conditions. U.S. Pat. Nos. 8,691,184, 9,096,625, and 9,403,856 (Wang et al.) describe Bcl inhibitors in a small-molecule library.

It has now been discovered that compounds based on the new scaffold described here fits into the active site of Bcl protein to provide strong Bcl inhibition and/or promote apoptosis of target cells. These compounds can be developed as highly potent and specific drugs to target senescent cells and cancer cells, as described in the sections that follow.

Phospholidine Inhibitor Compounds

This disclosure includes Bcl inhibitor phospholidine compounds having a scaffold based on a core N-substituted phospholidine linking moiety that can provide for a favorable binding conformation in the active site of a Bcl protein and gives compounds that have potent inhibition activity and/or promote apoptosis of target cells. The N-substituted phospholidine linking moiety can link a N-aryl or N-heteroaryl substituent with a P-aryl or P-heteroaryl substituent via a core cyclic group that includes a N—P(=X) group where X is O or S.

Phospholidine compounds of the disclosure can include a P-phenyl phospholidine moiety which is substituted with an N-aryl or N-heteroaryl group. The P-phenyl phospholidine moiety can be optionally substituted at phosphorus with thio (=S) instead of oxo (=O). In the core cyclic phospholidine group, the phosphorus can be further connected with a sulfur, oxygen or second nitrogen ring atom. Alternatively, the phosphorus can be linked to a saturated carbon atom. As such, the phospholidine compound may include a P-phenyl oxazaphospholidine group, a P-phenyl thiazaphospholidine group or a P-phenyl imidazaphospholidine group. The phosphorus atom of the core N-substituted phospholidine linking moiety is tetrahedral and can be chiral. As such, the phospholidine compounds of this disclosure can be present as a stereoisomer.

A second heteroatom attached to phosphorus can be cyclically linked to the N-substituted nitrogen atom of the phospholidine that is attached to the phosphorus to provide, together with the phosphorus atom through which they are connected, a heterocyclic ring. By incorporating such a cyclic constraint between two phosphorus substituents of the core linking moiety a favorable binding conformation can be promoted in the compounds.

The phenyl ring of the P-phenyl phospholidine moiety is further substituted to provide a desirable configuration of substituents that can fit into particular locations of the active site of Bcl protein. The nitrogen of the P-phenyl phospholidine moiety is substituted with an N-aryl or N-heteroaryl group which is itself further substituted to provide a desirable configuration of substituents that fit into particular locations of the active site of Bcl protein. The N-aryl or N-heteroaryl group can be N-phenyl which phenyl ring is further substituted.

This technology includes a compound described by Formula (I):

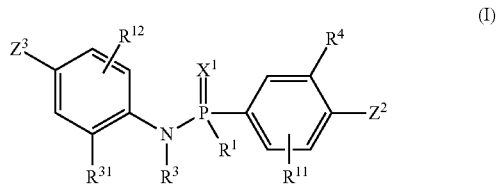

where:
$X^1$ is O or S;
$R^1$ is selected from $R^{21}$, $SR^{21}$, $OR^{21}$, and $NR^{21}R^{22}$;
$R^3$ is selected from hydrogen, alkyl, substituted alkyl, alkanoyl, substituted alkanoyl, alkoxycarbonyl and substituted alkoxycarbonyl; and/or $R^1$ and $R^3$ together with the N and P atoms through which they are connected form a 5-, 6- or 7-membered heterocyclic ring, optionally substituted with one or more $R^{23}$;
$R^4$ is selected from hydrogen, alkyl, substituted alkyl, nitro, alkylsulfonyl, substituted alkylsulfonyl, alkylsulfinyl, substituted alkylsulfinyl, cyano, alkylcarbonyl, substituted alkylcarbonyl, C(O)OH, C(O)NH$_2$, halogen, SO$_2$NH$_2$, alkylaminosulfonyl, substituted alkylaminosulfonyl, alkylsulfonylamino and substituted alkylsulfonylamino, alkanoyl, substituted alkanoyl, alkylaminocarbonyl, substituted alkylaminocarbonyl, alkyloxycarbonyl and substituted alkyloxycarbonyl;
$R^{21}$ and $R^{22}$ are independently selected from hydrogen, alkyl and substituted alkyl; or $R^{21}$ and $R^{22}$ together with the N atom through which they are connected form a 5- or 6-membered heterocyclic ring, optionally substituted with one or more $R^{23}$;
each $R^{23}$ is independently selected from alkyl, substituted alkyl, —CONH$_2$, COOH, CONHR$^{21}$, hydroxyl, halogen, alkoxy and substituted alkoxy;
$Z^2$ is selected from —NR$^5$R$^6$, hydrogen, alkyl, substituted alkyl, alkenyl, substituted alkenyl, alkoxy, substituted alkoxy, alkylsulfanyl, substituted alkylsulfanyl, alkynyl, substituted alkynyl, aryl, substituted aryl, heteroaryl, substituted heteroaryl, carbocycle, substituted carbocycle, heterocycle, substituted heterocycle, arylalkoxy, substituted arylalkoxy, aryloxy, substituted aryloxy, aryloxyalkoxy, substituted aryloxyalkoxy, arylsulfanyl, substituted arylsulfanyl, arylsulfanylalkoxy, substituted arylsulfanylalkoxy, cycloalkylalkoxy, substituted cycloalkylalkoxy, cycloalkyloxy, substituted cycloalkyloxy, halogen, carbonyloxy, haloalkoxy, haloalkyl, hydroxy and nitro;
$Z^3$ is selected from heterocycle, substituted heterocycle, —NR$^5$R$^6$, aryl, substituted aryl, heteroaryl, substituted heteroaryl, carbocycle and substituted carbocycle;
$R^5$ and $R^6$ are independently selected from hydrogen, alkyl and substituted alkyl;
$R^{11}$ and $R^{12}$ are each one or more optional substituents each independently selected from alkyl, substituted alkyl, alkoxy, substituted alkoxy, halogen, cyano, nitro, carboxy, C(O)NH$_2$, SO$_2$NH$_2$, sulfonate, hydroxyl, alkylsulfonyl, substituted alkylsulfonyl, alkylaminosulfonyl, substituted alkylaminosulfonyl, alkylsulfonylamino, substituted alkylsulfonylamino, alkyloxycarbonyl, substituted alkyloxycarbonyl and —NR$^5$R$^6$; and
$R^{31}$ is selected from H, $R^{12}$ and $L^3$-$Y^3$ wherein $L^3$ is a linker and $Y^3$ is selected from aryl, substituted aryl, heteroaryl and substituted heteroaryl.

This disclosure includes phospholidine compounds with $R^1$ and $R^3$ being cyclically linked to provide a heterocycle ring. Phospholidine compounds of Formula (I) include $R^1$ and $R^3$ being connected to provide a 5-, 6- or 7-membered heterocyclic ring together with the N and P atoms through which they are connected. In addition to the N and P atoms, this heterocyclic ring can further include an O, S or a second N ring atom. This disclosure includes $R^1$ being $R^{21}$, $SR^{21}$, $OR^{21}$ or $NR^{21}R^{22}$ where $R^{21}$ and $R^3$ together with the atoms through which they are connected form a 5-, 6- or 7-membered heterocyclic ring, optionally substituted with one or more $R^{23}$. For example, $R^1$ and $R^3$ can be cyclically linked (—$R^{1*}R^3$—) to provide a —$X^2(CH_2)_p$— linker between the phosphorus atom and the adjacent nitrogen atom, where p is 2 or 3 and $X^2$ is O, S or NH. Optionally, the heterocyclic ring can include a carbonyl group as part of the ring, and the heterocyclic ring can be optionally substituted, e.g., with one or more $R^3$ groups.

As such, the phospholidine compound of Formula (I) can be further described by Formula (II):

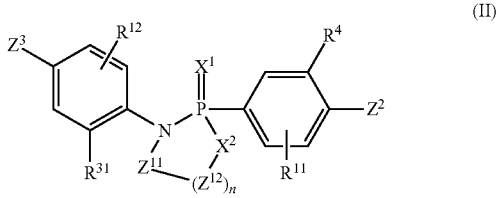

(II)

where:
$X^2$ is selected from $Z^{12}$, S, O, and $NR^{22}$;
$Z^{11}$ is selected from —C(=O)—, —C(=O)$X^3$— and $Z^{12}$;
each $Z^{12}$ is independently $CR^{24}R^{25}$;
$X^3$ is O or S;
n is 0, 1, 2 or 3; and
each $R^{24}$ and each $R^{25}$ is independently selected from hydrogen, alkyl and substituted alkyl.

This disclosure includes $X^1$ being O. Alternatively, $X^1$ can be S. In Formula (II), $Z^{11}$ can be $Z^{12}$. Sometimes, Z can be a carbonyl (C=O) or carbonyloxy (—C(=O)O—). When $Z^{11}$ is selected from —C(=O)$X^3$— n is 0, 1 or 2. When $Z^{12}$ is —C(=O)— or $Z^{12}$ n is 1, 2 or 3. This disclosure includes $X^2$ being NH or $NR^{22}$. $R^{22}$ can be alkyl or substituted alkyl. Optionally, $R^{22}$ is $C_{1-6}$alkyl, such as methyl. This disclosure includes $X^2$ being $Z^{12}$. This disclosure includes $X^2$ being O. $X^2$ can also be S. Sometimes, every $Z^{12}$ of the ring is $CH_2$. Optionally, one or more $Z^{12}$ groups of the ring can be substituted with a $R^{24}$ and/or $R^{25}$ substituent.

This disclosure includes compounds of formula (I) or (II) where the 5-, 6- or 7-membered heterocyclic ring connecting the N and P atoms includes a sidechain substituent that derives from an amino acid residue. For example, one of $R^{24}$ and $R^{25}$ of a $Z^{12}$ group can be a group corresponding to an amino acid sidechain. For each $Z^{12}$ group, one of $R^{24}$ and $R^{25}$ can be a sidechain group of an amino acid residue such as alanine, valine, leucine, isoleucine, glutamine, glutamic acid, aspartic acid, asparagine, serine, threonine, cysteine, methionine, lysine, arginine, ornithine, phenylalanine, tyrosine, tryptophan or histidine, or a substituted version thereof. In general, the heterocyclic ring includes only one $Z^{12}$ group that includes an amino acid derived sidechain, where the remaining $Z^{12}$ groups $R^{24}$ and $R^{25}$ are each hydrogen.

As such, $Z^{12}$ can include a chiral center having a chirality corresponding to an L-amino acid residue. Alternatively, $Z^{12}$ can have a chirality corresponding to a D-amino acid residue. Certain moieties of an amino acid synthon (e.g., the alpha-amino group or the backbone carboxylic acid group) may be modified or removed upon incorporation into the heterocyclic ring of the compound, while still providing for retention or incorporation of an amino acid-derived sidechain group of interest.

A stereoisomer of a phospholidine compound includes a chiral phosphorus stereocenter. Any of the formula or structures of this disclosure can include stereoisomer(s) at the tetrahedral phosphorus stereocenter of the phospholidine moiety. As such, the phospholidine compound of Formula (II) can be enriched in a stereoisomer of Formula (IIa) or (IIb):

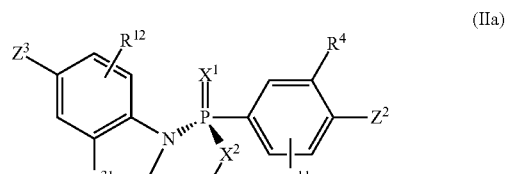

(IIa)

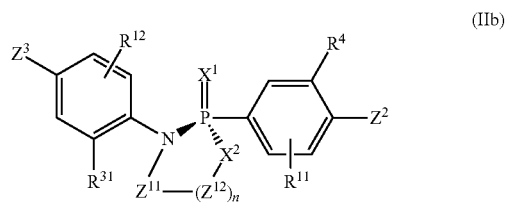

(IIb)

This disclosure includes an optically pure compound of Formula (IIa). This disclosure includes an optically pure compound of Formula (IIb).

In the core N-substituted phospholidine linking moiety of any of the formulas of this disclosure (e.g., Formulas (I)-(VIIb)), $R^3$ and $R^1$ can be cyclically linked via —$Z^{11}$—$(Z^{12})_n$—$X^2$— as shown in Formula (II) where together with the N and P atoms through which they are connected provide a phosphorus-containing heterocyclic ring. This ring can be 5- or 6-membered and optionally substituted with one or more groups independently selected from alkyl, substituted alkyl, alkoxy, substituted alkoxy, halogen, cyano, nitro, carboxy, $C(O)NH_2$, $SO_2NH_2$, sulfonate, hydroxyl, alkylsulfonyl, substituted alkylsulfonyl, alkylaminosulfonyl, substituted alkylaminosulfonyl, alkylsulfonylamino and substituted alkylsulfonylamino, alkoxycarbonyl, substituted alkoxycarbonyl, alkylamino, dialkylamino, substituted alkylamino and substituted dialkylamino.

The phospholidine compound of Formula (I) or (II) can be further described by one of Formulas (IIIa)-(IIIh):

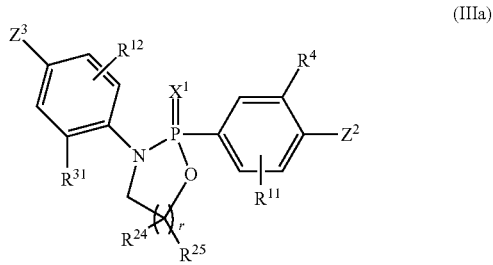

(IIIa)

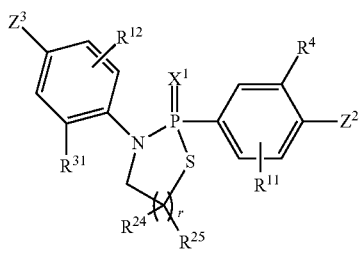
(IIIb)

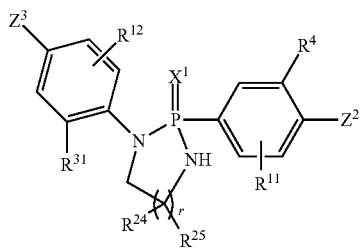
(IIIc)

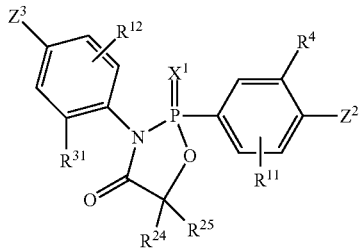
(IIId)

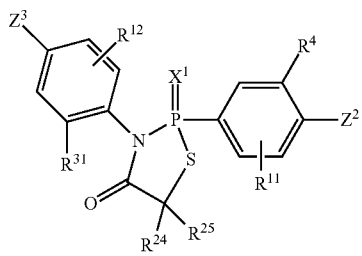
(IIIe)

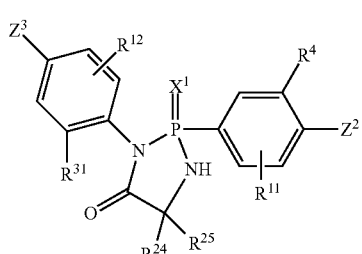
(IIIf)

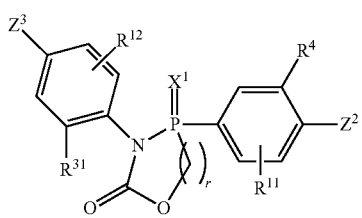
(IIIg)

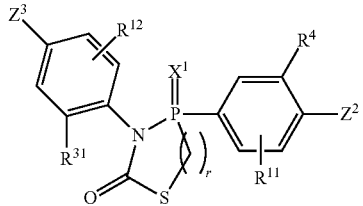
(IIIh)

where $R^{24}$ and $R^{25}$ are independently selected from H, alkyl, and substituted alkyl, and r is 1 or 2. Sometimes r is 1. Alternatively r is 2. This disclosure includes compounds of Formula (IIIa) to (IIIh) with $X^1$ being O. Optionally, $X^1$ can be S.

The phospholidine compound of Formula (IIIa) can be further described by one of Formulas (IIIa1)-(IIIa2):

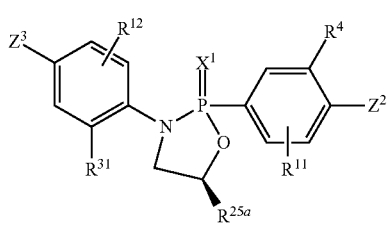
(IIIa1)

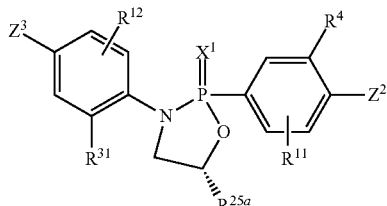
(IIIa2)

where $R^{25a}$ is selected from alkyl, and substituted alkyl.

In the core phospholidine linking moiety of any of the formulas of this disclosure (e.g., Formulas (I)-(VIIIb)), $R^4$ can be nitro, alkylsulfonyl or substituted alkylsulfonyl. Sometimes, $R^4$ is nitro. Alternatively, $R^4$ can be an alkylsulfonyl. Optionally, $R^4$ is $CH_3SO_2$—. This disclosure includes compounds and formula where $R^4$ can be a substituted alkylsulfonyl. Optionally, $R^4$ is $CF_3SO_2$—. $R^4$ can also be cyano. Optionally, $R^4$ can be alkylcarbonyl, substituted alkylcarbonyl, —C(O)OH or —C(O)NH$_2$.

This disclosure includes $R^4$ being alkylaminosulfonyl or substituted alkylaminosulfonyl. Also included is $R^4$ being alkoxycarbonyl or substituted alkoxycarbonyl. Also included is $R^4$ being alkylsulfonylamino or substituted alkylsulfonylamino. Alternatively, $R^4$ can be alkyl or substituted alkyl.

In any of the formulas of this disclosure, $Z^2$ can be —NR$^5$R$^6$ where $R^5$ and $R^6$ are independently selected from hydrogen, alkyl and alkyl substituted with one or more groups selected from arylsulfanylalkyl, heteroarylsulfanylalkyl, alkenyl, alkoxyalkyl, alkoxycarbonylalkyl, alkyl, alkylsulfonylalkyl, aryl, arylalkyl, arylsulfonylalkyl, aryloxyalkyl, arylsulfinylalkyl, arylsulfonylalkyl, heteroaryl, heteroarylalkyl, heteroarylsulfonylalkyl, heteroaryloxyalkyl, heteroarylsulfinylalkyl, heteroarylsulfonylalkyl, carboxyalkyl, cycloalkenyl, cycloalkenylalkyl, cycloalkyl, (cycloalkyl)alkyl, cycloalkylcarbonyl, (heterocycle)sulfanylalkyl, hydroxyalkyl, alkylamino, dialkylamino and heterocycle (e.g., piperidinyl, piperazinyl or morpholinyl), wherein said one or more groups are optionally further substituted. This disclosure includes $Z^2$ being —$NR^5R^6$ where $R^5$ is hydrogen. $R^6$ can be arylsulfanylalkyl, heteroarylsulfanylalkyl, aryloxyalkyl or heteroaryloxyalkyl, which $R^6$ is optionally further substituted, e.g., substituted with a heterocycle or substituted heterocycle. The heterocycle or substituted heterocycle can be a substituent of an alkyl moiety of $R^6$ and in some cases is a piperidinyl, piperazinyl or morpholinyl heterocycle.

In the formulas of this disclosure, $Z^3$ can be a substituted heterocycle. $Z^3$ can be a monocyclic 6-membered saturated heterocycle that is further substituted. This disclosure includes $Z^3$ being a substituted piperidinyl. Optionally, $Z^3$ can be a substituted piperazinyl. The $Z^3$ heterocycle group can be substituted with a group including three linked cyclic groups (e.g., three aryl, heteroaryl, carbocycle and/or heterocycle) connected via optional linkers to each other and in a linear fashion to first heterocycle of $Z^3$. $Z^3$ can be piperidinyl or piperazinyl substituted with a tri-(arylene and/or heteroarylene) group. Optionally, $Z^3$ can be piperidinyl or piperazinyl substituted with a tri-arylene, tri-heteroarylene, aryl-heteroaryl-aryl, heteroaryl-heteroaryl-aryl, aryl-heteroaryl-heteroaryl, aryl-cycloalkyl-aryl or aryl-heterocycle-aryl, where each ring of said group is optionally further substituted.

Alternatively, in the formulas of this disclosure, $Z^3$ can be a substituted carbocycle. $Z^3$ can be a monocyclic 6-membered saturated carbocyclic that is further substituted. The $Z^3$ carbocycle group can be substituted with a group including three linked cyclic groups (e.g., three aryl, heteroaryl, carbocycle and/or heterocycle) connected via optional linkers to each other and in a linear fashion to the first carbocycle of $Z^3$. $Z^3$ can be cyclohexyl substituted with a tri-arylene, tri-heteroarylene, aryl-heteroaryl-aryl, heteroaryl-heteroaryl-aryl, aryl-heteroaryl-heteroaryl, aryl-cycloalkyl-aryl or aryl-heterocycle-aryl, where each ring of said group is optionally further substituted.

This disclosure includes compounds having a $Y^3$ aryl or heteroaryl group that is capable of pi stacking interactions with the phenyl of the P-phenyl phospholidine moiety in the core structure. Pi stacking (or π-π stacking) interactions refer to attractive, noncovalent interactions between aromatic rings. This disclosure includes compounds of Formula (I) where $R^{31}$ is $L^3$-$Y^3$ where $L^3$ is a linker and $Y^3$ is aryl, substituted aryl, heteroaryl or substituted heteroaryl. Alternatively, a $Y^3$ group capable of similar pi stacking interactions can be linked (via $L^3$) to the $Z^2$ substituent group. The linker $L^3$ can provide for a configuration of the $Y^3$ group adjacent to the phenyl ring of the P-phenyl phospholidine moiety such that the two aromatic groups are capable of intramolecular pi stacking interactions.

As such, the phospholidine compound of Formula (I) can be further described by Formula (IVa) or Formula (IVb):

(IVa)

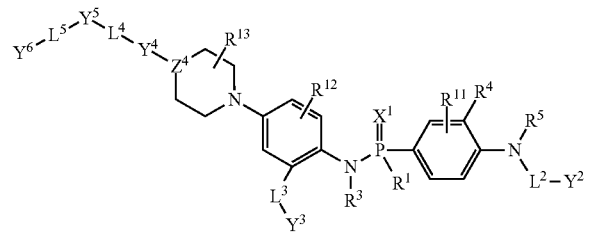

-continued (IVb)

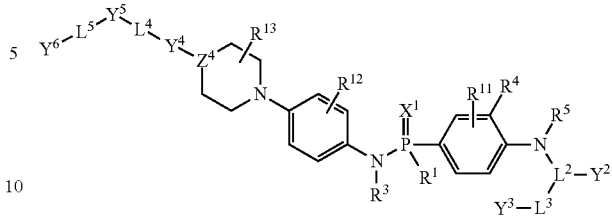

where:
$Z^4$ is selected from CH, $CR^{13}$ and N;
$L^2$, L, $L^4$ and $L^5$ are each independently a linker;
$Y^2$ is selected from alkyl, substituted alkyl, hydroxyl, alkoxy, substituted alkoxy, —$NR^7R^8$, aryl, substituted aryl, heteroaryl, substituted heteroaryl, carbocycle, substituted carbocycle, heterocycle and substituted heterocycle;
$Y^3$ is selected from aryl, substituted aryl, heteroaryl and substituted heteroaryl;
$Y^4$, $Y^5$ and $Y^6$ are independently selected from aryl, substituted aryl, heteroaryl, substituted heteroaryl, carbocycle, substituted carbocycle, heterocycle, and substituted heterocycle;
$R^7$ and $R^8$ are independently selected from hydrogen, alkyl and substituted alkyl, or $R^7$; and $R^8$ together with the nitrogen to which they are attached form a 5-, 6- or 7-membered heterocyclic ring or substituted 5-, 6- or 7-membered heterocyclic ring; and
$R^{13}$ is one or more optional substituents selected from alkyl, substituted heteroarkyl, substituted alkoxy, halogen, cyano, nitro, carboxy, $C(O)NH_2$, $SO_2NH_2$, sulfonate, hydroxyl, alkylsulfonyl, substituted alkylsulfonyl, alkylaminosulfonyd, substituted alkylaminosulfonyl, alkylsulfonylamino, substituted alkylsulfonylamino, alkyloxycarbonyl, substituted alkyloxycarbonyl, alkylamino, dialkylamino, substituted alkylamino and substituted dialkylamino.

This disclosure includes compounds of Formula (IVa), where $Y^3$ is a substituted or unsubstituted fused bicyclic heteroaryl. In Formula (IVa), $Y^3$ can be a pyrrolo-pyridine, optionally further substituted. This disclosure includes compounds of Formula (IVb), where $L^2$ is a trivalent linker connecting $Y_2$ and $Y_3$ to a nitrogen N, and $Y^3$ is a substituted or unsubstituted phenyl. The compounds of Formulas (IVa) and (IVb) can include a $Y^2$ group selected from OR and OP(=O)(OR)$_2$, where each R is independently H, alkyl or substituted alkyl. Each R can be a $C_{1-6}$alkyl such as ethyl or tert-butyl. Optionally, $Y^2$ can be $NR^7R^8$, where $R^7$ and $R^8$ together with the nitrogen to which they are attached can form a 5- or 6-membered heterocyclic ring, optionally further substituted. Where $Y^2$ is $NR^7R^8$, the 5- or 6-membered heterocyclic ring is optionally substituted on carbon with one or more $R^{40}$, and if the 5- or 6-membered heterocyclic ring contains a second nitrogen, that second nitrogen is optionally substituted with $R^{40*}$ to form a tertiary amine. Each $R^{40*}$, if present, can be selected from alkyl, substituted alkyl, —$(CH_2)_{m1}OR$ and —$(CH_2)_{m2}OP(=O)(OR)_2$, where m1 and m2 are independently an integer from 1 to 6 and each R is independently H, alkyl or substituted alkyl. R can be a $C_{1-4}$alkyl such as ethyl or tert-butyl. Each $R^{40}$, if present, is independently selected from —OR, —$N(R)_2$, —$(CH_2)_{m1}OR$, —$(CH_2)_{m3}N(R)_2$, —$(CH_2)_{m2}OP(=O)(OR)_2$, —OP(=O)(OH)$_2$, and —OP(=O)(OR)$_2$ where m1, m2 and m3 are each independently an integer from 1 to 6 and each R is independently H, alkyl or substituted alkyl. R can be a $C_{1-4}$alkyl such as ethyl or tert-butyl.

As described above, $Z^3$ can be a substituted heterocycle, such as a substituted piperidinyl or substituted piperazinyl. The $Z^3$ heterocycle group can be substituted with a group including three linked cyclic groups (e.g., three aryl, heteroaryl, carbocycle and/or heterocycle) connected via optional linkers to each other and in a linear fashion to $Z^3$. The disclosure includes compounds where the $Z^3$ substituent is a triheteroaryl, aryl-heterocycle-aryl, aryl-heteroaryl-aryl, heteroaryl-heteroaryl-aryl or aryl-heteroaryl-heteroaryl, where each ring of the $Z^3$ substituent is optionally further substituted. As such, one substituent of such a $Z^3$ substituted heterocycle can be described by the formula $Y^6$-$L^5$-$Y^5$-$L^4$-$Y^4$— where $Y^4$ and $Y^5$ are each independently aryl, substituted aryl, heteroaryl, substituted heteroaryl, carbocycle, substituted carbocycle, heterocycle or substituted heterocycle and $L^4$ and $L^5$ are optional linkers. This disclosure includes $L^4$ and $L^5$ being single covalent bonds. The compounds may include $Y^4$ and $Y^5$ groups that are monocyclic aromatic or non-aromatic 5-, 6- or 7-membered rings linked in sequence to the first heterocyclic group of $Z^3$. This disclosure includes a terminal $Y^6$ group being phenyl or substituted phenyl. The $Y^4$ group can be linked via a 1,2- or 1,3-configuration.

This disclosure also includes $Y^4$ being phenyl or substituted phenyl. Optionally, $Y^4$ is a 1,3-phenylene or substituted 1,3-phenylene. The compounds may include $Y^5$ being a heterocycle or substituted heterocycle. Optionally, $Y^5$ is a heterocycle or substituted heterocycle. $Y^5$ can be a 5-membered monocyclic heteroaryl, optionally further substituted. This disclosure includes $Y^5$ being pyrrole, substituted pyrrole, furan, substituted furan, thiophene or substituted thiophene. When $Y^5$ is a 5-membered monocyclic heteroaryl, it can be linked to the adjacent groups (e.g., $Y^6$-$L^5$- and -$L^4$-$Y^4$) with a cis-configuration, such as a 1,2- or 2,3-configuration. As such, this disclosure includes $Y^5$ being an optionally substituted 2,3-linked pyrrole.

The compounds of Formula (IVa) and Formula (IVb) can include an $L^3$ linker being a $C_{1-6}$alkylene or substituted $C_{1-6}$alkylene. In Formula (IVb) $L^2$ can be a trivalent linker. $L^2$ can be a $C_{1-6}$alkyl linker or substituted $C_{1-6}$alkyl linker that connects $Y^2$ to the nitrogen N and also includes a branching atom that connects $Y^3$-$L^3$ to the nitrogen N. The branching atom can be a carbon or a nitrogen atom. This disclosure includes compounds where $L^3$ and $L^2$ together provide a branched linker connecting $Y^2$ and $Y_3$ to the nitrogen N, where the branched linker is a substituted $C_{1-12}$alkylene, such as a $C_{1-6}$alkyl linker where one or more of the backbone carbon atoms are optionally replaced with a heteroatom (e.g., O, S or N).

The compounds of Formula (IVa) and Formula (IVb) can include a $Y^6$ group that is independently phenyl or substituted phenyl and a $Y^4$ that is selected from phenyl or substituted phenyl, e.g., an optionally substituted 1,3-linked phenylene. The $L^4$ linker can be a covalent bond. Sometimes, the $L^4$ linker has one backbone atom. This disclosure also includes $L^5$ linkers being a covalent bond, $C_{1-3}$alkyl linker, substituted $C_{1-3}$alkyl linker, O, NR, NH, S, S(=O), $SO_2$ or C(=O). Optionally, $L^5$ can be a single covalent bond.

The compound of Formula (IVb) can thus be further described by Formula (V):

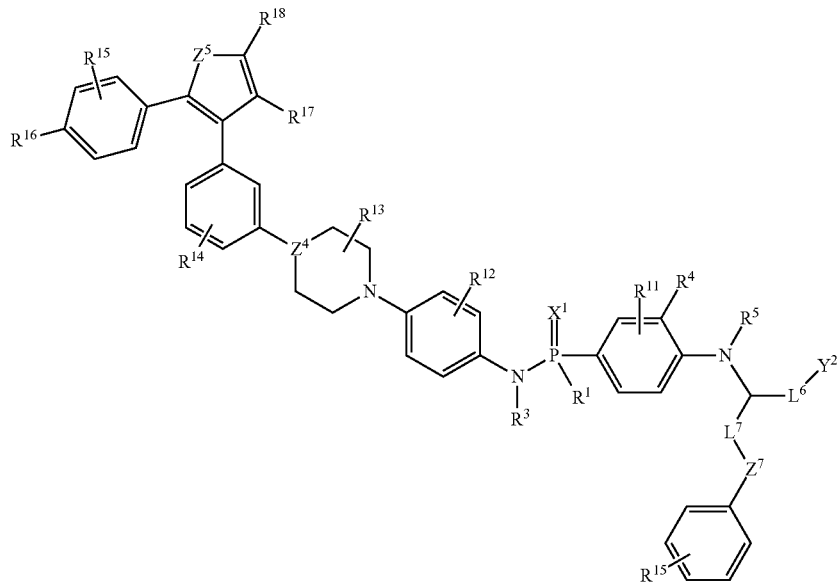

(V)

where:
$Y^2$ is selected from OR", OP(=O)(OR")$_2$ and NR$^7$R$^8$;
$Z^5$ is selected from NR$^{19}$, NH, O and S;
$Z^7$ is selected from S and O;
$L^6$ and $L^7$ are independently a covalent bond, $C_{1-6}$alkyl linker or substituted $C_{1-6}$alkyl linker;
R$^{13}$ and R$^{14}$ and each R$^{15}$ are independently one or more optional substituents selected from alkyl, substituted alkyl (e.g., CF$_3$), alkoxy, substituted alkoxy (e.g., —OCF$_3$), halogen, cyano, nitro, carboxy, C(O)NH$_2$, SO$_2$NH$_2$, sulfonate, hydroxyl, alkylsulfonyl, substituted alkylsulfonyl, alkylaminosulfonyl, substituted alkylaminosulfonyl, alkylsulfonylamino, substituted alkylsulfonylamino, alkyloxycarbonyl, substituted alkyloxycarbonyl, alkylamino, dialkylamino, substituted alkylamino and substituted dialkylamino;

$R^{16}$ is selected from hydrogen, halogen and $R^{15}$;

$R^{17}$ and $R^{18}$ are independently selected from hydrogen, cyano, nitro, halogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, substituted aryl, heteroaryl, substituted heteroaryl, heterocycle, substituted heterocycle, OR, SR, NRR', COR, OCOR, CO$_2$R, CONRR', CONRSO$_2$R', —C$_{1-3}$alkyleneCH(OH)CH$_2$OH, SO$_2$R and SO$_2$NRR'; and $R^{19}$ is selected from hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, substituted aryl, heteroaryl, substituted heteroaryl, heterocycle, substituted heterocycle, OR, SR, NRR', COR, OCOR, CO$_2$R, CONRR', CONRSO$_2$R', NRCOR, NRCONRR', NRC(=S)NRR', NRSO$_2$R and SO$_2$NRR';

each R" is independently H, alkyl or substituted alkyl (e.g., a C$_{1-6}$alkyl such as ethyl or tert-butyl); and R and R' are independently selected from hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, substituted aryl, heteroaryl, substituted heteroaryl, heterocycle, substituted heterocycle, heterocycle-alkyl- and substituted heterocycle-alkyl-.

Z$^4$ can be linked to an adjacent Y$^4$ group via a covalent bond. This disclosure includes compounds of Formula (V), where Z$^4$ can be CH or CR$^{13}$. This disclosure includes compounds of Formula (V), where Z$^4$ can be N.

This disclosure also includes Y$^5$ groups being pyrrole or substituted pyrrole. The pyrrole can be a 2,3-linked pyrrole. As such, in formula (V), Z$^5$ can be NH or NR$^{19}$. This disclosure includes L$^5$ being a single covalent bond, such that Y$^5$ (e.g., a 2,3-linked pyrrole) is directly linked to a terminal phenyl ring.

The compounds of Formula (V) can include L$^6$ and L$^7$ linkers being independently a C$_{1-6}$alkylene or substituted C$_{1-6}$alkylene connected via a chiral center. This disclosure includes compounds where L$^6$ is a covalent bond or a C$_{1-6}$alkyl linker (e.g., a C$_{1-3}$alkylene) where one or more of the backbone carbon atoms are optionally replaced with a heteroatom (e.g., O, S or N). Also included are compounds where L$^7$ is a covalent bond or a C$_{1-6}$alkyl linker (e.g., a C$_{1-3}$alkylene) where one or more of the backbone carbon atoms are optionally replaced with a heteroatom (e.g., O, S or N).

This disclosure includes compounds of Formula (V) where Y$^2$ is NR$^7$R$^8$ and R$^7$ and R$^8$ together with the nitrogen to which they are attached can form a 5- or 6-membered heterocyclic ring, optionally further substituted with one or more —OR, —N(R)$_2$, —(CH$_2$)$_{m1}$OR, —(CH$_2$)$_{m3}$N(R)$_2$, —(CH$_2$)$_{m2}$OP(=O)(OR)$_2$, —OP(=O)(OH)$_2$, and —OP(=O)(OR)$_2$ where m1, m2 and m3 are each independently an integer from 1 to 6 and each R is independently H, alkyl or substituted alkyl. R can be a C$_{1-4}$alkyl such as methyl, ethyl or tert-butyl. The 5- or 6-membered heterocyclic ring formed by R$^7$ and R$^8$ can be a 6-membered ring such as morpholinyl, piperidinyl or piperazinyl that is optionally further substituted.

The compound of Formula (V) can be further described by Formula (VIa):

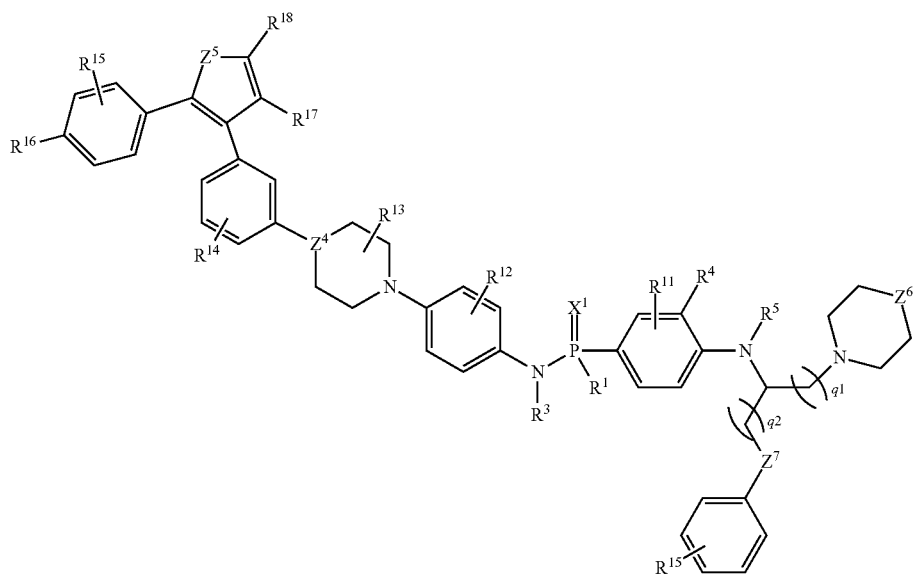

(VIa)

where:

Z$^6$ is selected from O, NR$^{40*}$, CHR$^{40*}$, C(R$^{40}$)$_2$ and CH$_2$;

R$^{40*}$ is selected from alkyl, substituted alkyl, —(CH$_2$)$_{m1}$OR and —(CH$_2$)$_{m2}$OP(=O)(OR)$_2$, wherein m1 and m2 are independently an integer from 1 to 6 and each R is independently H, alkyl or substituted alkyl (e.g., a C$_{1-4}$alkyl such as ethyl or tert-butyl);

each R$^{40}$ is independently selected from —OR, —N(R)$_2$, —C(O)OR, —(CH$_2$)$_{m1}$OR, —(CH$_2$)$_{m3}$N(R)$_2$, —(CH$_2$)$_{m2}$OP(=O)(OR)$_2$, —OP(=O)(OH)$_2$, and —OP(=O)(OR)$_2$ wherein m1, m2 and m3 are each independently an integer from 1 to 6 and each R is independently H, alkyl or substituted alkyl (e.g., a C$_{1-4}$alkyl such as ethyl or tert-butyl);

q$_1$ and q$_2$ are independently an integer from 1 to 6, or a stereoisomer thereof.

The compound of Formula (V) can be further described by Formula (VIb):

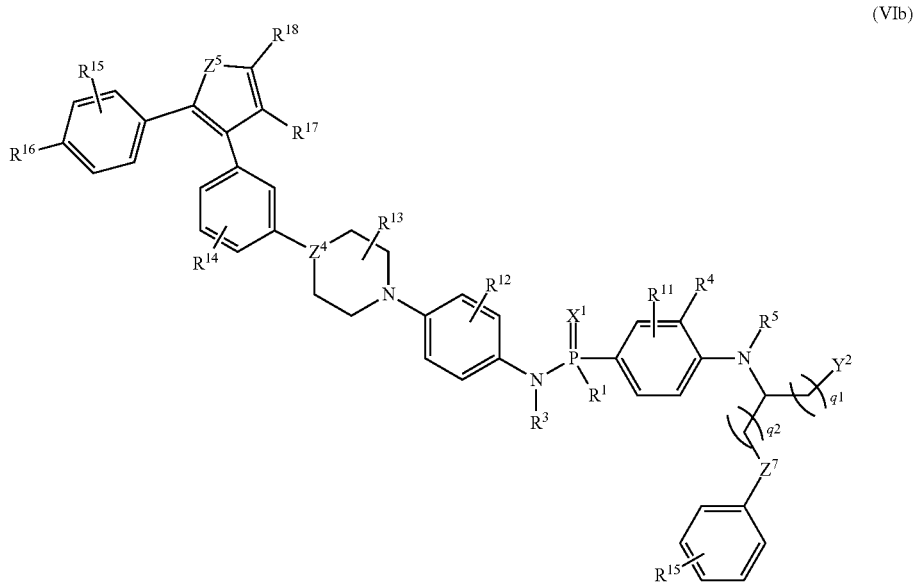

(VIb)

where $Y^2$ is selected from OH, OR, $NH_2$, NHR, $NR_2$, —OP(=O)(OR)$_2$ and —OP(=O)(OH)$_2$ where each R is independently $C_{1-6}$alkyl or substituted $C_{1-6}$alkyl; and $q_1$ and $q_2$ are independently an integer from 1 to 6.

Any of the Formula (I), (IVa), (IVb), (V), (VIa) and (VIb) can have a core phospholidine linking moiety as shown in Formula (II). This disclosure includes such compounds where $X^1$ is O. Optionally, $X^1$ is S. Sometimes, the compound is a stereoisomer of Formula (IIa) or (IIb).

Compounds of the Formulas (V) and (VIa) can include stereoisomers of compounds having a chiral center at the branching point of linker $L^2$. As such, the compound of Formulas (V) and (VIa) can be further described by Formula (VIIa):

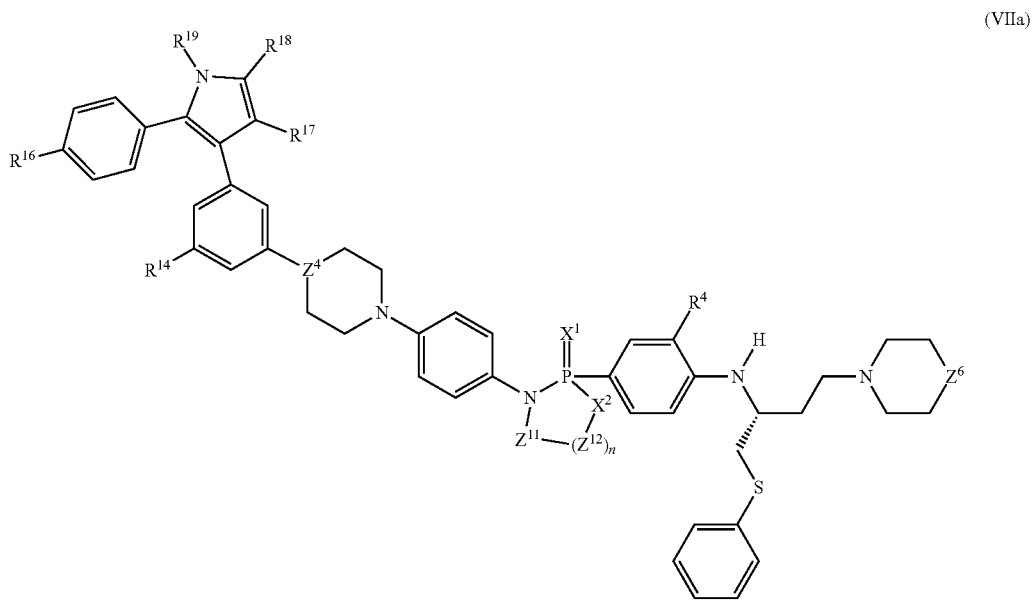

(VIIa)

where:
- $X^2$ is selected from $Z^{12}$, S, O, and $NR^{22}$;
- $Z^{11}$ is selected from —C(=O)—, —C(=O)$X^3$— and $Z^{12}$;
- each $Z^{12}$ is independently $CR^{24}R^{25}$;
- $X^3$ is O or S;
- n is 0, 1, 2 or 3;
- each $R^{24}$ and each $R^{25}$ are independently selected from hydrogen, alkyl and substituted alkyl;
- $R^4$ is selected from $NO_2$, $SO_2CH_3$, $SO_2CF_3$ and $COR^{51}$;
- $Z^4$ is selected from CH and N;
- $Z^6$ is selected from O, CHC(O)$R^{18}$, and $CH(CH_2)_p R^{18}$ wherein p is 0-6 and each $R^{18}$ is independently —OR, —N(R)$_2$, —OP(=O)(OH)$_2$, and —OP(=O)(OR)$_2$ wherein each R is independently H, alkyl or substituted alkyl (e.g., a $C_{1-4}$alkyl such as ethyl or tert-butyl);
- $R^{14}$ and $R^{16}$ are independently hydrogen or halogen; and
- $R^{17}$ is selected from $SO_2R^{52}$, $COR^{52}$, $CO_2R^{52}$, $CONR^{51}R^{52}$, $CONR^{52}SO_2R^{51}$ and $SO_2NR^{51}R^{52}$;
- $R^{18}$ and $R^{19}$ are independently selected from hydrogen, alkyl and substituted alkyl;
- $R^{51}$ is selected from $C_{1-6}$alkyl and substituted $C_{1-6}$alkyl; and
- $R^{52}$ is selected from hydrogen, $C_{1-6}$alkyl and substituted $C_{1-6}$alkyl.

This disclosure includes compounds of Formula (VIIa) as defined by the following compounds 1-18 of Table 1. For any of the compounds of Table 1, $X^1$ can be O. Alternatively, $X^1$ can be S.

TABLE 1

Compounds of Formula (VIIa)

| Compound | $X^2$ | $Z^{11}$-$(Z^{12})_n$ | $R^4$ | $R^{14}$ | $R^{16}$ | $R^{17}$ | $R^{18}$ | $R^{19}$ | $Z^4$ | $Z^6$ |
|---|---|---|---|---|---|---|---|---|---|---|
| 1 | O | $CH_2CH_2$ | $SO_2CF_3$ | F | Cl | $SO_2CH_3$ | $CH_3$ | $CH(CH_3)_2$ | N | CHOH |
| 2 | O | $CH_2CH_2$ | $SO_2CF_3$ | F | Cl | $SO_2CH_3$ | $CH_3$ | $CH(CH_3)_2$ | N | $CHOPO(OH)_2$ |
| 3 | O | $CH_2CH_2$ | $SO_2CF_3$ | F | Cl | $CO_2H$ | $CH_3$ | $CH(CH_3)_2$ | N | CHOH |
| 4 | O | $CH_2CH_2$ | $SO_2CF_3$ | F | Cl | $CO_2H$ | $CH_3$ | $CH(CH_3)_2$ | N | $CHOPO(OH)_2$ |
| 5 | O | $CH_2CH_2CH_2$ | $SO_2CF_3$ | F | Cl | $CO_2H$ | $CH_3$ | $CH(CH_3)_2$ | N | CHOH |
| 6 | O | $CH_2CH_2CH_2$ | $SO_2CF_3$ | F | Cl | $CO_2H$ | $CH_3$ | $CH(CH_3)_2$ | N | $CHOPO(OH)_2$ |
| 7 | O | $CH_2CH_2CH_2$ | $SO_2CH_3$ | F | Cl | $CO_2H$ | $CH_3$ | $CH(CH_3)_2$ | N | CHOH |
| 8 | O | $CH_2CH_2CH_2$ | $SO_2CH_3$ | F | Cl | $CO_2H$ | $CH_3$ | $CH(CH_3)_2$ | N | $CHOPO(OH)_2$ |
| 9 | O | $CH_2CH_2$ | $SO_2CH_3$ | F | Cl | $CO_2H$ | $CH_3$ | $CH(CH_3)_2$ | N | CHOH |
| 10 | O | $CH_2CH_2$ | $SO_2CH_3$ | F | Cl | $CO_2H$ | $CH_3$ | $CH(CH_3)_2$ | N | $CHOPO(OH)_2$ |
| 11 | O | $CH_2CH_2$ | $SO_2CH_3$ | F | Cl | $SO_2CH_3$ | $CH_3$ | $CH(CH_3)_2$ | N | CHOH |
| 12 | O | $CH_2CH_2$ | $SO_2CH_3$ | F | Cl | $SO_2CH_3$ | $CH_3$ | $CH(CH_3)_2$ | N | $CHOPO(OH)_2$ |
| 13 | O | $CH_2CH_2$ | $NO_2$ | F | Cl | $SO_2CH_3$ | $CH_3$ | $CH(CH_3)_2$ | N | CHOH |
| 14 | O | $CH_2CH_2$ | $NO_2$ | F | Cl | $SO_2CH_3$ | $CH_3$ | $CH(CH_3)_2$ | N | $CHOPO(OH)_2$ |
| 15 | O | $CH_2CH_2$ | $NO_2$ | F | Cl | $CO_2H$ | $CH_3$ | $CH(CH_3)_2$ | N | CHOH |
| 16 | O | $CH_2CH_2$ | $NO_2$ | F | Cl | $CO_2H$ | $CH_3$ | $CH(CH_3)_2$ | N | $CHOPO(OH)_2$ |
| 17 | O | $CH_2CH_2CH_2$ | $NO_2$ | F | Cl | $CO_2H$ | $CH_3$ | $CH(CH_3)_2$ | N | CHOH |
| 18 | O | $CH_2CH_2CH_2$ | $NO_2$ | F | Cl | $CO_2H$ | $CH_3$ | $CH(CH_3)_2$ | N | $CHOPO(OH)_2$ |

Compounds of the Formulas (V) and (VIb) can include stereoisomers of compounds having a chiral center at the branching point of linker $L^2$. As such, the compound of Formulas (V) and (VIb) can be further described by Formula (VIIIb):

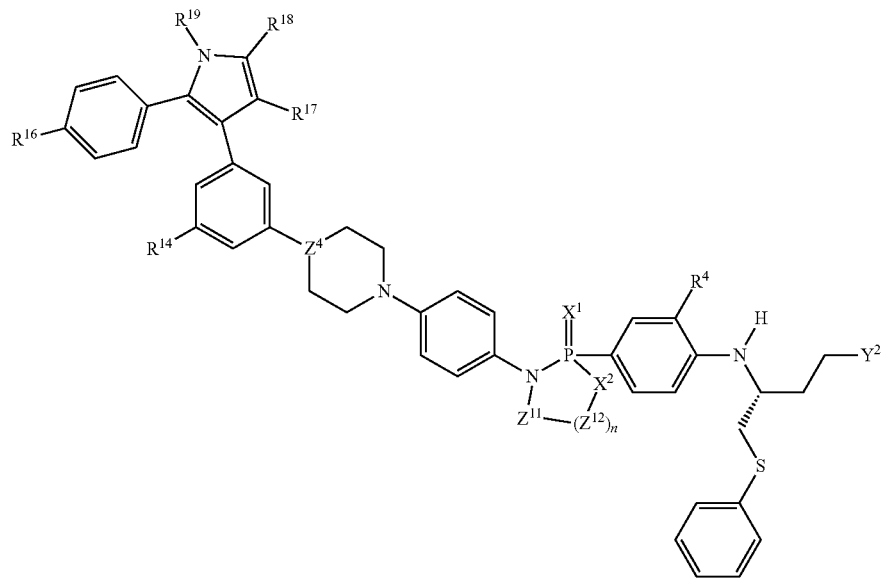

(VIIb)

where:
$Y^2$ is selected from —$OR^{52}$, —$N(R^{52})_2$, and —OP(=O)$(OR^{52})_2$;
$R^4$ is selected from $NO_2$, $SO_2CH_3$, $SO_2CF_3$ and $COR^{51}$;
$Z^4$ is selected from CH and N;
$R^{14}$ and $R^{16}$ are independently hydrogen or halogen; and
$R^{17}$ is selected from $SO_2R^{52}$, $COR^{52}$, $CO_2R^{52}$, $CONR^{51}R^{52}$, $CONR^{52}SO_2R^{51}$ and $SO_2NR^{51}R^{52}$;
$R^{18}$ and $R^{19}$ are independently selected from hydrogen, alkyl and substituted alkyl;
$R^{51}$ is selected from $C_{1-6}$alkyl and substituted $C_{1-6}$alkyl; and
$R^{52}$ is selected from hydrogen, $C_{1-6}$alkyl and substituted $C_{1-6}$alkyl.

This disclosure includes compounds of Formula (VIIb) as defined by the following compounds 19-36 of Table 2. For any of the compounds of Table 2, $X^1$ can be O. Alternatively, $X^1$ can be S.

TABLE 2

Compounds of Formula (VIIb)

| Compound | $X^2$ | $Z^{11}$-$(Z^{12})_n$ | $R^4$ | $R^{14}$ | $R^{16}$ | $R^{17}$ | $R^{19}$ | $R^{19}$ | $Z^4$ | $Y^2$ |
|---|---|---|---|---|---|---|---|---|---|---|
| 19 | O | $CH_2CH_2$ | $NO_2$ | F | Cl | $SO_2CH_3$ | $CH_3$ | $CH(CH_3)_2$ | N | $N(CH_3)_2$ |
| 20 | O | $CH_2CH_2$ | $SO_2CF_3$ | F | Cl | $SO_2CH_3$ | $CH_3$ | $CH(CH_3)_2$ | N | $N(CH_3)_2$ |
| 21 | O | $CH_2CH_2$ | $SO_2CF_3$ | F | Cl | $CO_2H$ | $CH_3$ | $CH(CH_3)_2$ | N | $N(CH_3)_2$ |
| 22 | O | $CH_2CH_2$ | $SO_2CF_3$ | H | Cl | $CO_2H$ | $CH_3$ | $CH(CH_3)_2$ | N | $N(CH_3)_2$ |
| 23 | O | $CH_2CH_2$ | $SO_2CH_3$ | F | Cl | $CO_2H$ | $CH_3$ | $CH(CH_3)_2$ | N | $N(CH_3)_2$ |
| 24 | O | $CH_2CH_2$ | $SO_2CH_3$ | H | Cl | $CO_2H$ | $CH_3$ | $CH(CH_3)_2$ | N | $N(CH_3)_2$ |
| 25 | O | $CH_2CH_2$ | $SO_2CH_3$ | F | Cl | $SO_2CH_3$ | $CH_3$ | $CH(CH_3)_2$ | N | $N(CH_3)_2$ |
| 26 | O | $CH_2CH_2$ | $NO_2$ | F | Cl | $CO_2H$ | $CH_3$ | $CH(CH_3)_2$ | N | $N(CH_3)_2$ |
| 27 | O | $CH_2CH_2$ | $NO_2$ | H | Cl | $CO_2H$ | $CH_3$ | $CH(CH_3)_2$ | N | $N(CH_3)_2$ |
| 28 | O | $CH_2CH_2$ | $NO_2$ | F | Cl | $SO_2CH_3$ | $CH_3$ | $CH(CH_3)_2$ | N | OH |
| 29 | O | $CH_2CH_2$ | $SO_2OF_3$ | F | Cl | $SO_2CH_3$ | $CH_3$ | $CH(CH_3)_2$ | N | OH |
| 30 | O | $CH_2CH_2$ | $SO_2OF_3$ | F | Cl | $CO_2H$ | $CH_3$ | $CH(CH_3)_2$ | N | OH |
| 31 | O | $CH_2CH_2$ | $SO_2OF_3$ | H | Cl | $CO_2H$ | $CH_3$ | $CH(CH_3)_2$ | N | OH |
| 32 | O | $CH_2CH_2$ | $SO_2CH_3$ | F | Cl | $CO_2H$ | $CH_3$ | $CH(CH_3)_2$ | N | OH |
| 33 | O | $CH_2CH_2$ | $SO_2CH_3$ | H | Cl | $CO_2H$ | $CH_3$ | $CH(CH_3)_2$ | N | OH |
| 34 | O | $CH_2CH_2$ | $SO_2CH_3$ | F | Cl | $SO_2CH_3$ | $CH_3$ | $CH(CH_3)_2$ | N | OH |
| 35 | O | $CH_2CH_2$ | $NO_2$ | F | Cl | $CO_2H$ | $CH_3$ | $CH(CH_3)_2$ | N | OH |
| 36 | O | $CH_2CH_2$ | $NO_2$ | H | Cl | $CO_2H$ | $CH_3$ | $CH(CH_3)_2$ | N | OH |

The compound of Formula (VIIa) can be further described by Formula (VIIIa):

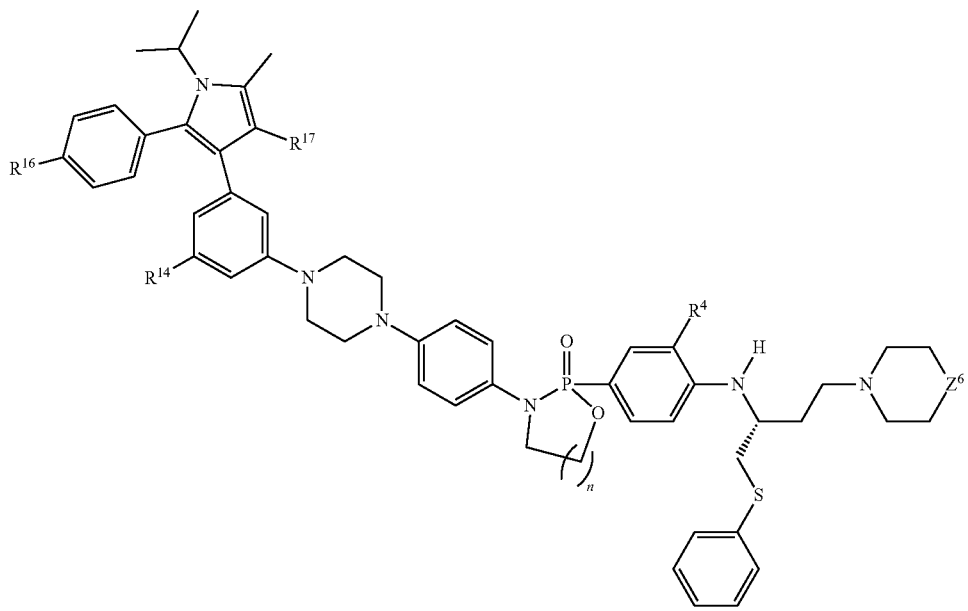

(VIIIa)

where:

R$^4$ is selected from NO$_2$, SO$_2$CH$_3$, SO$_2$CF$_3$ and COR$^{51}$;

n is 1 or 2;

Z$^6$ is selected from O, CHC(O)R$^{18}$, and CH(CH$_2$)$_p$R$^{18}$ wherein p is 0-6 and each R$^{18}$ is independently —OR, —N(R)$_2$, —OP(=O)(OH)$_2$, and —OP(=O)(OR)$_2$ wherein each R is independently H, alkyl or substituted alkyl (e.g., a C$_{1-4}$alkyl such as ethyl or tert-butyl);

R$^{14}$ and R$^{16}$ are independently hydrogen or halogen; and

R$^{17}$ is selected from SO$_2$R$^{52}$, COR$^{52}$, CO$_2$R$^{52}$, CONR$^{51}$R$^{52}$, CONR$^{52}$SO$_2$R$^{51}$ and SO$_2$NR$^{51}$R$^{52}$;

R$^{51}$ is selected from C$_{1-6}$alkyl and substituted C$_{1-6}$alkyl; and

R$^{52}$ is selected from hydrogen, C$_{1-6}$alkyl and substituted C$_{1-6}$alkyl.

This disclosure includes compounds of Formula (VIIIa) as defined by the following compounds of Table 3.

TABLE 3

| Compounds of Formula (VIIIa) | | | | | | |
|---|---|---|---|---|---|---|
| Compound | R$^4$ | R$^{14}$ | R$^{16}$ | R$^{17}$ | n | Z$^6$ |
| 37 | SO$_2$CF$_3$ | H | Cl | CO$_2$H | 1 | CHOPO(OH)$_2$ |
| 38 | SO$_2$CF$_3$ | H | Cl | CO$_2$H | 1 | CHCH$_2$OPO(OH)$_2$ |
| 39 | SO$_2$CF$_3$ | H | Cl | CO$_2$H | 1 | CHOH |
| 40 | SO$_2$CF$_3$ | H | Cl | CO$_2$H | 1 | CHCH$_2$OH |
| 41 | SO$_2$CF$_3$ | F | Cl | SO$_2$CH$_3$ | 1 | CHC(O)OH |
| 42 | SO$_2$CF$_3$ | F | Cl | SO$_2$CH$_3$ | 2 | CHOH |

The compound of Formula (VIIb) can be further described by Formula (VIIIb):

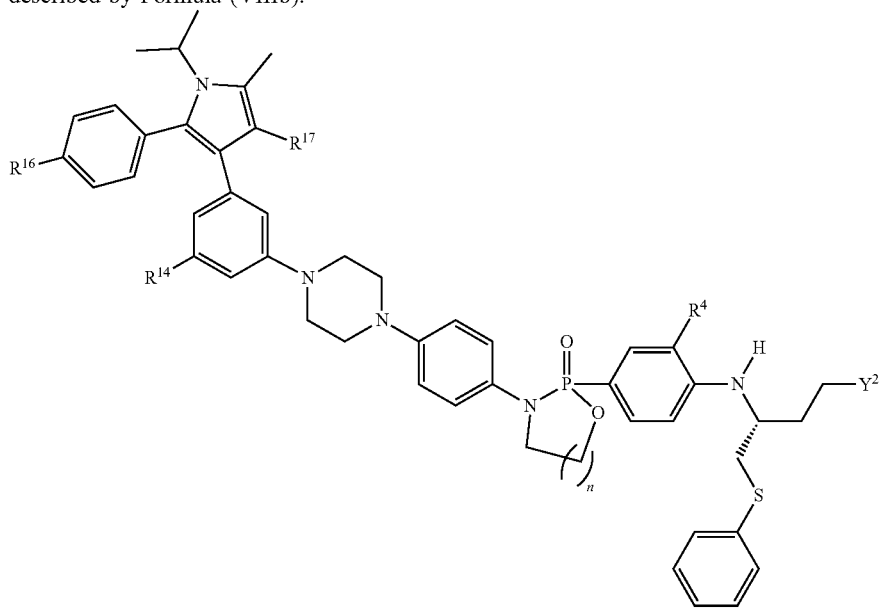

(VIIIb)

where:
Y² is selected from —OR⁵², —N(R⁵²)₂, and —OP(=O)(OR⁵²)₂;
R⁴ is selected from NO₂, SO₂CH₃, SO₂CF₃ and COR⁵¹;
n is 1 or 2;
R¹⁴ and R¹⁶ are independently hydrogen or halogen;
R¹⁷ is selected from SO₂R⁵², COR⁵², CO₂R⁵², CONR⁵¹R⁵², CONR⁵²SO₂R⁵¹ and SO₂NR⁵¹R⁵²;
R⁵¹ is selected from $C_{1-6}$alkyl and substituted $C_{1-6}$alkyl; and
R⁵² is selected from hydrogen, $C_{1-6}$alkyl and substituted $C_{1-6}$alkyl.

This disclosure includes compounds of Formula (VIIIb) as defined by the following compounds of Table 4.

TABLE 4

Compounds of Formula (VIIIb)

| Compound | R⁴ | R¹⁴ | R¹⁶ | R¹⁷ | n | Y² |
|---|---|---|---|---|---|---|
| 19 | NO₂ | F | Cl | SO₂CH₃ | 1 | N(CH₃)₂ |

This disclosure includes compounds with R¹⁶ being hydrogen, halogen, $C_{1-6}$alkyl, substituted $C_{1-6}$alkyl (e.g., CF₃) or CN. In Formulas (V), (VIa), (VIb), (VIIa), (VIIb), (VIIIa) and (VIIIb) R¹⁶ can be halogen. Optionally, R¹⁶ can be chloro. This disclosure includes compounds where R¹⁶ is not hydrogen. This disclosure includes compounds where R¹⁴ is absent. Alternatively, in Formulas (V), (VIa), (VIb), (VIIa), (VIIb), (VIIIa) and (VIIIb) R¹⁴ can be one halogen substituent. Optionally, R¹⁴ can be fluoro.

This disclosure includes compounds where R¹⁷ is SO₂R⁵², CO₂R⁵² or COR⁵². Alternatively, R¹⁷ can be CONR⁵¹R⁵², CONR⁵²SO₂R⁵¹ or SO₂NR⁵¹R⁵². R⁵¹ is $C_{1-6}$alkyl or substituted $C_{1-6}$alkyl and R⁵² is hydrogen, $C_{1-6}$alkyl or substituted $C_{1-6}$alkyl. In addition, R¹⁸ can be hydrogen. Sometimes, R¹⁸ is alkyl. Optionally, R¹⁸ can be substituted alkyl. In addition, R¹⁹ can be hydrogen. Sometimes, R¹⁹ can be alkyl. Optionally, R¹⁹ can be substituted alkyl.

The disclosure includes compounds of Formulas (VIIa), (VIIb), (VIIIa) and (VIIIb) including a stereoisomer of a chiral phosphorus stereocenter. As such, the compound of any one of Formulas (VIIa)-(VIIIb) can have either of the following chirality at phosphorus:

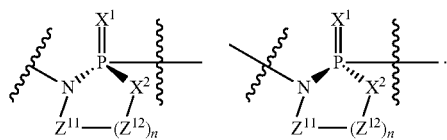

Any of the Formula (I), (IVa), (IVb), (V), (VIa), (VIb), (VIIa) and (VIIb) can have a core phospholidine linking moiety as shown in Formula (IIIa). This disclosure includes such compounds where $X^1$ is O. Optionally, $X^1$ is S. This disclosure includes such compounds where r is 1. Alternatively r is 2. Sometimes, the compound is a stereoisomer of Formula (IIIa).

Any of the Formula (I), (IVa), (IVb), (V), (VIa), (VIb), (VIIa) and (VIIb) can have a core phospholidine linking moiety as shown in Formula (IIIb). This disclosure includes such compounds where $X^1$ is O. Optionally, $X^1$ is S. Sometimes, the compound is a stereoisomer of Formula (IIIb).

Any of the Formula (I), (IVa), (IVb), (V), (VIa), (VIb), (VIIa) and (VIIb) can have a core phospholidine linking moiety as shown in Formula (IIIc). This disclosure includes such compounds where $X^1$ is O. Optionally, $X^1$ is S. This disclosure includes such compounds where r is 1. Alternatively r is 2. Sometimes, the compound is a stereoisomer of Formula (IIIc).

Any of the Formula (I), (IVa), (IVb), (V), (VIa), (VIb), (VIIa) and (VIIb) can have a core phospholidine linking moiety as shown in Formula (IIId). This disclosure includes such compounds where $X^1$ is O. Optionally, $X^1$ is S. Sometimes, the compound is a stereoisomer of Formula (IIId).

Any of the Formula (I), (IVa), (IVb), (V), (VIa), (VIb), (VIIa) and (VIIIb) can have a core phospholidine linking moiety as shown in Formula (IIIe). This disclosure includes such compounds where $X^1$ is O. Optionally, $X^1$ is S. Sometimes, the compound is a stereoisomer of Formula (IIIe).

Any of the Formula (I), (IVa), (IVb), (V), (VIa), (VIb), (VIIa) and (VIIb) can have a core phospholidine linking moiety as shown in Formula (IIIf). This disclosure includes such compounds where $X^1$ is O. Optionally, $X^1$ is S. Sometimes, the compound is a stereoisomer of Formula (IIIf).

Any of the Formula (I), (IVa), (IVb), (V), (VIa), (VIb), (VIIa) and (VIIb) can have a core phospholidine linking moiety as shown in Formula (IIIg). This disclosure includes such compounds where $X^1$ is O. Optionally, $X^1$ is S. This disclosure includes such compounds where r is 1. Alternatively r is 2. Sometimes, the compound is a stereoisomer of Formula (IIIg).

Any of the Formula (I), (IVa), (IVb), (V), (VIa), (VIb), (VIIa) and (VIIb) can have a core phospholidine linking moiety as shown in Formula (IIIh). This disclosure includes such compounds where $X^1$ is O. Optionally, $X^1$ is S. This disclosure includes such compounds where r is 1. Alternatively r is 2. Sometimes, the compound is a stereoisomer of Formula (IIIh).

This disclosure includes compounds of formula (VIIa) or (VIIb) where the 5-, 6- or 7-membered heterocyclic ring connecting the N and P atoms includes a sidechain substituent that derives from an amino acid residue. For example, one of $R^{24}$ and $R^{25}$ of a $Z^{12}$ group can be a group corresponding to an amino acid sidechain. For each $Z^{12}$ group, one of $R^{24}$ and $R^{25}$ can be a sidechain group of an amino acid residue such as alanine, valine, leucine, isoleucine, glutamine, glutamic acid, aspartic acid, asparagine, serine, threonine, cysteine, methionine, lysine, arginine, ornithine, phenylalanine, tyrosine, tryptophan or histidine, or a substituted version thereof. In general, the heterocyclic ring includes only one $Z^{12}$ group that includes an amino acid derived sidechain, where the remaining $Z^{12}$ groups $R^{24}$ and $R^{25}$ are each hydrogen. As such, $Z^{12}$ can include a chiral center having a chirality corresponding to an L-amino acid residue. Alternatively, $Z^{12}$ can have a chirality corresponding to a D-amino acid residue.

For any of the formulas and structures depicted herein, such formulas and structures may also include salt forms where the structure provides for an acidic or basic group. The core phospholidine linking moiety of the compounds of this disclosure can be neutral. The compound can include a charged moiety (e.g., a basic amino group) at other location(s) of the compound. Where applicable, neutral forms of the groups are generally depicted in the structures for simplicity, however various salt forms are also meant to be included. A salt of the compound could include a monovalent cation salt, such as sodium or potassium salt. Other tautomeric arrangements of the groups depicted in these formulas and structures are possible, and are meant to be included in this disclosure.

Evaluating Compounds for Senolytic Activity

These and other compounds can be evaluated on the molecular level for their ability to perform in a way that indicates they are candidate agents for use according to this disclosure.

For example, where the therapy includes triggering apoptosis of senescent cells by way of Bcl-2, Bcl-xL, Bcl-w, or other Bcl family protein, compounds can be tested for their ability to inhibit binding between one or more Bcl proteins and their respective cognate ligand. Example 1 provides an illustration of a homogeneous assay (an assay that does not require a separation step) for purposes of determining binding to the Bcl isoforms. Compounds can be screened on the molecular level for their ability to interact with the target isoform, thereby causing senolysis. Examples 2 and 3 provide illustrations of assays designed for this purpose.

Alternatively or in addition, compounds can be evaluated for an ability to kill senescent cells specifically. Cultured cells are contacted with the compound, and the degree of cytotoxicity or inhibition of the cells is determined. The ability of the compound to kill or inhibit senescent cells can be compared with the effect of the compound on normal cells that are freely dividing at low density, and normal cells that are in a quiescent state at high density. Examples 2 and 3 provide illustrations of senescent cell killing using the human target tissue fibroblast IMR90 cell line and HUVEC cells. Similar protocols are known and can be developed or optimized for testing the ability of the cells to kill or inhibit other senescent cells and other cell types, such as cancer cells.

Candidate Bcl inhibitors that are effective in selectively killing senescent cells in vitro can be further screened in animal models for particular disease. Examples 4, 5, 6, and 7 of the Experimental Section below provide illustrations for osteoarthritis, eye disease, lung disease, and atherosclerosis, respectively.

Formulation of Medicaments

Preparation and formulation of pharmaceutical agents for use according to this disclosure can incorporate standard technology, as described, for example, in the current edition of *Remington: The Science and Practice of Pharmacy*. The formulation will typically be optimized for administration to the target tissue, for example, by local administration, in a manner that enhances access of the active agent to the target senolytic cells and providing the optimal duration of effect, while minimizing side effects or exposure to tissues that are not involved in the condition being treated.

Pharmaceutical preparations for use in treating senescence-related conditions and other diseases can be prepared by mixing a Bcl inhibitor with a pharmaceutically acceptable base or carrier and as needed one or more pharmaceutically acceptable excipients. Depending on the target tissue, it may be appropriate to formulate the pharmaceutical composition for sustained or timed release. Oral timed release formulations may include a mixture of isomeric variants, binding agents, or coatings. Injectable time release formulations may include the active agent in combination with a binding agent, encapsulating agent, or microparticle. For treatment of joint diseases such as osteoarthritis, the pharmaceutical composition is typically formulated for intra-articular administration. For treatment of eye disease such as glaucoma, diabetic retinopathy or age-related macular degeneration (AMD), the composition may be formulated for intravitreal or intracameral administration. For treatment of lung diseases, the composition may be formulated as an aerosol, or for intratracheal administration.

This disclosure provides commercial products that are kits that enclose unit doses of one or more of the agents or compositions described in this disclosure. Such kits typically comprise a pharmaceutical preparation in one or more containers. The preparations may be provided as one or more unit doses (either combined or separate). The kit may contain a device such as a syringe for administration of the agent or composition in or around the target tissue of a subject in need thereof. The product may also contain or be accompanied by an informational package insert describing the use and attendant benefits of the drugs in treating the senescent cell associated condition, and optionally an appliance or device for therapeutic delivery of the composition.

Treatment Design

Senescent cells accumulate with age, which is why conditions mediated by senescent cells occur more frequently in older adults. In addition, different types of stress on pulmonary tissues may promote the emergence of senescent cells and the phenotype they express. Cell stressors include oxidative stress, metabolic stress, DNA damage (for example, as a result of environmental ultraviolet light exposure or genetic disorder), oncogene activation, and telomere shortening (resulting, for example, from hyperproliferation). Tissues that are subject to such stressors may have a higher prevalence of senescent cells, which in turn may lead to presentation of certain conditions at an earlier age, or in a more severe form. An inheritable susceptibility to certain conditions suggests that the accumulation of disease-mediating senescent cells may directly or indirectly be influenced by genetic components, which can lead to earlier presentation.

One of the benefits of the senescent cell paradigm is that successful removal of senescent cells may provide the subject with a long-term therapeutic effect. Senescent cells are essentially non-proliferative, which means that subsequent repopulation of a tissue with more senescent cells can only occur by conversion of non-senescent cells in the tissue to senescent cells—a process that takes considerably longer than simple proliferation. As a general principle, a period of therapy with a senolytic agent that is sufficient to remove senescent cells from a target tissue (a single dose, or a plurality of doses given, for example, every day, semi-weekly, or weekly, given over a period of a few days, a week, or several months) may provide the subject with a period of efficacy (for example, for two weeks, a month, two months, or more) during which the senolytic agent is not administered, and the subject experiences alleviation, reduction, or reversal of one or more adverse signs or symptoms of the condition being treated.

To treat a particular senescence-related condition with a senolytic agent according to this disclosure, the therapeutic regimen will depend on the location of the senescent cells, and the pathophysiology of the disease.

Senescence-Related Conditions Suitable for Treatment

The Bcl inhibitors of this disclosure can be used for prevention or treatment of various senescence-related conditions. Such conditions will typically (although not necessarily) characterized by an overabundance of senescent cells (such as cells expressing p16 and other senescence markers) in or around the site of the condition, or an overabundance of expression of p16 and other senescence markers, in comparison with the frequency of such cells or the level of such expression in unaffected tissue. Non-limiting examples of current interest include the treatment of osteoarthritis, eye disease, and lung disease, as illustrated in the following sections.

Treatment of Osteoarthritis

Any of the Bcl inhibitors listed in this disclosure can be developed for treating osteoarthritis in accordance with this disclosure. Similarly, of the Bcl inhibitors listed in this disclosure can be developed for selectively eliminating senescent cells in or around a joint of a subject in need thereof, including but not limited to a joint affected by osteoarthritis.

Osteoarthritis degenerative joint disease is characterized by fibrillation of the cartilage at sites of high mechanical stress, bone sclerosis, and thickening of the synovium and the joint capsule. Fibrillation is a local surface disorganization involving splitting of the superficial layers of the cartilage. The early splitting is tangential with the cartilage surface, following the axes of the predominant collagen bundles. Collagen within the cartilage becomes disorganized, and proteoglycans are lost from the cartilage surface. In the absence of protective and lubricating effects of proteoglycans in a joint, collagen fibers become susceptible to degradation, and mechanical destruction ensues. Predisposing risk factors for developing osteoarthritis include increasing age, obesity, previous joint injury, overuse of the joint, weak thigh muscles, and genetics. Symptoms of osteoarthritis include sore or stiff joints, particularly the hips, knees, and lower back, after inactivity or overuse; stiffness after resting that goes away after movement; and pain that is worse after activity or toward the end of the day.

Compounds according to this disclosure can be used to reduce or inhibit loss or erosion of proteoglycan layers in a joint, reduces inflammation in the affected joint, and promotes, stimulates, enhances, or induces production of collagen, for example, type 2 collagen. The compound may causes a reduction in the amount, or level, of inflammatory cytokines, such as IL-6, produced in a joint and inflammation is reduced. The compounds can be used for treating osteoarthritis and/or inducing collagen, for example, Type 2 collagen, production in the joint of a subject. A compound also can be used for decreasing, inhibiting, or reducing production of metalloproteinase 13 (MMP-13), which degrades collagen in a joint, and for restoring proteoglycan layer or inhibiting loss and/or degradation of the proteoglycan layer. Treatment with a compound thereby may also reduce the likelihood of, inhibits, or decreases erosion, or slows erosion of the bone. The compound may be administered directly to an osteoarthritic joint, for example, intra-articularly, topically, transdermally, intradermally, or subcutaneously. The compound may also restore, improve, or inhibit deterioration of strength of a join, and reduce joint pain.

Treatment of Ophthalmic Conditions

Any of the Bcl inhibitors listed in this disclosure can be used for preventing or treating an ophthalmic condition in a subject in need thereof by removing senescent cells in or around an eye of the subject, whereby at least one sign or symptom of the disease is decreased in severity. Such conditions include both back-of-the-eye diseases, and front-of-the-eye diseases. Similarly, of the Bcl inhibitors listed in this disclosure can be developed for selectively eliminating senescent cells in or around ocular tissue in a subject in need thereof.

Diseases of the eye that can be treated according to this disclosure include presbyopia, macular degeneration (including wet or dry AMD), diabetic retinopathy, and glaucoma.

Macular degeneration is a neurodegenerative condition that can be characterized as a back-of-the-eye disease. It causes the loss of photoreceptor cells in the central part of retina, called the macula. Macular degeneration can be dry or wet. The dry form is more common than the wet, with about 90% of age-related macular degeneration (AMD) patients diagnosed with the dry form. Dry AMD is associated with atrophy of the retinal pigment epithelium (RPE) layer, which causes loss of photoreceptor cells. With wet AMD, new blood vessels may grow beneath the retina and leak blood and fluid. Abnormally leaky choroidal neovascularization can cause the retinal cells to die, creating blind spots in central vision. The formation of exudates, or "drusen," underneath the Bruch's membrane of the macula is can be a physical sign that macular degeneration is emerging. Symptoms of macular degeneration include, for example, perceived distortion of straight lines, dark, blurry areas and color perception changes.

Another back-of-the-eye disease is diabetic retinopathy (DR). According to Wikipedia, the first stage of DR is non-proliferative, and typically has no substantial symptoms or signs. NPDR is detectable by fundus photography, in which microaneurysms (microscopic blood-filled bulges in the artery walls) can be seen. If there is reduced vision, fluorescein angiography can be done to see the back of the eye. Narrowing or blocked retinal blood vessels can be seen clearly and this is called retinal ischemia (lack of blood flow). Macular edema in which blood vessels leak their contents into the macular region can occur at any stage of NPDR. The symptoms of macular edema are blurred vision and darkened or distorted images that are not the same in both eyes. Optical Coherence Tomography can show the areas of retinal thickening (due to fluid accumulation) of macular edema. In the second stage of DR, abnormal new blood vessels (neovascularization) form at the back of the eye as part of proliferative diabetic retinopathy (PDR), which may burst and bleed (vitreous hemorrhage) and blur the vision. On funduscopic exam, a clinician will see cotton wool spots, flame hemorrhages (similar lesions are also caused by the alpha-toxin of *Clostridium novyi*), and dot-blot hemorrhages.

Benefits of treatment of back-of-the-eye disease with a senolytic agent of this disclosure may include inhibition or delay of adverse features of the condition, such as abnormal neovascularization, pathogenic angiogenesis, vaso-obliteration, intraocular bleeding, retinal damage, and vision loss. The senolytic agent may be administered in or around the eye, for example, by intraocular, intravitreal, or retrobulbar injection. Optimally, there will be a reversal in some of the pathophysiology, such as restoration of functional vasculature, functional angiogenesis, retinal regrowth or restoration, with a partial degree of vision improvement.

Presbyopia is an age-related condition where the eye exhibits a progressively diminished ability to focus on near objects as the speed and amplitude of accommodation of a normal eye decreases with advancing age. Loss of elasticity of the crystalline lens and loss of contractility of the ciliary muscles can cause presbyopia. Age-related changes in the mechanical properties of the anterior lens capsule and posterior lens capsule suggest that the mechanical strength of the posterior lens capsule decreases significantly with age as a consequence of change in the composition of the tissue. The major structural component of the lens capsule is basement membrane type IV collagen that is organized into a three-dimensional molecular network. Adhesion of the collagen IV, fibronectin, and lamina to the intraocular lens can inhibit cell migration and can reduce the risk of PCO.

Senolytic agents provided by this disclosure may slow the disorganization of the type IV collagen network, decrease or inhibit epithelial cell migration and can also delay the onset of presbyopia or decrease or slow the progressive severity of the condition. They can also be useful for post-cataract surgery to reduce the likelihood of occurrence of PCO.

Glaucoma and other front-of-the-eye diseases may also be amenable to treatment with the senolytic agents provided in this disclosure. Normally, clear fluid flows into and out of the front part of the eye, known as the anterior chamber. In individuals who have open/wide-angle glaucoma, the clear fluid drains too slowly, leading to increased pressure within the eye. If left untreated, the high pressure in the eye can subsequently damage the optic nerve and can lead to complete blindness. The loss of peripheral vision is caused by the death of ganglion cells in the retina.

Possible benefits of therapy include a reduction in intraocular pressure, improved draining of ocular fluid through the trabecular network, and an inhibition or delay of vision loss that results. The senolytic agent may be administered in or around the eye, for example, by intraocular or intracameral injection or in a topical formulation. The effect of therapy can be monitored by automated perimetry, gonioscopy, imaging technology, scanning laser tomography, HRT3, laser polarimetry, GDX, ocular coherence tomography, ophthalmoscopy, and pachymeter measurements that determine central corneal thickness.

Treatment of Pulmonary Conditions

Any of the Bcl inhibitors listed in this disclosure can be developed for treating pulmonary disease in accordance with this disclosure. Similarly, of the Bcl inhibitors listed in this disclosure can be developed for selectively eliminating senescent cells in or around a lung of a subject in need thereof. Pulmonary conditions that can be treated include idiopathic pulmonary fibrosis (IPF), chronic obstructive pulmonary disease (COPD), asthma, cystic fibrosis, bronchiectasis, and emphysema.

COPD is a lung disease defined by persistently poor airflow resulting from the breakdown of lung tissue, emphysema, and the dysfunction of the small airways, obstructive bronchiolitis. Primary symptoms of COPD include shortness of breath, wheezing, chest tightness, chronic cough, and excess sputum production. Elastase from cigarette smoke-activated neutrophils and macrophages can disintegrate the extracellular matrix of alveolar structures, resulting in enlarged air spaces and loss of respiratory capacity. COPD can be caused by, for example, tobacco smoke, cigarette smoke, cigar smoke, secondhand smoke, pipe smoke, occupational exposure, exposure to dust, smoke, fumes, and pollution, occurring over decades thereby implicating aging as a risk factor for developing COPD.

The processes that cause lung damage include, for example, oxidative stress produced by the high concentrations of free radicals in tobacco smoke, cytokine release due to the inflammatory response to irritants in the airway, and impairment of anti-protease enzymes by tobacco smoke and free radicals, allowing proteases to damage the lungs. Genetic susceptibility can also contribute to the disease. In about 1% percent of people with COPD, the disease results from a genetic disorder that causes low level production of alpha-1-antitrypsin in the liver. Alpha-1-antitrypsin is normally secreted into the bloodstream to help protect the lungs.

Pulmonary fibrosis is a chronic and progressive lung disease characterized by stiffening and scarring of the lung, which can lead to respiratory failure, lung cancer, and heart failure. Fibrosis is associated with repair of epithelium. Fibroblasts are activated, production of extracellular matrix proteins is increased, and transdifferentiation to contractile myofibroblasts contribute to wound contraction. A provisional matrix plugs the injured epithelium and provides a scaffold for epithelial cell migration, involving an epithelial-mesenchymal transition (EMT). Blood loss associated with epithelial injury induces platelet activation, production of growth factors, and an acute inflammatory response. Normally, the epithelial barrier heals and the inflammatory response resolves. However, in fibrotic disease the fibroblast response continues, resulting in unresolved wound healing. Formation of fibroblastic foci is a feature of the disease, reflecting locations of ongoing fibrogenesis.

Subjects at risk of developing pulmonary fibrosis include, for example, those exposed to environmental or occupational pollutants, such as asbestosis and silicosis; those who smoke cigarettes; those who have a connective tissue diseases such as RA, SLE, scleroderma, sarcoidosis, or Wegener's granulomatosis; those who have infections; those who take certain medications, including, for example, amiodarone, bleomycin, busufan, methotrexate, and nitrofurantoin; those subject to radiation therapy to the chest; and those whose family member have pulmonary fibrosis.

Other pulmonary conditions that can be treated by using a compound according to this condition include emphysema, asthma, bronchiectasis, and cystic fibrosis. Pulmonary diseases can also be exacerbated by tobacco smoke, occupational exposure to dust, smoke, or fumes, infection, or pollutants that contribute to inflammation.

Symptoms of lung disease can include of shortness of breath, wheezing, chest tightness, having to clear one's throat first thing in the morning because of excess mucus in the lungs, a chronic cough that produces sputum that can be clear, white, yellow or greenish, cyanosis, frequent respiratory infections, lack of energy, and unintended weight loss. Symptoms of pulmonary fibrosis may include shortness of breath, particularly during exercise; dry, hacking cough; fast, shallow breathing; gradual, unintended weight loss; fatigue; aching joints and muscles; and clubbing of the fingers or toes.

Lung function before, during, and after treatment can be determined, for example, by measuring expiratory reserve volume (ERV), forced vital capacity (FVC), forced expiratory volume (FEV), total lung capacity (TLC), vital capacity (VC), residual volume (RV), and functional residual capacity (FRC). Gas exchange across alveolar capillary membrane can be measured using diffusion capacity for carbon monoxide (DLCO). Exercise capacity can be measured as a proxy. Peripheral capillary oxygen saturation ($SpO_2$) can also be measured: normal oxygen levels are typically between 95% and 100%. An $SpO_2$ level below 90% suggests the subject has hypoxemia. Values below 80% are considered critical and require intervention to maintain brain and cardiac function and avoid cardiac or respiratory arrest.

Benefits of treatment may include inhibiting progression or reversing of any of these effects. Administration of the senolytic agent may be systemic, or local at a site in or around the lung: for example, by inhalation as an aerosol or powder, or by intubation. Optimally, the agent will improve the $SpO_2$ level and exercise capacity.

Treatment of Atherosclerosis

The senolytic compounds can be used for the treatment of atherosclerosis: for example, by inhibiting formation, enlargement, or progression of atherosclerotic plaques in a subject. The senolytic compounds can also be used to enhance stability of atherosclerotic plaques that are present in one or more blood vessels of a subject, thereby inhibiting them from rupturing and occluding the vessels.

Atherosclerosis is characterized by patchy intimal plaques, atheromas, that encroach on the lumen of medium-sized and large arteries; the plaques contain lipids, inflammatory cells, smooth muscle cells, and connective tissue. Atherosclerosis can affect large and medium-sized arteries, including the coronary, carotid, and cerebral arteries, the aorta and branches thereof, and major arteries of the extremities.

Atherosclerosis may lead to an increase in artery wall thickens. Symptoms develop when growth or rupture of the plaque reduces or obstructs blood flow; and the symptoms can vary depending on which artery is affected. Atherosclerotic plaques can be stable or unstable. Stable plaques regress, remain static, or grow slowly, sometimes over several decades, until they can cause stenosis or occlusion. Unstable plaques are vulnerable to spontaneous erosion, fissure, or rupture, causing acute thrombosis, occlusion, and infarction long before they cause hemodynamically significant stenosis. Clinical events can result from unstable plaques, which do not appear severe on angiography; thus, plaque stabilization can be a way to reduce morbidity and mortality. Plaque rupture or erosion can lead to major cardiovascular events such as acute coronary syndrome and stroke. Disrupted plaques can have a greater content of lipid, macrophages, and have a thinner fibrous cap than intact plaques.

Diagnosis of atherosclerosis and other cardiovascular disease can be based on symptoms, for example, angina, chest pressure, numbness or weakness in arms or legs, difficulty speaking or slurred speech, drooping muscles in face, leg pain, high blood pressure, kidney failure and/or erectile dysfunction, medical history, and/or physical examination of a patient. Diagnosis can be confirmed by angiography, ultrasonography, or other imaging tests. Subjects at risk of developing cardiovascular disease include those having any one or more of predisposing factors, such as a family history of cardiovascular disease and those having other risk factors, for example, predisposing factors including high blood pressure, dyslipidemia, high cholesterol, diabetes, obesity and cigarette smoking, sedentary lifestyle, and hypertension. The condition can be assessed, for example, by angiography, electrocardiography, or stress test.

Potential benefits of treatment with a senolytic agent include alleviating or halting progression of one or more signs or symptoms of the condition, such as the frequency of plaques, the surface area of vessels covered by plaques, angina, and reduced exercise tolerance.

Exemplary Phospholidines

Included in the formulas presented above are the following exemplary compounds, which can be screened and developed for the various uses described as part of this disclosure.

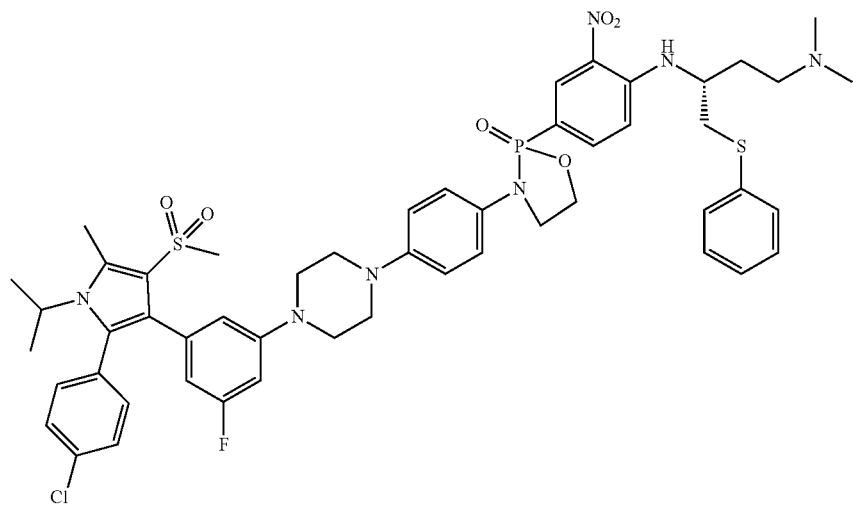

3-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)-2-(4-(((R)-4-(dimethylamino)-1-(phenylthio)butan-2-yl)amino)-3-nitrophenyl)-1,3,2-oxazaphospholidine 2-oxide

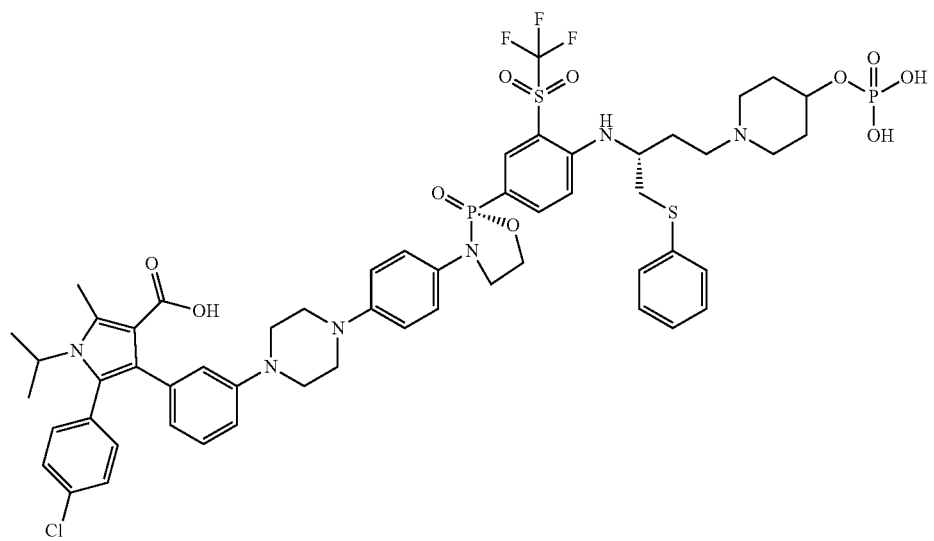

5-(4-chlorophenyl)-1-isopropyl-2-methyl-4-(3-(4-(4-(4-((R)-2-oxido-2-(4-(((R)-1-(phenylthio)-4-(4-(phosphonooxy)piperidin-1-yl)butan-2-yl)amino)-3-((trifluoromethyl)sulfonyl)phenyl)-1,3,2-oxazaphospholidin-3-yl)phenyl)piperazin-1-yl)phenyl)-1H-pyrrole-3-carboxylic acid

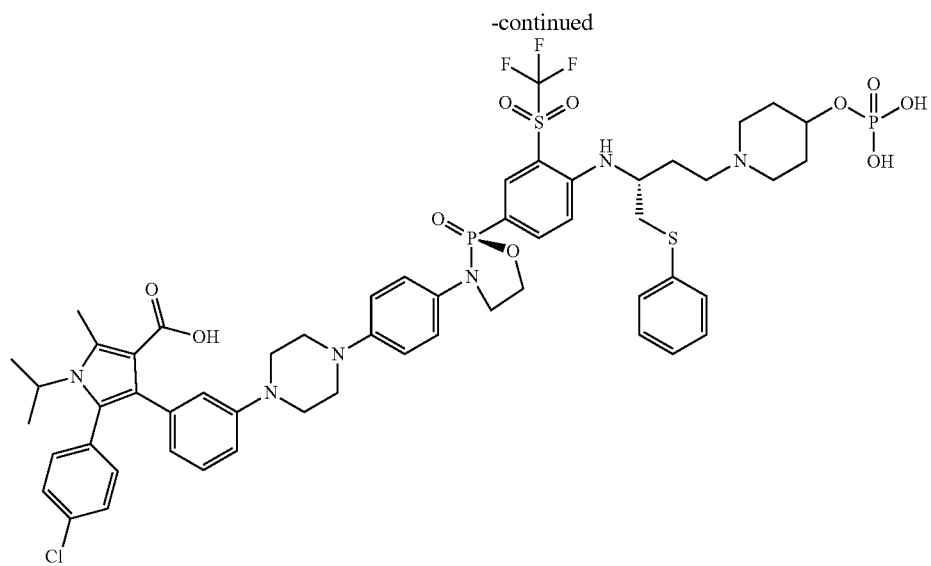

5-(4-chlorophenyl)-1-isopropyl-2-methyl-4-(3-(4-(4-(((S)-2-oxido-2-(4-(((R)-1-(phenylthio)-4-(4-(phosphonooxy)piperidin-1-yl)butan-2-yl)amino)-3-((trifluoromethyl)sulfonyl)phenyl)-1,3,2-oxazaphospholidin-3-yl)phenyl)piperazin-1-yl)phenyl)-1H-pyrrole-3-carboxylic acid

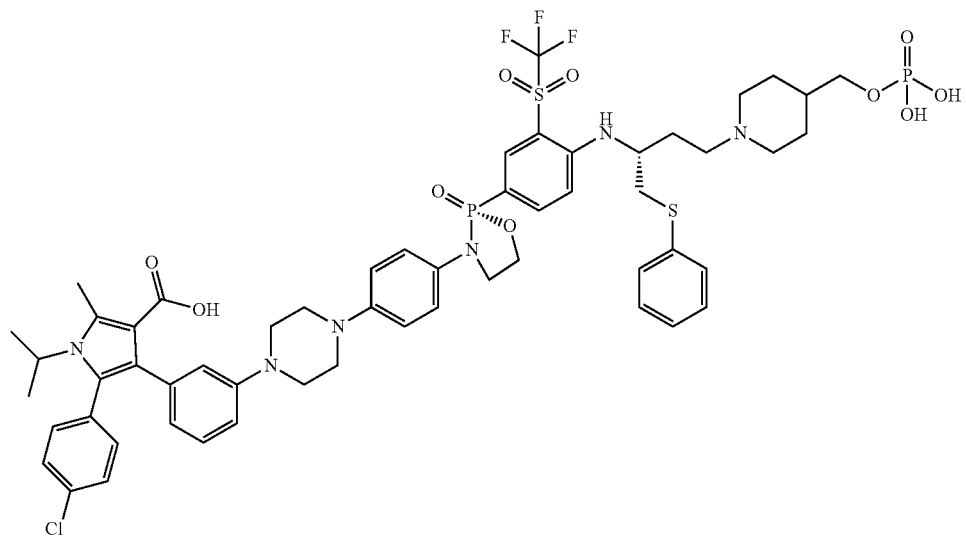

5-(4-chlorophenyl)-1-isopropyl-2-methyl-4-(3-(4-(4-(((R)-2-oxido-2-(4-(((R)-1-(phenylthio)-4-(4-((phosphonooxy)methyl)piperidin-1-yl)butan-2-yl)amino)-3-((trifluoromethyl)sulfonyl)phenyl)-1,3,2-oxazaphospholidin-3-yl)phenyl)piperazin-1-yl)phenyl)-1H-pyrrole-3-carboxylic acid

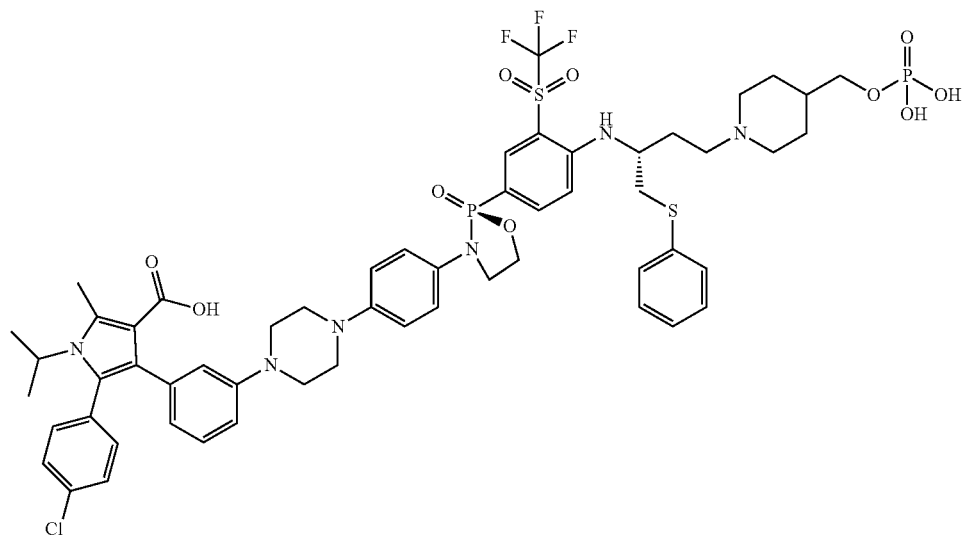

5-(4-chlorophenyl)-1-isopropyl-2-methyl-4-(3-(4-(4-(((S)-2-oxido-2-(4-(((R)-1-(phenylthio)-4-(4-((phosphonooxy)methyl)piperidin-1-yl)butan-2-yl)amino)-3-((trifluoromethyl)sulfonyl)phenyl)-1,3,2-oxazaphospholidin-3-yl)phenyl)piperazin-1-yl)phenyl)-1H-pyrrole-3-carboxylic acid

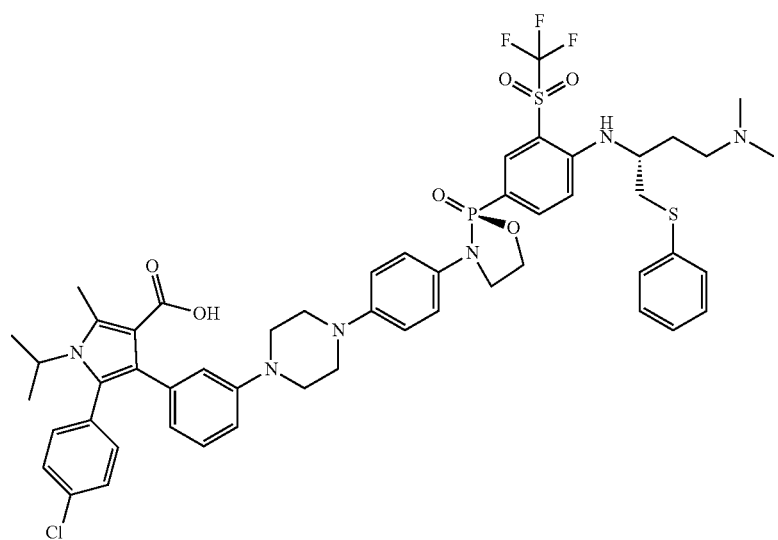

5-(4-chlorophenyl)-4-(3-(4-(4-(((S)-2-(4-(((R)-4-(dimethylamino)-1-(phenylthio)butan-2-yl)amino)-3-((trifluoromethyl)sulfonyl)phenyl)-2-oxido-1,3,2-oxazaphospholidin-3-yl)phenyl)piperazin-1-yl)phenyl)-1-isopropyl-2-methyl-1H-pyrrole-3-carboxylic acid -continued

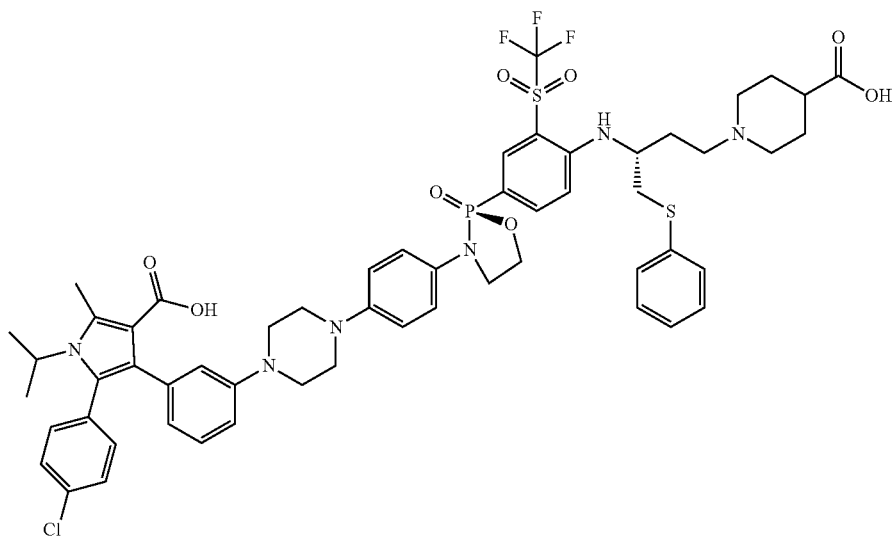

1-((R)-3-((4-((S)-3-(4-(4-(3-(4-carboxy-2-(4-chlorophenyl)-1-isopropyl-5-methyl-1H-pyrrol-3-yl)phenyl)piperazin-1-yl)phenyl)-2-oxido-1,3,2-oxazaphospholidin-2-yl)-2-((trifluoromethyl)sulfonyl)phenyl)amino)-4-(phenylthio)butyl)piperidine-4-carboxylic acid

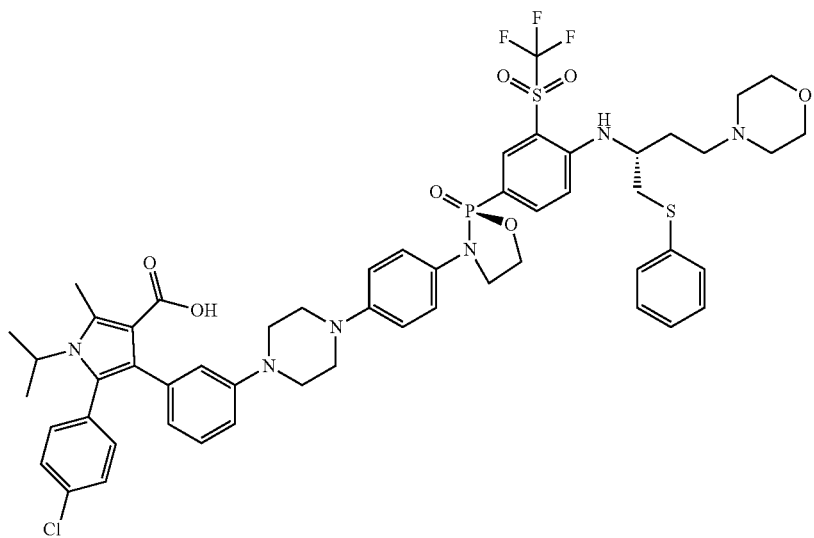

5-(4-chlorophenyl)-1-isopropyl-2-methyl-4-(3-(4-(4-((S)-2-(4-(((R)-4-morpholino-1-(phenylthio)butan-2-yl)amino)-3-((trifluoromethyl)sulfonyl)phenyl)-2-oxido-1,3,2-oxazaphospholidin-3-yl)phenyl)piperazin-1-yl)phenyl)-1H-pyrrole-3-carboxylic acid

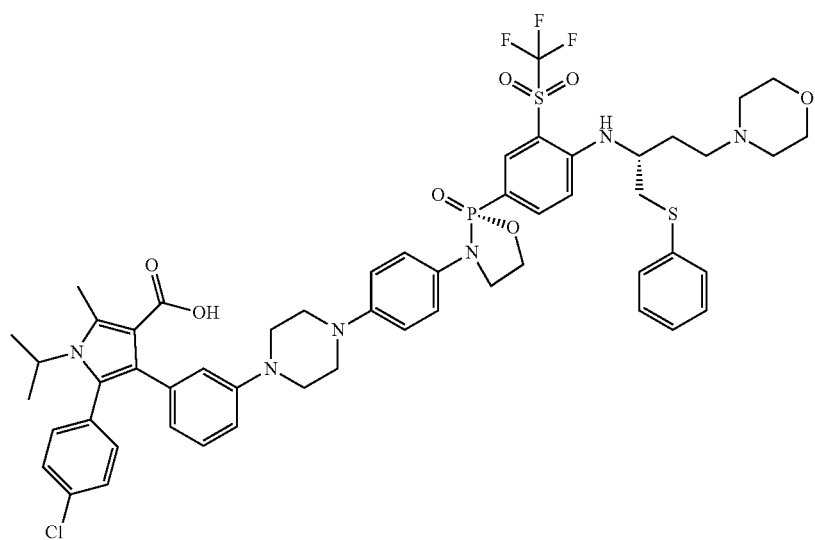

5-(4-chlorophenyl)-1-isopropyl-2-methyl-4-(3-(4-(4-((R)-2-(4-(((R)-4-morpholino-1-(phenylthio)butan-2-yl)amino)-3-((trifluoromethyl)sulfonyl)phenyl)-2-oxido-1,3,2-oxazaphospholidin-3-yl)phenyl)piperazin-1-yl)phenyl)-1H-pyrrole-3-carboxylic acid

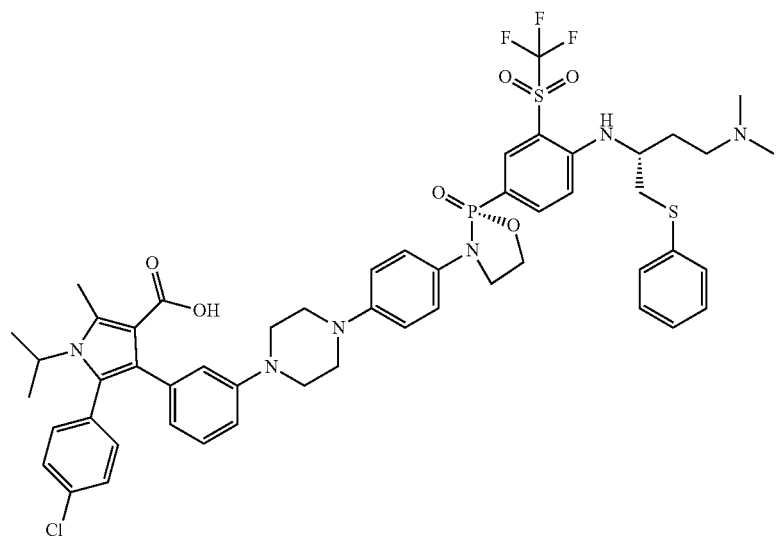

5-(4-chlorophenyl)-4-(3-(4-(4-((R)-2-(4-(((R)-4-(dimethylamino)-1-(phenylthio)butan-2-yl)amino)-3-((trifluoromethyl)sulfonyl)phenyl)-2-oxido-1,3,2-oxazaphospholidin-3-yl)phenyl)piperazin-1-yl)phenyl)-1-isopropyl-2-methyl-1H-pyrrole-3-carboxylic acid

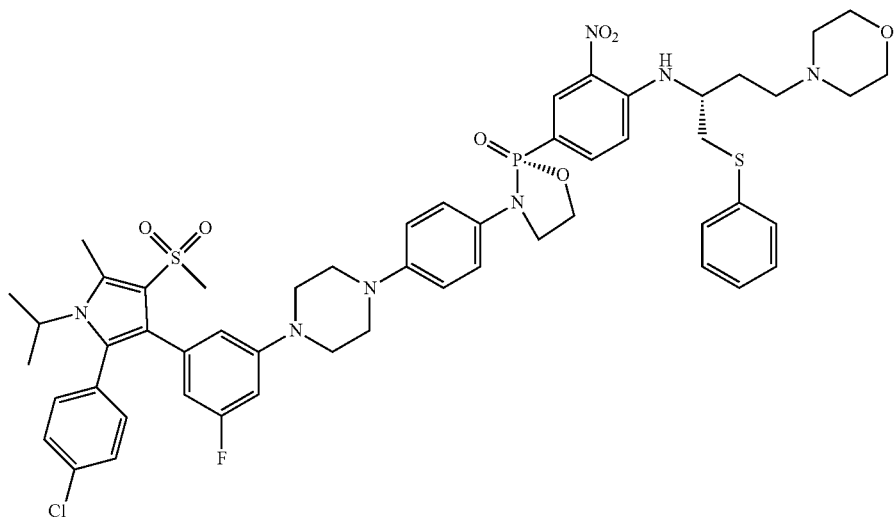
(R)-3-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)-2-(4-(((R)-4-morpholino-1-(phenylthio)butan-2-yl)amino)-3-nitrophenyl)-1,3,2-oxazaphospholidine 2-oxide
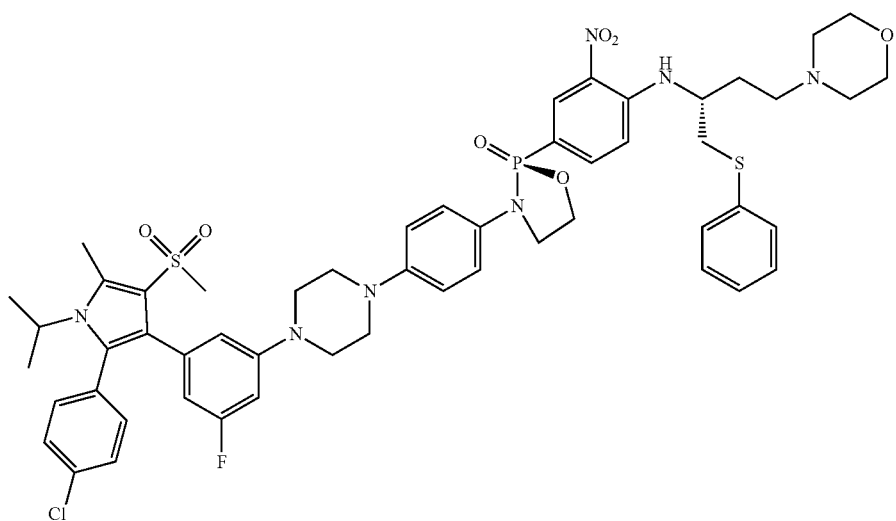
(S)-3-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)-2-(4-(((R)-4-morpholino-1-(phenylthio)butan-2-yl)amino)-3-nitrophenyl)-1,3,2-oxazaphospholidine 2-oxide

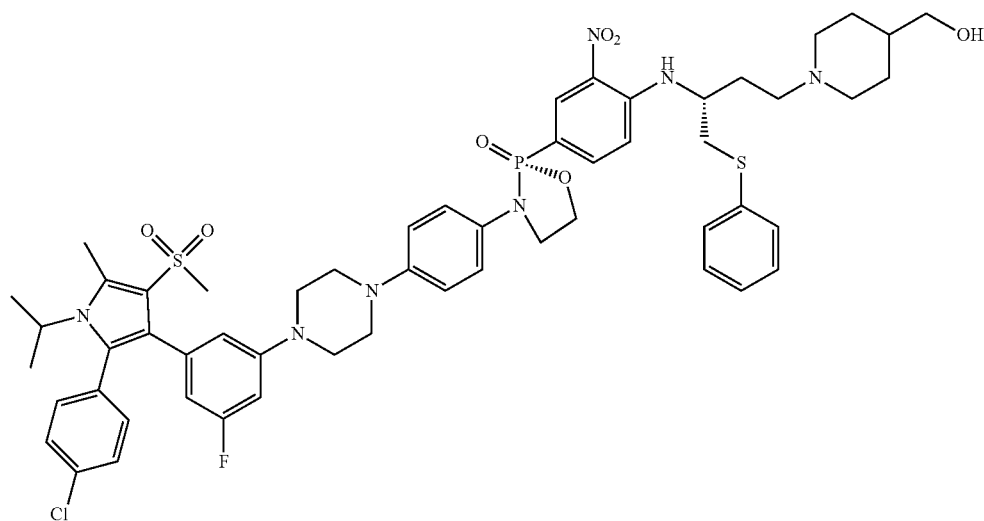

(R)-3-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)-2-(4-(((R)-4-(4-(hydroxymethyl)piperidin-1-yl)-1-(phenylthio)butan-2-yl)amino)-3-nitrophenyl)-1,3,2-oxazaphospholidine 2-oxide

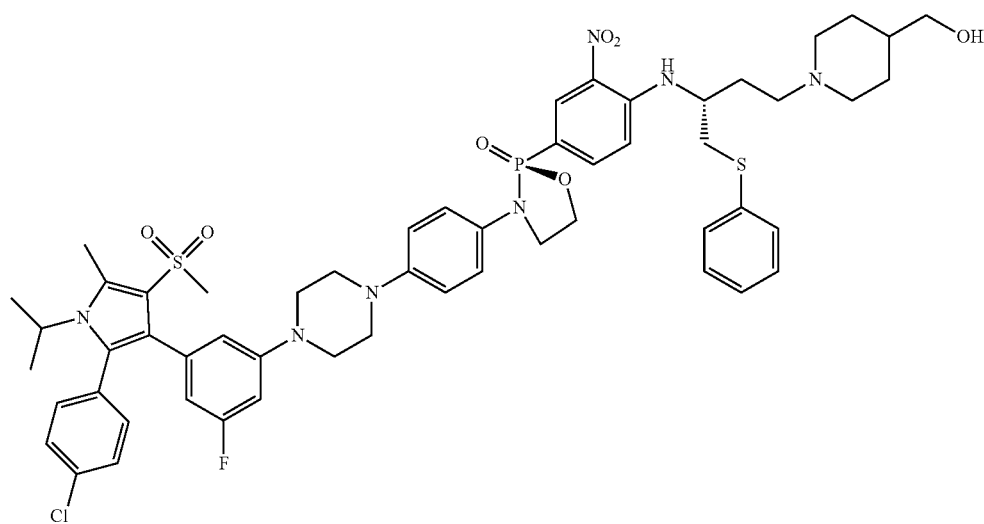

(S)-3-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)-2-(4-(((R)-4-(4-(hydroxymethyl)piperidin-1-yl)-1-(phenylthio)butan-2-yl)amino)-3-nitrophenyl)-1,3,2-oxazaphospholidine 2-oxide -continued

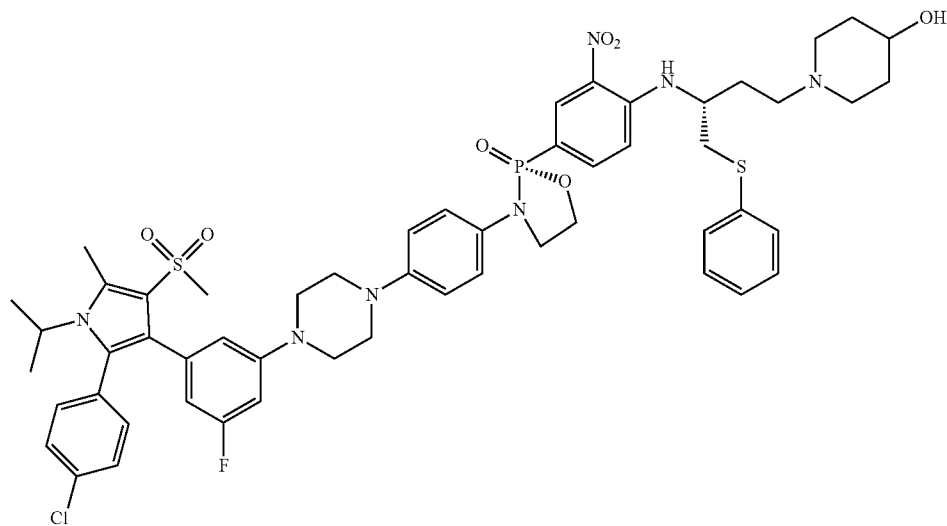

(R)-3-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)-2-(4-(((R)-4-(4-(hydroxymethyl)piperidin-1-yl)-1-(phenylthio)butan-2-yl)amino)-3-nitrophenyl)-1,3,2-oxazaphospholidine 2-oxide

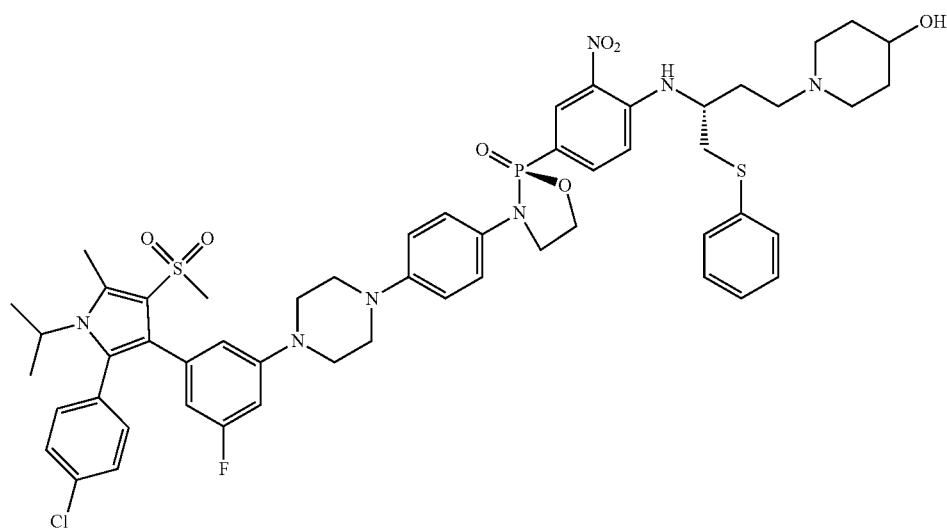

(S)-3-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)-2-(4-(((R)-4-(4-(hydroxymethyl)piperidin-1-yl)-(phenylthio)butan-2-yl)amino)-3-nitrophenyl)-1,3,2-oxazaphospholidine 2-oxide

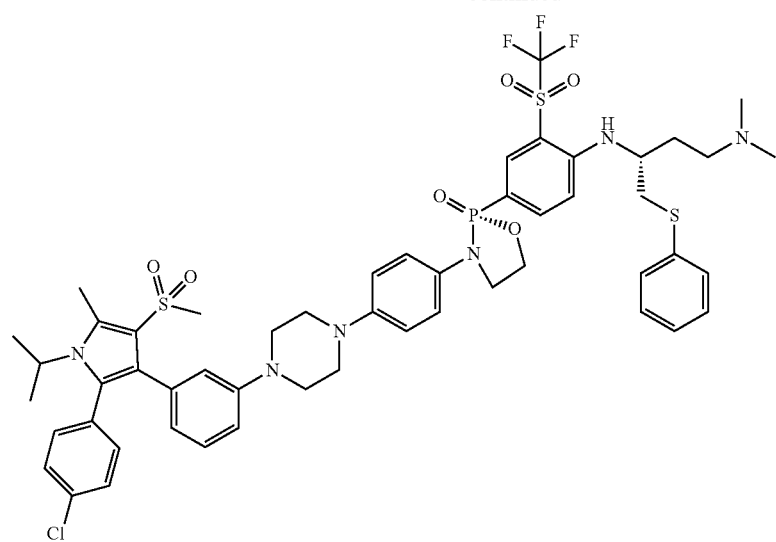

(R)-3-(4-(4-(3-(2-(4-chlorophenyl)-1-isopropyl-5-methyl-4-(methylsulfonyl)-1H-pyrrol-3-yl)phenyl)piperazin-1-yl)phenyl)-2-(4-(((R)-4-(dimethylamino)-1-(phenylthio)butan-2-yl)amino)-3-((trifluoromethyl)sulfonyl)phenyl)-1,3,2-oxazaphospholidine 2-oxide

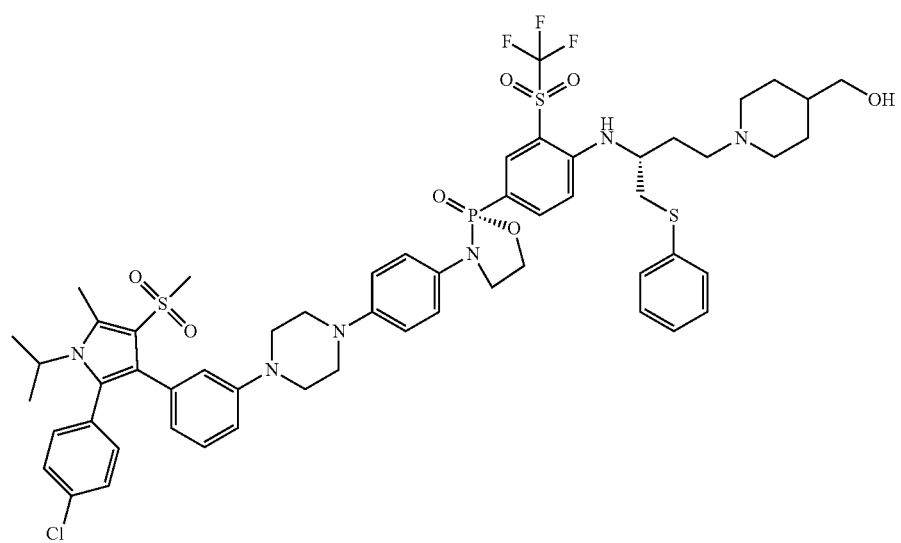

(R)-3-(4-(3-(2-(4-chlorophenyl)-1-isopyropyl-5-methyl-4-(methylsulfonyl)-1H-pyrrol-3-yl)phenyl)piperazin-1-yl)phenyl)-2-(4-(((R)-4-(4-(hydroxymethyl)piperidin-1-yl)-1-(phenylthio)butan-2-yl)amino)-3-((trifluoromethyl)sulfonyl)phenyl)-1,3,2-oxazaphospholidine 2-oxide

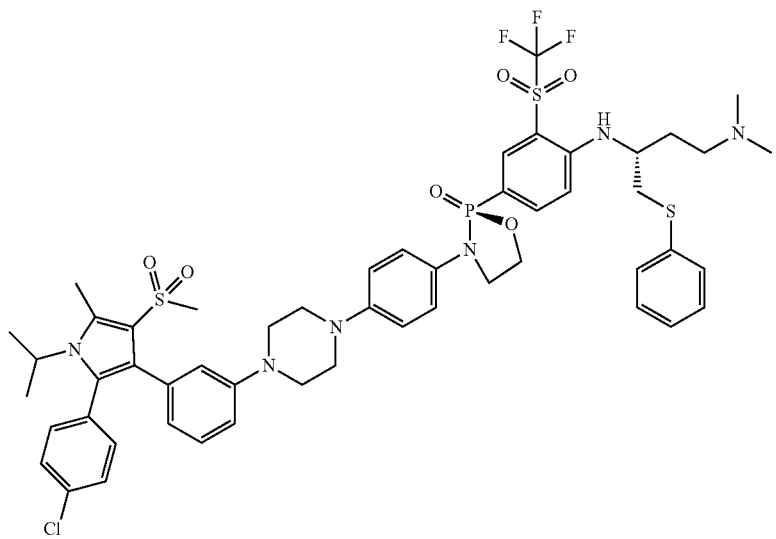

(S)-3-(4-(4-(3-(2-(4-chlorophenyl)-1-isopyropyl-5-methyl-4-(methylsulfonyl)-1H-pyrrol-3-yl)phenyl)piperazin-1-yl)phenyl)-2-(4-(((R)-4-(dimethylamino)-1-(phenylthio)butan-2-yl)amino)-3-((trifluoromethyl)sulfonyl)phenyl)-1,3,2-oxazaphospholidine 2-oxide

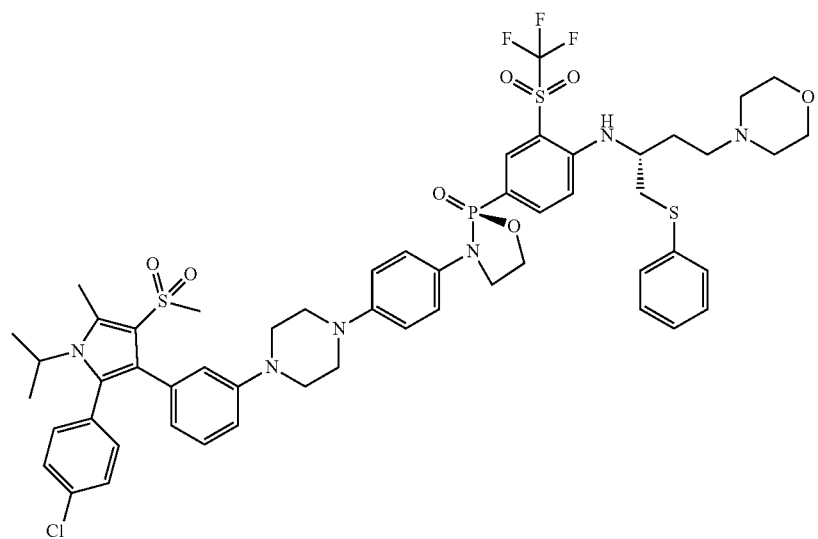

(S)-3-(4-(4-(3-(2-(4-chlorophenyl)-1-isopyropyl-5-methyl-4-(methylsulfonyl)-1H-pyrrol-3-yl)phenyl)piperazin-1-yl)phenyl)-2-(4-(((R)-4-morpholino-1-(phenylthio)butan-2-yl)amino)-3-((trifluoromethyl)sulfonyl)phenyl)-1,3,2-oxazaphospholidine 2-oxide -continued

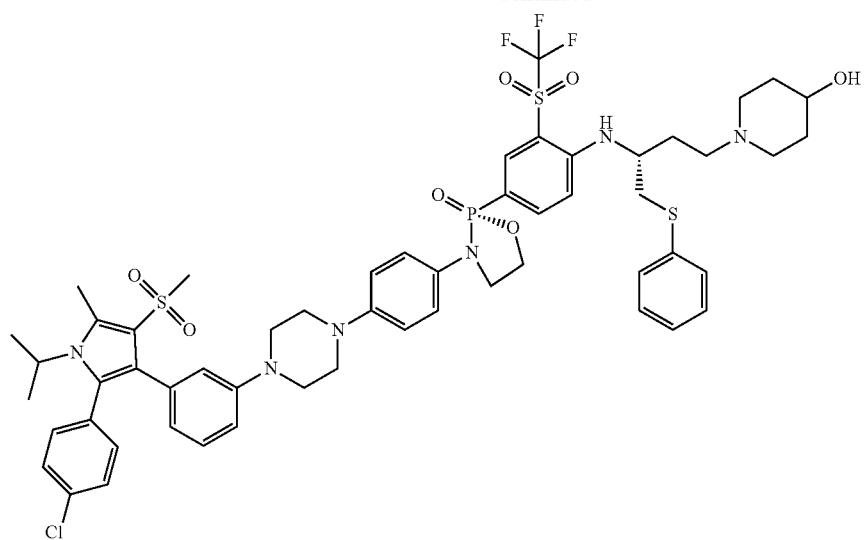

(R)-3-(4-(4-(3-(2-(4-chlorophenyl)-1-isopyropyl-5-methyl-4-(methylsulfonyl)-1H-pyrrol-3-yl)phenyl)piperazin-1-yl)phenyl)-2-(4-(((R)-4-(4-(hydroxypiperidin-1-yl)-1-(phenylthio)butan-2-yl)amino)-3-((trifluoromethyl)sulfonyl)phenyl)-1,3,2-oxazaphospholidine 2-oxide

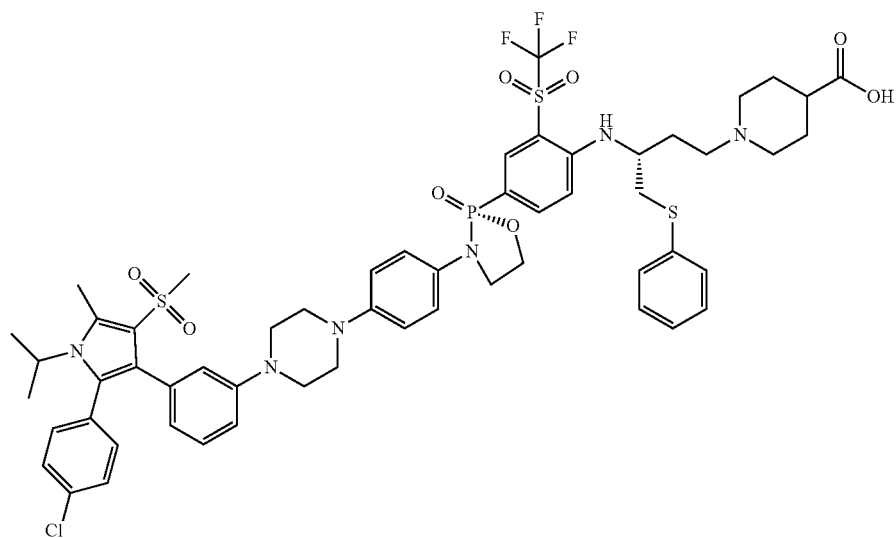

1-((R)-3-((4-((R)-3-(4-(4-(3-(2-(4-chlorophenyl)-1-isopyropyl-5-methyl-4-(methylsulfonyl)-1H-pyrrol-3-yl)phenyl)piperazin-1-yl)phenyl)-2-oxido-1,3,2-oxazaphospholidin-2-yl)-2-((trifluoromethyl)sulfonyl)phenyl)amino)-4-(phenylthio)butyl)piperidine-4-carboxylic acid

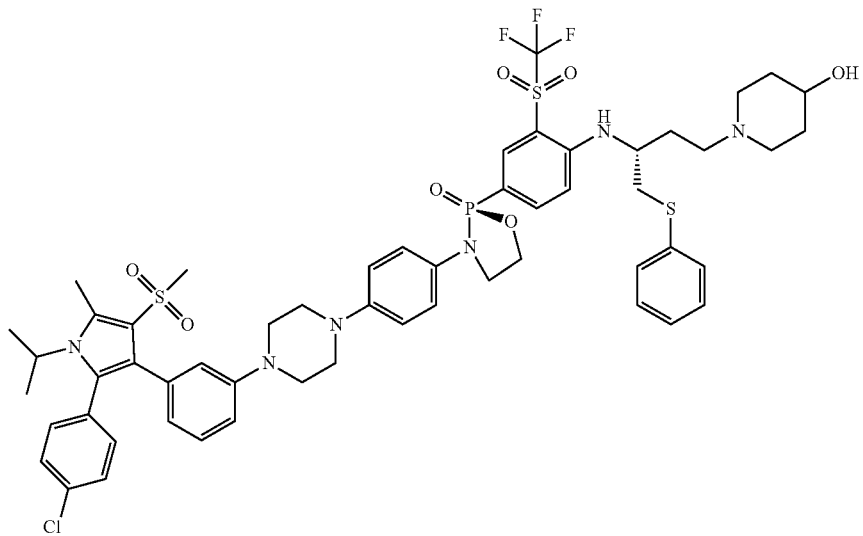

(S)-3-(4-(4-(3-(2-(4-chlorophenyl)-1-isopropyl-5-methyl-4-(methylsulfonyl)-1H-pyrrol-3-yl)phenyl)piperazin-1-yl)phenyl)-2-(4-(((R)-4-(4-hydroxypiperidin-1-yl)-1-(phenylthio)butan-2-yl)amino)-3-((trifluoromethyl)sulfonyl)phenyl)-1,3,2-oxazaphospholidine 2-oxide

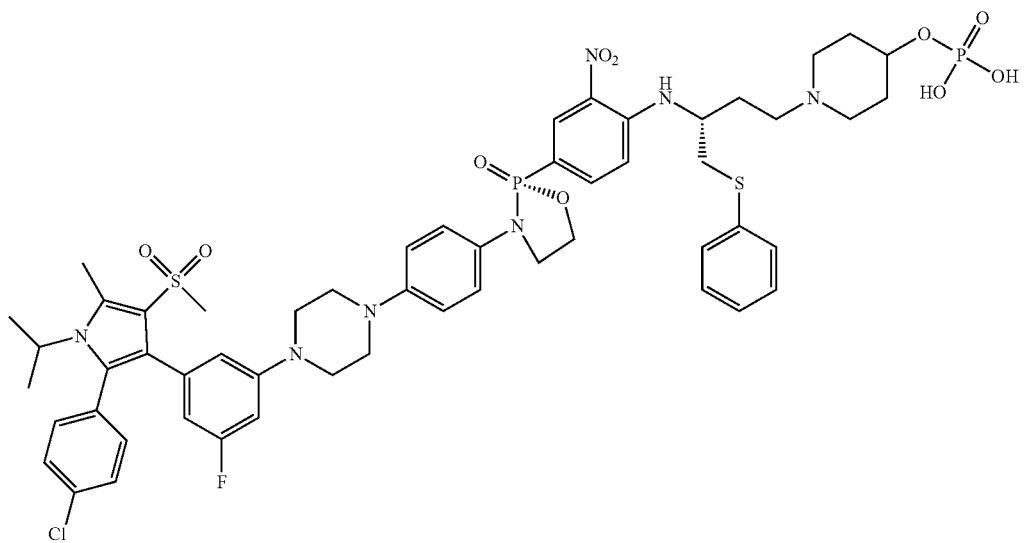

1-((R)-3-((4-((R)-3-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)-2-oxido-1,3,2-oxazaphospholidin-2-yl)-2-nitrophenyl)amino)-4-(phenylthio)butyl)piperidin-4-yl dihydrogen phosphate -continued

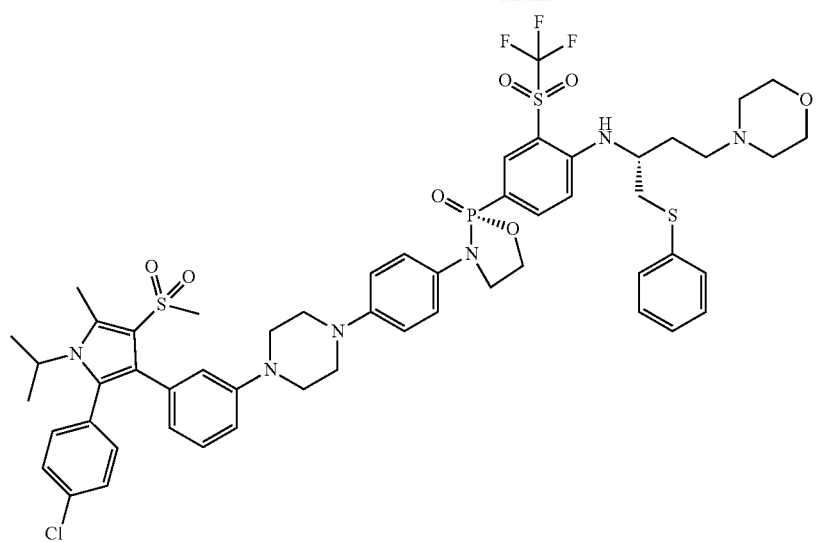

(R)-3-(4-(4-(3-(2-(4-chlorophenyl)-1-isopropyl-5-methyl-4-(methylsulfonyl)-1H-pyrrol-3-yl)phenyl)piperazin-1-yl)phenyl)-2-(4-(((R)-4-morpholino-1-(phenylthio)butan-2-yl)amino)-3-((trifluoromethyl)sulfonyl)phenyl)-1,3,2-oxazaphospholidine 2-oxide

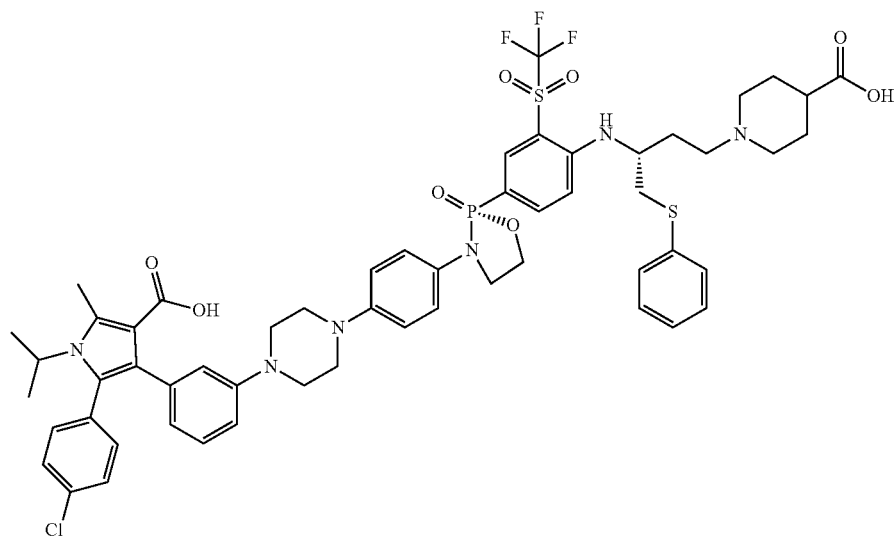

1-((R)-3-((4-((R)-3-(4-(4-(3-(4-carboxy-2-(4-chlorophenyl)-1-isopropyl-5-methyl-1H-pyrrol-3-yl)phenyl)piperazin-1-yl)phenyl)-2-oxido-1,3,2-oxazaphospholidin-2-yl)-2-((trifluoromethyl)sulfonyl)phenyl)amino)-4-(phenylthio)butyl)piperidine-4-carboxylic acid -continued

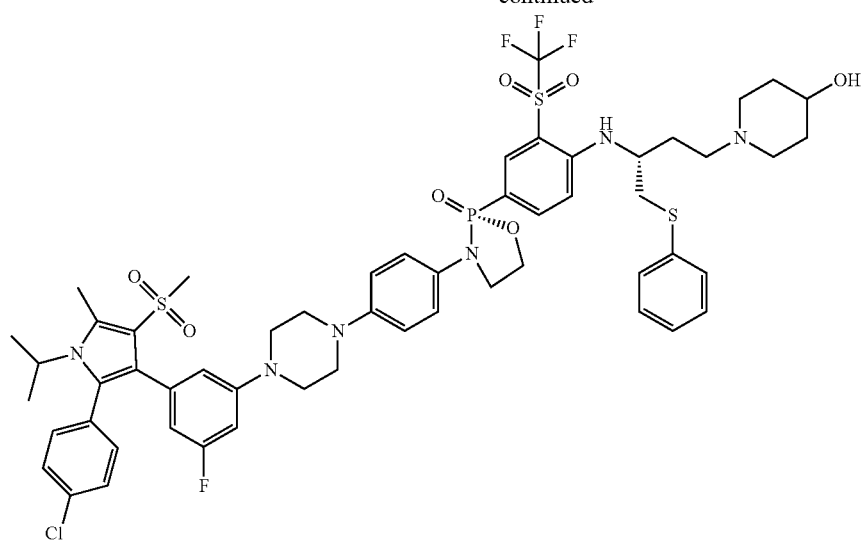

(R)-3-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)-2-(4-(((R)-4-(4-hydroxypiperidin-1-yl)-1-(phenylthio)butan-2-yl)amino)-3-((trifluoromethyl)sulfonyl)phenyl)-1,3,2-oxazaphospholidine 2-oxide

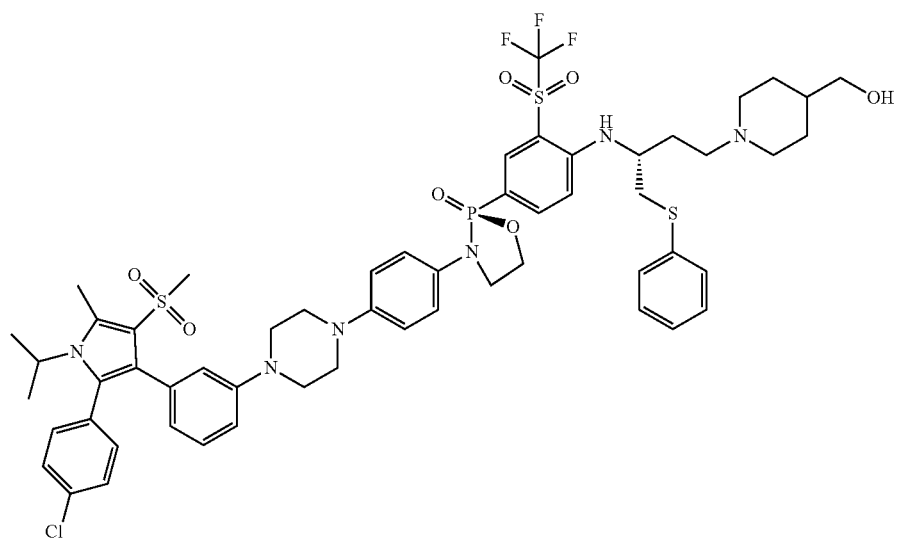

(S)-3-(4-(4-(3-(2-(4-chlorophenyl)-1-isopropyl-5-methyl-4-(methylsulfonyl)-1H-pyrrol-3-yl)phenyl)piperazin-1-yl)phenyl)-2-(4-(((R)-4-(4-(hydroxymethyl)piperidin-1-yl)-1-(phenylthio)butan-2-yl)amino)-3-((trifluoromethyl)sulfonyl)phenyl)-1,3,2-oxazaphospholidine 2-oxide

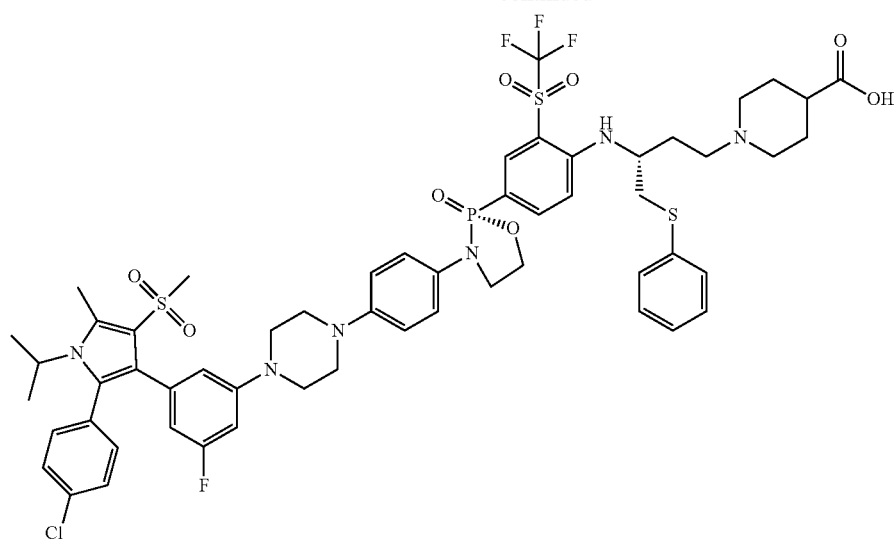

1-((R)-3-((4-((R)-3-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)-2-oxido-1,3,2-oxazaphospholidin-2-yl)-2-((trifluoromethyl)sulfonyl)phenyl)amino)-4-(phenylthio)butyl)piperidine-4-carboxylic acid

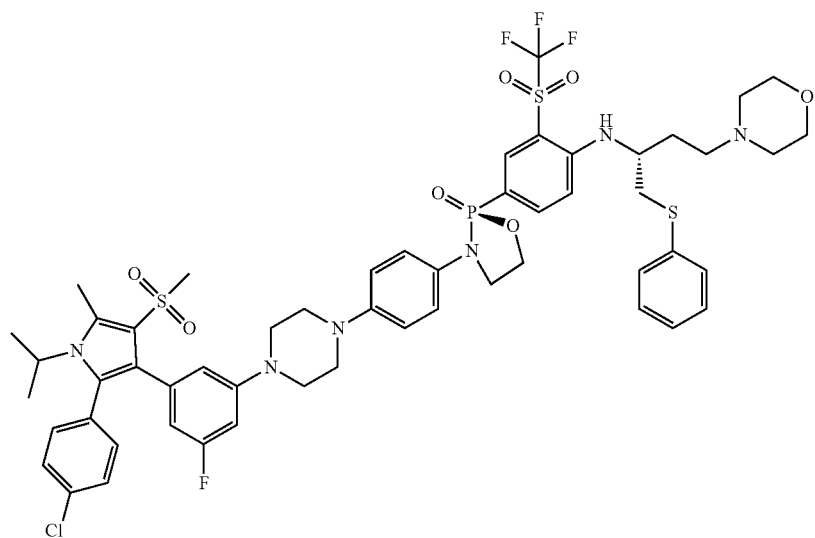

(S)-3-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)-2-(4-(((R)-4-morpholino-1-(phenylthio)butan-2-yl)amino)-3-((trifluoromethyl)sulfonyl)phenyl)-1,3,2-oxazaphospholidine 2-oxide -continued

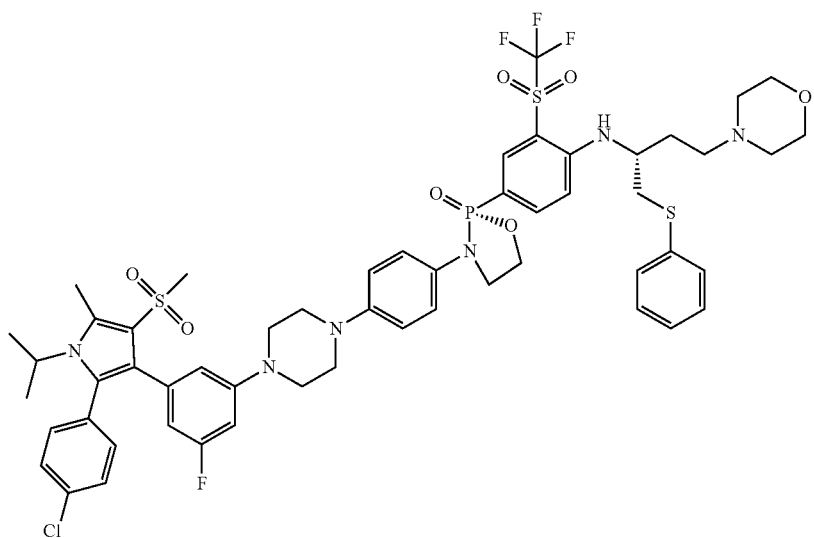

(R)-3-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)-2-(4-(((R)-4-morpholino-1-(phenylthio)butan-2-yl)amino)-3-((trifluoromethyl)sulfonyl)phenyl)-1,3,2-oxazaphospholidine 2-oxide

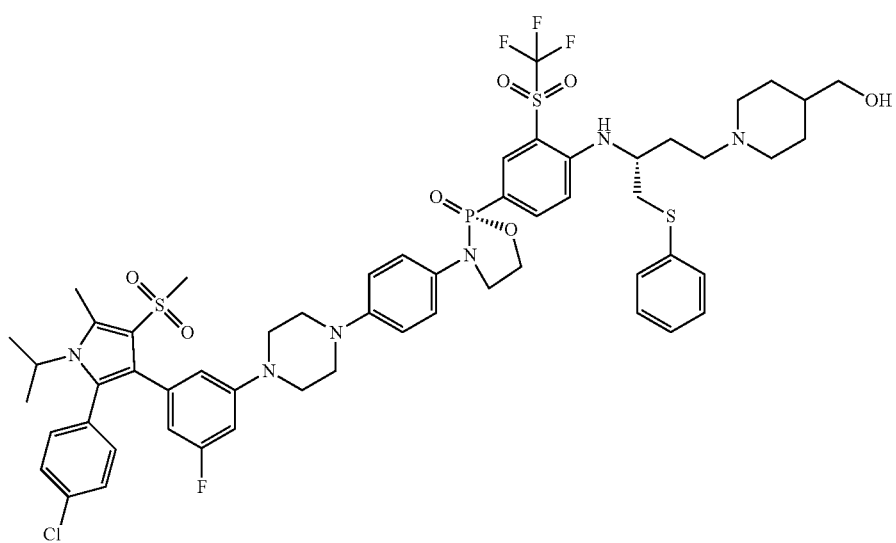

(R)-3-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)-2-(4-(((R)-4-(4-(hydroxymethyl)piperidin-1-yl)-1-(phenylthio)butan-2-yl)amino)-3-((trifluoromethyl)sulfonyl)phenyl)-1,3,2-oxazaphospholidine 2-oxide

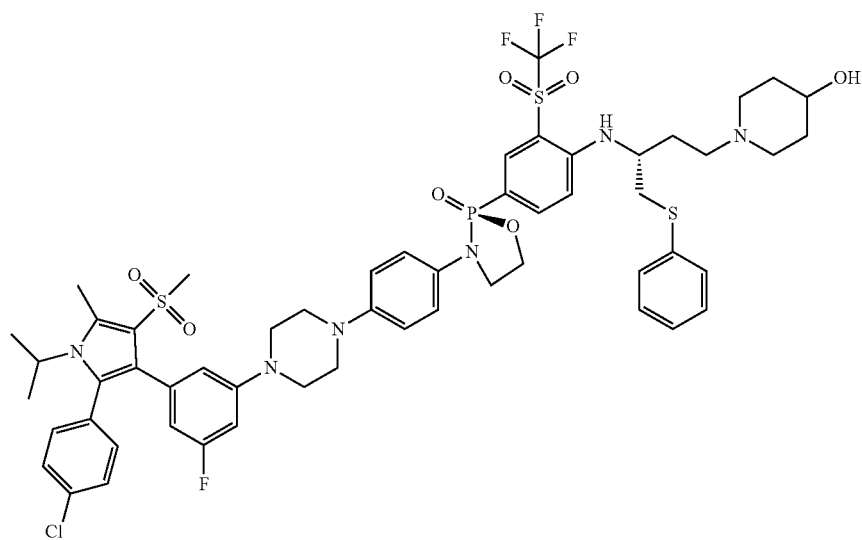

(S)-3-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)-2-(4-(((R)-4-(4-(hydroxypiperidin-1-yl)-1-(phenylthio)butan-2-yl)amino)-3-((trifluoromethyl)sulfonyl)phenyl)-1,3,2-oxazaphospholidine 2-oxide

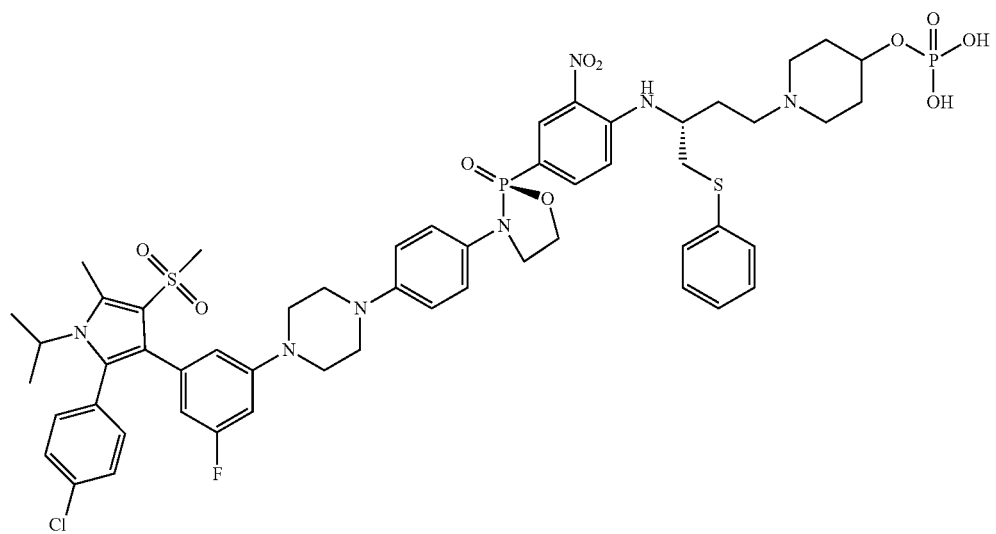

1-((R)-3-((4-((S)-3-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)-2-oxido-1,3,2-oxazaphospholidin-2-yl)-2-nitrophenyl)amino)-4-(phenylthio)butyl)piperidin-4-yl dihydrogen phosphate

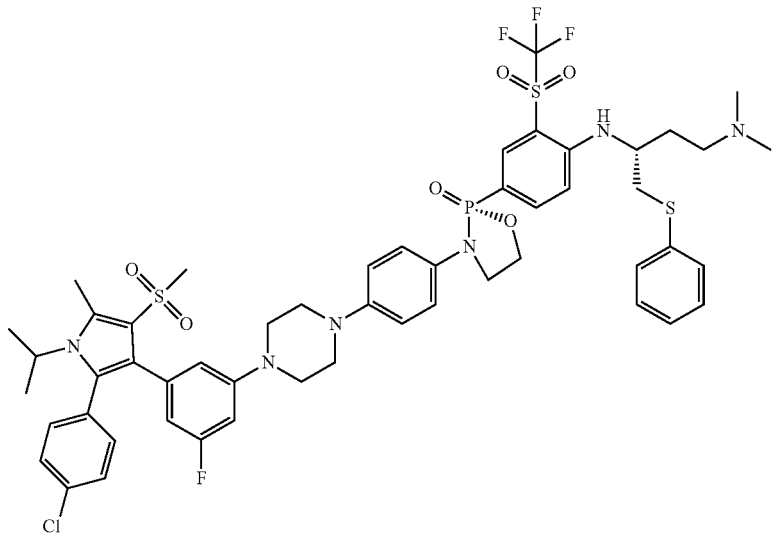

(R)-3-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)-2-(4-(((R)-4-(dimethylamino)-1-(phenylthio)butan-2-yl)amino)-3-((trifluoromethyl)sulfonyl)phenyl)-1,3,2-oxazaphospholidine 2-oxide

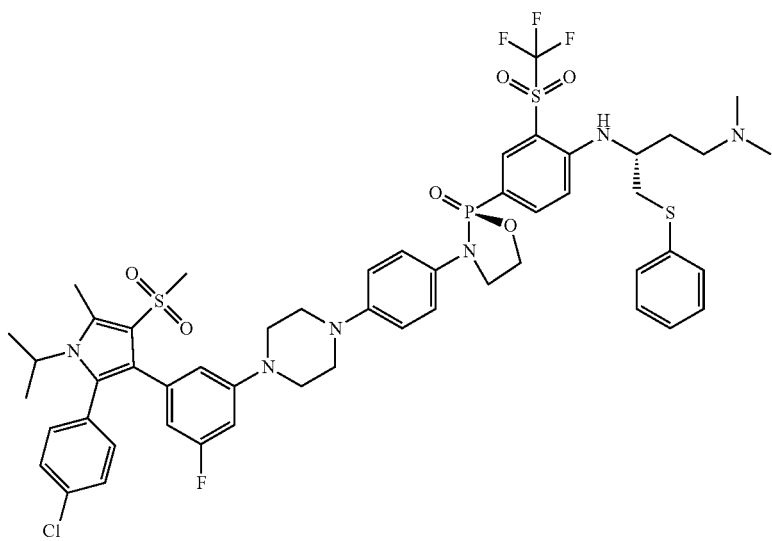

(S)-3-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)-2-(4-(((R)-4-(dimethylamino)-1-(phenylthio)butan-2-yl)amino)-3-((trifluoromethyl)sulfonyl)phenyl)-1,3,2-oxazaphospholidine 2-oxide

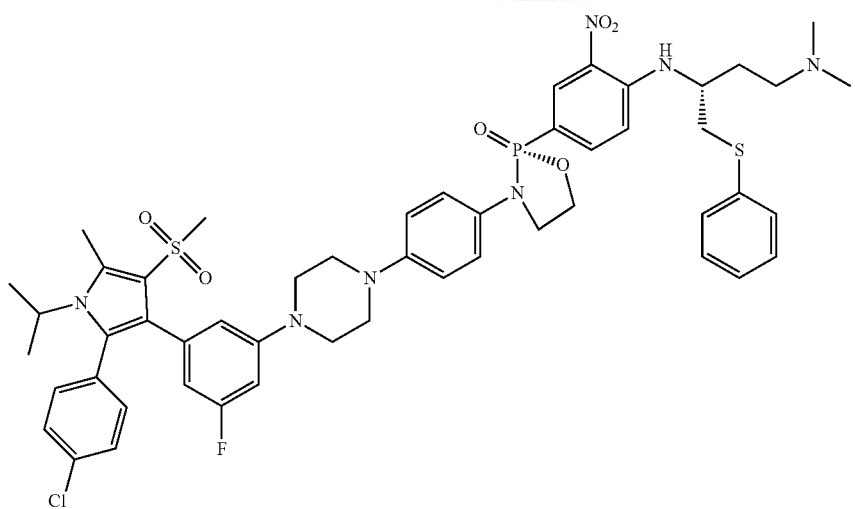

(R)-3-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)-2-(4-(((R)-4-(dimethylamino)-1-(phenylthio)butan-2-yl)amino)-3-nitrophenyl)-1,3,2-oxazaphospholidine 2-oxide

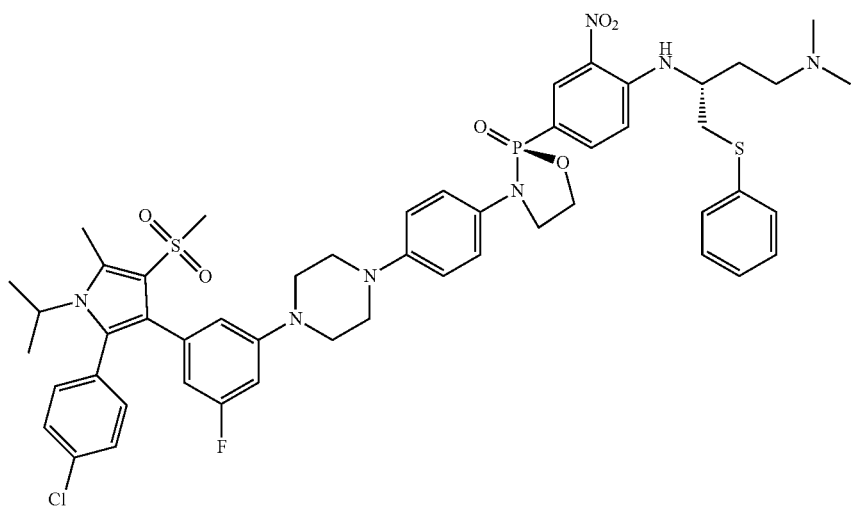

(S)-3-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)-2-(4-(((R)-4-(dimethylamino)-1-(phenylthio)butan-2-yl)amino)-3-nitrophenyl)-1,3,2-oxazaphospholidine 2-oxide -continued

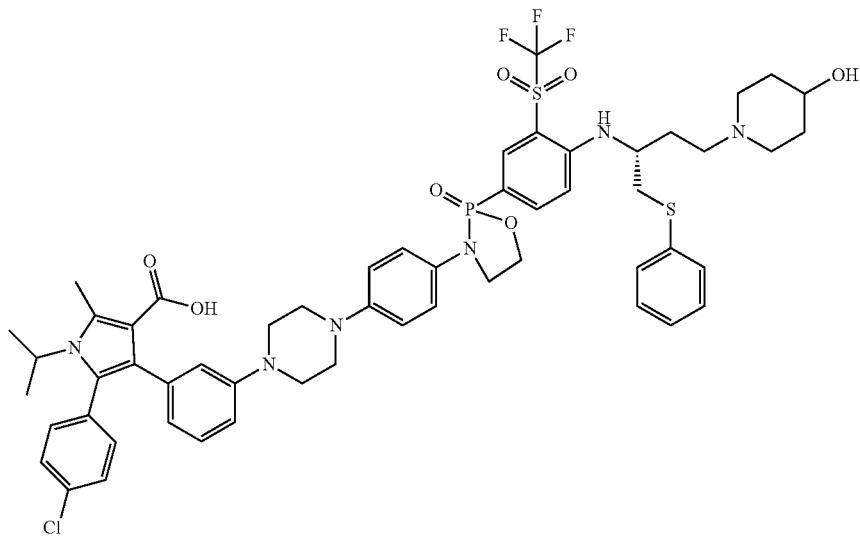

5-(4-chlorophenyl)-4-(3-(4-(4-(2-(4-(((R)-4-(4-hydroxypiperidin-1-yl)-1-(phenylthio)butan-2-yl)amino-3-((trifluoromethyl)sulfonyl)phenyl)-2-oxido-1,3,2-oxazaphospholidin-3-yl)phenyl)piperazin-1-yl)phenyl)-1-isopropyl-2-methyl-1H-pyrrole-3-carboxylic acid

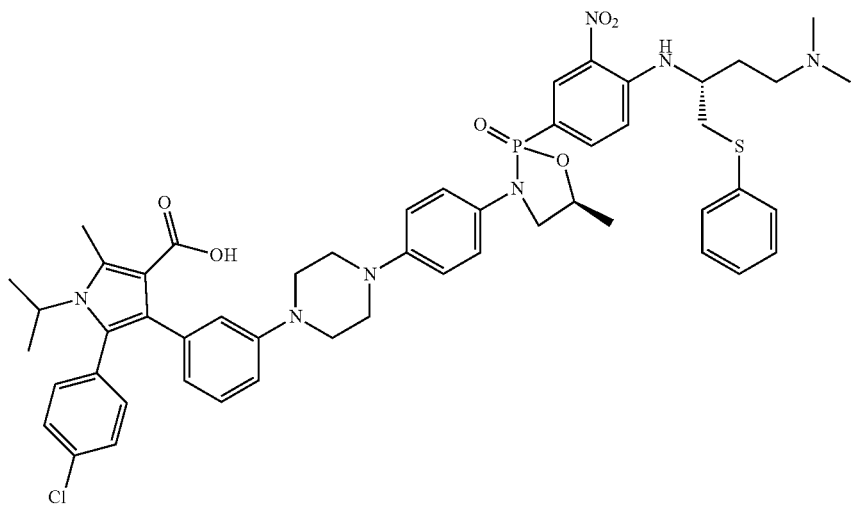

5-(4-chlorophenyl)-4-(3-(4-(4-((5S)-2-(4-(((R)-4-dimethylamino)-1-(phenylthio)butan-2-yl)amino-3-nitrophenyl)-5-methyl-2-oxido-1,3,2-oxazaphospholidin-3-yl)phenyl)piperazin-1-yl)phenyl)-1-isopropyl-2-methyl-1H-pyrrole-3-carboxylic acid

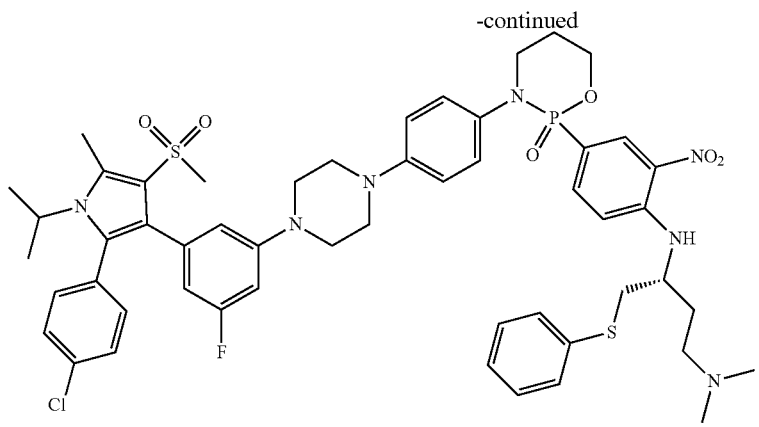

3-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)-2-(4-(((R)-4-(dimethylamino)-1-(phenylthio)butan-2-yl)amino)-3-nitrophenyl)-1,3,2-oxazaphospholidine 2-oxide

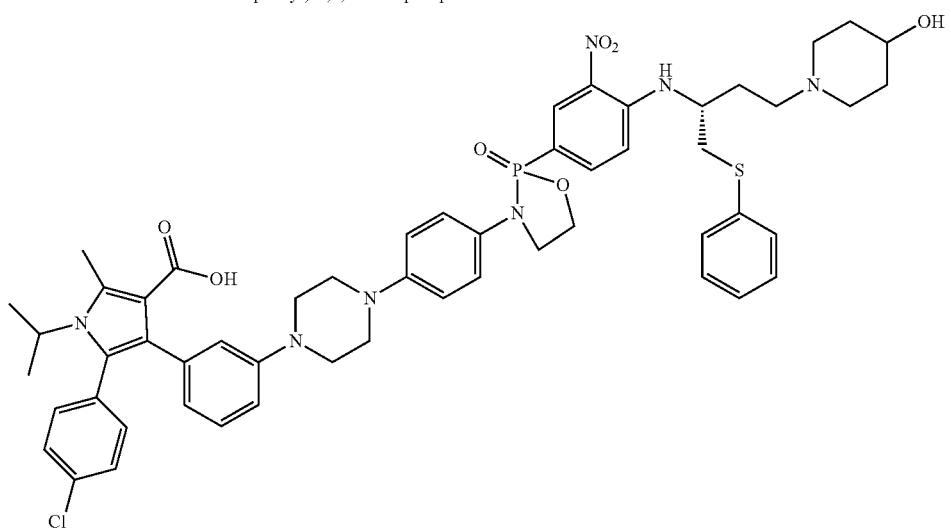

5-(4-chlorophenyl)-4-(3-(4-(4-(2-(4-(((R)-4-(4-hydroxypiperidin-1-yl)-1-(phenylthio)butan-2-yl)amino)-3-nitrophenyl)-2-oxido-1,3,2-oxazaphospholidin-3-yl)phenyl)piperazin-1-yl)phenyl)-1-isopropyl-2-methyl-1H-pyrrole-3-carboxylic acid

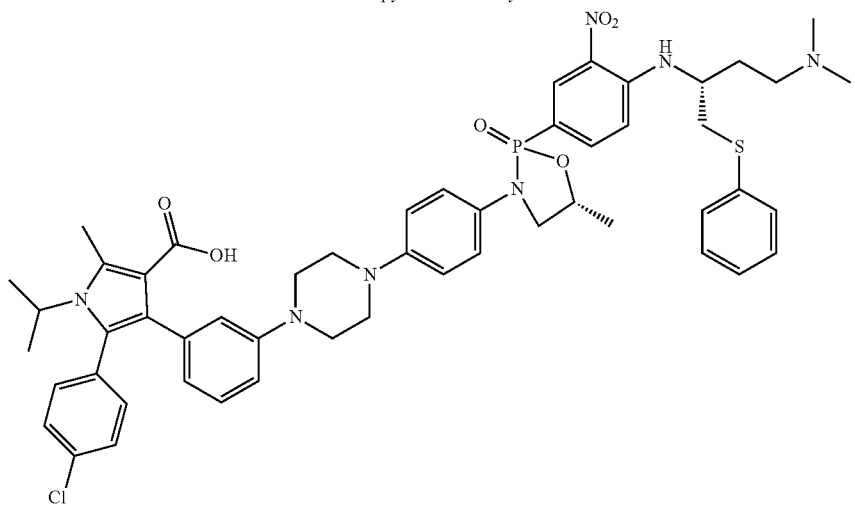

5-(4-chlorophenyl)-4-(3-(4-(4-((5R)-2-(4-(((R)-4-dimethylamino)-1-(phenylthio)butan-2-yl)amino)-3-nitrophenyl)-5-methyl-2-oxido-1,3,2-oxazaphospholidin-3-yl)phenyl)piperazin-1-yl)phenyl)-1-isopropyl-2-methyl-1H-pyrrole-3-carboxylic acid -continued

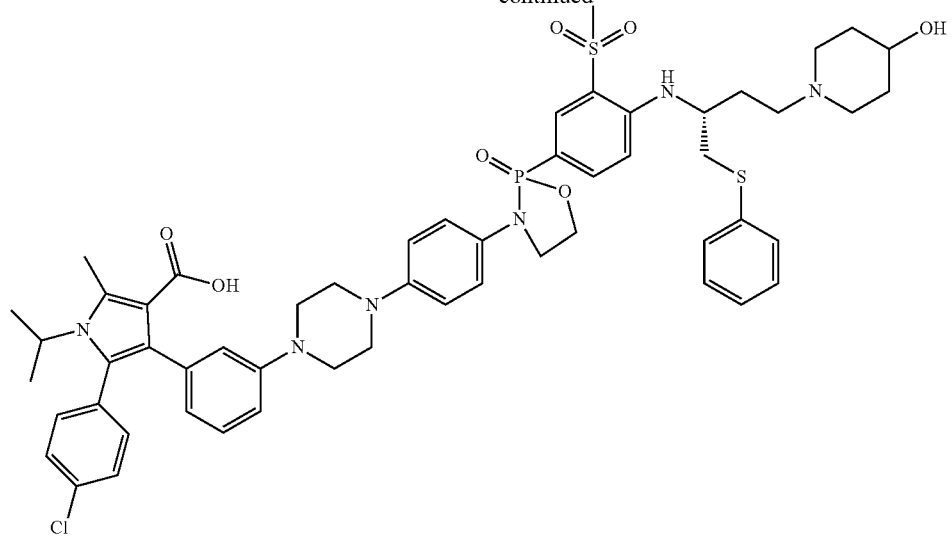

5-(4-chlorophenyl)-4-(3-(4-(4-(2-(4-(((R)-4-(4-hydroxypiperidin-1-yl)-1-(phenylthio)butan-2-yl)amino)-3-(methylsulfonyl)phenyl)-2-oxido-1,3,2-oxazaphospholidin-3-yl)phenyl)piperazin-1-yl)phenyl)-1-isopyropy-2-methyl-1H-pyrrole-3-carboxylic acid

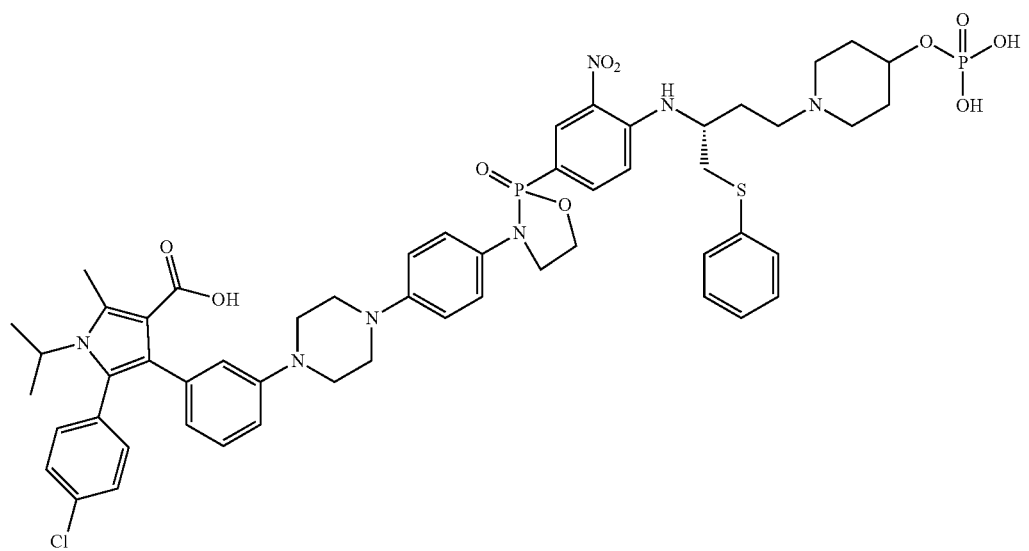

5-(4-chlorophenyl)-1-isopropyl-2-methyl-4-(3-(4-(4-(2-(3-nitro-4-(((R)-1-(phenylthio)-4-(4-(phosphonooxy)piperidin-1-yl)butan-2-yl)amino)phenyl)-2-oxido-1,3,2-oxazaphospholidin-3-yl)phenyl)piperazin-1-yl)phenyl)-1H-pyrrole-3-carboxylic acid

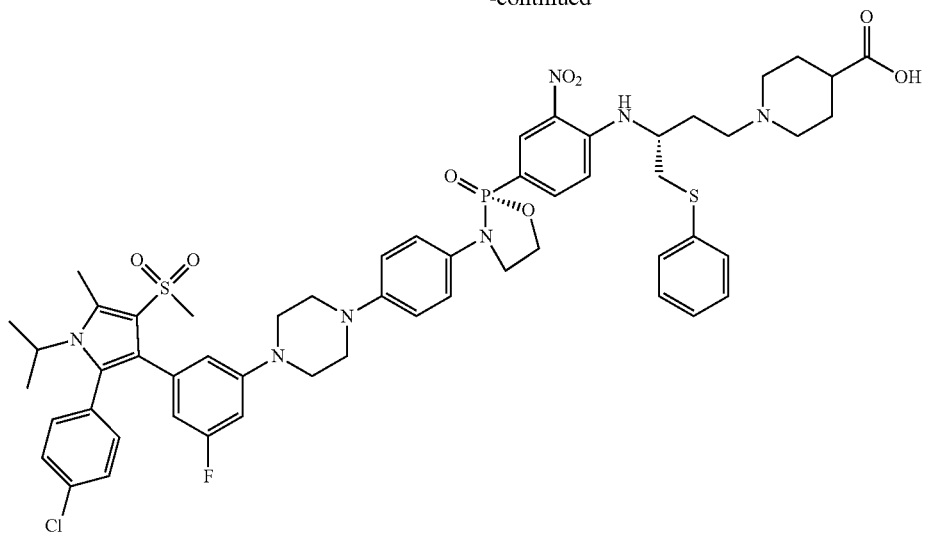

1-((R)-3-((4-((R)-3-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)-2-oxido-1,3,2-oxazaphospholidin-2-yl)-2-nitrophenyl)amino)-4-(phenylthio)butyl)piperidine-4-carboxylic acid

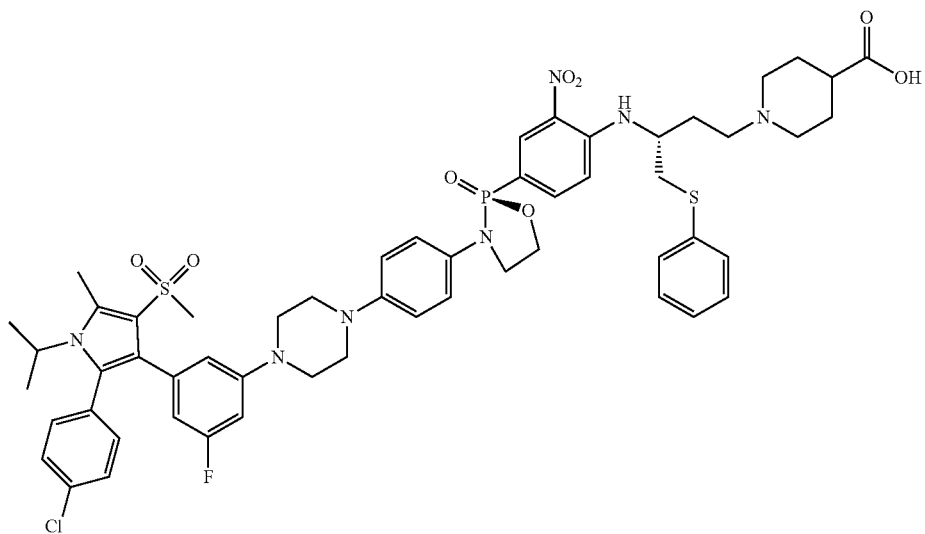

1-((R)-3-((4-((S)-3-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)-2-oxido-1,3,2-oxazaphospholidin-2-yl)-2-nitrophenyl)amino)-4-(phenylthio)butyl)piperidine-4-carboxylic acid -continued

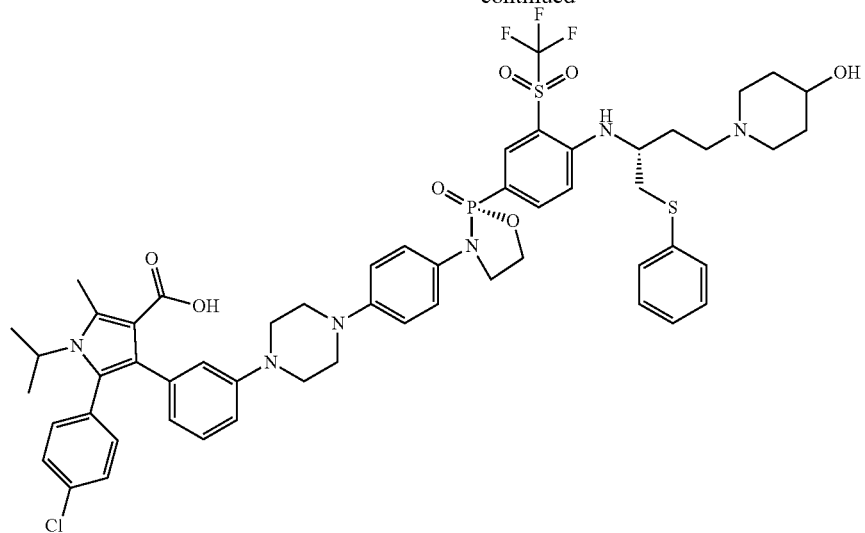

5-(4-chlorophenyl)-4-(3-(4-(4-(((R)-2-(4-(((R)-4-(((R)-4-(4-hydroxypiperidin-1-yl)-1-(phenylthio)butan-2-yl)amino)-3-((trifluoromethyl)sulfonyl)phenyl)-2-oxido-1,3,2-oxazaphospholidin-3-yl)phenyl)piperazin-1-yl)phenyl)-1-isopropyl-2-methyl-1H-pyrrole-3-carboxylic acid

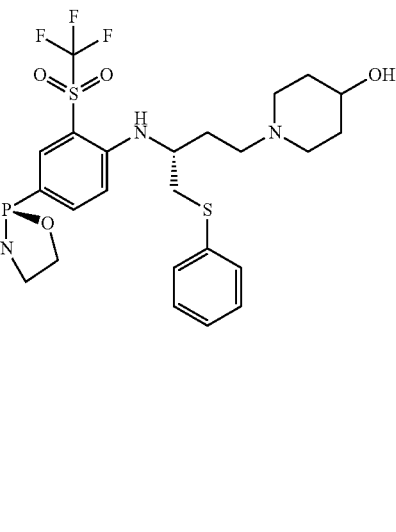

5-(4-chlorophenyl)-4-(3-(4-(4-(((S)-2-(4-(((R)-4-(((R)-4-(4-hydroxypiperidin-1-yl)-1-(phenylthio)butan-2-yl)amino)-3-((trifluoromethyl)sulfonyl)phenyl)-2-oxido-1,3,2-oxazaphospholidin-3-yl)phenyl)piperazin-1-yl)phenyl)-1-isopropyl-2-methyl-1H-pyrrole-3-carboxylic acid -continued

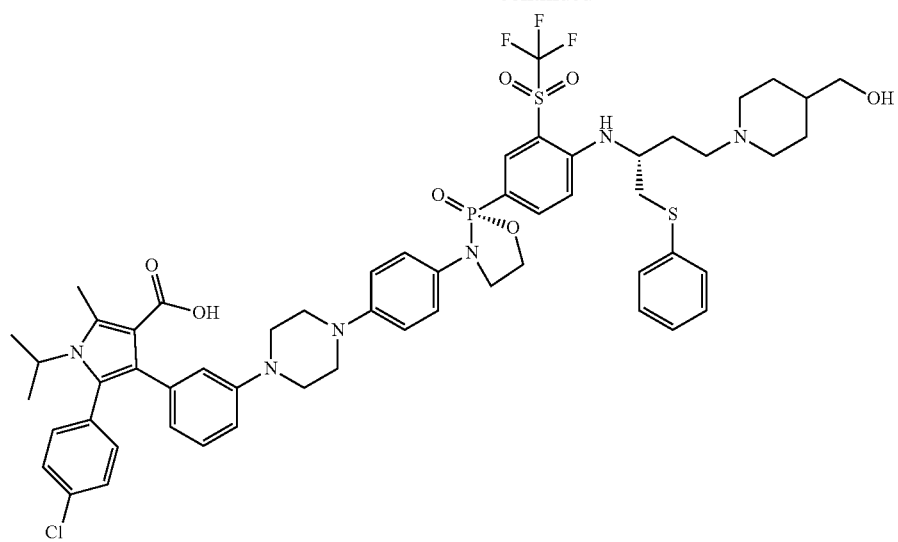

5-(4-chlorophenyl)-4-(3-(4-(4-((R)-2-(4-(((R)-4-(4-hydroxymethyl)piperidin-1-yl)-1-(phenylthio)butan-2-yl)amino)-3-(trifluoromethyl)sulfonyl)phenyl)-2-oxido-1,3,2-oxazaphospholidin-3-yl)phenyl)piperazin-1-yl)phenyl)-1-isopropyl-2-methyl-1H-pyrrole-3-carboxylic acid

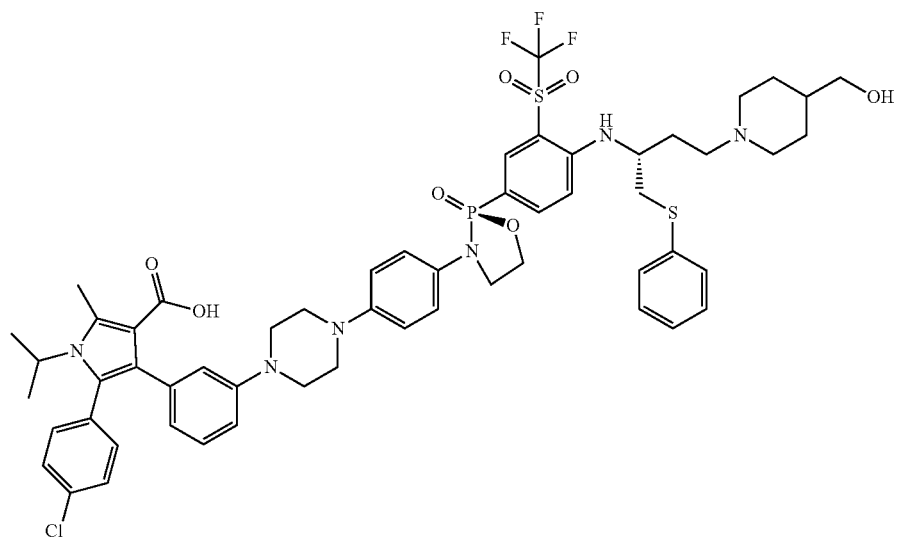

5-(4-chlorophenyl)-4-(3-(4-(4-((S)-2-(4-(((R)-4-(((R)-4-(4-hydroxypiperidin-1-yl)-1-(phenylthio)butan-2-yl)amino)-3-(trifluoromethyl)sulfonyl)phenyl)-2-oxido-1,3,2-oxazaphospholidin-3-yl)phenyl)piperazin-1-yl)phenyl)-1-isopropyl-2-methyl-1H-pyrrole-3-carboxylic acid

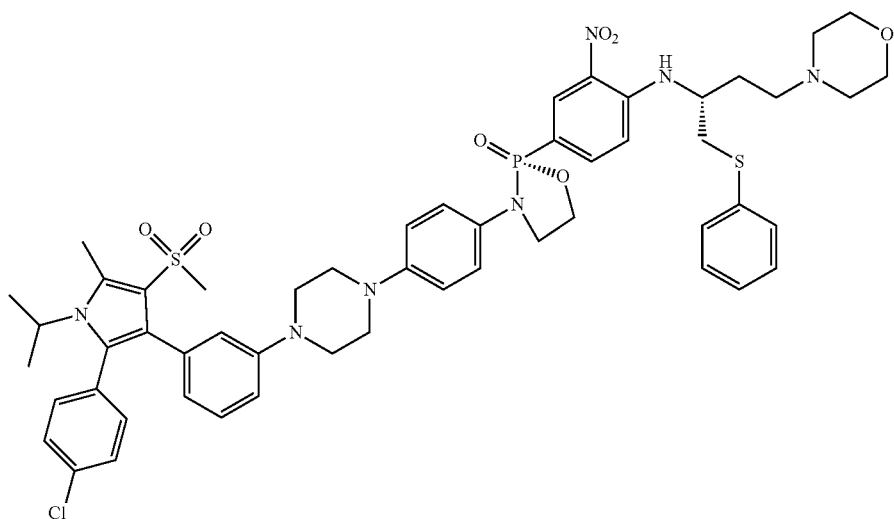
(R)-3-(4-(4-(3-(2-(4-chlorophenyl)-1-isopropyl-5-methyl-4-(methylsulfonyl)-1H-pyrrol-3-yl)phenyl)piperazin-1-yl)phenyl)-2-(4-(((R)-4-morpholino-1-(phenylthio)butan-2-yl)amino)-3-nitrophenyl)-1,3,2-oxazaphospholidine 2-oxide
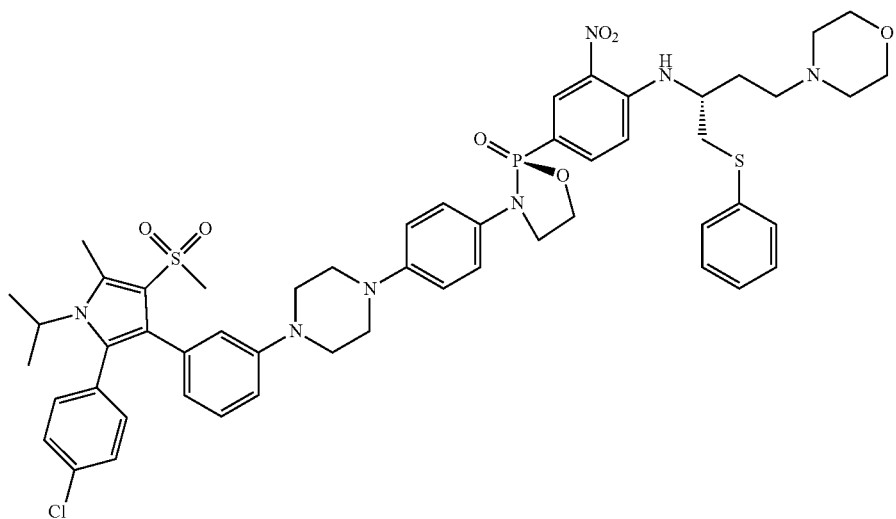
(S)-3-(4-(4-(3-(2-(4-chlorophenyl)-1-isopropyl-5-methyl-4-(methylsulfonyl)-1H-pyrrol-3-yl)phenyl)piperazin-1-yl)phenyl)-2-(4-(((R)-4-morpholino-1-(phenylthio)butan-2-yl)amino)-3-nitrophenyl)-1,3,2-oxazaphospholidine 2-oxide

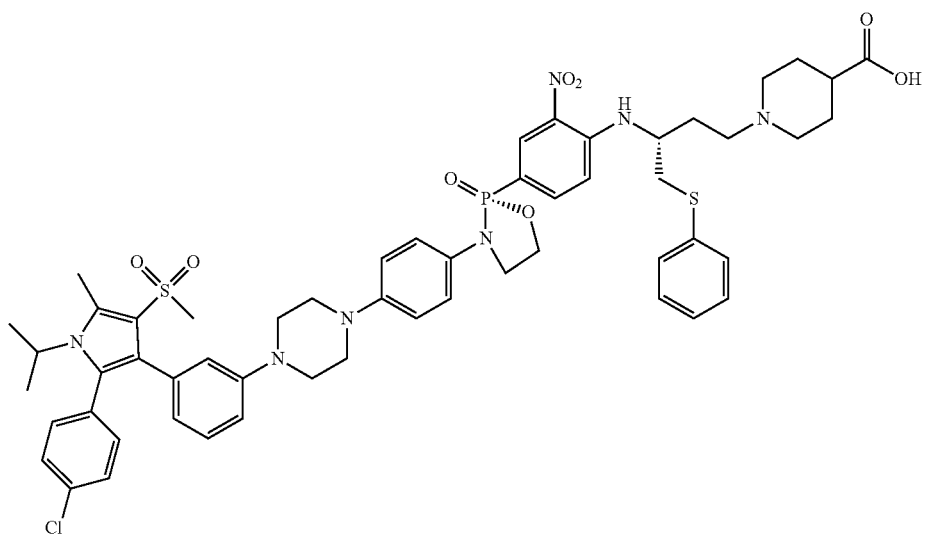

1-((R)-3-((4-((R)-3-(4-(4-(3-(2-(4-chlorophenyl)-1-isopropyl-5-methyl-4-(methylsulfonyl)-1H-pyrrol-3-yl)phenyl)piperazin-1-yl)phenyl)-2-oxido-1,3,2-oxazaphospholidin-2-yl)-2-nitrophenyl)amino)-4-(phenylthio)butyl)piperidine-4-carboxylic acid

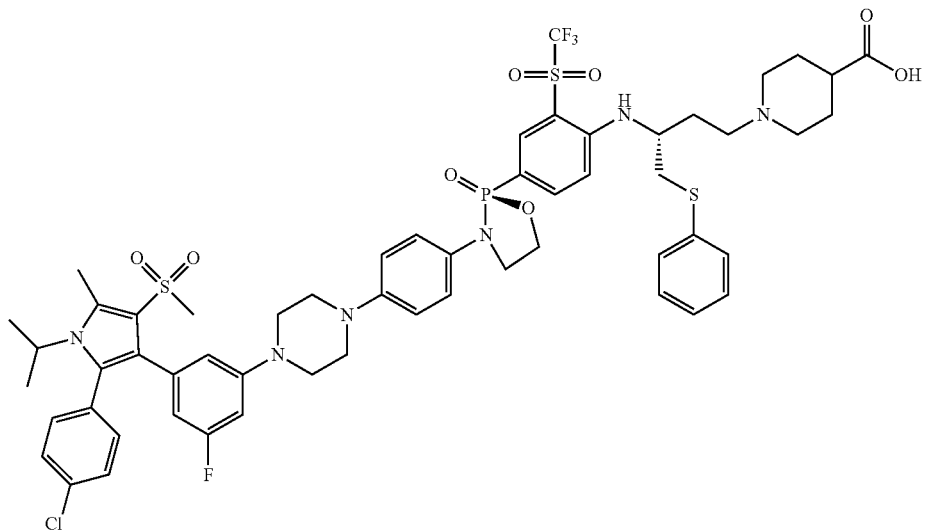

1-((R)-3-((4-((S)-3-(4-(4-(3-(2-(4-chlorophenyl)-1-isopropyl-5-methyl-4-(methylsulfonyl)-1H-pyrrol-3-yl)phenyl)piperazin-1-yl)phenyl)-2-oxido-1,3,2-oxazaphospholidin-2-yl)-2-((trifluoromethyl)sulfonyl)phenyl)amino)-4-(phenylthio)butyl)piperidine-4-carboxylic acid

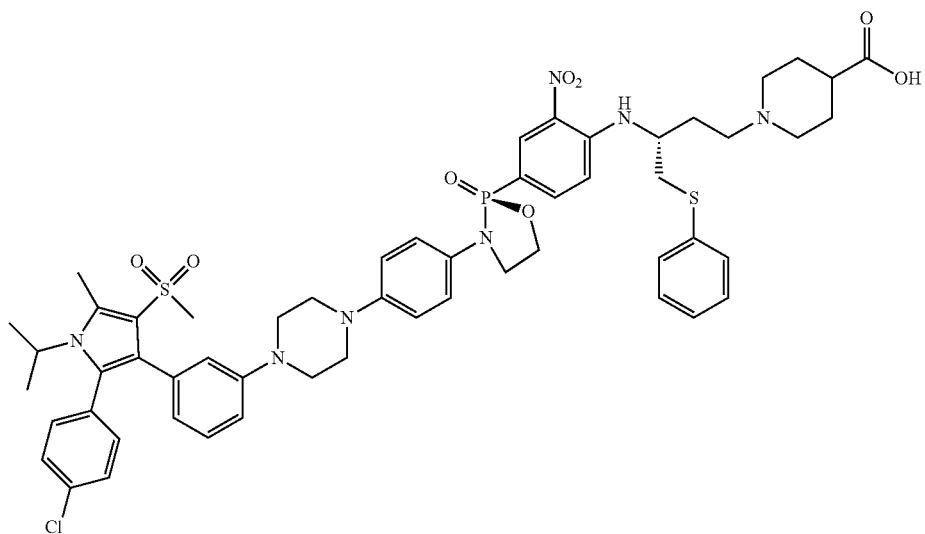

1-((S)-3-((4-((R)-3-(4-(4-(3-(2-(4-chlorophenyl)-1-isopropyl-5-methyl-4-(methylsulfonyl)-1H-pyrrol-3-yl)phenyl)piperazin-1-yl)phenyl)-2-oxido-1,3,2-oxazaphospholidin-2-yl)-2-nitrophenyl)amino)-4-(phenylthio)butyl)piperidine-4-carboxylic acid

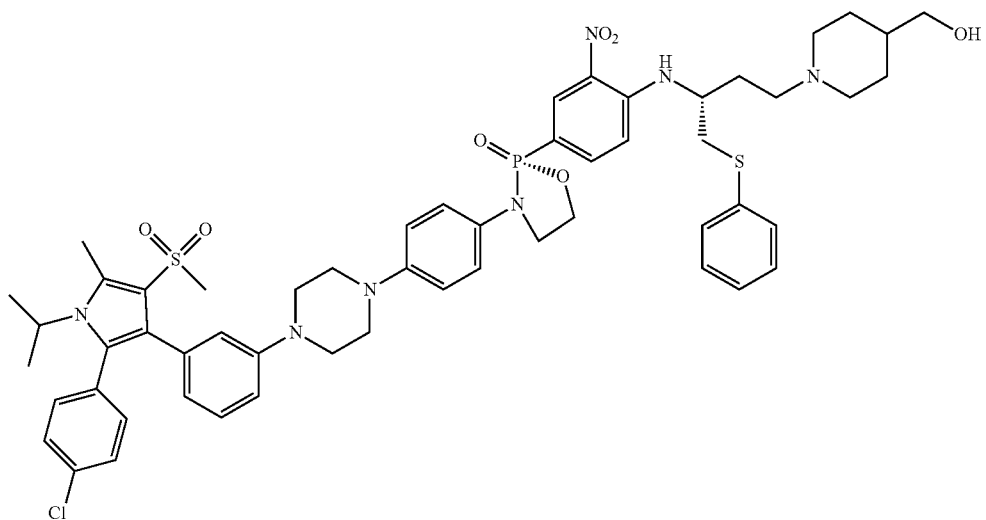

(R)-3-(4-(4-(3-(2-(4-chlorophenyl)-1-isopropyl-5-methyl-4-(methylsulfonyl)-1H-pyrrol-3-yl)phenyl)piperazin-1-yl)phenyl)-2-(4-(((R)-4-(4-(hydroxymethyl)pieridin-1-yl)-1-(phenylthio)butan-2-yl)amino)-3-nitrophenyl)-1,3,2-oxazaphospholidine 2-oxide -continued
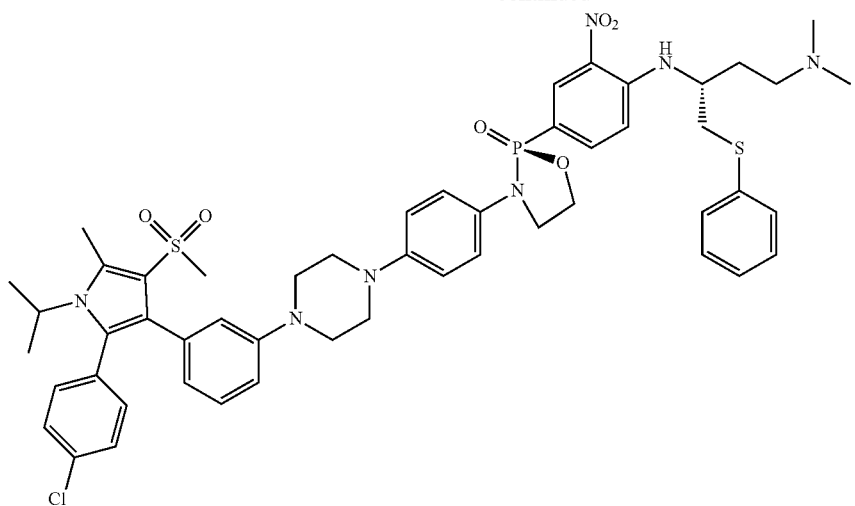
(S)-3-(4-(4-(3-(2-(4-chlorophenyl)-1-isopropyl-5-methyl-4-(methylsulfonyl)-1H-pyrrol-3-yl)phenyl)piperazin-1-yl)phenyl)-2-(4-(((R)-4-(dimethylamino)-1-(phenylthio)butan-2-yl)amino)-3-nitrophenyl)-1,3,2-oxazaphospholidine 2-oxide
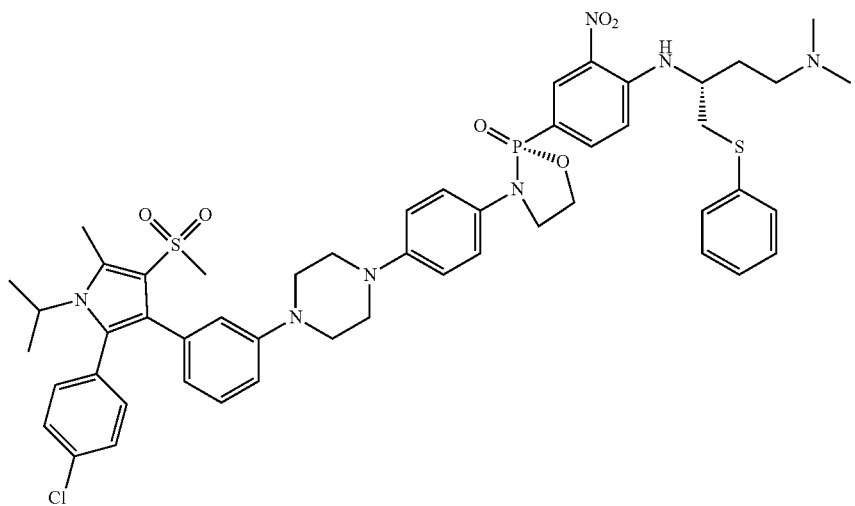
(R)-3-(4-(4-(3-(2-(4-chlorophenyl)-1-isopropyl-5-methyl-4-(methylsulfonyl)-1H-pyrrol-3-yl)phenyl)piperazin-1-yl)phenyl)-2-(4-(((R)-4-(dimethylamino)-1-(phenylthio)butan-2-yl)amino)-3-nitrophenyl)-1,3,2-oxazaphospholidine 2-oxide

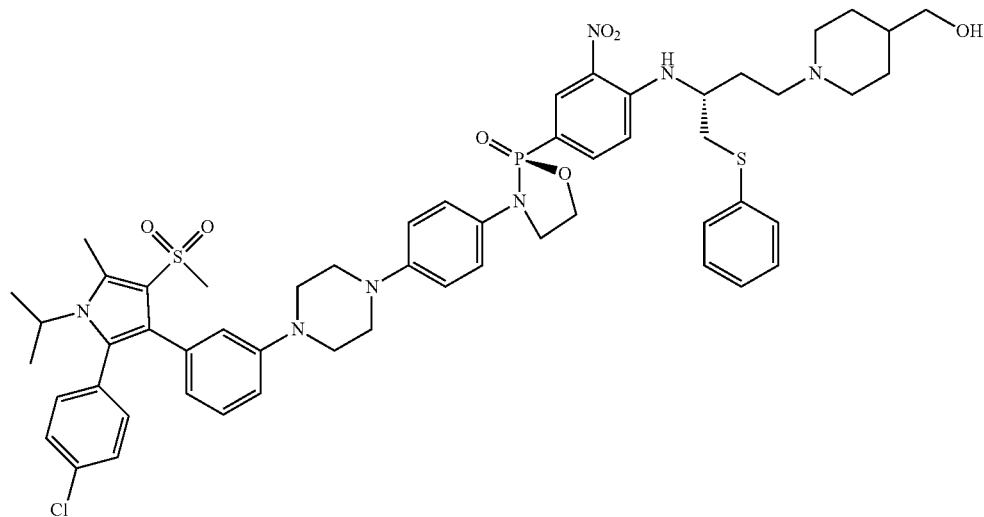

(S)-3-(4-(4-(3-(2-(4-chlorophenyl)-1-isopropyl-5-methyl-4-(methylsulfonyl)-1H-pyrrol-3-yl)phenyl)piperazin-1-yl)phenyl)-2-(4-(((R)-4-(hydroxymethyl)piperidin-1-yl)-1-(phenylthio)butan-2-yl)amino)-3-nitrophenyl)-1,3,2-oxazaphospholidine 2-oxide

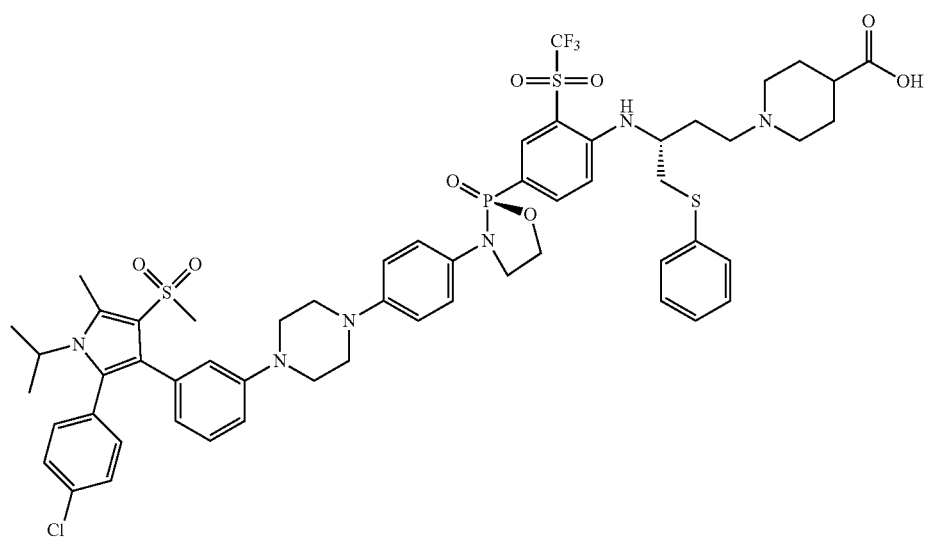

1-((R)-3-((4-((S)-3-(4-(4-(3-(2-(4-chlorophenyl)-1-isopropyl-5-methyl-4-(methylsulfonyl)-1H-pyrrol-3-yl)phenyl)piperazin-1-yl)phenyl)-2-oxido-1,3,2-oxazaphospholidin-2-yl)-2-((trifluoromethyl)sulfonyl)phenyl)amino)-4-(phenylthio)butyl)piperidine-4-carboxylic acid

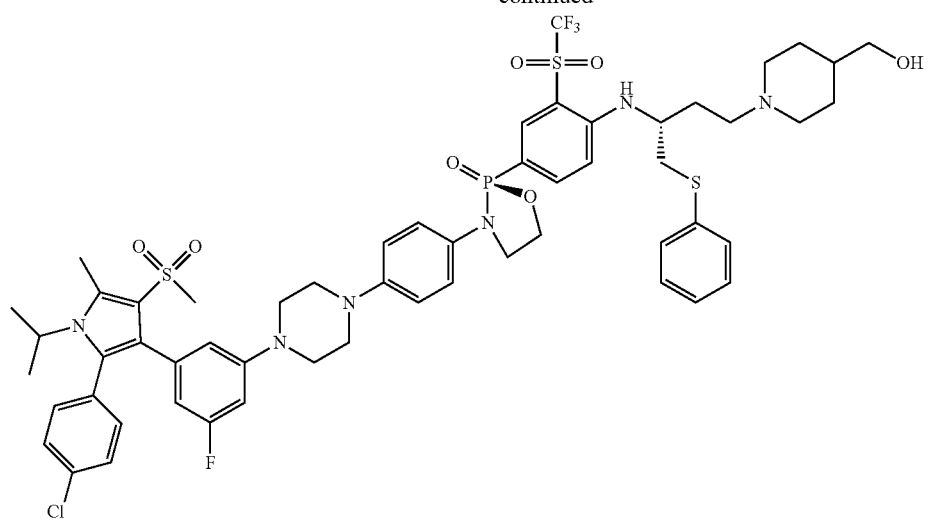

(S)-3-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)-2-(4-(((R)-4-(4-hydroxymethyl)piperidin-1-yl)-1-(phenylthio)butan-2-yl)amino)-3-((trifluoromethyl)sulfonyl)phenyl)-1,3,2-oxazaphospholidine 2-oxide

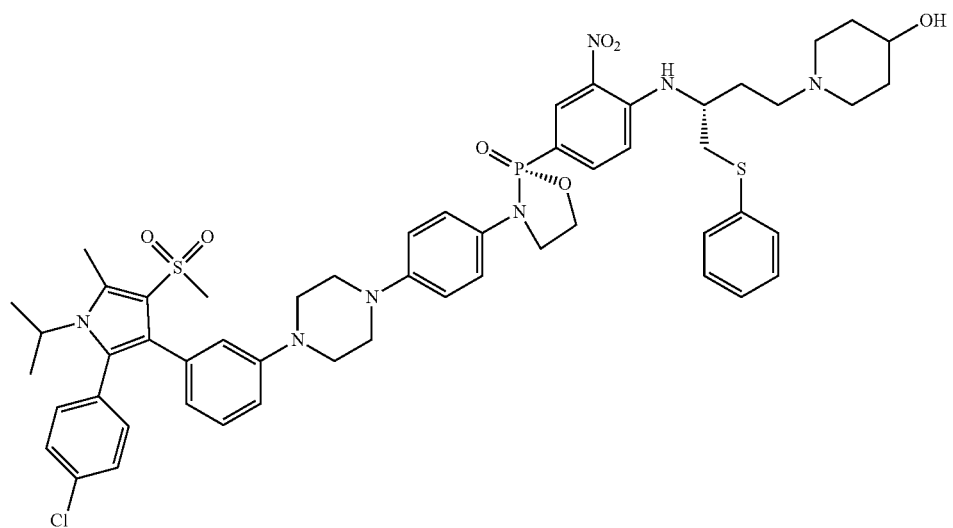

(R)-3-(4-(4-(3-(2-(4-chlorophenyl)-1-isopropyl-5-methyl-4-(methylsulfonyl)-1H-pyrrol-3-yl)-phenyl)piperezin-1-yl)phenyl)-2-(4-(((R)-4-(4-hydroxypiperidin-1-yl)-1-(phenylthio)butan-2-yl)amino)-3-nitrophenyl)-1,3,2-oxazaphospholidine 2-oxide -continued

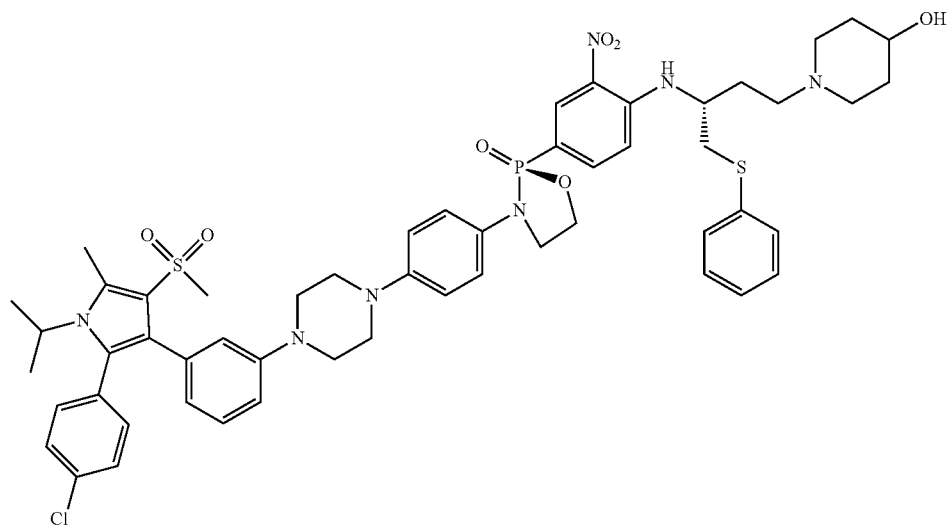

(S)-3-(4-(4-(3-(2-(4-chlorophenyl)-1-isopropyl-5-methyl-4-(methylsulfonyl)-1H-pyrrol-3-yl)-phenyl)piperezin-1-yl)phenyl)-2-(4-(((R)-4-(4-hydroxypiperidin-1-yl)-1-(phenylthio)butan-2-yl)amino)-3-nitrophenyl)-1,3,2-oxazaphospholidine 2-oxide

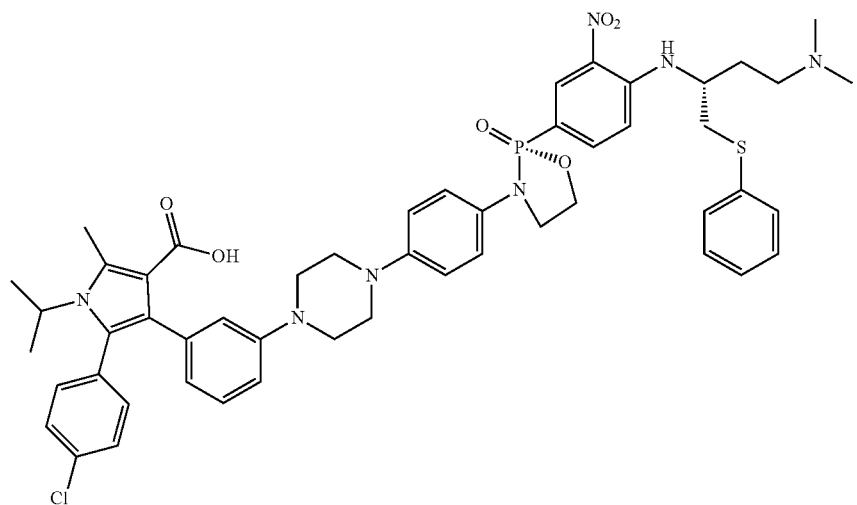

5-(4-chlorophenyl)-4-(3-(4-(4-((R)-2-(4-(((R)-4-(dimethylamino)-1-(phenylthio)butan-2-yl)amino)-3-nitrophenyl)-2-oxido-1,3,2-oxazaphospholidin-3-yl)phenyl)piperazin-1-yl)phenyl)-1-isopropyl-2-methyl-1H-pyrrole-3-carboxylic acid

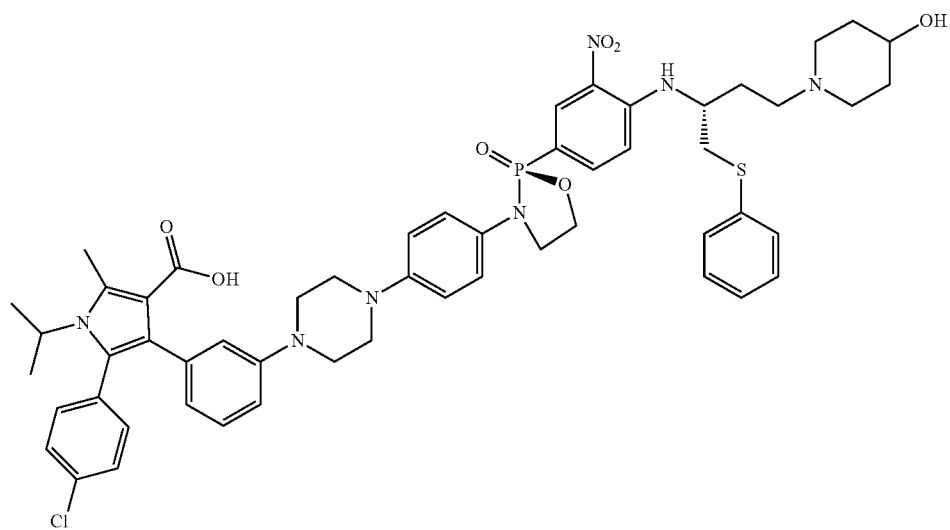

5-(4-chlorophenyl)-4-(3-(4-(4-((S)-2-(4-(((R)-4-(4-hydroxypiperidin-1-yl)-1-(phenylthio)butan-2-yl)amino)-3-nitrophenyl)-2-oxido-1,3,2-oxazaphospholidin-3-yl)phenyl)piperazin-1-yl)phenyl)-1-isopropyl-2-methyl-1H-pyrrole-3-carboxylic acid

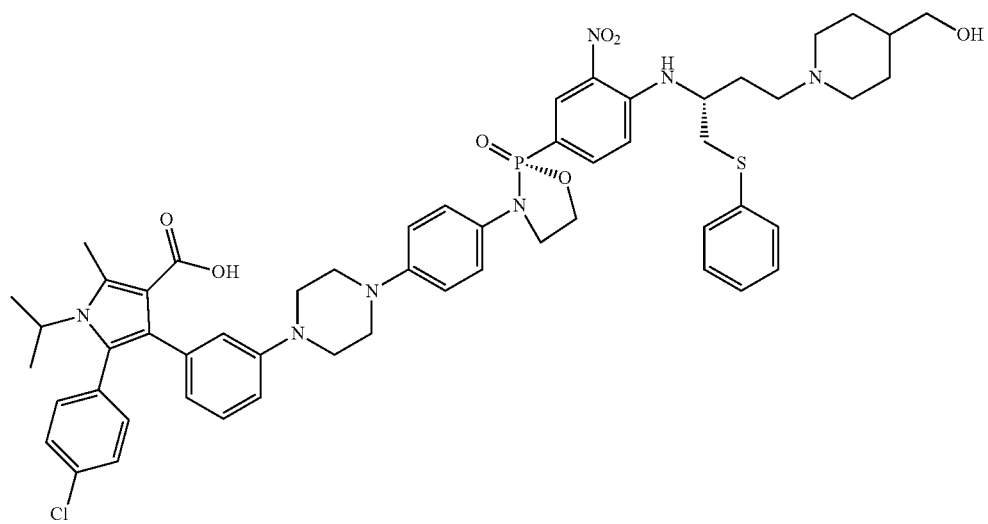

5-(4-chlorophenyl)-4-(3-(4-(4-((R)-2-(4-(((R)-4-(4-(hydroxymethyl)piperidin-1-yl)-1-(phenylthio)butan-2-yl)amino)-3-nitrophenyl)-2-oxido-1,3,2-oxazaphospholidin-3-yl)phenyl)piperazin-1-yl)phenyl)-1-isopropyl-2-methyl-1H-pyrrole-3-carboxylic acid

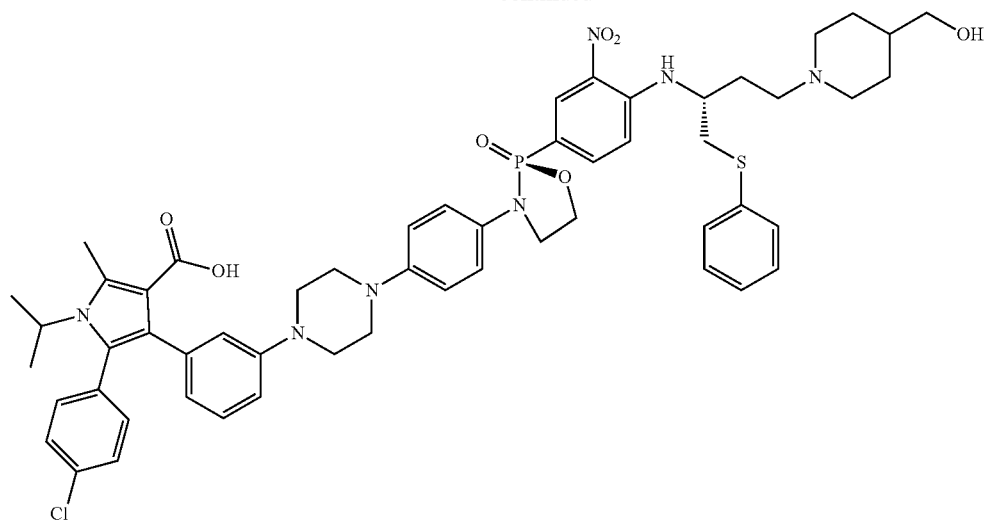

5-(4-chlorophenyl)-4-(3-(4-(4-((S)-2-(4-(((R)-4-(4-hydroxymethyl)piperidin-1-yl)-1-(phenylthio)butan-2-yl)amino)-3-nitrophenyl)-2-oxido-1,3,2-oxazaphospholidin-3-yl)phenyl)piperazin-1-yl)phenyl)-1-isopropyl-2-methyl-1H-pyrrole-3-carboxylic acid

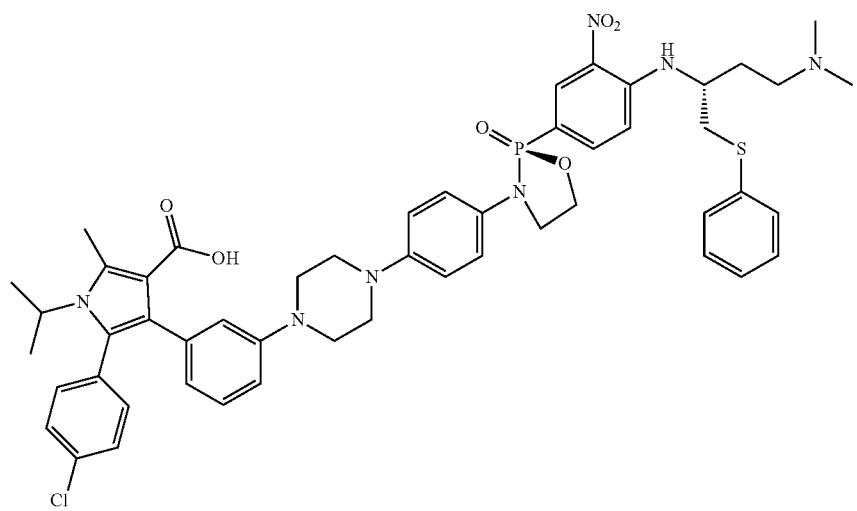

5-(4-chlorophenyl)-4-(3-(4-(4-((S)-2-((S)-2-(4-(((R)-4-(dimethylamino)-1-(phenylthio)butan-2-yl)amino)-3-nitrophenyl)-2-oxido-1,3,2-oxazaphospholidin-3-yl)phenyl)piperazin-1-yl)phenyl)-1-isopropyl-2-methyl-1H-pyrrole-3-carboxylic acid

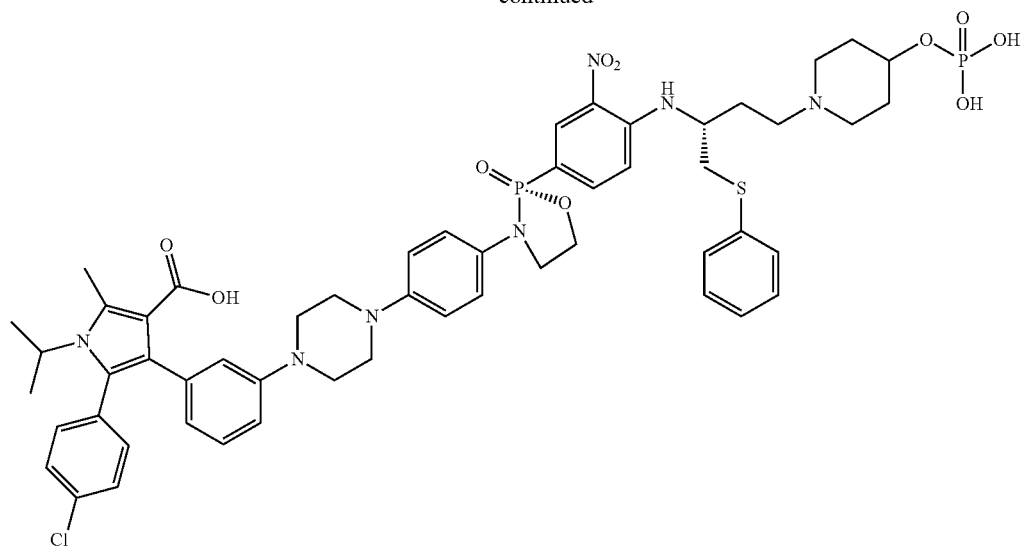
5-(4-chlorophenyl)-1-isopropyl-2-methyl-4-(3-(4-(4-((R)-2-(3-nitro-4-(((R)-1-(phenylthio)-4-(4-(phosphonooxy)piperidin-1-yl)butan-2-yl)amino)phenyl)-2-oxido-1,3,2-oxazaphospholidin-3-yl)phenyl)piperazin-1-yl)phenyl)-1H-pyrrole-3-carboxylic acid
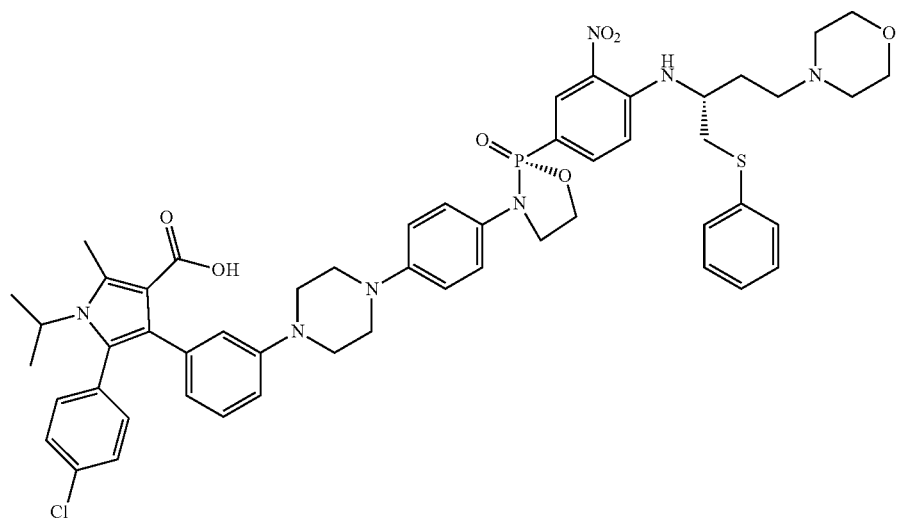
5-(4-chlorophenyl)-1-isopropyl-2-methyl-4-(3-(4-(4-((R)-2-(4-(((R)-4-morpholino-1-(phenylthio)butan-2-yl)amino)-3-nitrophenyl)-2-oxido-1,3,2-oxazaphospholidin-3-yl)phenyl)piperezin-1-yl)phenyl)-1H-pyrrole-3-carboxylic acid

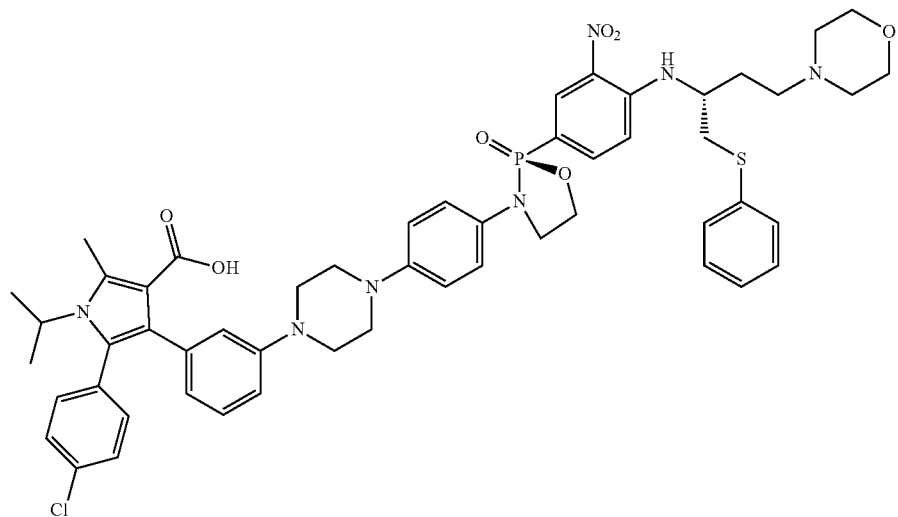

5-(4-chlorophenyl)-1-isopropyl-2-methyl-4-(3-(4-(4-((S)-2-(4-(((R)-4-morpholino-1-(phenylthio)butan-2-yl)amino)-3-nitrophenyl)-2-oxido-1,3,2-oxazaphospholidin-3-yl)phenyl)piperezin-1-yl)phenyl)-1H-pyrrole-3-carboxylic acid

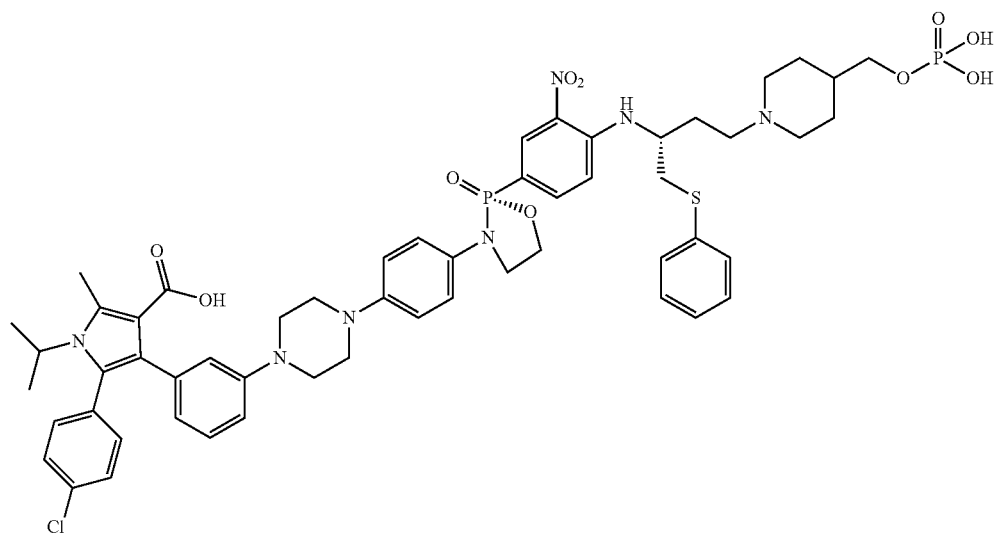

5-(4-chlorophenyl)-1-isopropyl-2-methyl-4-(3-(4-(4-((R)-2-(3-nitro-4-(((R)-1-(phenylthio)-4-(4-((phosphonooxy)methyl)piperidin-1-yl)butan-2-yl)amino)phenyl)-2-oxido-1,3,2-oxazaphospholidin-3-yl)phenyl)piperazin-1-yl)phenyl)-1H-pyrrole-3-carboxylic acid

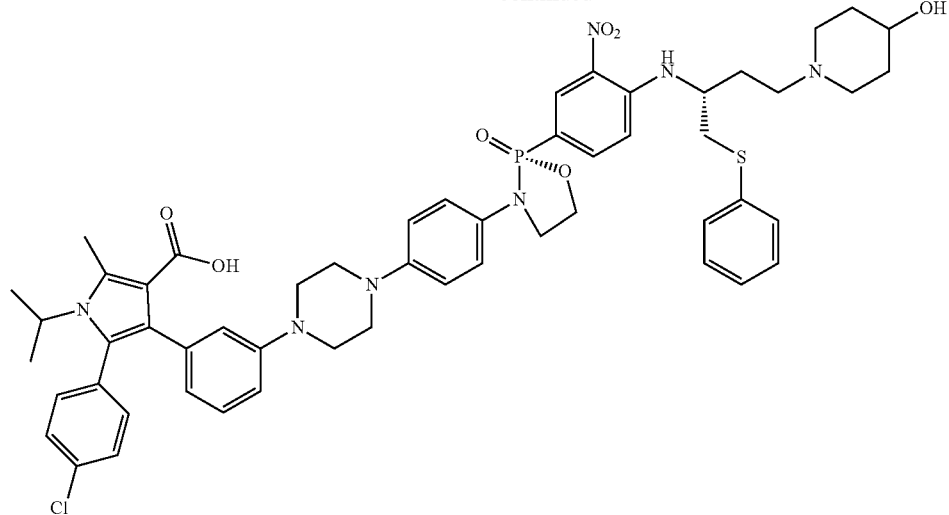

5-(4-chlorophenyl)-4-(3-(4-(4-((R)-2-(4-(((R)-2-(4-(((R)-4-(4-hydroxypiperidin-1-yl)-1-(phenylthio)butan-2-yl)amino)-3-nitrophenyl)-2-oxido-1,3,2-oxazaphospholidin-3-yl)phenyl)piperazin-1-yl)phenyl)-1-isopropyl-2-methyl-1H-pyrrole-3-carboxylic acid

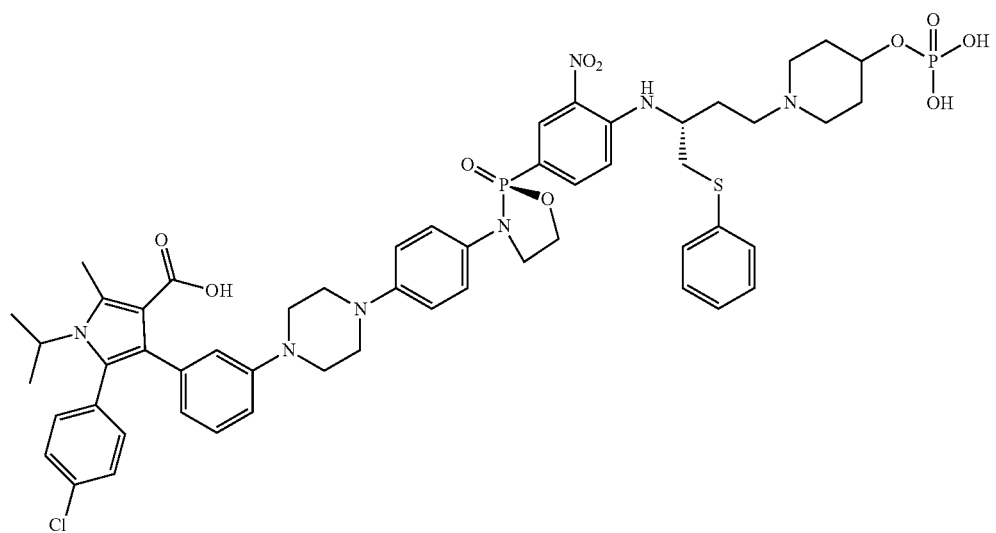

5-(4-chlorophenyl)-1-isopropyl-2-methyl-4-(3-(4-(4-((S)-2-(3-nitro-4-(((R)-1-(phenylthio)-4-(4-(phosphonooxy)piperidin-1-yl)butan-2-yl)amino)phenyl)-2-oxido-1,3,2-oxazaphospholidin-3-yl)phenyl)piperazin-1-yl)phenyl)-1H-pyrrole-3-carboxylic acid

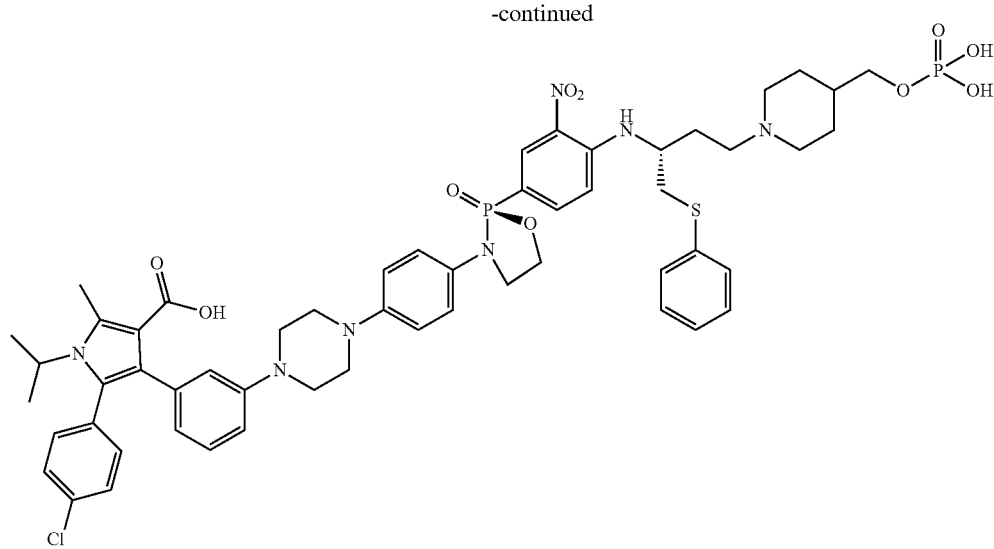

5-(4-chlorophenyl)-1-isopropyl-2-methyl-4-(3-(4-(4-((S)-2-(3-nitro-4-(((R)-1-(phenylthio)-4-(4-(phosphonooxy)piperidin-1-yl)butan-2-yl)amino)phenyl)-2-oxido-1,3,2-oxazaphospholidin-3-yl)phenyl)piperazin-1-yl)phenyl)-1H-pyrrole-3-carboxylic acid

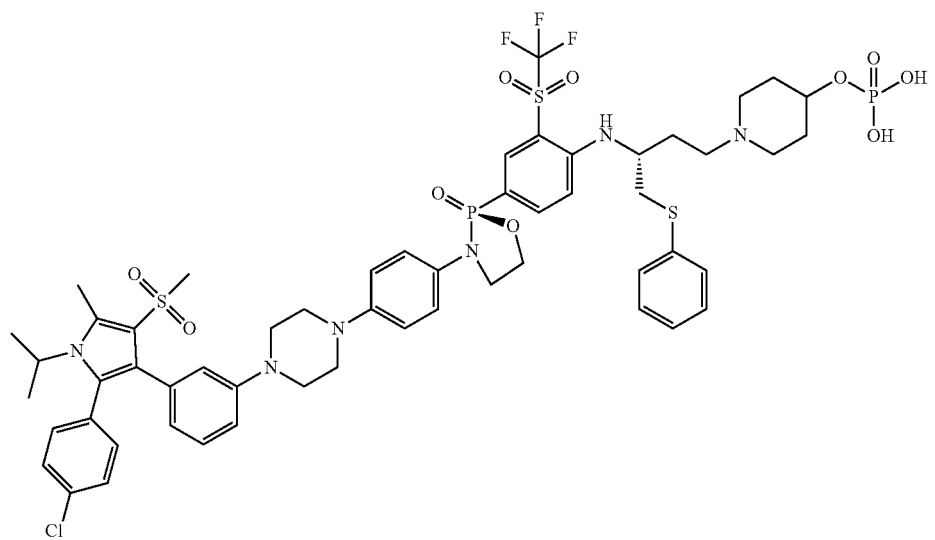

1-((R)-3-((4-((S)-3-(4-(4-(3-(2-(4-chlorophenyl)-1-isopropyl-5-methyl-4-(methylsulfonyl)-1H-pyrrol-3-yl)phenyl)piperazin-1-yl)phenyl)-2-oxido-1,3,2-oxazaphospholidin-2-yl)-2-((trifluoromethyl)sulfonyl)phenyl)amino)-4-(phenylthio)butyl)piperidin-4-yl dihydrogen phosphate

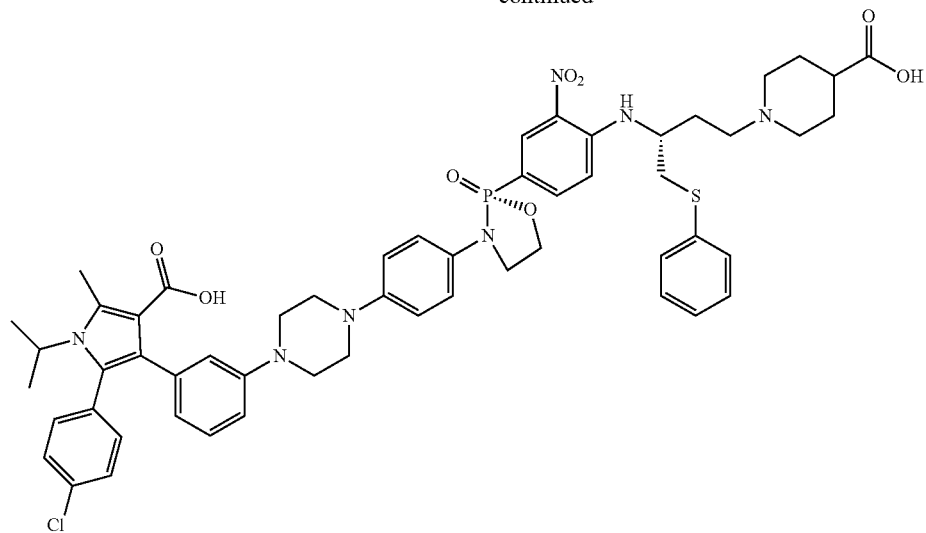
1-((R)-3-((4-((R)-3-(4-(4-(3-(4-carboxy-2-(4-chlorophenyl)-1-isopropyl-5-methyl-1H-pyrrol-3-yl)phenyl)piperazin-1-yl)phenyl)-2-oxido-1,3,2-oxazaphospholidin-2-yl)-1-nitrophenyl)amino)-4-(phenylthio)butyl)piperidine-4-carboxylic acid
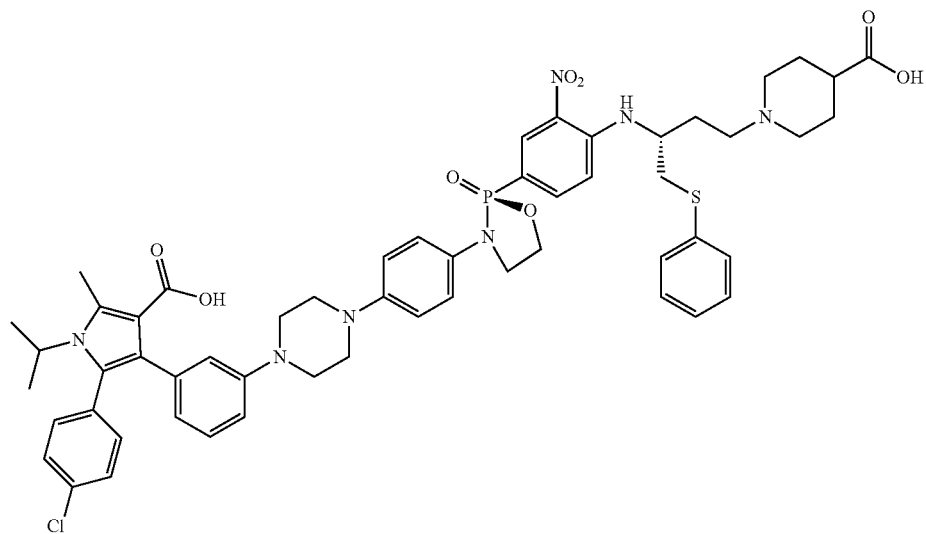
1-((S)-3-((4-((R)-3-(4-(4-(3-(4-carboxy-2-(4-chlorophenyl)-1-isopropyl-5-methyl-1H-pyrrol-3-yl)phenyl)piperazin-1-yl)phenyl)-2-oxido-1,3,2-oxazaphospholidin-2-yl)-1-nitrophenyl)amino)-4-(phenylthio)butyl)piperidine-4-carboxylic acid -continued

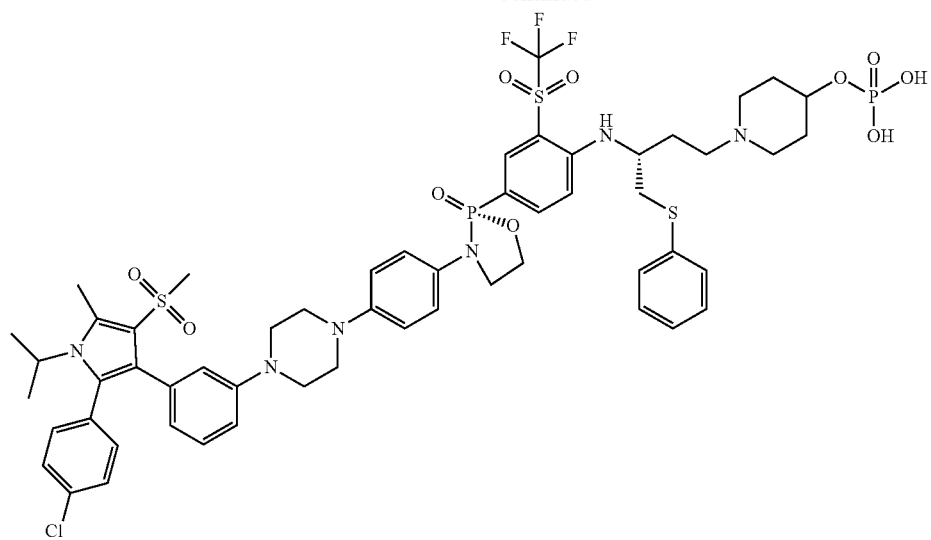

1-((R)-3-((4-((R)-3-(4-(4-(3-(2-(4-chlorophenyl)-1-isopropyl-5-methyl-4-(methylsulfonyl)-1H-pyrrol-3-yl)phenyl)piperazin-1-yl)phenyl)-2-oxido-1,3,2-oxazaphospholidin-2-yl)-2-((trifluoromethyl)sulfonyl)phenyl)amino)-4-(phenylthio)butyl)piperidin-4-yl dihydrogen phosphate

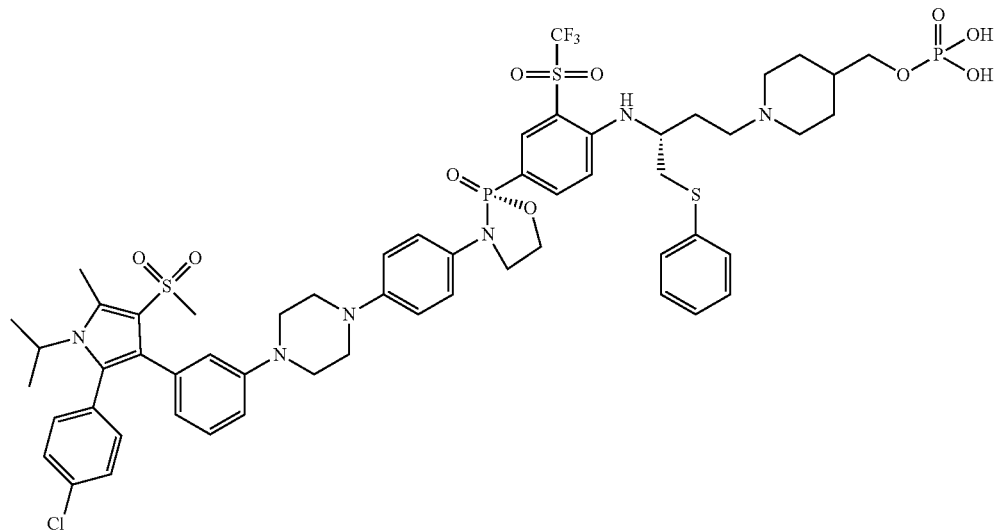

1-((R)-3-((4-((R)-3-(4-(4-(3-(2-(4-chlorophenyl)-1-isopropyl-5-methyl-4-(methylsulfonyl)-1H-pyrrol-3-yl)phenyl)piperazin-1-yl)phenyl)-2-oxido-1,3,2-oxazaphospholidin-2-yl)-2-((trifluoromethyl)sulfonyl)phenyl)amino)-4-(phenylthio)butyl)piperidin-4-yl)methyl dihydrogen phosphate

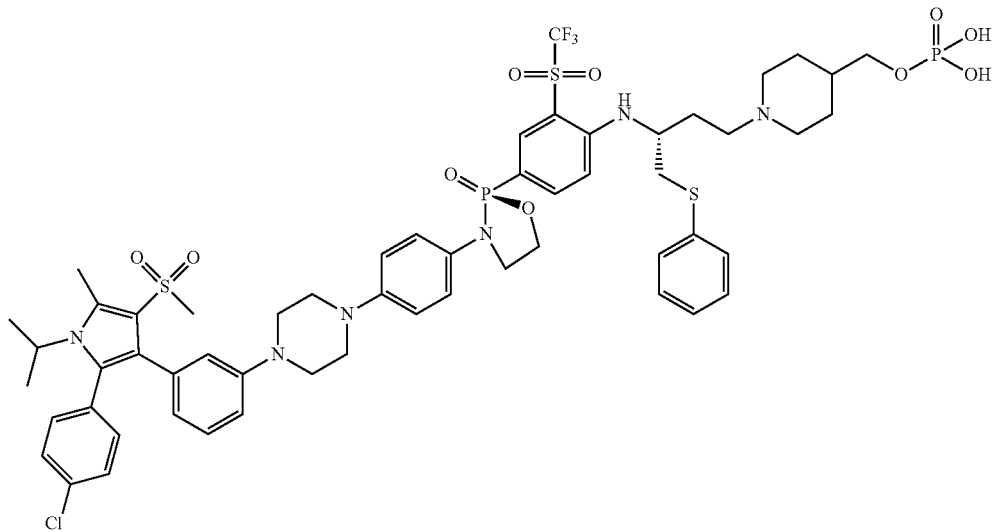

1-((R)-3-((4-((S)-3-(4-(4-(3-(2-(4-chlorophenyl)-1-isopropyl-5-methyl-4-(methylsulfonyl)-1H-pyrrol-3-yl)phenyl)piperazin-1-yl)phenyl)-2-oxido-1,3,2-oxazaphospholidin-2-yl)-2-((trifluoromethyl)sulfonyl)phenyl)amino)-4-(phenylthio)butyl)piperidin-4-yl)methyl dihydrogen phosphate

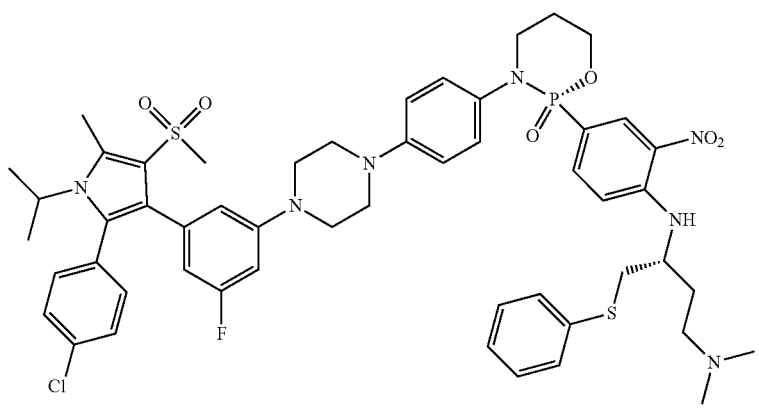

(S)-3-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)-2-(4-(((R)-4-(dimethylamino)-1-(phenylthio)butan-2-yl)amino)-3-nitrophenyl)-1,3,2-oxazaphosphinane 2-oxide

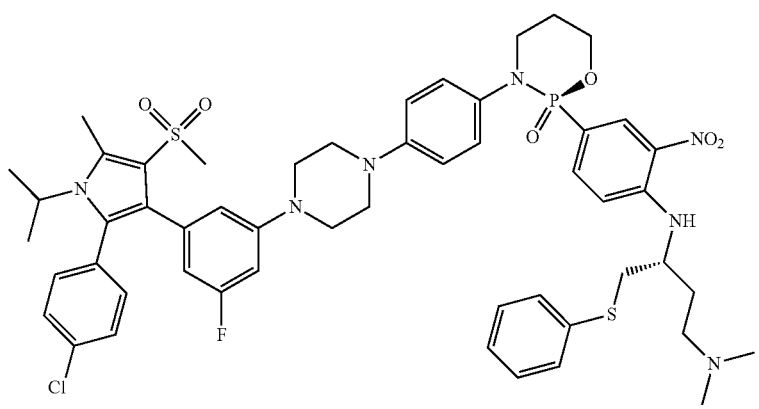

(R)-3-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)-2-(4-(((R)-4-(dimethylamino)-1-(phenylthio)butan-2-yl)amino)-3-nitrophenyl)-1,3,2-oxazaphosphinane 2-oxide -continued

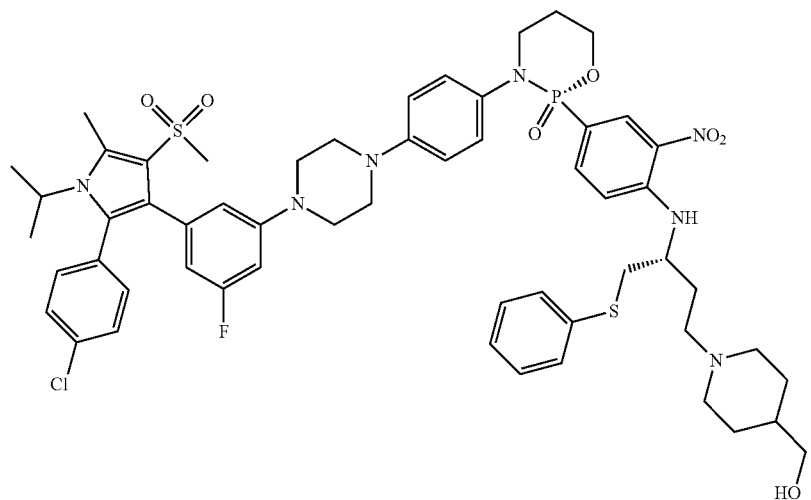

(S)-3-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)-2-(4-(((R)-4-(4-hydromethyl)piperidin-1-yl)-1 (phenylthio)butan2-yl)amino)-3-nitrophenyl)-1,3,2-oxazaphosphinane 2-oxide

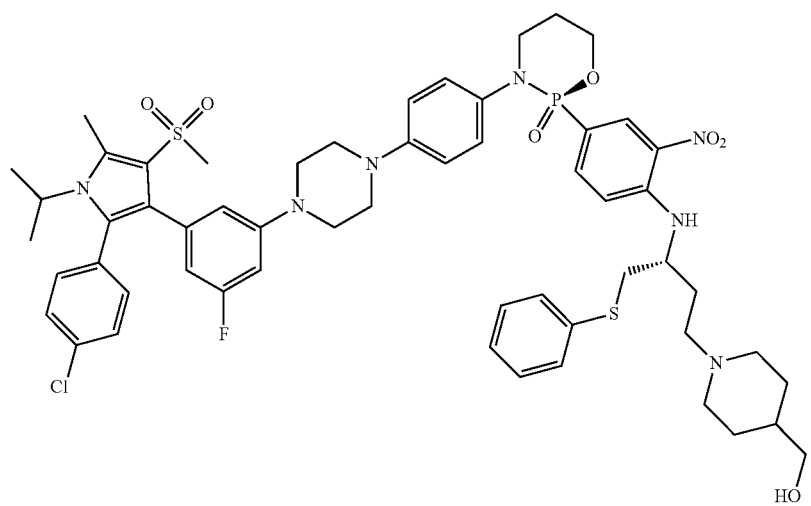

(R)-3-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)-2-(4-(((R)-4-(4-hydromethyl)piperidin-1-yl)-1 (phenylthio)butan2-yl)amino)-3-nitrophenyl)-1,3,2-oxazaphosphinane 2-oxide -continued

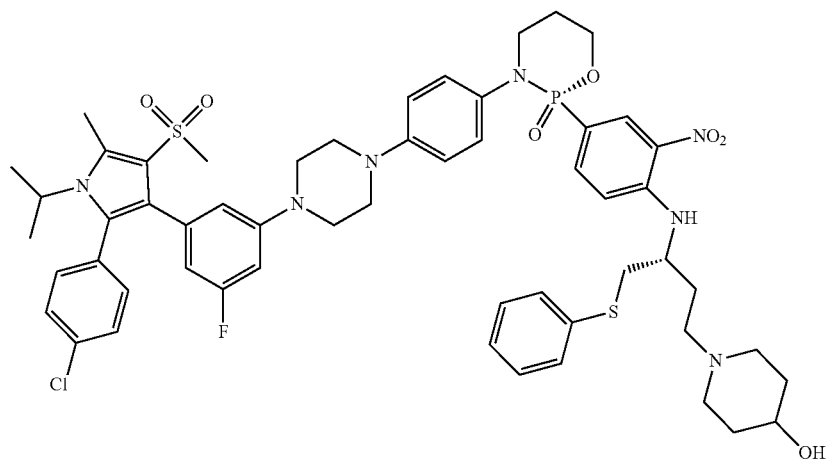

(S)-3-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)-2-(4-(((R)-4-(4-hydroxypiperidin-1-yl)-1-(phenylthio)butan-2-yl)amino)-3-nitrophenyl)-1,3,2-oxazaphosphinane 2-oxide

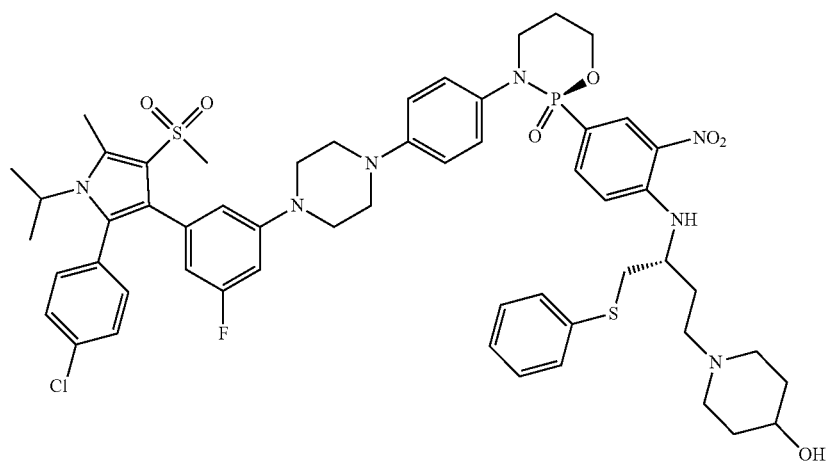

(R)-3-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)-2-(4-(((R)-4-(4-hydroxypiperidin-1-yl)-1-(phenylthio)butan-2-yl)amino)-3-nitrophenyl)-1,3,2-oxazaphosphinane 2-oxide -continued

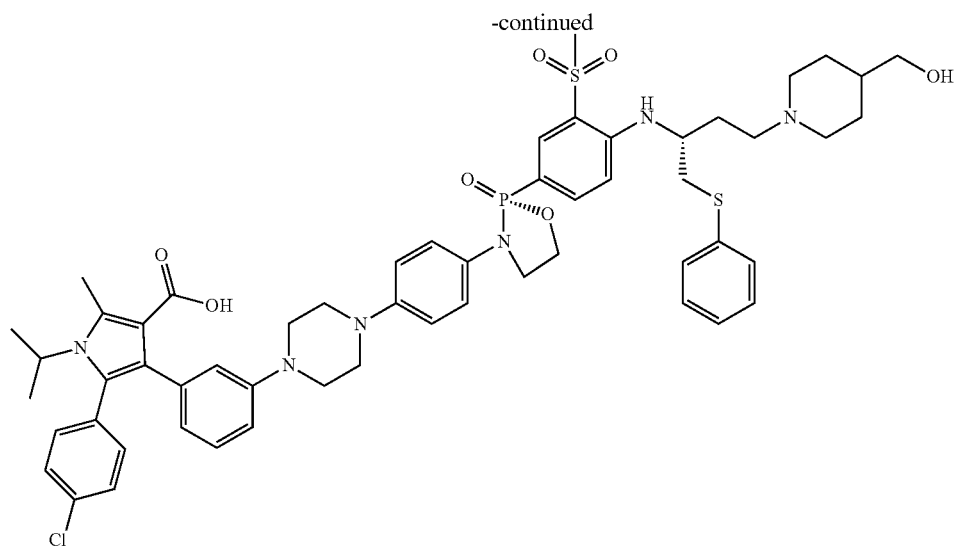

5-(4-chlorophenyl)-4-(3-(4-(4-((R)-2-(4-(((R)-4-(4-(hydroxymethyl)piperidin-1-yl)-1-(phenylthio)butan-2-yl)amino)-3-(methylsulfonyl)phenyl)-2-oxido-1,3,2-oxazaphospholidin-3-yl)phenyl)piperazin-1-yl)phenyl)-1-isopropyl-2-methyl-1H-pyrrole-3-carboxylic acid

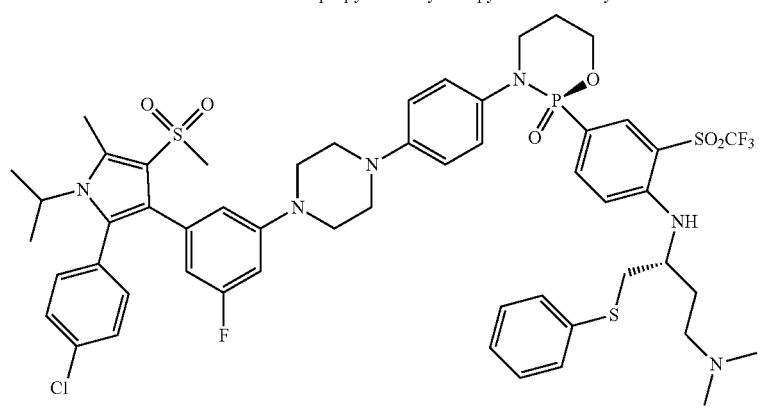

(R)-3-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)-2-(4-(((R)-4-(dimethylamino)-1-(phenylthio)butan-2-yl)amino)-3-((trifluoromethyl)sulfonyl)phenyl)-1,3,2-oxazaphosphinane 2-oxide

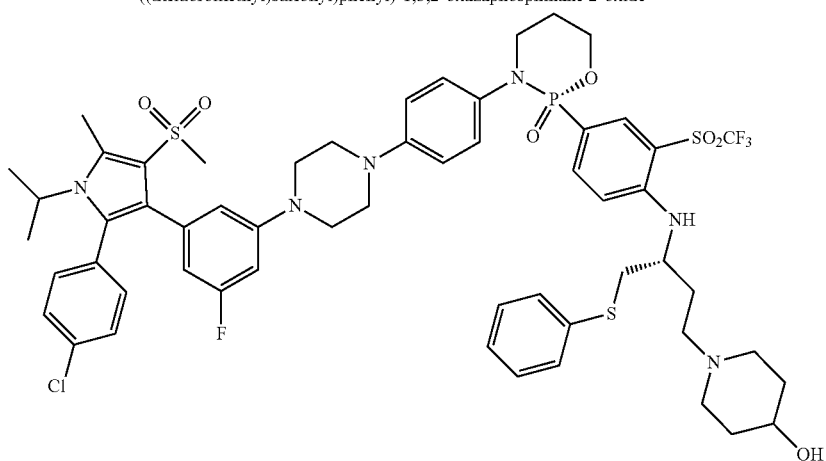

(S)-3-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)-2-(4-(((R)-4-(4-hydroxypiperidin-1-yl)-1-(phenylthio)butan-2-yl)amino)-3-((trifluoromethyl)sulfonyl)phenyl)-1,3,2-oxazaphosphinane 2-oxide

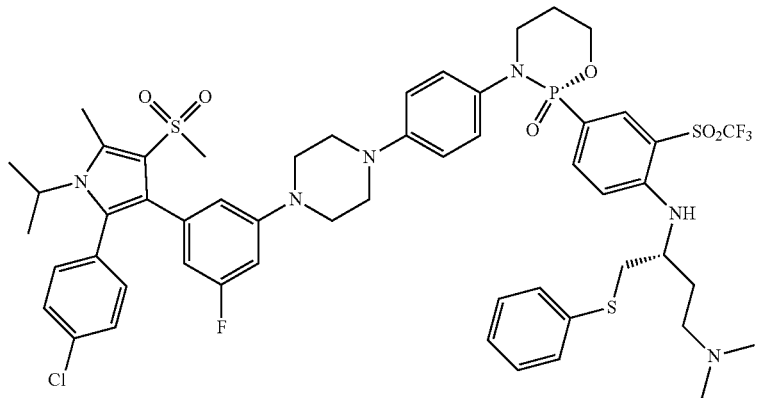

(S)-3-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)-2-(4-(((R)-4-(dimethylamino)-1-(phenylthio)butan-2-yl)amino)-3-((trifluoromethyl)sulfonyl)phenyl)-1,3,2-oxazaphosphinane 2-oxide

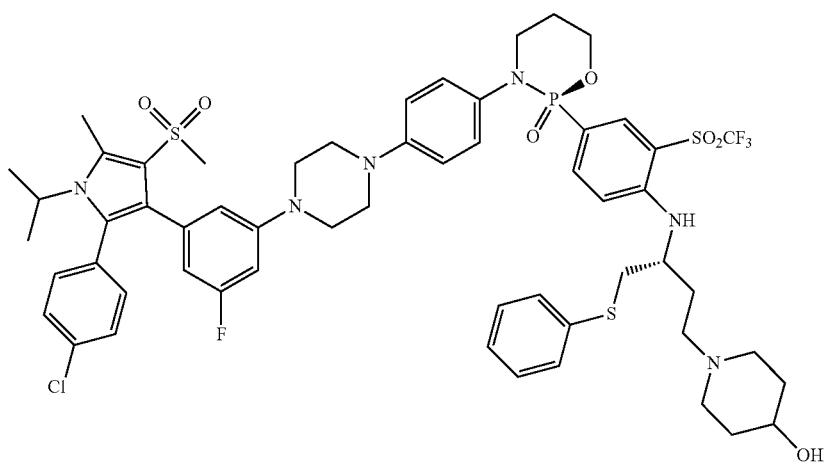

(R)-3-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)-2-(4-(((R)-4-(4-hydroxypiperidin-1-yl)-1-(phenylthio)butan-2-yl)amino)-3-((trifluoromethyl)sulfonyl)phenyl)-1,3,2-oxazaphosphinane 2-oxide

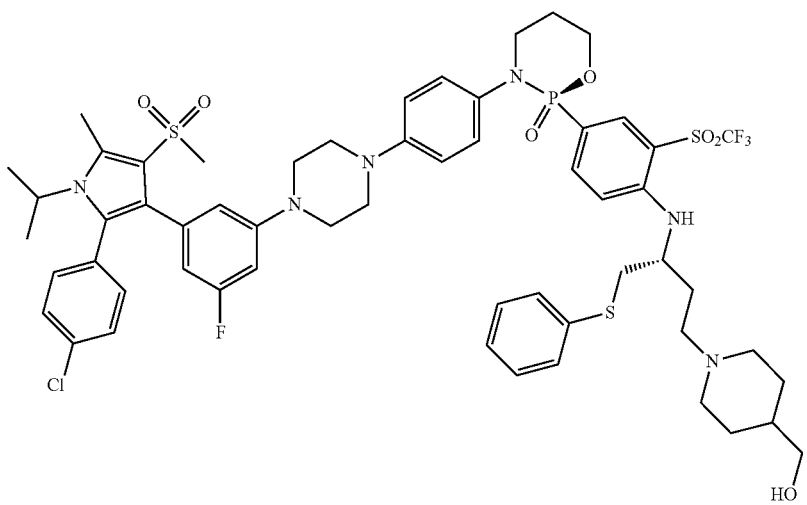

(R)-3-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)-2-(4-(((R)-4-(4-hydroxymethyl)piperidin-1-yl)-1-(phenylthio)butan-2-yl)amino)-3-((trifluoromethyl)sulfonyl)phenyl)-1,3,2-oxazaphosphinane 2-oxide -continued

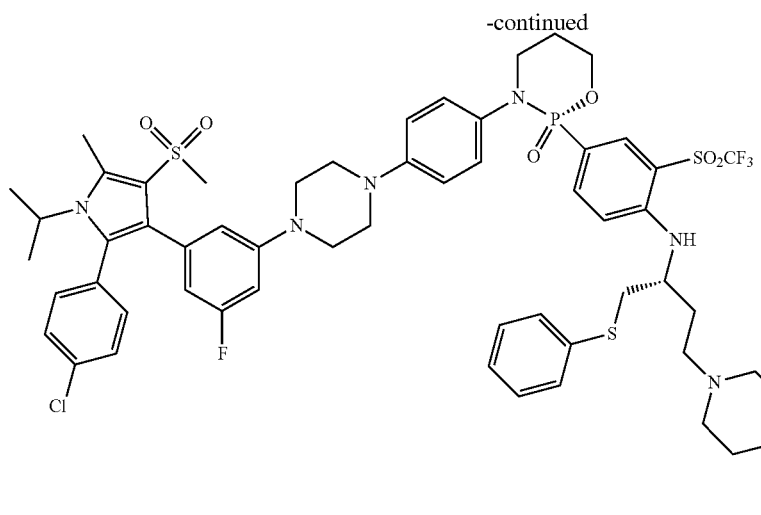

(S)-3-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)-2-(4-(((R)-4-(4-hydroxymethyl)piperidin-1-yl)-1-(phenylthio)butan-2-yl)amino)-3-((trifluoromethyl)sulfonyl)phenyl)-1,3,2-oxazaphosphinane 2-oxide

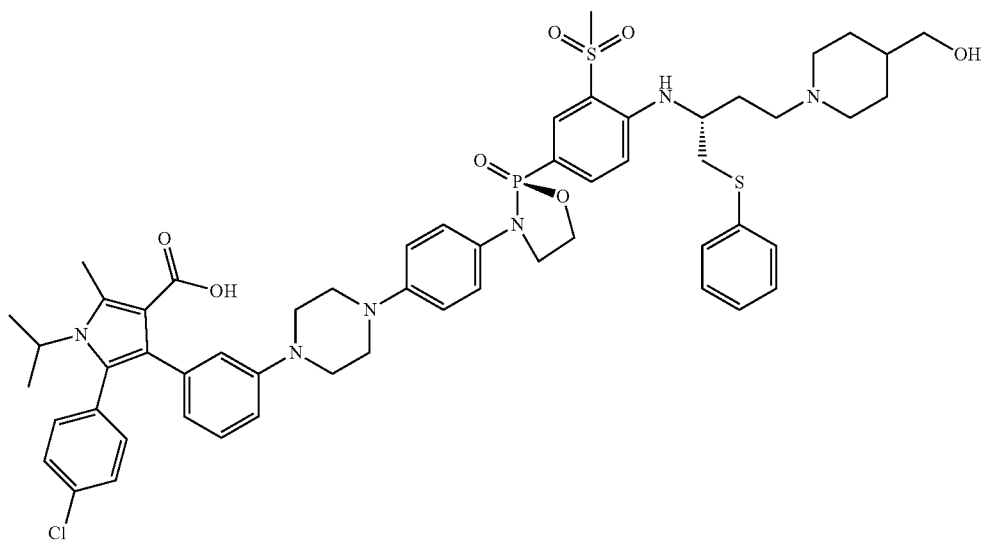

5-(4-chlorophenyl)-4-(3-(4-(4-((S)-2-(4-(((R)-4-(4-(hydroxymethyl)piperidin-1-yl)-1-(phenylthio)butan-2-yl)amino)-3-(methylsulfonyl)phenyl)-2-oxido-1,3,2-oxazaphospholidin-3-yl)phenyl)piperazin-1-yl)phenyl)-1-isopropyl-2-methyl-1H-pyrrole-3-carboxylic acid

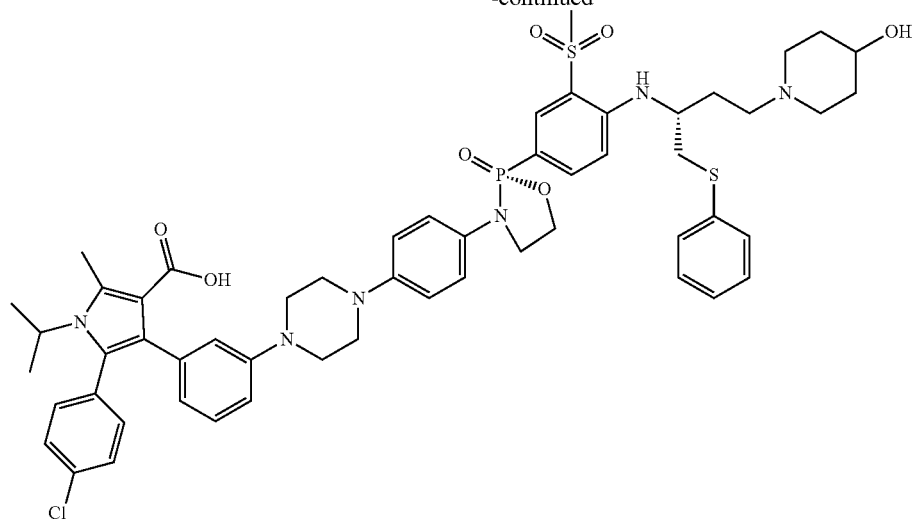

5-(4-chlorophenyl)-4-(3-(4-(4-((R)-2-(4-(((R)-4-(4-(hydroxypiperidin-1-yl)-1-(phenylthio)butan-2-yl)amino)-3-(methylsulfonyl)phenyl)-2-oxido-1,3,2-oxazaphospholidin-3-yl)phenyl)piperazin-1-yl)phenyl)-1-isopropyl-2-methyl-1H-pyrrole-3-carboxylic acid

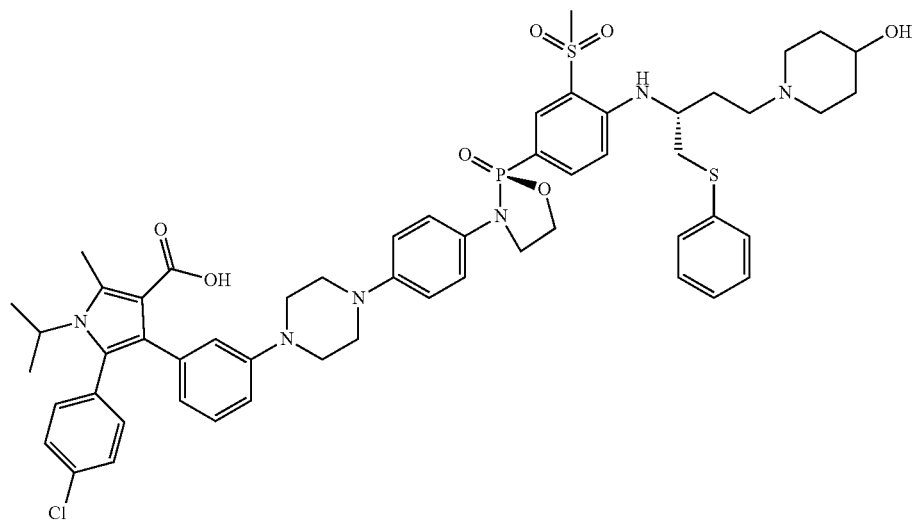

5-(4-chlorophenyl)-4-(3-(4-(4-((S)-2-(4-(((R)-4-(4-(hydroxypiperidin-1-yl)-1-(phenylthio)butan-2-yl)amino)-3-(methylsulfonyl)phenyl)-2-oxido-1,3,2-oxazaphospholidin-3-yl)phenyl)piperazin-1-yl)phenyl)-1-isopropyl-2-methyl-1H-pyrrole-3-carboxylic acid -continued

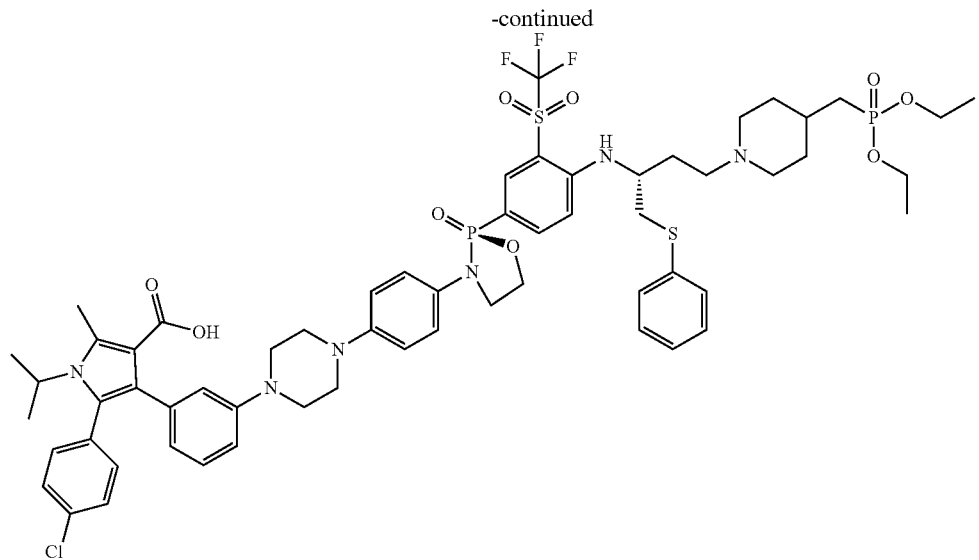

5-(4-chlorophenyl)-4-(3-(4-(4-(4-((S)-2-(4-(((R)-4-(4-((diethoxyphosphoryl)methyl)piperidin-1-yl)-1-(phenylthio)butan-2-yl)amino)-3-((trifluoromethyl)sulfonyl)phenyl)-2-oxido-1,3,2-oxazaphospholidin-3-yl)phenyl)piperazin-1-yl)phenyl)-1-isopropyl-2-methyl-1H-pyrrole-3-carboxylic acid

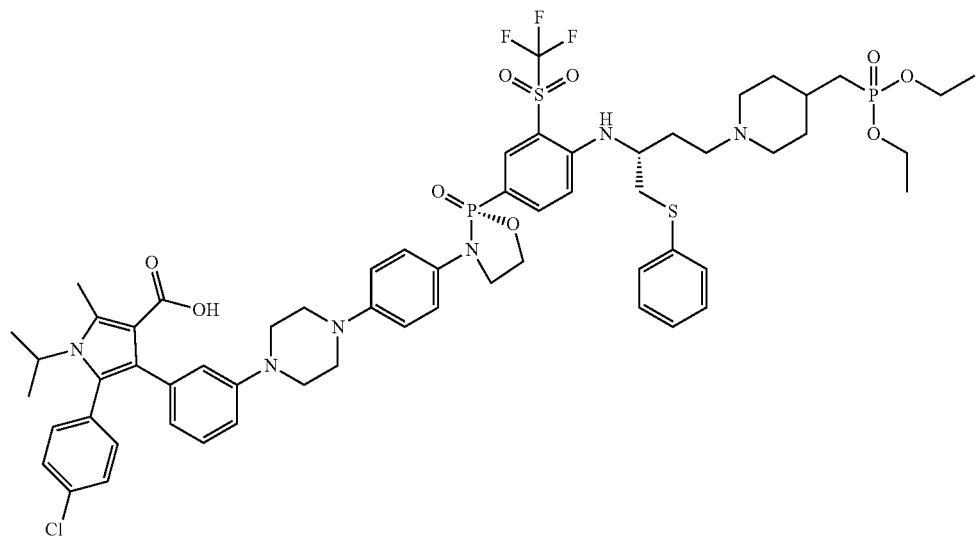

5-(4-chlorophenyl)-4-(3-(4-(4-(4-((R)-2-(4-(((R)-4-(4-((diethoxyphosphoryl)methyl)piperidin-1-yl)-1-(phenylthio)butan-2-yl)amino)-3-((trifluoromethyl)sulfonyl)phenyl)-2-oxido-1,3,2-oxazaphospholidin-3-yl)phenyl)piperazin-1-yl)phenyl)-1-isopropyl-2-methyl-1H-pyrrole-3-carboxylic acid -continued

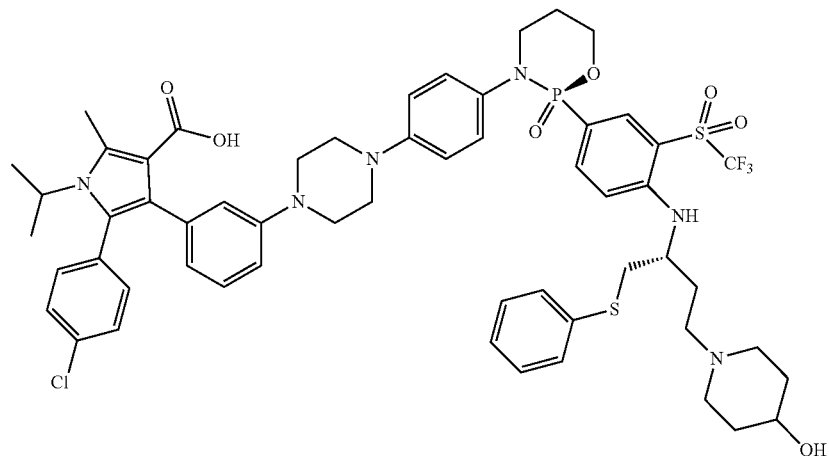

5-(4-chlorophenyl)-4-(3-(4-(4-(((R)-2-(4-(((R)-4-(4-hydroxypiperidin-1-yl)-1-(phenylthio)butan-2-yl)amino)-3-((trifluoromethyl)sulfonyl)phenyl)-2-oxido-1,3,2-oxazaphosphinan-3-yl)phenyl)piperazin-1-yl)phenyl)-1-isopropyl-2-methyl-1H-pyrrold-3-carboxylic acid

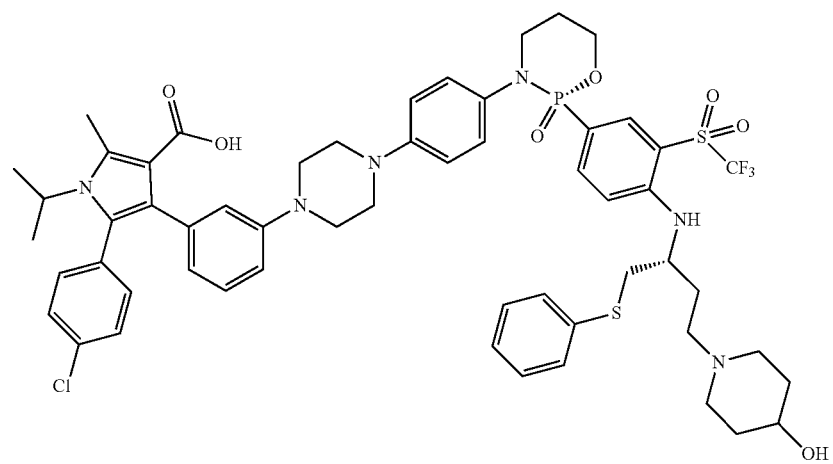

5-(4-chlorophenyl)-4-(3-(4-(4-(((S)-2-(4-(((R)-4-(4-hydroxypiperidin-1-yl)-1-(phenylthio)butan-2-yl)amino)-3-((trifluoromethyl)sulfonyl)phenyl)-2-oxido-1,3,2-oxazaphosphinan-3-yl)phenyl)piperazin-1-yl)phenyl)-1-isopropyl-2-methyl-1H-pyrrole-3-carboxylic acid -continued

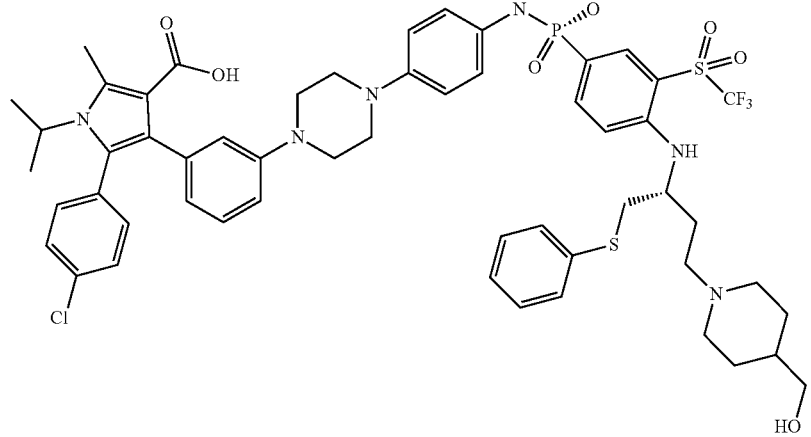

5-(4-chlorophenyl)-4-(3-(4-(4-(4-((S)-2-(4-(((R)-4-(4-(hydroxymethyl)piperidin-1-yl)-1-(phenylthio)butan-2-yl)amino)-3-((trifluoromethyl)sulfonyl)phenyl)-2-oxido-1,3,2-oxazaphosphinan-3-yl)phenyl)piperazin-1-yl)phenyl)-1-isopropyl-2-methyl-1H-pyrrole-3-carboxylic acid

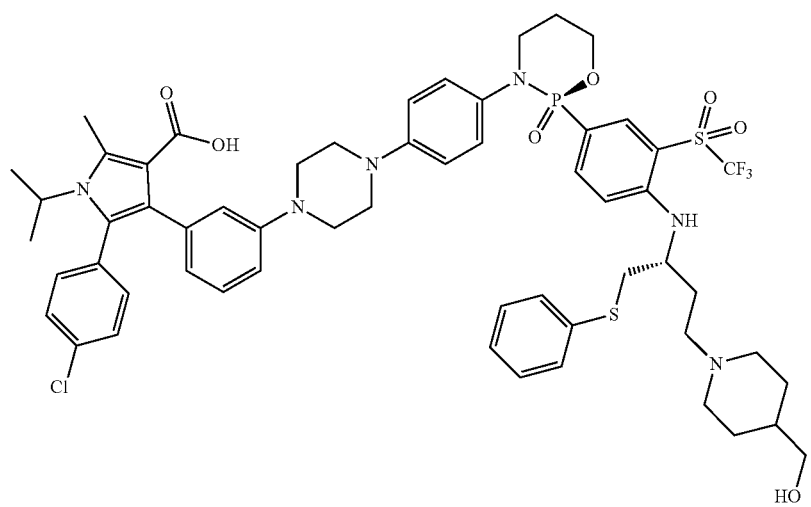

5-(4-chlorophenyl)-4-(3-(4-(4-(4-((R)-2-(4-(((R)-4-(4-(hydroxymethyl)piperidin-1-yl)-1-(phenylthio)butan-2-yl)amino)-3-((trifluoromethyl)sulfonyl)phenyl)-2-oxido-1,3,2-oxazaphosphinan-3-yl)phenyl)piperazin-1-yl)phenyl)-1-isopropyl-2-methyl-1H-pyrrole-3-carboxylic acid -continued

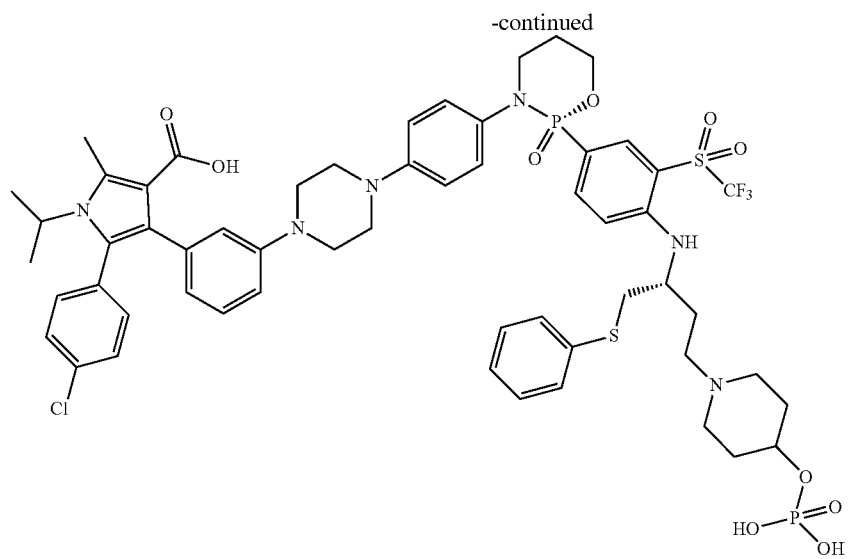

5-(4-chlorophenyl)-1-isopropyl-2-methyl-4-(3-(4-(4-((S)-2-oxido-2-(4-(((R)-1-(phenylthio)-4-(4-(phosphonooxy)piperidin-1-yl)butan-2-yl)amino)-3-((trifluoromethyl)sulfonyl)phenyl)-1,3,2-oxazaphosphinan-3-yl)phenyl)piperazin-1-yl)phenyl)-1H-pyrrole-3-carboxylic acid

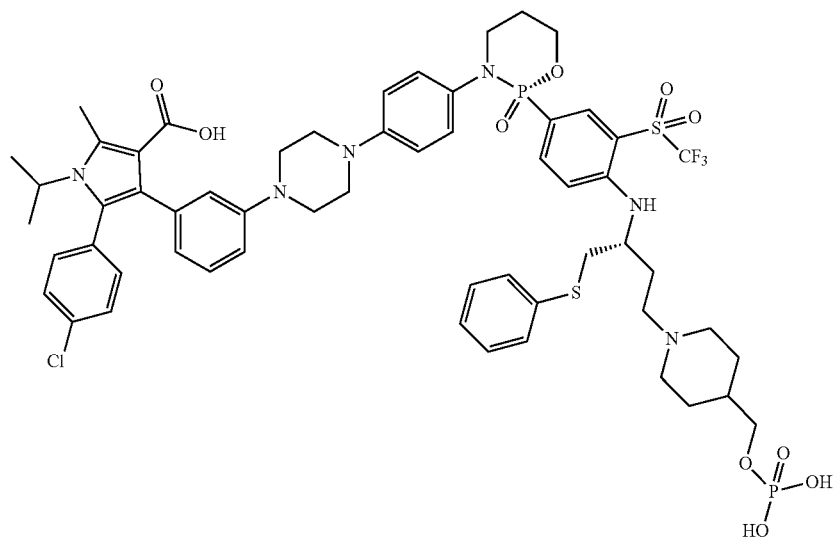

5-(4-chlorophenyl)-1-isopropyl-2-methyl-4-(3-(4-(4-((S)-2-oxido-2-(4-(((R)-1-(phenylthio)-4-(4-((phosphonooxy)methyl)piperidin-1-yl)butan-2-yl)amino)-3-((trifluoromethyl)sulfonyl)phenyl)-1,3,2-oxazaphosphinan-3-yl)phenyl)piperazin-1-yl)phenyl)-1H-pyrrole-3-carboxylic acid

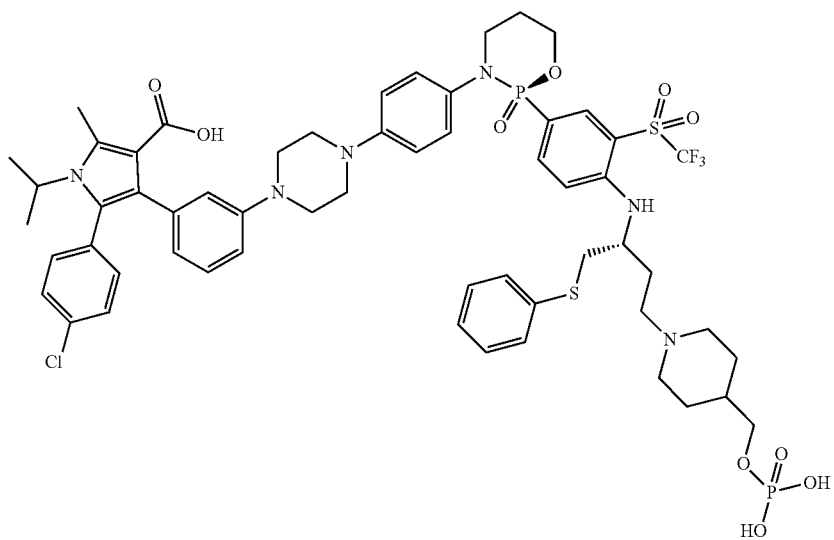

5-(4-chlorophenyl)-1-isopropyl-2-methyl-4-(3-(4-(4-((R)-2-oxido-2-(4-(((R)-1-(phenylthio)-4-(4-((phosphonooxy)methyl)piperidin-1-yl)butan-2-yl)amino)-3-((trifluoromethyl)sulfonyl)phenyl)-1,3,2-oxazaphosphinan-3-yl)phenyl)piperazin-1-yl)phenyl)-1H-pyrrole-3-carboxylic acid

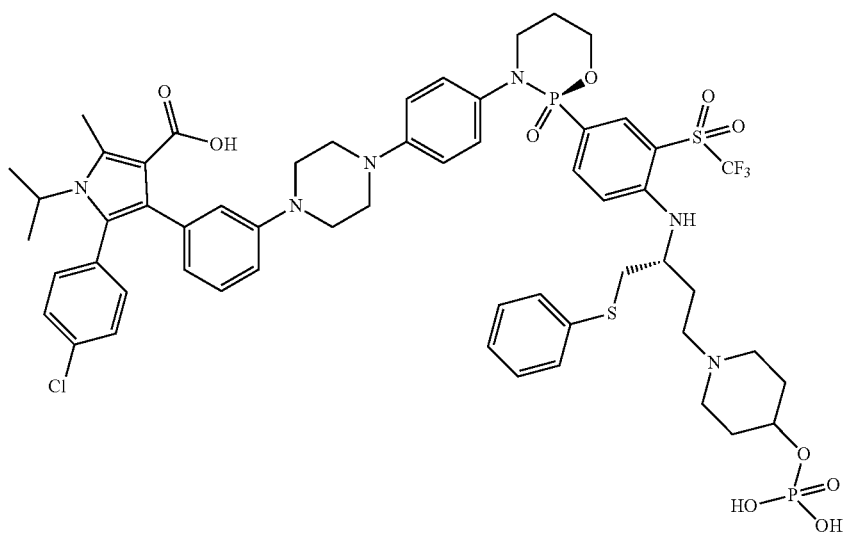

5-(4-chlorophenyl)-1-isopropyl-2-methyl-4-(3-(4-(4-((R)-2-oxido-2-(4-(((R)-1-(phenylthio)-4-(4-(phosphonooxy)piperidin-1-yl)butan-2-yl)amino)-3-((trifluoromethyl)sulfonyl)phenyl)-1,3,2-oxazaphosphinan-3-yl)phenyl)piperazin-1-yl)phenyl)-1H-pyrrole-3-carboxylic acid

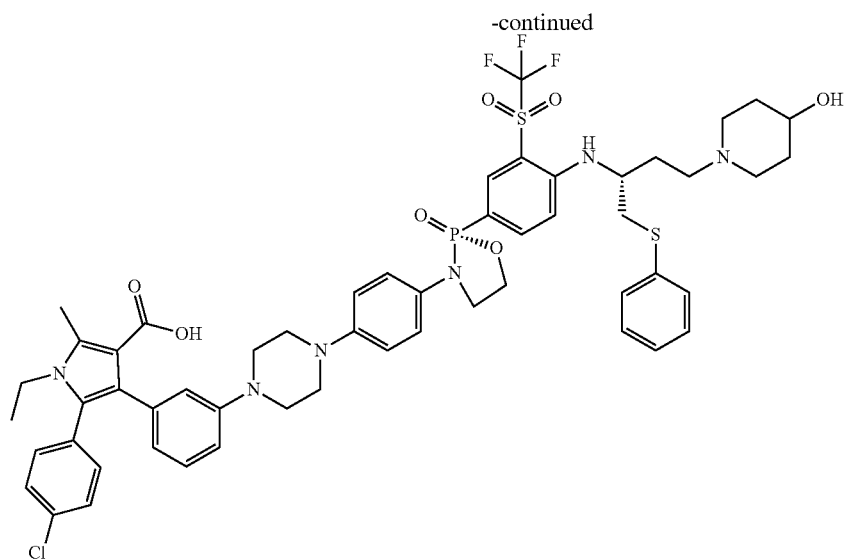

5-(4-chlorophenyl)-1-ethyl-4-(3-(4-(4-((R)-2-(4-(((R)-4-(4-hydroxypiperidin-1-yl)-1-(phenylthio)butan-2-yl)amino)-3-((trifluoromethyl)sulfonyl)phenyl)-2-oxido-1,3,2-oxazaphospholidin-3-yl)phenyl)piperazin-1-yl)phenyl)-2-methyl-1H-pyrrole-3-carboxylid acid

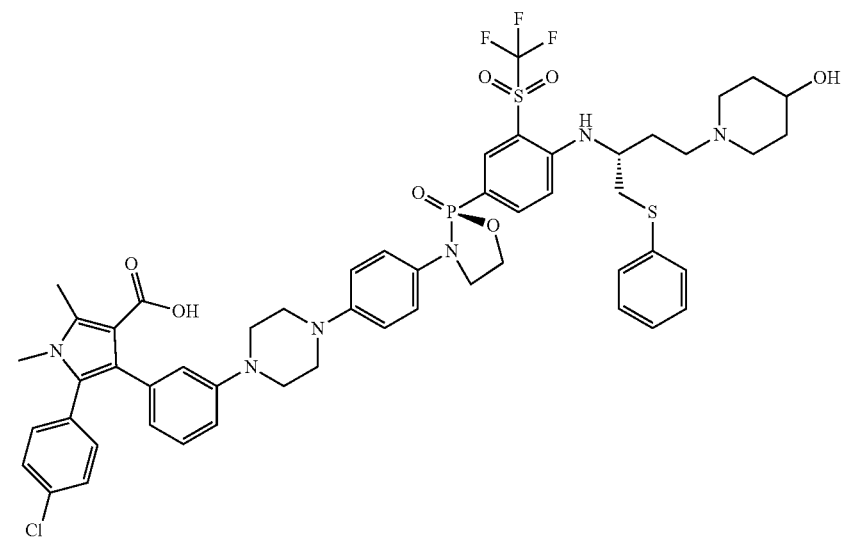

5-(4-chlorophenyl)-1-ethyl-4-(3-(4-(4-((S)-2-(4-(((R)-4-(4-hydroxypiperidin-1-yl)-1-(phenylthio)butan-2-yl)amino)-3-((trifluoromethyl)sulfonyl)phenyl)-2-oxido-1,3,2-oxazaphospholidin-3-yl)phenyl)piperazin-1-yl)phenyl)-2-dimethyl-1H-pyrrole-3-carboxylid acid

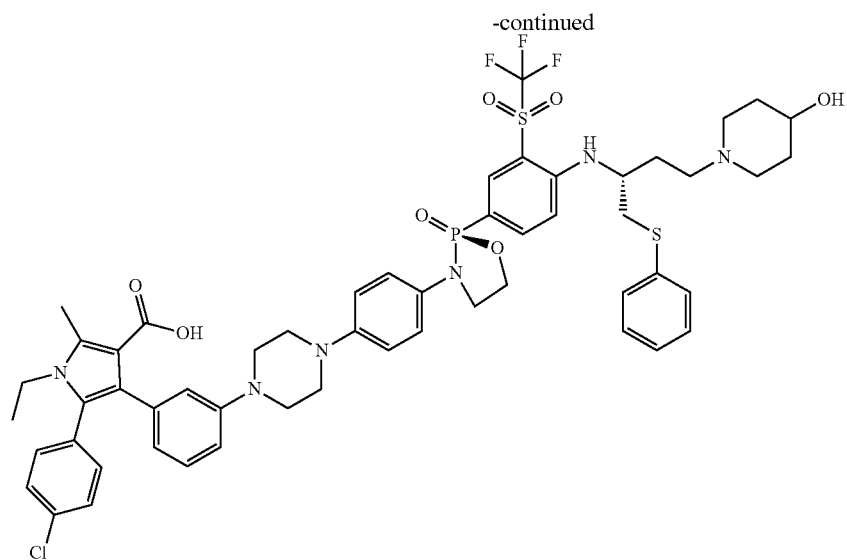

5-(4-chlorophenyl)-1-ethyl-4-(3-(4-(4-(((S)-2-(4-(((R)-4-(4-hydroxypiperidin-1-yl)-1-(phenylthio)butan-2-yl)amino)-3-((trifluoromethyl)sulfonyl)phenyl)-2-oxido-1,3,2-oxazaphospholidin-3-yl)phenyl)piperazin-1-yl)phenyl)-2-methyl-1H-pyrrole-3-carboxylid acid

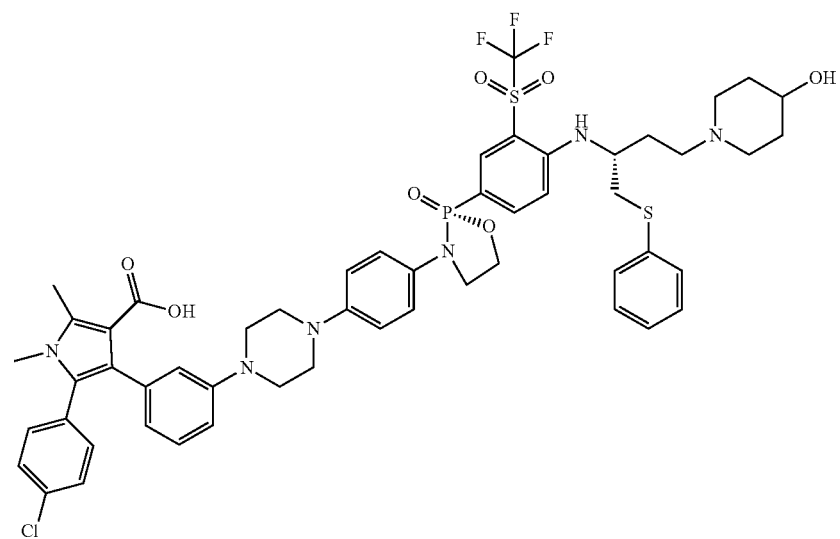

5-(4-chlorophenyl)-4-(3-(4-(4-((R)-2-(4-(((R)-4-(4-hydroxypiperidin-1-yl)-1-(phenylthio)butan-2-yl)amino)-3-((trifluoromethyl)sulfonyl)phenyl)-2-oxido-1,3,2-oxazaphospholidin-3-yl)phenyl)piperazin-1-yl)phenyl)-1,2-dimethyl-1H-pyrrole-3-carboxylic acid

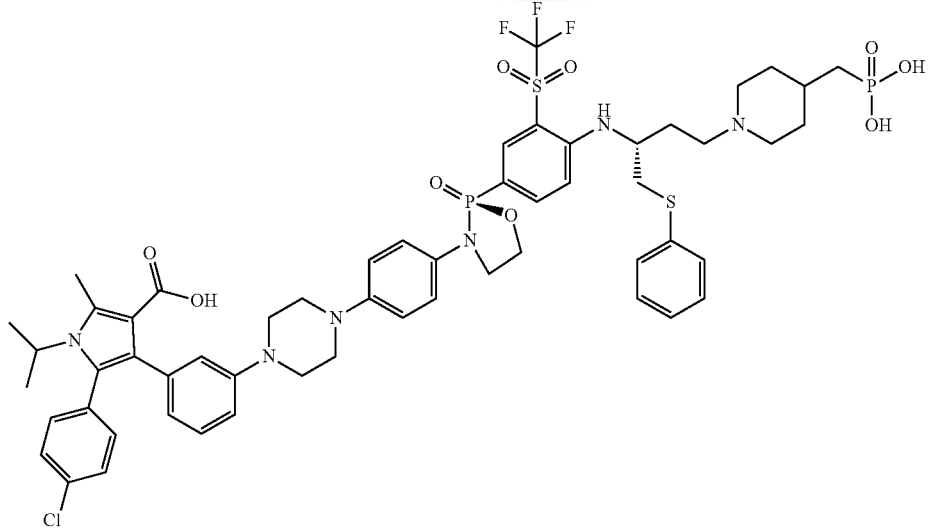

5-(4-chlorophenyl)-1-isopropyl-2-methyl-4-(3-(4-(4-((S)-2-oxido-2-(4-(((R)-1-(phenylthio)-4-(4-(phosphonomethyl)piperidin-1-yl)butan-2-yl)amino)-3-((trifluoromethyl)sulfonyl)phenyl)-1,3,2-oxazaphospholidin-3-yl)phenyl)piperazin-1-yl)phenyl)-1H-pyrrole-3-carboxylic acid

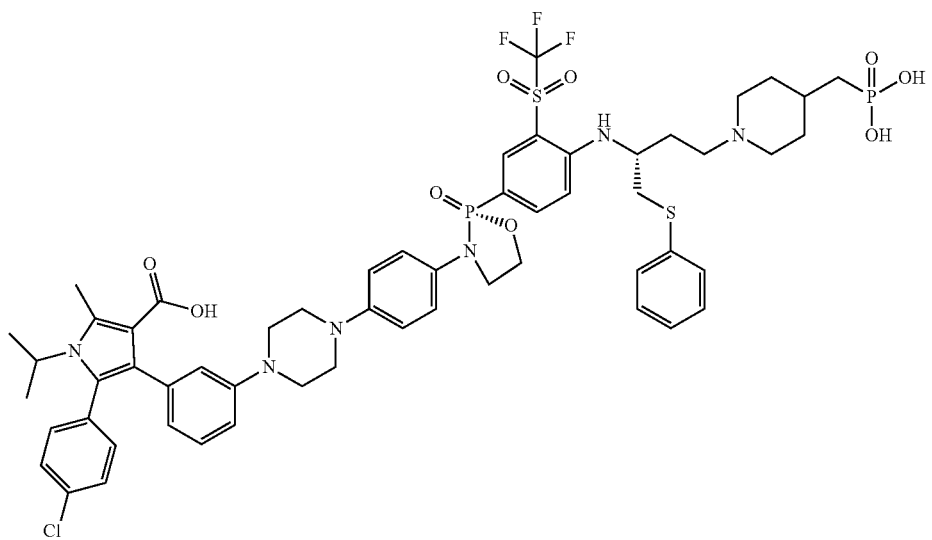

5-(4-chlorophenyl)-1-isopropyl-2-methyl-4-(3-(4-(4-((R)-2-oxido-2-(4-(((R)-1-(phenylthio)-4-(4-(phosphonomethyl)piperidin-1-yl)butan-2-yl)amino)-3-((trifluoromethyl)sulfonyl)phenyl)-1,3,2-oxazaphospholidin-3-yl)phenyl)piperazin-1-yl)phenyl)-1H-pyrrole-3-carboxylic acid -continued

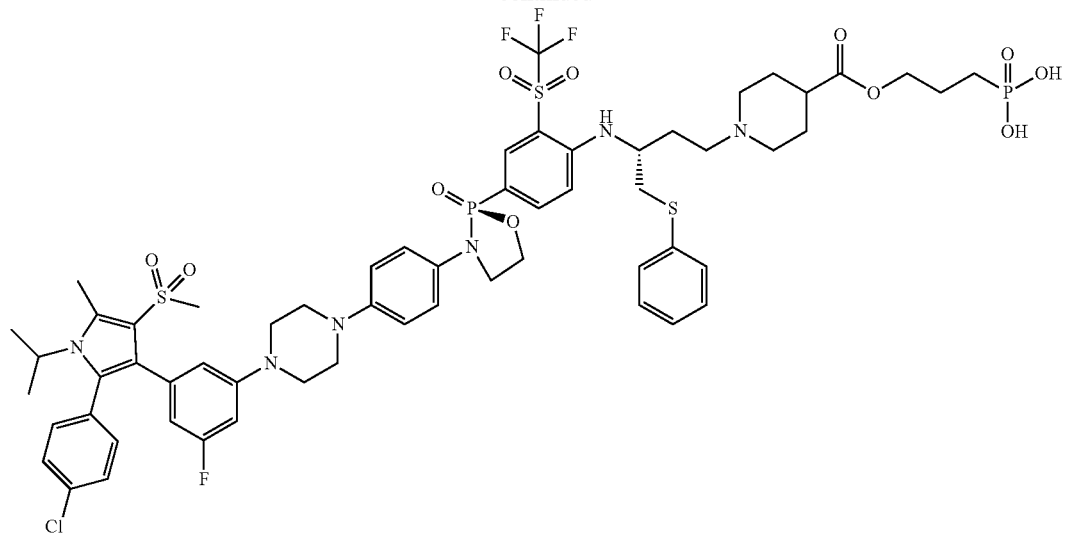

(3-((1-((R)-3-((4-((S)-3-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)-2-oxido-1,3,2-oxazaphospholidin-2-yl)-2-((trifluoromethyl)sulfonyl)phenyl)amino)-4-(phenylthio)butyl)piperidine-4-carbonyl)oxy)propyl)phosphonic acid

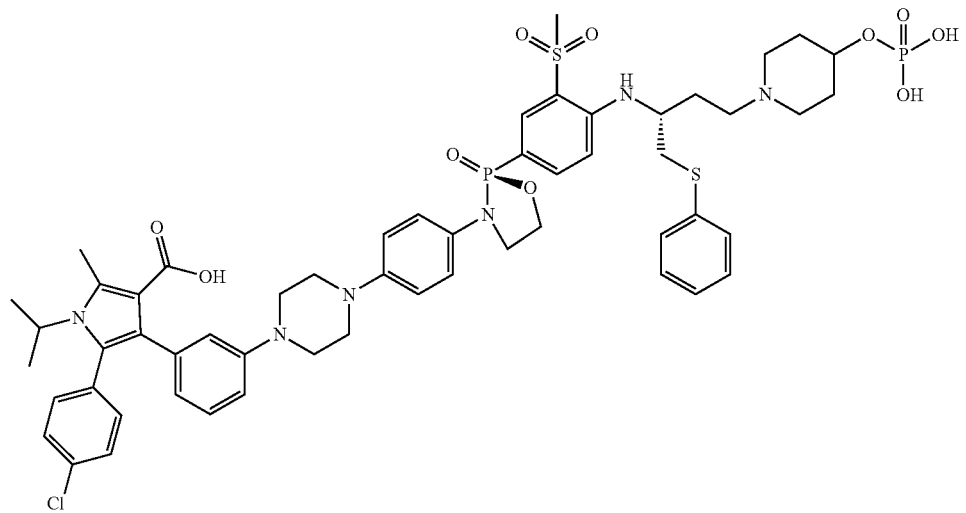

5-(4-chlorophenyl)-1-isopropyl-2-methyl-4-(3-(4-(4-((S)-2-(3-(methylsulfonyl)-4-(((R)-1-(phenylthio)-4-(4-(phosphonooxy)piperidin-1-yl)butan-2-yl)amino)phenyl)-2-oxido-1,3,2-oxazaphospholidin-3-yl)phenyl)piperazin-1-yl)phenyl)-1H-pyrrole-3-carboxylic acid

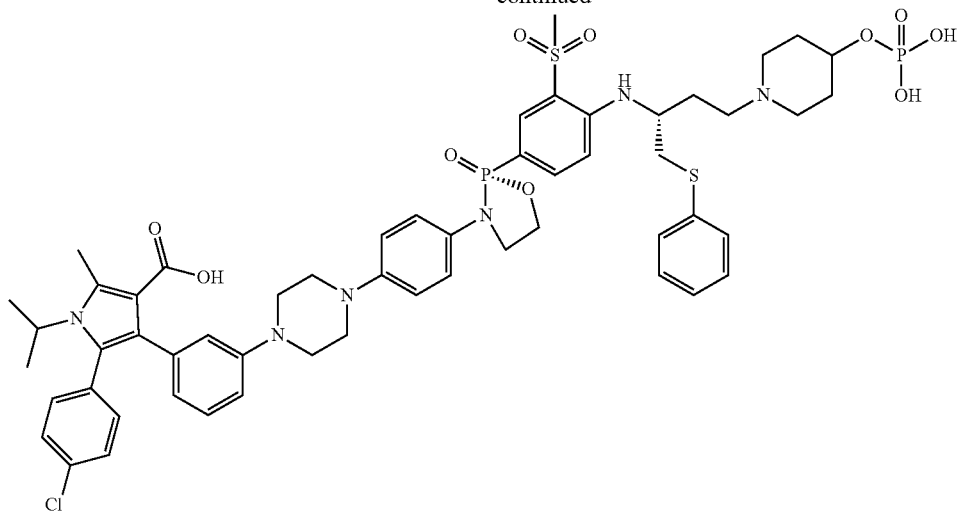

5-(4-chlorophenyl)-1-isopropyl-2-methyl-4-(3-(4-(4-((R)-2-(3-(methylsulfonyl)-4-(((R)-1-(phenylthio)-4-(4-(phosphonooxy)piperidin-1-yl)butan-2-yl)amino)phenyl)-2-oxido-1,3,2-oxazaphospholidin-3-yl)phenyl)piperazin-1-yl)phenyl)-1H-pyrrole-3-carboxylic acid

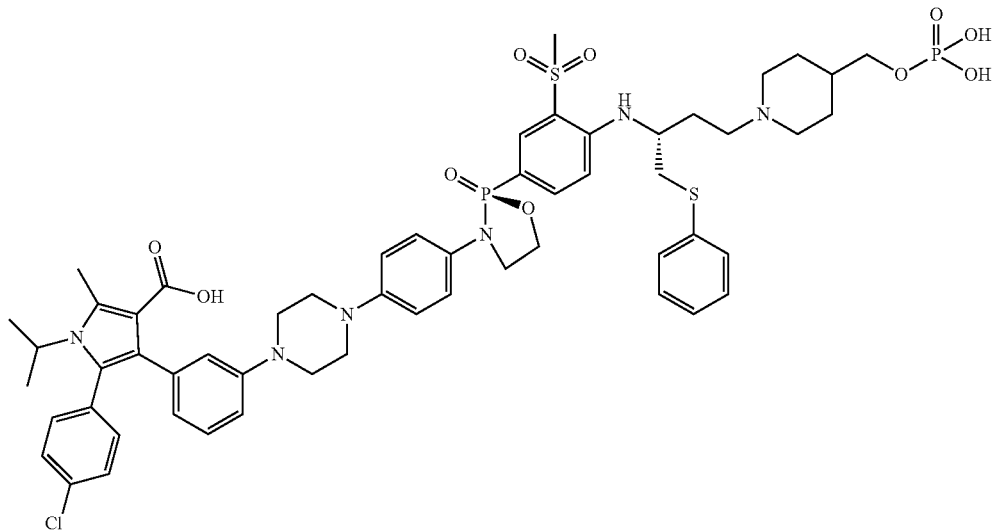

5-(4-chlorophenyl)-1-isopropyl-2-methyl-4-(3-(4-(4-((S)-2-(3-(methylsulfonyl)-4-(((R)-1-(phenylthio)-4-(4-((phosphonooxy)piperidin-1-yl)butan-2-yl)amino)phenyl)-2-oxido-1,3,2-oxazaphospholidin-3-yl)phenyl)piperazin-1-yl)phenyl)-1H-pyrrole-3-carboxylic acid

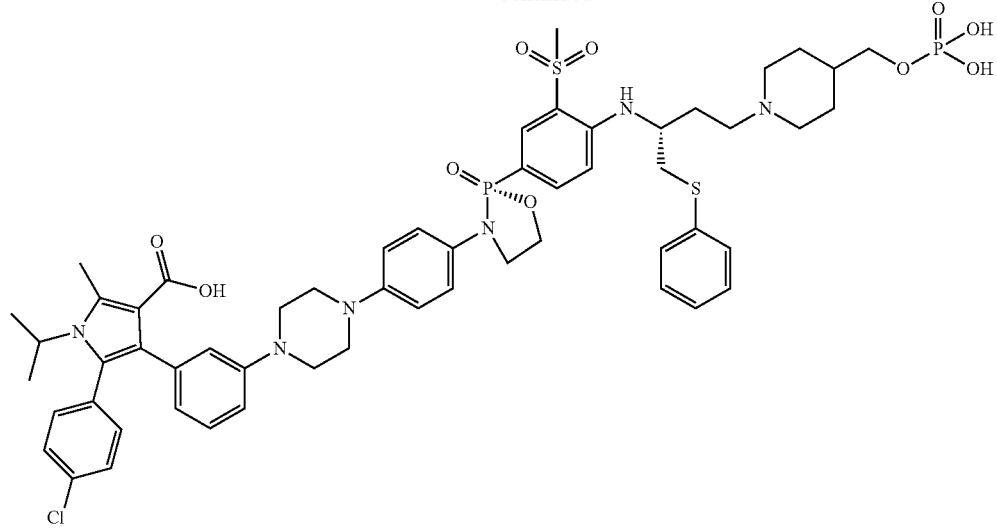

5-(4-chlorophenyl)-1-isopropyl-2-methyl-4-(3-(4-(4-(((R)-2-(3-(methylsulfonyl)-4-(((R)-1-(phenylthio)-4-(4-((phosphonooxy)piperidin-1-yl)butan-2-yl)amino)phenyl)-2-oxido-1,3,2-oxazaphospholidin-3-yl)phenyl)piperazin-1-yl)phenyl)-1H-pyrrole-3-carboxylic acid Definitions A "senescent cell" is generally thought to be derived from a cell type that typically replicates, but as a result of aging or other event that causes a change in cell state, can no longer replicate. Depending on the context, senescent cells can be identified as expressing p16, or at least one marker selected from p16, senescence-associated β-galactosidase, and lipofuscin; sometimes two or more of these markers, and other markers of the senescence-associated secretory profile (SASP) such as but not limited to interleukin 6, and inflammatory, angiogenic and extracellular matrix modifying proteins. Unless explicity stated otherwise, the senescent cells referred to in the claims do not include cancer cells.

A "senescence associated", "senescence related" or "age related" disease, disorder, or condition is a physiological condition that presents with one or more symptoms or signs that are adverse to the subject. The condition is "senescence associated" if it is "caused or mediated at least in part by senescent cells." This means that at least one component of the SASP in or around the affected tissue plays a role in the pathophysiology of the condition such that elimination of at least some of the senescent cells in the affected tissue results in substantial relief or lessening of the adverse symptoms or signs, to the patient's benefit. Senescence associated disorders that can potentially be treated or managed using the methods and products according to this disclosure include disorders referred to in this disclosure and in previous disclosures referred to in the discussion. Unless explicitly stated otherwise, the term does not include cancer.

An inhibitor of protein function or Bcl function is a compound that to a substantial degree prevents the target protein already expressed in a target cell from performing an enzymatic, binding, or regulatory function that the protein or Bcl family member normally performs in the target cell. This results in elimination of the target cell or rendering the cell more susceptible to the toxicity of another compound or event. A compound qualifies as a "Bcl inhibitor" or a compound that "inhibits Bcl activity" in this disclosure if it has an $IC_{50}$ when tested in an assay according to Example 1 below that is less than 1,000 nM (1.0 µM). Activity that is less than 100 nM or 10 nM, or between 100 nM and 1 nM is often preferred, depending on the context.

The term "Bcl" or "Bcl protein" refers to the family of Bcl proteins, exemplified by Bcl-2, Bcl-xL, and Bcl-w. A Bcl inhibitor of this disclosure will be able to inhibit at least one of Bcl-2, Bcl-xL, and Bcl-w. Typically but not necessarily, an inhibitor of one of these Bcl proteins will to some extent inhibit the other two. The compounds provided in this disclosure can be tested for activity of any Bcl family members, to identify compounds that have inhibitory activity and are potentially specific for Bcl-2, Bcl-xL, or Bcl-w. Such an inhibitor will have an $IC_{50}$ for a target Bcl from this list that is at least 10-fold better than its $IC_{50}$ for the other two Bcl family members on the list.

A compound, composition or agent is typically referred to as "senolytic" if it eliminates senescent cells, in preference replicative cells of the same tissue type, or quiescent cells lacking SASP markers. Alternatively or in addition, a compound or combination may effectively be used if it decreases the release of pathological soluble factors or mediators as part of the senescence associated secretory phenotype that play a role in the initial presentation or ongoing pathology of a condition, or inhibit its resolution. In this respect, the term "senolytic" refers to functional inhibition, such that compounds that work primarily by inhibiting rather than eliminating senescent cells (senescent cell inhibitors) can be used in a similar fashion with ensuing benefits. Model senolytic compositions and agents in this disclosure have an $EC_{50}$ when tested in an assay according to Example 2 below that is less than 1 µM. Activity that is less than 0.1 µM, or between 1 µM and 0.1 µM may be preferred. The selectivity index (SI) ($EC_{50}$ of senescent cells compared with non-senescent cells of the same tissue type) may be better than 1, 2, 5, or 10, depending on the context.

Selective removal or "elimination" of senescent cells from a mixed cell population or tissue doesn't require that all cells bearing a senescence phenotype be removed: only that the proportion of senescent cells initially in the tissue that remain after treatment is substantially higher than the proportion of non-senescent cells initially in the tissue that remain after the treatment.

Successful "treatment" of a condition according to this disclosure may have any effect that is beneficial to the subject being treated. This includes decreasing severity, duration, or progression of a condition, or of any adverse signs or symptoms resulting therefrom. Treatment may also be unsuccessful, resulting in no improvement in typical signs and symptoms of the condition. A concurrent objective of therapy is to minimize adverse effects on the target tissue or elsewhere in the treated subject. In some circumstances, senolytic agents can also be used to prevent or inhibit presentation of a condition for which a subject is susceptible, for example, because of an inherited susceptibility of because of medical history.

A "therapeutically effective amount" is an amount of a compound of the present disclosure that (i) treats the particular disease, condition, or disorder, (ii) attenuates, ameliorates, or eliminates one or more symptoms of the particular disease, condition, or disorder, (iii) prevents or delays the onset of one or more symptoms of the particular disease, condition, or disorder described herein, (iv) prevents or delays progression of the particular disease, condition or disorder, or (v) at least partially reverses damage caused by the condition prior to treatment.

A "phosphorylated" form of a compound is a compound which bears one or more phosphate groups covalently bound to the core structure through an oxygen atom, which was typically but not necessarily present on the molecule before phosphorylation. For example, one or more —OH or —COOH groups may have been substituted in place of the hydrogen with a phosphate group which is either —OPO$_3$H$_2$ or —C$_n$PO$_3$H$_2$ (where n is 1 to 4). In some phosphorylated forms, the phosphate group may be removed in vivo (for example, by enzymolysis), in which case the phosphorylated form may be a pro-drug of the non-phosphorylated form. A non-phosphorylated form has no such phosphate group. A dephosphorylated form is a derivative of a phosphorylated molecule after at least one phosphate group has been removed.

"Small molecule" Bcl inhibitors according to this disclosure have molecular weights less than 20,000 daltons, and are often less than 10,000, 5,000, or 2,000 daltons. Small molecule inhibitors are not antibody molecules or oligonucleotides, and typically have no more than five hydrogen bond donors (the total number of nitrogen-hydrogen and oxygen-hydrogen bonds), and no more than 10 hydrogen bond acceptors (all nitrogen or oxygen atoms).

"Prodrug" refers to a derivative of an active agent that requires a transformation within the body to release the active agent. The transformation can be an enzymatic transformation. Sometimes, the transformation is a cyclization transformation, or a combination of an enzymatic transformation and a cyclization transformation. Prodrugs are frequently, although not necessarily, pharmacologically inactive until converted to the active agent.

"Promoiety" refers to a form of protecting group that when used to mask a functional group within an active agent converts the active agent into a prodrug. Typically, the promoiety will be attached to the drug via bond(s) that are cleaved by enzymatic or non-enzymatic means in vivo. Exemplary promoiety groups include acyl groups capable of forming an ester or thioester group with a hydroxyl or thiol functional group of a compound, and substituted alkyl groups capable of forming an ether or thioether group with a hydroxyl or thiol functional group of a compound, which groups can be cleaved in vivo as described above.

Unless otherwise stated or required, each of the compound structures referred to in the disclosure include conjugate acids and bases having the same structure, crystalline and amorphous forms of those compounds, pharmaceutically acceptable salts, and prodrugs. This includes, for example, tautomers, polymorphs, solvates, hydrates, unsolvated polymorphs (including anhydrates).

Unless otherwise stated or implied, the term "substituted" when used to modify a specified group or radical means that one or more hydrogen atoms of the specified group or radical are each independently replaced with the same or different substituent groups which is not hydrogen. Unless indicated otherwise, the nomenclature of substituents is arrived at by naming the terminal portion of the functionality followed by the adjacent functionality toward the point of attachment. For example, the substituent "arylalkyloxycarbonyl" refers to the group (aryl)-(alkyl)-O—C(O)—.

A "linker" is a moiety that covalently connects two or more chemical structures, and has a backbone of 100 atoms or less in length between the two structures. The linker may be cleavable or non-cleavable. The linker typically has a backbone of between 1 and 20 or between 1 and 100 atoms in length, in linear or branched form. The bonds between backbone atoms may be saturated or unsaturated. The linker backbone may include a cyclic group, for example, an optionally substituted aryl, heteroaryl, heterocycle or cycloalkyl group.

For any Bcl inhibitor compound of this disclosure having one or more chiral centers, if an absolute stereochemistry is not expressly indicated, then each chiral center may independently be of R-configuration or S-configuration or a racemic mixture thereof. The compound may be any stereoisomer of the structure shown, either as an alternative form or as a mixture, unless a particular stereoisomer is explicity referred to.

Except where otherwise stated or required, other terms used in the specification have their ordinary meaning.

INCORPORATION BY REFERENCE

For all purposes in the United States and in other jurisdictions where effective, each and every publication and patent document cited in this disclosure is hereby incorporated herein by reference in its entirety for all purposes to the same extent as if each such publication or document was specifically and individually indicated to be incorporated herein by reference.

US 2016/0339019 A1 (Laberge et al.) and US 20170266211 A1 (David et al.) are hereby incorporated herein for all purposes, including but not limited to the identification, formulation, and use of compounds capable of eliminating or reducing the activity of senescent cells and treating particular senescence-related conditions, including but not limited to those referred to in this disclosure. Pre-grant patent publications US 2018/0000816 A1 (David et al.) and EP 3441069 A1 (Hopkins et al.) are hereby incorporated herein for all purposes, including but not limited to the identification, formulation, and use of compounds capable of eliminating or reducing the activity of senescent cells and treating various ophthalmic conditions.

EXAMPLES

Example 1: Measuring Bcl Inhibition

The ability of candidate compounds to inhibit Bcl-2 and Bcl-xL activity can be measured on the molecular level by direct binding. This assay uses a homogenous assay technology based on oxygen channeling that is marketed by PerkinElmer Inc., Waltham, Mass.: see Eglin et al., Current Chemical Genomics, 2008, 1, 2-10. The test compound is combined with the target Bcl protein and a peptide representing the corresponding cognate ligand, labeled with biotin. The mixture is then combined with streptavidin bearing luminescent donor beads and luminescent acceptor beads, which proportionally reduces luminescence if the compound has inhibited the peptide from binding to the Bcl protein.

Bcl-2, Bcl-xL and Bcl-w are available from Sigma-Aldrich Co., St. Louis, Mo. Biotinylated BIM peptide (ligand for Bcl-2) and BAD peptide (ligand for Bcl-xL) are described in US 2016/0038503 A1. AlphaScreen® Streptavidin donor beads and Anti-6xHis AlphaLISA® acceptor beads are available from PerkinElmer.

To conduct the assay, a 1:4 dilution series of the compound is prepared in DMSO, and then diluted 1:100 in assay buffer. In a 96-well PCR plate, the following are combined in order: 10 µL peptide (120 nM BIM or 60 nM BIM), 10 µL test compound, and 10 µL Bcl protein (0.8 nM Bcl-2/W or 0.4 nM Bcl-XL). The assay plate is incubated in the dark at room temperature for 24 h. The next day, donor beads and acceptor beads are combined, and 5 µL is added to each well. After incubating in the dark for 30 minute, luminescence is measured using a plate reader, and the affinity or degree of inhibition by each test compound is determined.

Example 2: Measuring Senolytic Activity in Fibroblasts

Human fibroblast IMR90 cells can be obtained from the American Type Culture Collection (ATCC®) with the designation CCL-186. The cells are maintained at <75% confluency in DMEM containing FBS and Pen/Strep in an atmosphere of 3% O2, 10% $CO_2$, and ~95% humidity. The cells are divided into groups: irradiated cells (cultured for 14 days after irradiation prior to use) and quiescent cells (cultured at high density for four day prior to use).

On day 0, the irradiated cells are prepared as follows. IMR90 cells are washed, placed in T175 flasks at a density of 50,000 cells per mL, and irradiated at 10-15 Gy. Following irradiation, the cells are plated at 100 µL in 96-well plates. On days 1, 3, 6, 10, and 13, the medium in each well is aspirated and replaced with fresh medium.

On day 10, the quiescent healthy cells are prepared as follows. IMR90 cells are washed, combined with 3 mL of TrypLE trypsin-containing reagent (Thermofisher Scientific, Waltham, Mass.) and cultured for 5 min until the cells have rounded up and begin to detach from the plate. Cells are dispersed, counted, and prepared in medium at a concentration of 50,000 cells per mL. 100 µL of the cells is plated in each well of a 96-well plate. Medium is changed on day 13. On day 14, test inhibitor compounds are combined with the cells as follows. A DMSO dilution series of each test compound is prepared at 200 times the final desired concentration in a 96-well PCR plate. Immediately before use, the DMSO stocks are diluted 1:200 into prewarmed complete medium. Medium is aspirated from the cells in each well, and 100 µL/well of the compound containing medium is added.

Candidate senolytic agents for testing are cultured with the cells for 6 days, replacing the culture medium with fresh medium and the same compound concentration on day 17. Bcl 2 inhibitors are cultured with the cells for 3 days. The assay system uses the properties of a thermostable luciferase to enable reaction conditions that generate a stable luminescent signal while simultaneously inhibiting endogenous ATPase released during cell lysis. At the end of the culture period, 100 µL of CellTiter-GloB reagent (Promega Corp., Madison, Wis.) is added to each of the wells. The cell plates are placed for 30 seconds on an orbital shaker, and luminescence is measured.

Example 3: Measuring Senolytic Activity in HUVEC Cells and Other Senescent Cells Human umbilical vein (HUVEC) cells from a single lot were expanded in Vascular Cell Basal Media supplemented with the Endothelial Cell Growth Kit™-VEGF from ATCC to approximately eight population doublings then cryopreserved. Nine days prior to the start of the assay, cells for the senescent population were thawed and seeded at approximately 27,000/$cm_2$. All cells were cultured in humidified incubators with 5% $CO_2$ and 3% O2 and media was changed every 48 hr. Two days after seeding, the cells were irradiated, delivering 12 Gy radiation from an X-ray source. Three days prior to the start of the assay, cells for the non-senescent populations are thawed and seeded as for the senescent population. One day prior to the assay, all cells were trypsinized and seeded into 384-well plates, 5,000/well senescent cells and 10,000/well non-senescent in separate plates in a final volume of 55 µL/well. In each plate, the central 308 wells contained cells and the outer perimeter of wells was filled with 70 µL/well deionized water.

On the day of the assay, compounds were diluted from 10 mM stocks into media to provide the highest concentration working stock, aliquots of which were then further diluted in media to provide the remaining two working stocks. To initiate the assay, 5 µL of the working stock was added to the cell plates. The final test concentrations were 20, 2, and 0.2 µM. In each plate, 100 test compounds were assayed in triplicate at a single concentration along with a three wells of a positive control and five no treatment (DMSO) controls. Following compound addition, the plates are returned to the incubators for three days.

Cell survival was assessed indirectly by measuring total ATP concentration using CellTiter-Glo™ reagent (Promega). The resultant luminescence was quantitated with an EnSpire™ plate reader (Perkin Elmer). The relative cell viability for each concentration of a compound was calculated as a percentage relative to the no-treatment controls for the same plate.

For follow-up dose responses of potential lead compounds, 384-well plates of senescent and non-senescent cells were prepared as described above. Compounds were prepared as 10-point 1:3 dilution series in DMSO, then diluted to 12× in media. Five microliters of this working stock was then added to the cell plates. After three days of incubation, cell survival relative to DMSO control was calculated as described above. All measurements were performed in quadruplicate.

Other cell lines and primary cell cultures may be used as an alternative to IMR90 fibroblasts or HUVEC cells that align with the intended target tissue in vivo. An example is the use of cultured human retinal microvascular endothelial cells (HRMEC) for screening compounds intended for treatment of eye disease. The cells are cultured according to known protocols for the chosen cell line, and irradiated in a similar fashion to render them senescent.

Example 4: Efficacy of Senolytic Agents in an Osteoarthritis Model

This example illustrates the testing of an MDM2 inhibitor in a mouse model for treatment of osteoarthritis. It can be adapted mutatis mutandis to test and develop Bcl inhibitors for use in clinical therapy.

The model was implemented as follows. C57BL/6J mice underwent surgery to cut the anterior cruciate ligament of one rear limb to induce osteoarthritis in the joint of that limb. During week 3 and week 4 post-surgery, the mice were treated with 5.8 µg of Nutlin-3A (n=7) per operated knee by intra-articular injection, q.o.d. for 2 weeks. At the end of 4 weeks post-surgery, joints of the mice were monitored for presence of senescent cells, assessed for function, monitored for markers of inflammation, and underwent histological assessment.

Two control groups of mice were included in the studies performed: one group comprising C57BL/6J or 3MR mice that had undergone a sham surgery (n=3) (i.e., surgical procedures followed except for cutting the ACL) and intra-articular injections of vehicle parallel to the GCV (ganciclovir) treated group; and one group comprising C57BL/6J or 3MR mice that had undergone an ACL surgery and received intra-articular injections of vehicle (n=5) parallel to the GCV-treated group. RNA from the operated joints of mice from the Nutlin-3A treated mice was analyzed for expression of SASP factors (mmp3, IL-6) and senescence markers (p16). qRT-PCR was performed to detect mRNA levels.

FIGS. 5A, 5B, and 5C show expression of p16, IL-6, and MMP13 in the tissue, respectively. The OA inducing surgery was associated with increased expression of these markers. Treatment with Nutlin-3A reduced the expression back to below the level of the controls. Treatment with Nutlin-3A cleared senescent cells from the joint.

Function of the limbs was assessed 4 weeks post-surgery by a weight bearing test to determine which leg the mice favored. The mice were allowed to acclimate to the chamber on at least three occasions prior to taking measurements. Mice were maneuvered inside the chamber to stand with one hind paw on each scale. The weight that was placed on each hind limb was measured over a three second period. At least three separate measurements were made for each animal at each time point. The results were expressed as the percentage of the weight placed on the operated limb versus the contralateral unoperated limb.

FIG. 6A shows the results of the functional study. Untreated mice that underwent osteoarthritis inducing surgery favored the unoperated hind limb over the operated hind limb (Δ). However, clearing senescent cells with Nutlin-3A abrogated this effect in mice that have undergone surgery (∇).

FIGS. 6B, 6C, and 6D show histopathology of joint tissue from these experiments. Osteoarthritis induced by ACL surgery caused the proteoglycan layer was destroyed. Clearing of senescent cells using Nutlin-3A completely abrogated this effect.

Example 5: Efficacy of Senolytic Agents in Models for Diabetic Retinopathy

This example illustrates the testing of a Bcl inhibitor in a mouse model for treatment of a back-of-the eye disease, specifically diabetic retinopathy. It can be adapted mutatis mutandis to test senolytic agents for use in clinical therapy.

The efficacy of model compound UBX1967 (a Bcl-xL inhibitor) was studied in the mouse oxygen-induced retinopathy (OIR) model (Scott and Fruttiger, Eye (2010) 24, 416-421, Oubaha et al, 2016). C57Bl/6 mouse pups and their CD1 foster mothers were exposed to a high oxygen environment (75% $O_2$) from postnatal day 7 (P7) to P12. At P12, animals were injected intravitreally with 1 µl test compound (200, 20, or 2 uM) formulated in 1% DMSO, 10% Tween-80, 20% PEG-400, and returned to room air until P17. Eyes were enucleated at P17 and retinas dissected for either vascular staining or qRT-PCR. To determine avascular or neovascular area, retinas were flat-mounted, and stained with isolectin B4 (IB4) diluted 1:100 in 1 mM $CaCl_2$. For quantitative measurement of senescence markers (e.g., Cdkn2a, Cdkn1a, 116, Vegfa), qPCR was performed. RNA was isolated and cDNA was generated by reverse-transcription, which was used for qRT-PCR of the selected transcripts.

FIGS. 7A and 7B show that intravitreal ITT) administration UBX1967 resulted in statistically significant improvement in the degree of neovascularization and vaso-obliteration at all dose levels. The efficacy of UBX1967 was also studied in the streptozotocin (STZ) model. C57BL/6J mice of 6- to 7-week were weighted and their baseline glycemia was measured (Accu-Chek™, Roche). Mice were injected intraperitoneally with STZ (Sigma-Alderich, St. Louis, Mo.) for 5 consecutive days at 55 mg/Kg. Age-matched controls were injected with buffer only. Glycemia was measured again a week after the last STZ injection and mice were considered diabetic if their non-fasted glycemia was higher than 17 mM (300 mg/L). STZ treated diabetic C57BL/6J mice were intravitreally injected with 1 µl of UBX1967 (2 µM or 20 µM, formulated as a suspension in 0.015% polysorbate-80, 0.2% Sodium Phosphate, 0.75% Sodium Chloride, pH 7.2) at 8 and 9 weeks after STZ administration. Retinal Evans blue permeation assay was performed at 10 weeks after STZ treatment.

FIGS. 7C and 7D show results for this protocol. Retinal and choroidal vascular leakage after intravitreal (IVT) administration UBX1967 improved in vascular permeability at both dose levels.

Other models of retinal ganglion cell damage can be used in testing that are relevant to glaucoma, where increased intraocular pressure (IOP) is thought to cause retinal ganglion cell loss and optic nerve damage. In preclinical species, increased anterior chamber pressure can result in retinal neuron loss as reported in several established models, including the magnetic microbead occlusion (Ito et al., Vis Exp. 2016 (109): 53731) and other glaucoma models (Almasieh and Levin, Annu Rev Vis Sci. 2017). Additionally, ischemia-reperfusion has been demonstrated to cause retinal injury which may result in cellular senescence. Presence of retinal senescence in such models can be used to monitor the impact of senolysis after intravitreal injection of test compounds.

Example 6: Efficacy of Senolytic Agents in a Pulmonary Disease Model

This example illustrates the testing of inhibitors in a mouse model for treatment of lung disease: specifically, a model for idiopathic pulmonary fibrosis (IPF). It can be adapted mutatis mutandis to test and develop Bcl inhibitors for use in clinical therapy.

As a model for chronic obstructive pulmonary disease (COPD), mice were exposed to cigarette smoke.

The effect of a senolytic agent on the mice exposed to smoke is assessed by senescent cell clearance, lung function, and histopathology.

The mice used in this study include the 3MR strain, described in US 2017/0027139 A1 and in Demaria et al., Dev Cell. 2014 Dec. 22; 31(6): 722-733. The 3MR mouse has a transgene encoding thymidine kinase that converts the prodrug ganciclovir (GCV) to a compound that is lethal to cells. The enzyme in the transgene is placed under control of the p16 promoter, which causes it to be specifically expressed in senescent cells. Treatment of the mice with GCV eliminates senescent cells.

Other mice used in this study include the INK-ATTAC strain, described in US 2015/0296755 A1 and in Baker et al., Nature 2011 Nov. 2; 479(7372):232-236. The INK-ATTAC mouse has a transgene encoding switchable caspase 8 under control of the p16 promoter. The caspase 8 can be activated by treating the mice with the switch compound AP20187, whereupon the caspase 8 directly induces apoptosis in senescent cells, eliminating them from the mouse.

To conduct the experiment, six-week-old 3MR (n=35) or INK-ATTAC (n=35) mice were chronically exposed to cigarette smoke generated from a Teague TE-10 system, an automatically-controlled cigarette smoking machine that produces a combination of side-stream and mainstream cigarette smoke in a chamber, which is transported to a collecting and mixing chamber where varying amounts of air is mixed with the smoke mixture. The COPD protocol was adapted from the COPD core facility at Johns Hopkins University (Rangasamy et al., 2004, J. Clin. Invest. 114: 1248-1259; Yao et al., 2012, J. Clin. Invest. 122:2032-2045).

Mice received a total of 6 hours of cigarette smoke exposure per day, 5 days a week for 6 months. Each lighted cigarette (3R4F research cigarettes containing 10.9 mg of total particulate matter (TPM), 9.4 mg of tar, and 0.726 mg of nicotine, and 11.9 mg carbon monoxide per cigarette [University of Kentucky, Lexington, Ky.]) was puffed for 2 seconds and once every minute for a total of 8 puffs, with the flow rate of 1.05 L/min, to provide a standard puff of 35 cm3. The smoke machine was adjusted to produce a mixture of side stream smoke (89%) and mainstream smoke (11%) by smoldering 2 cigarettes at one time. The smoke chamber atmosphere was monitored for total suspended particulates (80-120 mg/m3) and carbon monoxide (350 ppm).

Beginning at day 7, (10) INK-ATTAC and (10) 3MR mice were treated with AP20187 (3× per week) or ganciclovir (5 consecutive days of treatment followed by 16 days off drug, repeated until the end of the experiment), respectively. An equal number of mice received the corresponding vehicle. The remaining 30 mice (15 INK-ATTAC and 15 3MR) were evenly split with 5 of each genetically modified strain placed into three different treatment groups. One group (n=10) received Nutlin-3A (25 mg/kg dissolved in 10% DMSO/3% Tween-20™ in PBS, treated 14 days consecutively followed by 14 days off drug, repeated until the end of the experiment). One group (n=10) received ABT-263 (Navitoclax) (100 mg/kg dissolved in 15% DMSO/5% Tween-20, treated 7 days consecutively followed by 14 days off drug, repeated until the end of the experiment), and the last group (n=10) received only the vehicle used for ABT-263 (15% DMSO/ 5% Tween-20), following the same treatment regimen as ABT-263. An additional 70 animals that did not receive exposure to cigarette smoke were used as controls for the experiment.

After two months of cigarette smoke (CS) exposure, lung function was assessed by monitoring oxygen saturation using the MouseSTAT PhysioSuite™ pulse oximeter (Kent Scientific). Animals were anesthetized with isoflurane (1.5%) and the toe clip was applied. Mice were monitored for 30 seconds and the average peripheral capillary oxygen saturation (SpO2) measurement over this duration was calculated.

FIG. 8 shows the results. Clearance of senescent cells via AP2018, ganciclovir, ABT-263 (Navitoclax), or Nutlin-3A resulted in statistically significant increases in $SpO_2$ levels in mice after two months of cigarette smoke exposure, compared with untreated controls.

Example 7: Efficacy of Senolytic Agents in Atherosclerosis when Administered Systemically This example illustrates the testing of an MDM2 inhibitor in a mouse model for treatment of atherosclerosis. The test compounds are administered systemically rather than locally. The model is done in an LDLR−/− strain of mice, which are deficient in the receptor for low-density lipoprotein. The experiments described here can be adapted mutatis mutandis to test and develop other types of inhibitors for use in clinical therapy.

Two groups of LDLR−/− mice (10 weeks) are fed a high fat diet (HFD) (Harlan Teklad TD.88137) having 42% calories from fat, beginning at Week 0 and throughout the study. Two groups of LDLR−/− mice (10 weeks) are fed normal chow (−HFD). From weeks 0-2, one group of HFD mice and −HFD mice are treated with Nutlin-3A (25 mg/kg, intraperitoneally). One treatment cycle is 14 days treatment, 14 days off. Vehicle is administered to one group of HFD mice and one group of −HFD mice. At week 4 (timepoint 1), one group of mice are sacrificed and to assess presence of senescent cells in the plaques. For the some of the remaining mice, Nutlin-3A and vehicle administration is repeated from weeks 4-6. At week 8 (timepoint 2), the mice are sacrificed and to assess presence of senescent cells in the plaques. The remaining mice are treated with Nutlin-3A or vehicle from weeks 8-10. At week 12 (timepoint 3), the mice are sacrificed and to assess the level of plaque and the number of senescent cells in the plaques.

Plasma lipid levels were measured in LDLR−/− mice fed a HFD and treated with Nutlin-3A or vehicle at timepoint 1 as compared with mice fed a −HFD (n=3 per group). Plasma was collected mid-afternoon and analyzed for circulating lipids and lipoproteins.

At the end of timepoint 1, LDLR−/− mice fed a HFD and treated with Nutlin-3A or vehicle were sacrificed (n=3, all groups), and the aortic arches were dissected for RT-PCR analysis of SASP factors and senescent cell markers. Values were normalized to GAPDH and expressed as fold-change versus age-matched, vehicle-treated LDLR−/− mice on a normal diet. The data show that clearance of senescent cells with Nutlin-3A in LDLR−/− mice fed a HFD reduced expression of several SASP factors and senescent cell markers, MMP3, MMP13, $PAI_1$, p21, IGFBP2, IL-1A, and IL-1B after one treatment cycle.

At the end of timepoint 2, LDLR−/− mice fed a HFD and treated with Nutlin-3A or vehicle (n=3 for all groups) were sacrificed, and aortic arches were dissected for RT-PCR analysis of SASP factors and senescent cell markers. Values were normalized to GAPDH and expressed as fold-change versus age-matched, vehicle-treated LDLR−/− mice on a normal diet. The data show expression of some SASP factors and senescent cell markers in the aortic arch within HFD mice. Clearance of senescent cells with multiple treatment cycles of Nutlin-3A in LDLR−/− mice fed a HFD reduced expression of most markers.

At the end of timepoint 3, LDLR−/− mice fed a HFD and treated with Nutlin-3A or vehicle (n=3 for all groups) were sacrificed, and aortas were dissected and stained with Sudan IV to detect the presence of lipid. Body composition of the mice was analyzed by MRI, and circulating blood cells were counted by Hemavet™.

FIG. 9 shows the results. Treatment with Nutlin-3A reduced the surface area covered by plaques in the descending aorta by about 45%. The platelet and lymphocyte counts were equivalent between the Nutlin-3A and vehicle treated mice. Treatment with Nutlin-3A also decreased mass and body fat composition in mice fed the high fat diet.

Example 8: Measuring Cytotoxicity for Cancer Cells In Vitro and In Vivo

The cellular activity of compounds can be evaluated in the interleukin-3 (IL-3)-dependent prolymphocytic FL5.12 murine cell line. Withdrawal of IL-3 induces FL5.12 apoptosis, by up-regulation of the proapoptotic factors Bim and Puma. Overexpression of Bcl-2 (FL5.12-Bcl-2) or Bcl-xL (FL5.12-Bcl-xL) protects against the effects of IL-3 withdrawal by sequestration of Bim and Puma. Compounds reverse the protection afforded by overexpression of Bcl-2 or Bcl-xL. Compounds are ineffective in eliciting cell death in the presence of IL-3 where FL5.12 cells are not subject to proapoptotic stimuli. The ability of compounds to kill FL5.12-Bcl-2 or FL5.12-Bcl-xL cells under IL-3 withdrawal can be attenuated in the presence of the caspase inhibitor ZVAD, indicating that cell killing is caspase dependent.

Co-immunoprecipitation studies can be done to determine if BH3 mimetic induced cytotoxicity can be attributed to the disruption of intracellular Bcl-2 family protein-protein interactions. Compounds induce a dose-dependent decrease in Bim:Bcl-xL interactions in FL5.12-Bcl-xL cells. Similar results are also observed for the disruption of Bim:Bcl-2 complexes in FL5.12-Bcl-2 cells indicating that compounds restore IL-3-dependent cell death by attenuating the ability of Bcl-xL and Bcl-2 to sequester proapoptotic factors such as Bim.

Testing of the ability of compounds listed in this disclosure to specifically kill cancer cells can be tested in similar assays using other established cell lines. These include HeLa cells, OVCAR-3, LNCaP, and any of the Authenticated Cancer Cell Lines available from Millipore Sigma, Burlington Mass., U.S.A. Compounds specifically kill cancer cells if they are lethal to the cells at a concentration that is at least 5-fold lower, and preferably 25- or 100-fold lower than a non-cancerous cell of the same tissue type. The control cell has morphologic features and cell surface markers similar to the cancer cell line being tested, but without signs of cancer.

In vivo, compounds are evaluated in flank xenograft models established from sensitive SCLC (H889) and hematologic (RS4;11) cell lines, or using other tumor-forming cancer cell lines, according to what type of cancer is of particular interest to the user. When dosed orally or intravenously, compounds induce rapid and complete tumor responses (CR) that are durable for several weeks after the end of treatment in all animals bearing H889 (SCLC) or RS4;11 (ALL) tumors. Similar treatment of mice bearing H146 SCLC tumors can induce rapid regressions in the animals.

Example 9: Synthesis of Phospholidine Compounds

Figures 1A, 1B, 1C:
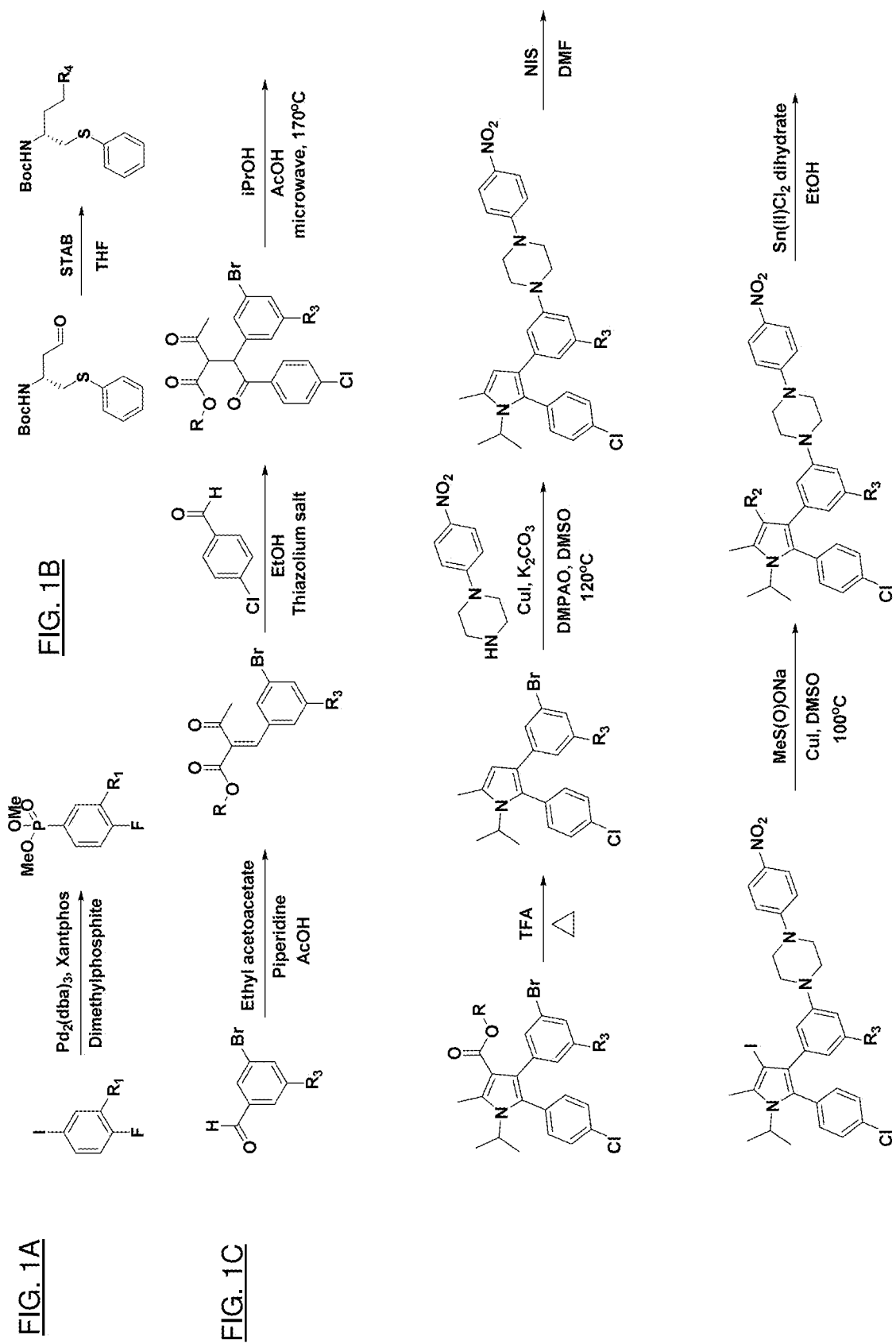
FIGS. 1A to 1C depict a synthesis scheme that is generally useful for preparing the phospholidine compounds.
Figure 1C:
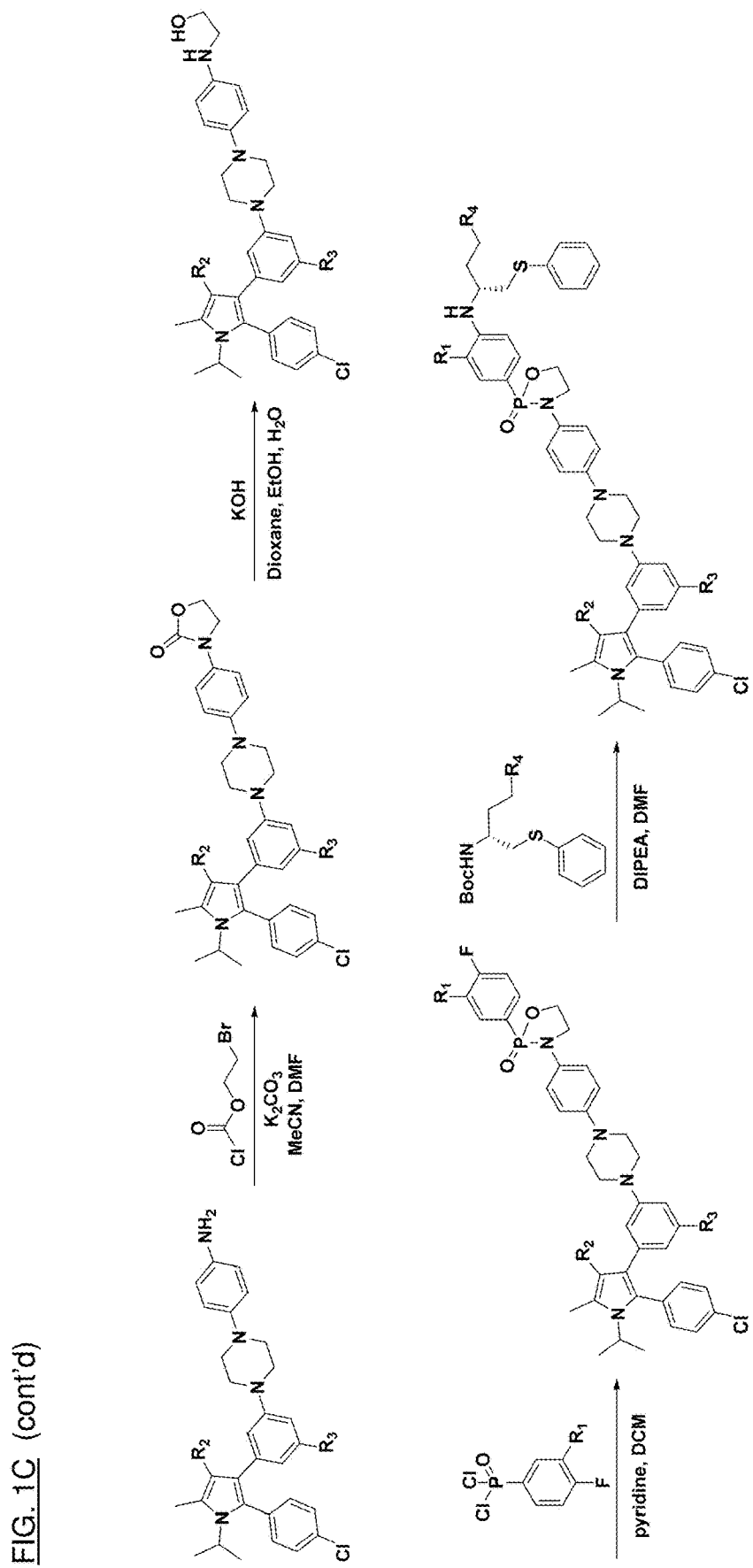
Figures 2A, 2B, 2C:
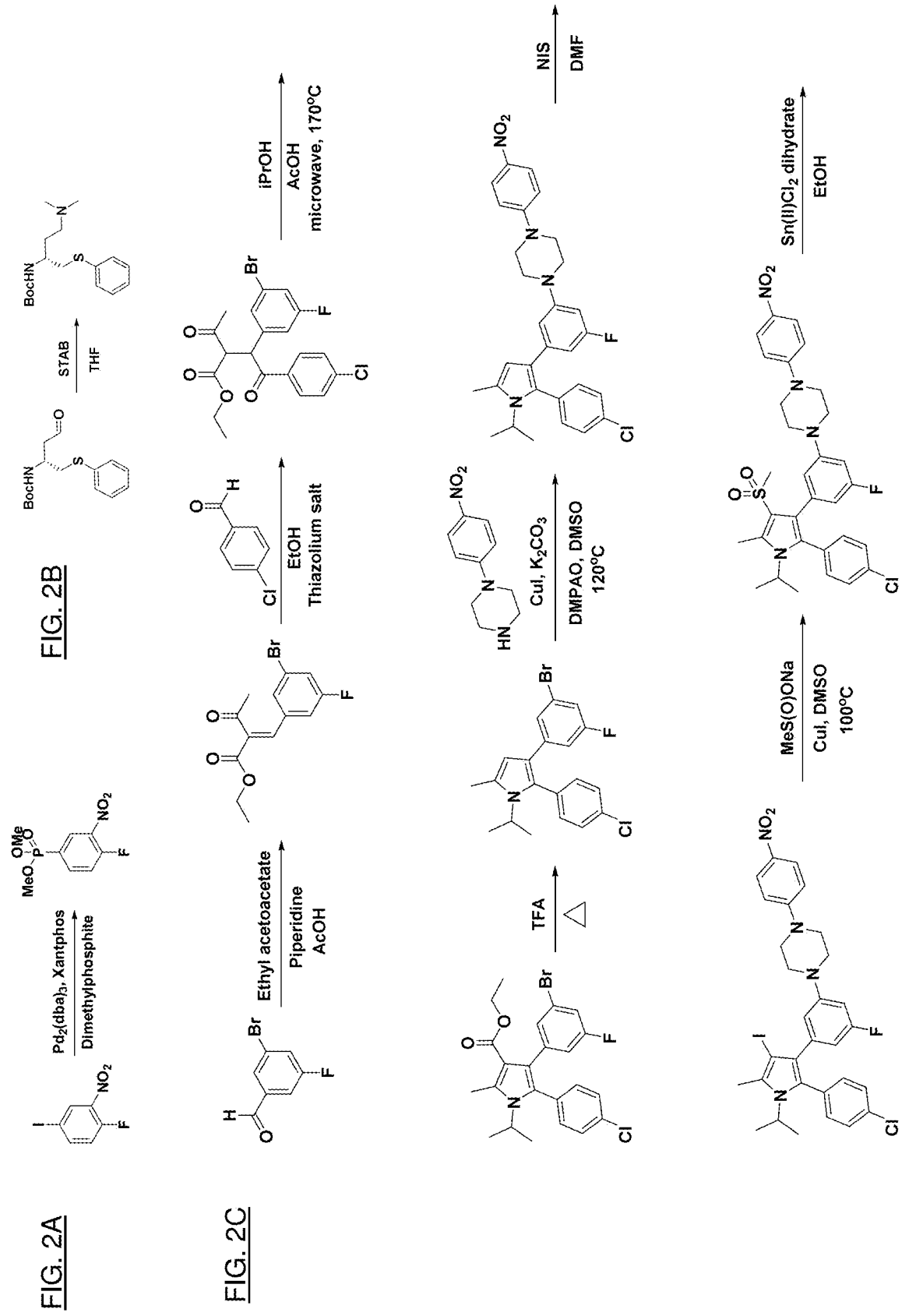
FIGS. 2A to 2C depict the synthesis of an exemplary compound an accordance with this disclosure.
Figure 2C:
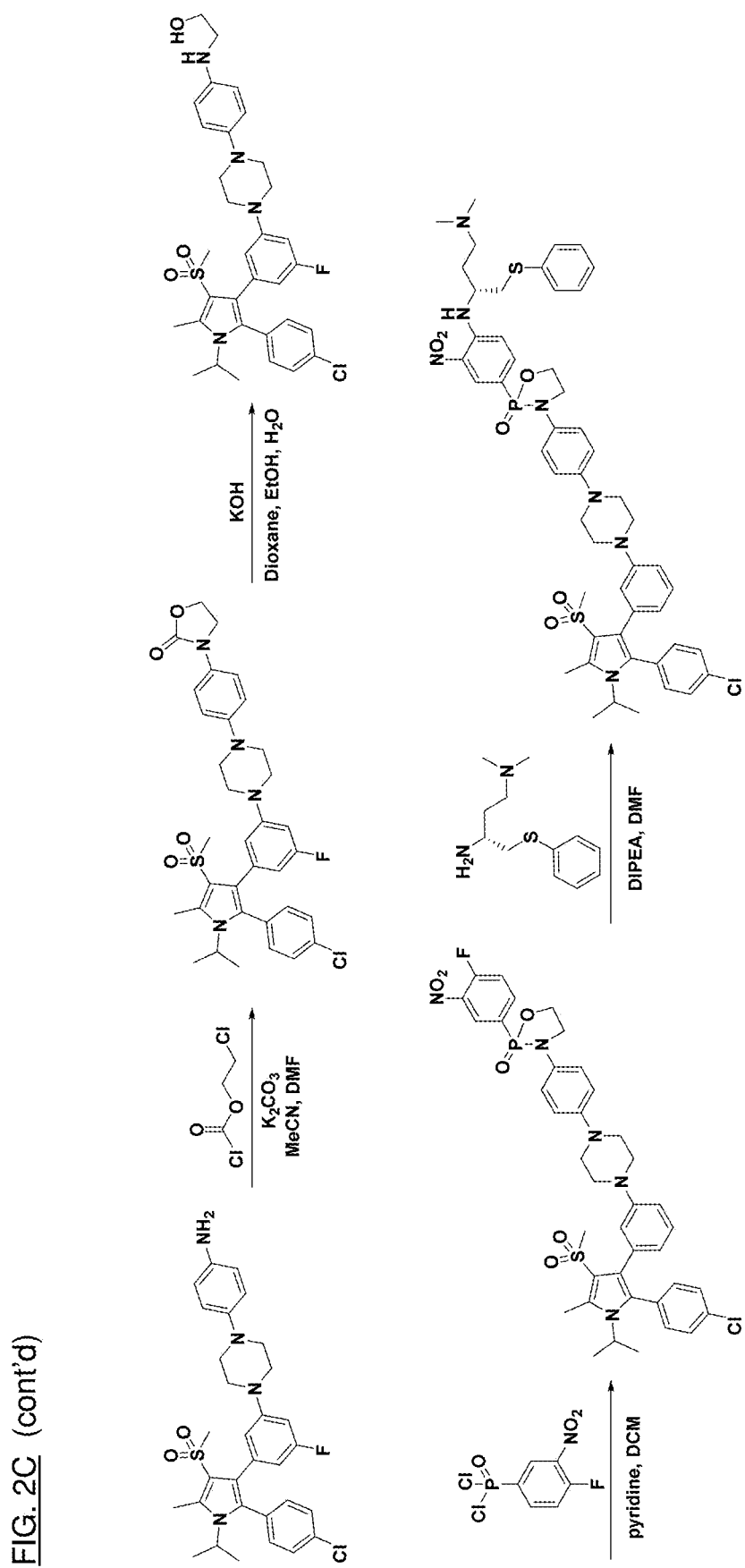

FIGS. 1A, 1B, and 1C show a general synthetic scheme that can be used to prepare acyl phosphonamidates FIGS. 2A, 2B, and 2C show a method that was used to synthesize ethyl N-(4-(4-((4'-chloro-[1,1'-biphenyl]-2-yl) methyl)piperazin-1-yl)benzoyl)-P-(4-(((R)-4-morpholino-1-(phenylthio)butan-2-yl)amino)-3-nitrophenyl)phosphonamidate. The steps were as follows:

Synthesis of dimethyl (4-fluoro-3-nitrophenyl)phosphonate

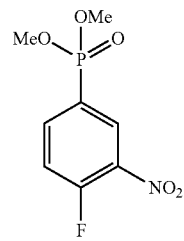 [SMILES: COP(=O)(OC)c1ccc(F)c([N+](=O)[O-])c1]

To a solution of 4-iodo-2-nitro-fluorobenzene (4.55 g, 17.0 mmol) in dry dioxane (40 mL) was added dimethyl phosphite (1.88 g, 17 mmol) and triethylamine (2.59 mL, 18.7 mmol). Xantphos (492 mg, 0.85 mmol) and $Pd_2(dba)_3$ (394 mg, 0.43 mmol) were then added under nitrogen atmosphere and the mixture was stirred at room temperature for 2.5 h. The mixture was diluted in water (100 mL) and 1 M aqueous hydrochloric acid (20 mL) and was extracted with ethyl acetate (2×100 mL). The combined organic extracts were washed with brine (40 mL), dried over $MgSO_4$, filtered and concentrated under vacuum. The crude residue was purified by silica flash chromatography (Reveleris, 50-100% ethyl acetate in hexanes) to give dimethyl (4-fluoro-3-nitrophenyl)phosphonate as a pale yellow solid (3.09 g, 73% yield). LCMS (ESI) M+H=250.1

Synthesis of tert-butyl (R)-(4-(dimethylamino)-1-(phenylthio)butan-2-yl)carbamate

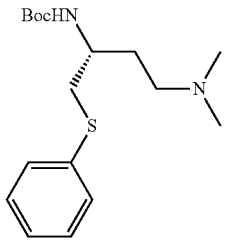 [SMILES: CN(C)CC[C@H](CSc1ccccc1)NC(=O)OC(C)(C)C]

To a solution of tert-butyl N-[(2R)-4-oxo-1-(phenylsulfanyl)butan-2-yl]carbamate (1 g, 3.39 mmol) in a mixture of THF (10 mL) and dimethylamine (0.95 mL of a 33% solution in ethanol, 5.1 mmol) was added sodium triacetoxyborohydride (1.44 g, 6.78 mmol). The mixture was stirred at room temperature for 30 min. The mixture was diluted in saturated aqueous ammonium chloride (10 mL), water (5 mL), brine (50 mL) and ethyl acetate (50 mL). The layers were separated and the aqueous phase pH was adjusted to ~10 by addition of saturated aqueous sodium carbonate and was extracted with ethyl acetate (2×60 mL). The combined organic extracts were washed with brine (30 mL), dried over $MgSO_4$, filtered and concentrated under vacuum. The crude residue was purified by silica flash chromatography (Reveleris, 20 g silica cartridge, 0-30% methanol in DCM) to give tert-butyl (R)-(4-(dimethylamino)-1-(phenylthio)butan-2-yl)carbamate as a colorless oil (921 mg, 84% yield). LCMS (ESI) M+H=325.2

Synthesis of ethyl-2-(3-bromo-5-fluorobenzylidene)-3-oxobutanoate (Mix of E and Z)

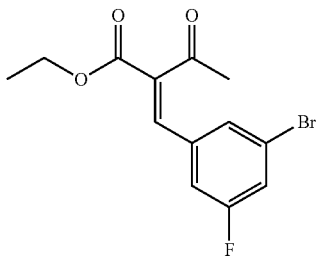 [SMILES: CCOC(=O)/C(=C/c1cc(F)cc(Br)c1)C(C)=O]

To a solution of 3-bromo-5-fluorobenzaldehyde (40.8 g, 201 mmol) in toluene (80 mL) and glacial acetic acid (4 mL) were added ethyl acetoacetate (28.5 mL, 225 mmol) and piperidine (1.2 mL). The mixture was heated to reflux for 2.5 h and the liberated water was collected with a Dean-Stark apparatus. The mixture was diluted in a mixture of toluene (100 mL), EtOAc (200 mL) and hexanes (100 mL). The resulting solution was washed with 1 M aqueous HCl (100 mL), water (100 mL), saturated aqueous NaHCO$_3$ (50 mL) and brine (50 mL). The organic layer was dried over MgSO$_4$, filtered and concentrated under vacuum. The crude residue was treated with hot hexanes (100 mL), cooled to room temperature and further cooled in an ice/acetone bath. The solid material was collected by filtration, washed with ice cold hexanes and dried under vacuum to give ethyl-2-(3-bromo-5-fluorobenzylidene)-3-oxobutanoate as a yellow solid (38.18 g, 60.3% yield). The filtrate was concentrated to 80 mL and the separated material was collected by filtration and purified by silica flash chromatography (Reveleris, 40 g cartridge, 0-100% DCM in hexanes) to give additional desired product as a yellow solid (8.8 g, 13.9% yield). LCMS (ESI) [M+H]+=315.0/317.0 [M+Na]+=337.0/339.0

Synthesis of ethyl 2-acetyl-3-(3-bromo-5-fluorophenyl)-4-(4-chlorophenyl)-4-oxobutanoate

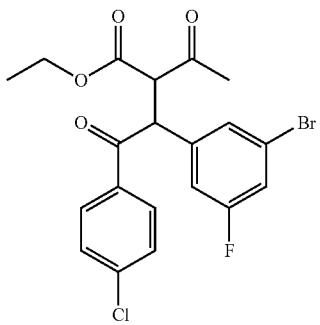 [SMILES: CCOC(=O)C(C(C)=O)C(C(=O)c1ccc(Cl)cc1)c1cc(F)cc(Br)c1]

To a solution of ethyl-2-(3-bromo-5-fluorobenzylidene)-3-oxobutanoate (46.8 g, 148.5 mmol) and 4-chlorobenzaldehyde (21.4 g, 152.2 mmol) in ethanol (240 mL) was added triethylamine (31 mL, 222 mmol). Nitrogen gas was bubbled through the mixture for 5 min and 3-benzyl-5-(2-hydroxyethyl)-4-methylthiazolium chloride (6 g, 22 mmol) was then added. The mixture was heated to 70° C. for 2 h under a nitrogen atmosphere. The solvent was removed under vacuum and the residual crude was dissolved in EtOAc (700 mL) and washed with 1 M aqueous HCl (130 mL), water (2×150 mL) and brine (2×20 mL). The organic extract was dried over MgSO$_4$, filtered and concentrated under vacuum to give ethyl 2-acetyl-3-(3-bromo-5-fluorophenyl)-4-(4-chlorophenyl)-4-oxobutanoate as an orange gum (73.1 g) which was used without purification. LCMS (ESI) [M+Na]+=477.0/479.0

Synthesis of ethyl 4-(3-bromo-5-fluorophenyl)-5-(4-chlorophenyl)-1-isopropyl-2-methyl-pyrrole-3-carboxylate

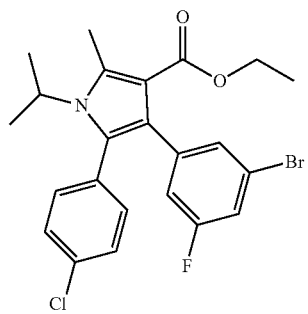 [SMILES: CCOC(=O)c1c(-c2cc(F)cc(Br)c2)c(-c2ccc(Cl)cc2)n(C(C)C)c1C]

To a solution of ethyl 2-acetyl-3-(3-bromo-5-fluorophenyl)-4-(4-chlorophenyl)-4-oxobutanoate (73.1 g) in glacial acetic acid (140 mL) was added isopropylamine (85 mL) dropwise over 15 min whilst nitrogen gas was bubbled through the mixture. The mixture was allowed to stir at room temperature for 10 min then heated to 130° C. for 2 h under a nitrogen atmosphere. The mixture was diluted with EtOAc (600 mL) and treated with water (500 mL) and brine (50 mL). 1 M aqueous HCl was added until reaching pH ~1. The organic layer was separated, washed with water (4×500 mL), saturated aqueous NaHCO$_3$ (100 mL) and brine (50 mL), dried over MgSO$_4$, filtered and concentrated under vacuum. The crude residue was treated with hot methanol (250 mL) and the resulting solution was allowed to cool to room temperature then further cooled in an ice-acetone bath. The precipitated solid was collected by filtration, washed with cold methanol and dried under vacuum to give ethyl 4-(3-bromo-5-fluorophenyl)-5-(4-chlorophenyl)-1-isopropyl-2-methyl-pyrrole-3-carboxylate as a pale yellow solid (44.4 g, 62% yield over 2 steps). LCMS (ESI) single major peak, poor ionization Synthesis of 3-(3-bromo-5-fluorophenyl)-2-(4-chlorophenyl)-5-methyl-1-(propan-2-yl)-1H-pyrrole

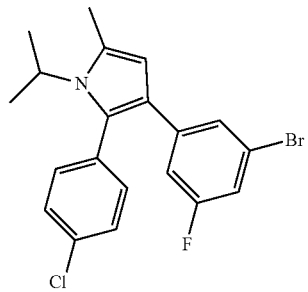 [SMILES: Cc1cc(-c2cc(F)cc(Br)c2)c(-c2ccc(Cl)cc2)n1C(C)C]

To trifluoroacetic acid (190 mL) was added ethyl 4-(3-bromo-5-fluorophenyl)-5-(4-chlorophenyl)-1-isopropyl-2-methyl-pyrrole-3-carboxylate (44.3 g, 92.5 mmol). The mixture was heated to reflux for 2 h. The mixture was poured into ice-water (800 mL) and was extracted with EtOAc (800 mL). The combined organic extracts were washed with water (4×500 mL) and saturated aqueous $Na_2CO_3$ until reaching pH >9. The organic layer was then washed with brine (50 mL), dried over $MgSO_4$, filtered and concentrated under vacuum to give 3-(3-bromo-5-fluorophenyl)-2-(4-chlorophenyl)-5-methyl-1-(propan-2-yl)-1H-pyrrole as a pale yellow solid (36.1 g, 96% yield) which was used without purification. LCMS (ESI) [M+H]+=406.1/408.1

Synthesis of 1-[3-[2-(4-chlorophenyl)-1-isopropyl-5-methyl-pyrrol-3-yl]-5-fluoro-phenyl]-4-(4-nitrophenyl)piperazine

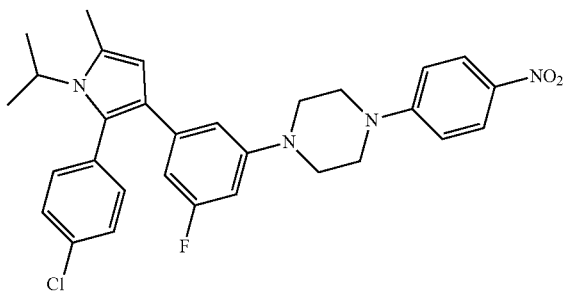 [SMILES: Cc1cc(-c2cc(F)cc(N3CCN(c4ccc([N+](=O)[O-])cc4)CC3)c2)c(-c2ccc(Cl)cc2)n1C(C)C]

To a solution of 3-(3-bromo-5-fluorophenyl)-2-(4-chlorophenyl)-5-methyl-1-(propan-2-yl)-1H-pyrrole (24 g, 59.0 mmol) in anhydrous DMSO (200 mL) was added 4-nitrophenylpiperazine (33 g, 159 mmol) and DMPAO (11.6 g, 60 mmol) under nitrogen atmosphere. The mixture was warmed and sonicated to assist with solubilization and nitrogen gas was bubbled through the solution for several minutes. Potassium carbonate (32.44 g, 234.7 mmol) and copper (I) iodide (2.88 g, 15.1 mmol) were then added and nitrogen bubbling continued for another 5 min. The mixture was heated to 120° C. for 6 h under nitrogen. The mixture was treated with DCM (800 mL), water (1.5 L) and saturated aqueous $NH_4Cl$ (400 mL). The organic layer was separated and the aqueous layer extracted with DCM (2×200 mL). The combined organic extracts were washed with water (5×500 mL), saturated aqueous $NaHCO_3$ (200 mL), water (200 mL) and brine (50 mL), dried over $MgSO_4$, filtered and concentrated under vacuum.

The crude residue was dissolved in DCM (minimal amount) and treated with MeOH (excess). The mixture was heated to 70° C. until the volume was reduced by approximately half. The suspension was cooled at 0° C. and the solid was collected by filtration, washed with cold MeOH and dried under vacuum to give 1-[3-[2-(4-chlorophenyl)-1-isopropyl-5-methyl-pyrrol-3-yl]-5-fluoro-phenyl]-4-(4-nitrophenyl)piperazine as a yellow solid (19.2 g, 61% yield).

Additional solid was observed to precipitate in the filtrate and was collected by filtration, washed with cold MeOH and dried under vacuum to give additional desired product as a yellow solid (1.28 g, 4% yield). LCMS (ESI) single major peak, poor ionization Synthesis of 1-[3-[2-(4-chlorophenyl)-4-iodo-1-isopropyl-5-methyl-pyrrol-3-yl]-5-fluoro-phenyl]-4-(4-nitrophenyl)piperazine

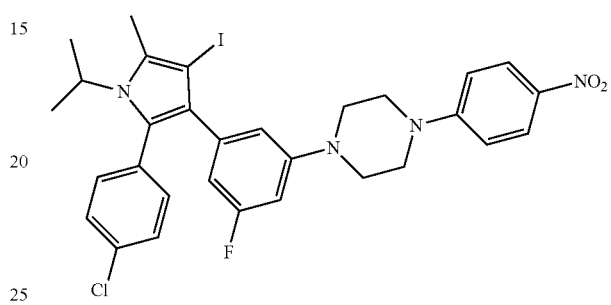

To a solution of 1-[3-[2-(4-chlorophenyl)-1-isopropyl-5-methyl-pyrrol-3-yl]-5-fluoro-phenyl]-4-(4-nitrophenyl)piperazine (20.4 g, 38.3 mmol) in DMF (250 mL) was added a solution of N-iodosuccinimide (10.45 g, 46.4 mmoL) in DMF (50 mL) at 0° C. The mixture was stirred at room temperature for 2.5 h. The mixture was diluted in ice/water (1.3 L). The precipitated solid was collected by filtration, washed with water then dissolved in DCM. The resulting solution was dried over $MgSO_4$, filtered and concentrated under vacuum. The crude residue was triturated with MeOH and the solid was collected by filtration and dried under vacuum to give 1-[3-[2-(4-chlorophenyl)-4-iodo-1-isopropyl-5-methyl-pyrrol-3-yl]-5-fluoro-phenyl]-4-(4-nitrophenyl)piperazine as a yellow solid (23.0 g, 91% yield) which was used without purification. LCMS (ESI) single major peak, poor ionization Synthesis of 1-[3-[2-(4-chlorophenyl)-1-isopropyl-5-methyl-4-methylsulfonyl-pyrrol-3-yl]-5-fluoro-phenyl]-4-(4-nitrophenyl)piperazine

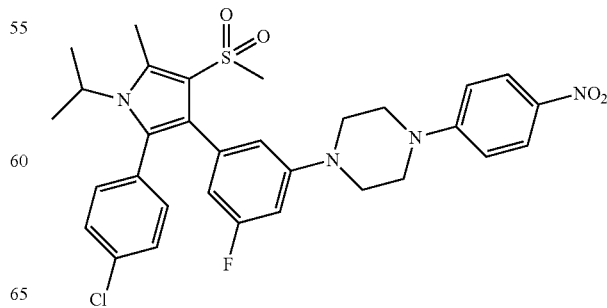

To a solution of 1-[3-[2-(4-chlorophenyl)-4-iodo-1-isopropyl-5-methyl-pyrrol-3-yl]-5-fluoro-phenyl]-4-(4-nitrophenyl)piperazine (13.35 g, 18.23 mmol) in anhydrous DMSO (120 mL) was added proline sodium salt (3.1 g, 22.3 mmol) and methanesulfinic acid sodium salt (20.2 g, 198 mmol) under nitrogen atmosphere. Copper (I) iodide (3.52 g, 18.5 mmol) was then added and the mixture was heated to 105° C. for 19 h. The mixture was diluted with EtOAc (1.5 L), water (500 mL) and saturated aqueous NH$_4$Cl (300 mL). The organic layer was separated and the aqueous layer was extracted with EtOAc (500 mL). The combined organic extracts were washed with water (2×500 mL), saturated aqueous NaHCO$_3$ (200 mL), water (200 mL) and brine (200 mL), dried over MgSO$_4$, filtered and concentrated under vacuum.

The crude residue was purified by silica flash chromatography (0-60% EtOAc in hexanes). Desired product-containing fractions were combined and concentrated and further purified by recrystallization from EtOAc/hexanes to give 1-[3-[2-(4-chlorophenyl)-1-isopropyl-5-methyl-4-methylsulfonyl-pyrrol-3-yl]-5-fluoro-phenyl]-4-(4-nitrophenyl) piperazine as an orange solid (9.18 g, 41%). Additional desired product (2.7 g, 12%) was obtained via repetition of the process of silica chromatography and recrystallization from EtOAc/hexanes. LCMS (ESI) [M+H]+=611.2

Synthesis of 4-(4-(3-(2-(4-chlorophenyl)-1-isopropyl-5-methyl-4-(methylsulfonyl)-1H-pyrrol-3-yl)-5-fluorophenyl)piperazin-1-yl)aniline

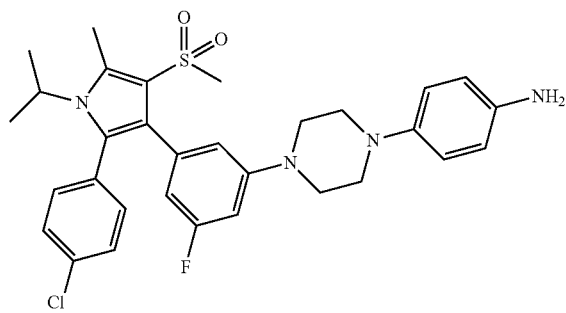 [SMILES: Cc1c(S(C)(=O)=O)c(-c2cc(F)cc(N3CCN(c4ccc([N+](=O)[O-])cc4)CC3)c2)c(-c2ccc(Cl)cc2)n1C(C)C]

To a solution of 1-[3-[2-(4-chlorophenyl)-1-isopropyl-5-methyl-4-methylsulfonyl-pyrrol-3-yl]-5-fluoro-phenyl]-4-(4-nitrophenyl)piperazine (2.34 g, 3.82 mmol) in ethanol (50 mL) was added concentrated hydrochloric acid (4 mL) and tin(II) dichloride dihydrate (4.32 g, 19.1 mmol) under nitrogen atmosphere. The mixture was heated to reflux for 5 h. The mixture was concentrated to ⅓ volume and partitioned between ethyl acetate (200 mL) and saturated aqueous sodium bicarbonate (200 mL). The layers were separated and the aqueous was washed with ethyl acetate (2×100 mL). The combined organic extracts were washed with water (3×80 mL) and brine (50 mL), dried over MgSO$_4$, filtered and concentrated under vacuum to give 4-(4-(3-(2-(4-chlorophenyl)-1-isopropyl-5-methyl-4-(methylsulfonyl)-1H-pyrrol-3-yl)-5-fluorophenyl)piperazin-1-yl)aniline as a tan foam solid (2.30 g, >100%) which was used without purification. LCMS (ESI) M+H=581.2

Synthesis of 3-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)oxazolidin-2-one

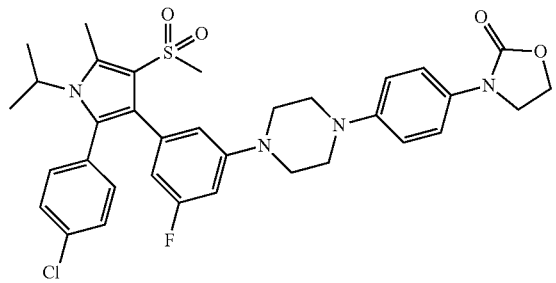 [SMILES: Cc1c(S(C)(=O)=O)c(-c2cc(F)cc(N3CCN(c4ccc(N5CCOC5=O)cc4)CC3)c2)c(-c2ccc(Cl)cc2)n1C(C)C]

To a solution of 4-(4-(3-(2-(4-chlorophenyl)-1-isopropyl-5-methyl-4-(methylsulfonyl)-1H-pyrrol-3-yl)-5-fluorophenyl)piperazin-1-yl)aniline (581 mg, 1.0 mmol) in anhydrous acetonitrile (20 mL) was added potassium carbonate (691 mg, 5.0 mmol, fine powder) under nitrogen atmosphere. A solution of 2-bromoethyl chloroformate (281 mg, 1.5 mmol) in anhydrous acetonitrile (5 mL) was then added and the resulting mixture was heated to reflux for 18 h. The mixture was diluted with brine (50 mL) and water (50 mL) and extracted with ethyl acetate (2×50 mL). The combined organic extracts were washed with water (50 mL) then brine (20 mL), dried over MgSO$_4$, filtered and concentrated under vacuum. The crude residue was purified by silica flash chromatography (Revelaris, 20 g silica cartridge, 40-100% ethyl acetate in DCM) to provide 3-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)oxazolidin-2-one as an off-white solid (365 mg, 58% yield). LCMS (ESI) M+H=651.2, M+Na=673.2

Synthesis of 2-((4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)amino) ethan-1-ol

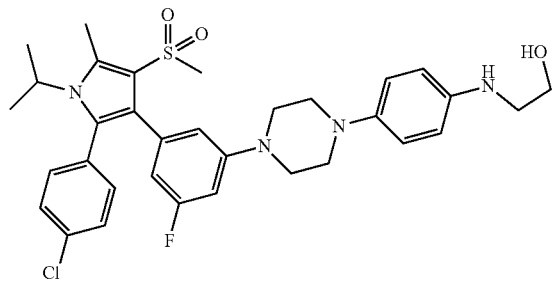 [SMILES: Cc1c(S(C)(=O)=O)c(-c2cc(F)cc(N3CCN(c4ccc(NCCO)cc4)CC3)c2)c(-c2ccc(Cl)cc2)n1C(C)C]

To a solution of 3-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)oxazolidin-2-one (365 mg) in ethanol (50 mL) was added a solution of potassium hydroxide (1.5 g, 27 mmol) in water (5 mL). The mixture was heated to reflux for 1 h. The mixture was concentrated under vacuum and the residue partitioned between ethyl acetate (50 mL) and water (100 mL). The layers were separated and the aqueous washed with ethyl acetate (50 mL). The combined organic extracts were washed with brine (30 mL), dried over MgSO$_4$, filtered and concentrated under vacuum to give 2-((4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)amino)ethan-1-ol as a tan foam (391 mg, 63% yield). LCMS (ESI) M+H=625.3, M+Na=647.2

Synthesis of 3-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)-2-(4-fluoro-3-nitrophenyl)-1,3,2-oxazaphospholidine 2-oxide

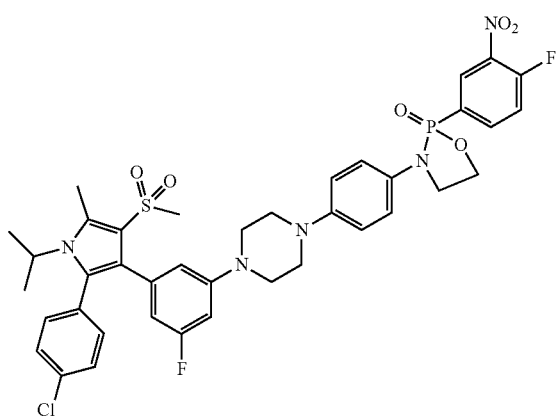 [SMILES: Cc1c(S(C)(=O)=O)c(-c2cc(F)cc(N3CCN(c4ccc(N5CCOP5(=O)c5ccc(F)c([N+](=O)[O-])c5)cc4)CC3)c2)c(-c2ccc(Cl)cc2)n1C(C)C]

1st Step

To a suspension of (4-fluoro-3-nitrophenyl)phosphonic acid (pre-dried before use by co-evaporation from toluene and drying under high vacuum, 1.33 g, 6.0 mmol) in anhydrous DCM (15 mL) was added oxalyl chloride (2 mL, 24 mmol) and DMF (2 drops) under a nitrogen atmosphere. After gas evolution had subsided, the mixture was heated to 40° C. for 45 min, cooled and concentrated under vacuum. The resulting residue was coevaporated from toluene to remove excess oxalyl chloride. The crude residue was then redissolved in anhydrous DCM (15 mL) and treated again with oxalyl chloride (1.5 mL) and DMF (2 drops) and heated to reflux for 30 min under nitrogen. The mixture was concentrated under vacuum and the residue co-evaporated from toluene to give the crude intermediate as an orange oil which was used directly in the next step.

2nd Step

To a solution of 2-((4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)amino)ethan-1-ol (2.5 g, 4.0 mmol) in anhydrous DCM (15 mL) and anhydrous pyridine (3.23 mL, 40 mmol) was added a solution of the crude residue from the last step in anhydrous DCM (15 mL) under a nitrogen atmosphere and cooled in an ice/water bath. The resulting mixture was stirred for 30 min then warmed to room temperature and stirred for an additional 30 min. The mixture was diluted in DCM (50 mL) and treated with saturated aqueous NaHCO$_3$ (50 mL). The layers were separated and the aqueous was washed with DCM (2×50 mL). The combined organic extracts were washed with water (100 mL), dried over MgSO$_4$, filtered and concentrated under vacuum.

The crude residue was purified by silica flash chromatography (Reveleris, 70-100% DCM in hexanes then 0-100% EtOAc in DCM) to give 3-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)-2-(4-fluoro-3-nitrophenyl)-1,3,2-oxazaphospholidine 2-oxide as an orange foam solid (2.23 g, 69% yield). LCMS (ESI) [M+H]+=810.1

Synthesis of 3-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)-2-(4-(((R)-4-(dimethylamino)-1-(phenylthio)butan-2-yl)amino)-3-nitrophenyl)-1,3,2-oxazaphospholidine 2-oxide

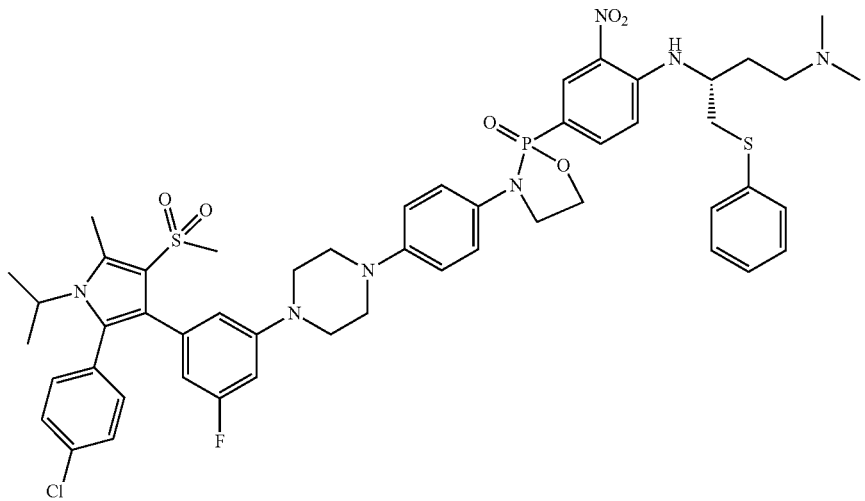 [SMILES: Cc1c(S(C)(=O)=O)c(-c2cc(F)cc(N3CCN(c4ccc(N5CCOP5(=O)c5ccc(N[C@H](CCN(C)C)CSc6ccccc6)c([N+](=O)[O-])c5)cc4)CC3)c2)c(-c2ccc(Cl)cc2)n1C(C)C]

To a solution of tert-butyl (R)-(4-(dimethylamino)-1-(phenylthio)butan-2-yl)carbamate (120 mg, 0.370 mmol) in ethyl acetate (3 mL) was added concentrated aqueous hydrochloric acid (3 mL). The mixture was stirred at room temperature for 2 h. The mixture was then concentrated to dryness and the resulting residue was dissolved in anhydrous DMF (10 mL) under a nitrogen atmosphere. N,N-diisopropylethylamine (485 mg, 3.75 mmol) followed by 3-(4-(4-(3-(2-(4-chlorophenyl)-1-isopropyl-5-methyl-4-(methylsulfonyl)-1H-pyrrol-3-yl)-5-fluorophenyl)piperazin-1-yl)

phenyl)-2-(4-fluoro-3-nitrophenyl)-1,3,2-oxazaphospholidine 2-oxide (200 mg, 0.25 mmol) were added and the resulting mixture was stirred at room temperature for 4 h. The mixture was diluted in brine (50 mL) and water (50 mL) and was extracted with ethyl acetate (2×50 mL). The combined organic extracts were washed with water (50 mL) and brine (20 mL), dried over $MgSO_4$, filtered and concentrated under vacuum.

The crude residue was purified by silica flash chromatography (Reveleris, 20 g $SiO_2$ column, 0-10% methanol in DCM) to give 3-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)-2-(4-(((R)-4-(dimethylamino)-1-(phenylthio)butan-2-yl)amino)-3-nitrophenyl)-1,3,2-oxazaphospholidine 2-oxide as a mixture of diastereoisomers and as a yellow foam (157 mg, 62% yield). LCMS (ESI) M+H=1014.2, M+2H/2=507.8

Example 10: Biochemical and Cellular Activity of Phospholidine Compounds

Selected compounds were assessed for inhibition of ligand binding to Bcl-2 in an in vitro assay, according to the method described in Example 1. The compounds were also assessed for senescent cell killing activity in HRMEC cell line and IMR90 fibroblasts according to the method described in Example 3 and 2, respectively.

FIGS. 3A and 3B show the results of both the Bcl binding assay and the cell culture assay.

FIG. 4 is a drawing that depicts a three-dimensional model in which the Bcl inhibitors described in this disclosure are fit into the crystal structure of Bcl family proteins. The annotations in the drawing can be used as a guide to the reader for developing additional compounds that fall within the formulas shown above, that would retain Bcl inhibition activity and senolytic activity. Regions that interact closely with Bcl or its binding partners are less tolerant to variation. Regions that interact with solvent are more tolerant to variation in terms of Bcl inhibition, and can be modified to adjust other properties of the molecule, such as solubility and detection.

The several hypotheses presented in this disclosure provide a premise by way of which the reader may understand various aspects of the invention. This premise is provided for the intellectual enrichment of the reader. Practice of the invention does not require detailed understanding or application of the hypothesis. Except where stated otherwise, features of the hypothesis presented in this disclosure do not limit application or practice of the claimed invention.

For example, except where the elimination of senescent cells is explicitly required, the compounds may be used for treating the conditions described regardless of their effect on senescent cells. Although many of the senescence-related conditions referred to in this disclosure occur predominantly in older patients, the occurrence of senescent cells and the pathophysiology they mediate can result from other events, such as irradiation, other types of tissue damage, other types of disease, and genetic abnormalities. The invention may be practiced on patients of any age having the condition indicated, unless otherwise explicitly indicated or required.

Discussions about the mechanism of action of the compounds of the disclosure are also provided for the intellectual enrichment of the reader, and do not imply any limitation. Except where stated otherwise, the compounds may be used for removing senescent or cancer cells or for the treatment of disease conditions as claimed below, regardless of how they operate inside the target cells or in the treated subject.

Although the compounds and compositions referred to in this disclosure are illustrated in the context of eliminating senescent cells and treating senescence-associated conditions and cancer, compounds and their derivatives described herein that are novel can be prepared for any purpose, including but not limited to laboratory use, the treatment of senescence-related conditions, and for diagnostic purposes.

While the invention has been described with reference to the specific examples and illustrations, changes can be made and equivalents can be substituted to adapt to a particular context or intended use as a matter of routine development and optimization and within the purview of one of ordinary skill in the art, thereby achieving benefits of the invention without departing from the scope of what is claimed and their equivalents.

The invention claimed is:
1. A compound of Formula (VIIa):

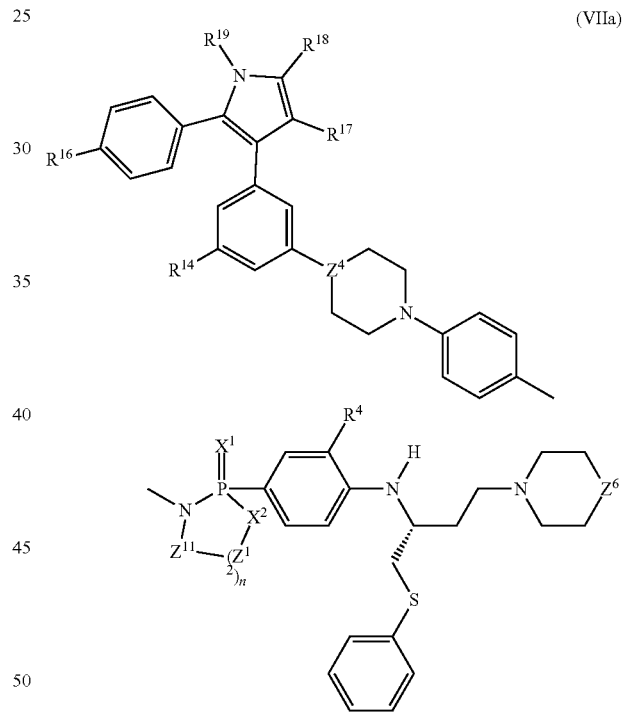

(VIIa)

wherein:
$X^1$ is O or S;
$X^2$ is selected from $Z^{12}$, S, O and $NR^{22}$;
$R^{22}$ is selected from hydrogen and $C_{1-6}$alkyl;
$Z^{11}$ is selected from C(=O), —C(=O)$X^3$— and $Z^{12}$;
each $Z^{12}$ is independently $CR^{24}R^{25}$;
$X^3$ is O or S;
n is 0, 1, 2 or 3;
each $R^{24}$ and each $R^{25}$ are independently selected from hydrogen and $C_{1-6}$alkyl;
$R^4$ is selected from $NO_2$, $SO_2CH_3$, and $SO_2CF_3$;
$Z^4$ is selected from CH and N;
$Z^6$ is selected from O, CHC(O)$R^{18a}$, and CH(CH$_2$)$_p$$R^{18a}$ wherein p is 0-6 and each $R^{18a}$ is independently selected from —OR, —N(R)$_2$, —OP(=O)(OH)$_2$, and —OP(=O)(OR)$_2$, wherein each R is independently H or C$_{1-4}$alkyl;

$R^{14}$ and $R^{16}$ are independently hydrogen or halogen;

$R^{17}$ is selected from SO$_2$R$^{52}$, COR$^{52}$, CO$_2$R$^{52}$, CONR$^{51}$R$^{52}$, CONR$^{52}$SO$_2$R$^{51}$ and SO$_2$NR$^{51}$R$^{52}$;

$R^{18}$ and $R^{19}$ are independently selected from hydrogen and alkyl;

$R^{51}$ is C$_{1-6}$alkyl; and $R^{52}$ is selected from hydrogen and C$_{1-6}$alkyl, and salt forms thereof.

2. The compound of claim 1, selected from the following table:

| Compound | $X^2$ | $Z^{11}$-$(Z^{12})_n$ | $R^4$ | $R^{14}$ | $R^{16}$ | $R^{17}$ | $R^{18}$ | $R^{19}$ | $Z^4$ | $Z^6$ |
|---|---|---|---|---|---|---|---|---|---|---|
| 1 | O | CH$_2$CH$_2$ | SO$_2$OF$_3$ | F | Cl | SO$_2$CH$_3$ | CH$_3$ | CH(CH$_3$)$_2$ | N | CHOH |
| 2 | O | CH$_2$CH$_2$ | SO$_2$OF$_3$ | F | Cl | SO$_2$CH$_3$ | CH$_3$ | CH(CH$_3$)$_2$ | N | CHOPO(OH)$_2$ |
| 3 | O | CH$_2$CH$_2$ | SO$_2$OF$_3$ | F | Cl | CO$_2$H | CH$_3$ | CH(CH$_3$)$_2$ | N | CHOH |
| 4 | O | CH$_2$CH$_2$ | SO$_2$CF$_3$ | F | Cl | CO$_2$H | CH$_3$ | CH(CH$_3$)$_2$ | N | CHOPO(OH)$_2$ |
| 5 | O | CH$_2$CH$_2$CH$_2$ | SO$_2$OF$_3$ | F | Cl | CO$_2$H | CH$_3$ | CH(CH$_3$)$_2$ | N | CHOH |
| 6 | O | CH$_2$CH$_2$CH$_2$ | SO$_2$OF$_3$ | F | Cl | CO$_2$H | CH$_3$ | CH(CH$_3$)$_2$ | N | CHOPO(OH)$_2$ |
| 7 | O | CH$_2$CH$_2$CH$_2$ | SO$_2$CH$_3$ | F | Cl | CO$_2$H | CH$_3$ | CH(CH$_3$)$_2$ | N | CHOH |
| 8 | O | CH$_2$CH$_2$CH$_2$ | SO$_2$CH$_3$ | F | Cl | CO$_2$H | CH$_3$ | CH(CH$_3$)$_2$ | N | CHOPO(OH)$_2$ |
| 9 | O | CH$_2$CH$_2$ | SO$_2$CH$_3$ | F | Cl | CO$_2$H | CH$_3$ | CH(CH$_3$)$_2$ | N | CHOH |
| 10 | O | CH$_2$CH$_2$ | SO$_2$CH$_3$ | F | Cl | CO$_2$H | CH$_3$ | CH(CH$_3$)$_2$ | N | CHOPO(OH)$_2$ |
| 11 | O | CH$_2$CH$_2$ | SO$_2$CH$_3$ | F | Cl | SO$_2$CH$_3$ | CH$_3$ | CH(CH$_3$)$_2$ | N | CHOH |
| 12 | O | CH$_2$CH$_2$ | SO$_2$CH$_3$ | F | Cl | SO$_2$CH$_3$ | CH$_3$ | CH(CH$_3$)$_2$ | N | CHOPO(OH)$_2$ |
| 13 | O | CH$_2$CH$_2$ | NO$_2$ | F | Cl | SO$_2$CH$_3$ | CH$_3$ | CH(CH$_3$)$_2$ | N | CHOH |
| 14 | O | CH$_2$CH$_2$ | NO$_2$ | F | Cl | SO$_2$CH$_3$ | CH$_3$ | CH(CH$_3$)$_2$ | N | CHOPO(OH)$_2$ |
| 15 | O | CH$_2$CH$_2$ | NO$_2$ | F | Cl | CO$_2$H | CH$_3$ | CH(CH$_3$)$_2$ | N | CHOH |
| 16 | O | CH$_2$CH$_2$ | NO$_2$ | F | Cl | CO$_2$H | CH$_3$ | CH(CH$_3$)$_2$ | N | CHOPO(OH)$_2$ |
| 17 | O | CH$_2$CH$_2$CH$_2$ | NO$_2$ | F | Cl | CO$_2$H | CH$_3$ | CH(CH$_3$)$_2$ | N | CHOH |
| 18 | O | CH$_2$CH$_2$CH$_2$ | NO$_2$ | F | Cl | CO$_2$H | CH$_3$ | CH(CH$_3$)$_2$ | N | CHOPO(OH)$_2$. |

3. A compound of Formula (VIIb):

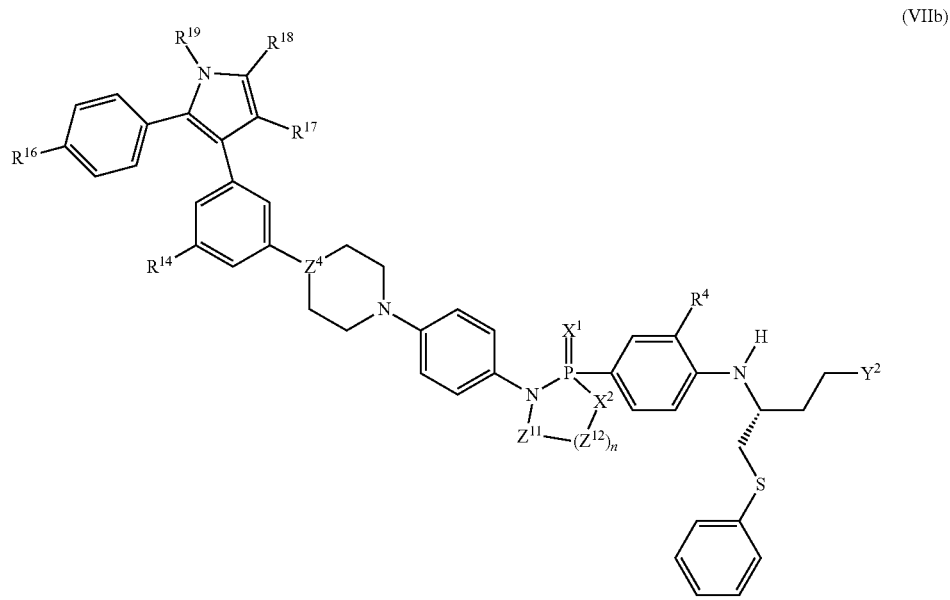

(VIIb)

wherein:

$X^1$ is O or S;

$X^2$ is selected from $Z^{12}$, S, O, and NR$^{22}$;

$R^{22}$ is selected from hydrogen and C$_{1-6}$alkyl;

$Z^{11}$ is selected from —C(=O)—, —C(=O)X$^3$— and $Z^{12}$;

each $Z^{12}$ is independently CR$^{24}$R$^{25}$;

$X^3$ is O or S;

$R^{17}$ is selected from $SO_2R^{52}$, $COR^{52}$, $CO_2R^{52}$, n is 0, 1, 2 or 3;

each $R^{24}$ and each $R^{25}$ are independently selected from hydrogen and $C_{1-6}$alkyl;

$Y^2$ is selected from —$OR^{52}$, —$N(R^{52})_2$, and —$OP(=O)(OR^{52})_2$;

$R^4$ is selected from $NO_2$, $SO_2CH_3$, and $SO_2CF_3$;

$Z^4$ is selected from CH and N;

$R^{14}$ and $R^{16}$ are independently hydrogen or halogen; $CONR^{51}R^{52}$, $CONR^{52}SO_2R^{51}$ and $SO_2NR^{51}R^{52}$;

$R^{18}$ and $R^{19}$ are independently selected from hydrogen and alkyl;

$R^{51}$ is $C_{1-6}$alkyl; and $R^{52}$ is selected from hydrogen and $C_{1-6}$alkyl, and salt forms thereof.

4. The compound of claim 3, selected from the following table:

| Compound | $X^2$ | $Z^{11}$-$(Z^{12})_n$ | $R^4$ | $R^{14}$ | $R^{16}$ | $R^{17}$ | $R^{18}$ | $R^{19}$ | $Z^4$ | $Y^2$ |
|---|---|---|---|---|---|---|---|---|---|---|
| 19 | O | $CH_2CH_2$ | $NO_2$ | F | Cl | $SO_2CH_3$ | $CH_3$ | $CH(CH_3)_2$ | N | $N(CH_3)_2$ |
| 20 | O | $CH_2CH_2$ | $SO_2OF_3$ | F | Cl | $SO_2CH_3$ | $CH_3$ | $CH(CH_3)_2$ | N | $N(CH_3)_2$ |
| 21 | O | $CH_2CH_2$ | $SO_2OF_3$ | F | Cl | $CO_2H$ | $CH_3$ | $CH(CH_3)_2$ | N | $N(CH_3)_2$ |
| 22 | O | $CH_2CH_2$ | $SO_2CF_3$ | H | Cl | $CO_2H$ | $CH_3$ | $CH(CH_3)_2$ | N | $N(CH_3)_2$ |
| 23 | O | $CH_2CH_2$ | $SO_2CH_3$ | F | Cl | $CO_2H$ | $CH_3$ | $CH(CH_3)_2$ | N | $N(CH_3)_2$ |
| 24 | O | $CH_2CH_2$ | $SO_2CH_3$ | H | Cl | $CO_2H$ | $CH_3$ | $CH(CH_3)_2$ | N | $N(CH_3)_2$ |
| 25 | O | $CH_2CH_2$ | $SO_2CH_3$ | F | Cl | $SO_2CH_3$ | $CH_3$ | $CH(CH_3)_2$ | N | $N(CH_3)_2$ |
| 26 | O | $CH_2CH_2$ | $NO_2$ | F | Cl | $CO_2H$ | $CH_3$ | $CH(CH_3)_2$ | N | $N(CH_3)_2$ |
| 27 | O | $CH_2CH_2$ | $NO_2$ | H | Cl | $CO_2H$ | $CH_3$ | $CH(CH_3)_2$ | N | $N(CH_3)_2$ |
| 28 | O | $CH_2CH_2$ | $NO_2$ | F | Cl | $SO_2CH_3$ | $CH_3$ | $CH(CH_3)_2$ | N | OH |
| 29 | O | $CH_2CH_2$ | $SO_2CF_3$ | F | Cl | $SO_2CH_3$ | $CH_3$ | $CH(CH_3)_2$ | N | OH |
| 30 | O | $CH_2CH_2$ | $SO_2OF_3$ | F | Cl | $CO_2H$ | $CH_3$ | $CH(CH_3)_2$ | N | OH |
| 31 | O | $CH_2CH_2$ | $SO_2OF_3$ | H | Cl | $CO_2H$ | $CH_3$ | $CH(CH_3)_2$ | N | OH |
| 32 | O | $CH_2CH_2$ | $SO_2CH_3$ | F | Cl | $CO_2H$ | $CH_3$ | $CH(CH_3)_2$ | N | OH |
| 33 | O | $CH_2CH_2$ | $SO_2CH_3$ | H | Cl | $CO_2H$ | $CH_3$ | $CH(CH_3)_2$ | N | OH |
| 34 | O | $CH_2CH_2$ | $SO_2CH_3$ | F | Cl | $SO_2CH_3$ | $CH_3$ | $CH(CH_3)_2$ | N | OH |
| 35 | O | $CH_2CH_2$ | $NO_2$ | F | Cl | $CO_2H$ | $CH_3$ | $CH(CH_3)_2$ | N | OH |
| 36 | O | $CH_2CH_2$ | $NO_2$ | H | Cl | $CO_2H$ | $CH_3$ | $CH(CH_3)_2$ | N | OH. |

5. The compound of claim 1, which has the structure shown in Formula (VIIIa):

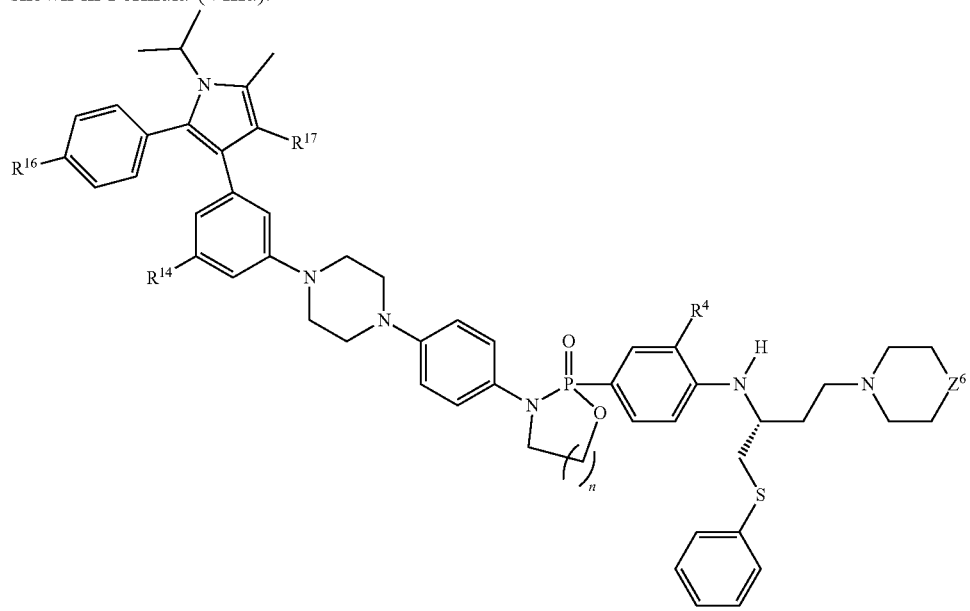

(VIIIa)

wherein:

$R^4$ is selected from $NO_2$, $SO_2CH_3$, and $SO_2CF_3$;

n is 1 or 2;

$Z^6$ is selected from O, $CHC(O)R^{18a}$, and $CH(CH_2)_pR^{18a}$ wherein p is 0-6 and each $R^{18a}$ is independently selected from —OR, —N(R)$_2$, —OP(=O)(OH)$_2$, and —OP(=O)(OR)$_2$, wherein each R is independently H or $C_{1-4}$alkyl;

$R^{14}$ and $R^{16}$ are independently hydrogen or halogen; and $R^{17}$ is selected from $SO_2R^{52}$, $COR^{52}$, $CO_2R^{52}$, and $CONR^{51}R^{52}$;

$R^{51}$ is $C_{1-6}$alkyl; and $R^{52}$ is selected from hydrogen and methyl, and salt forms thereof.

6. The compound of claim 3, which has the structure shown in Formula (VIIIb):

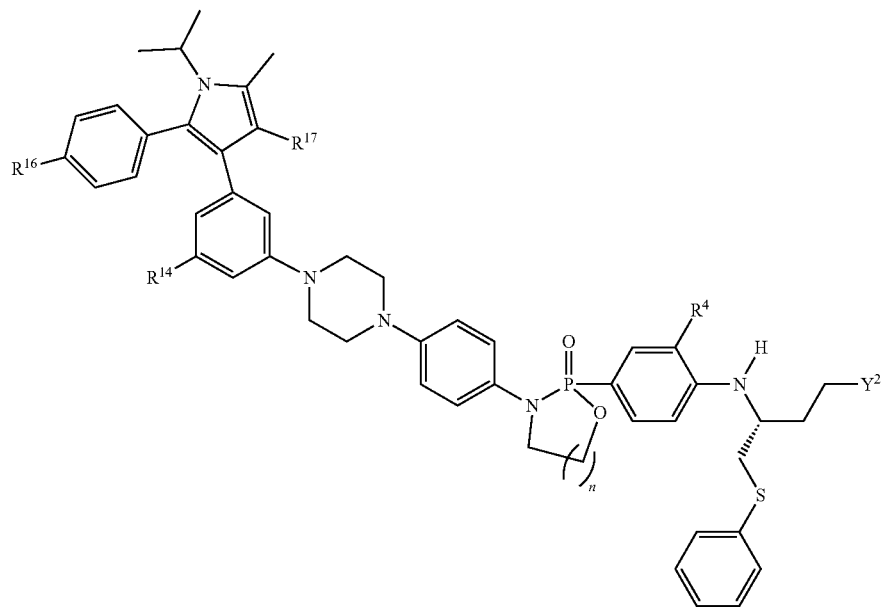

(VIIIb)

wherein:

$Y^2$ is selected from —OR$^{52}$, —N(R$^{52}$)$_2$, and —OP(=O)(OR$^{52}$)$_2$;

$R^4$ is selected from $NO_2$, $SO_2CH_3$, and $SO_2CF_3$;

n is 1 or 2;

$R^{14}$ and $R^{16}$ are independently hydrogen or halogen;

$R^{17}$ is selected from $SO_2R^{52}$, $COR^{52}$, $CO_2R^{52}$, and $CONR^{51}R^{52}$;

$R^{51}$ is $C_{1-6}$alkyl; and each $R^{52}$ is selected from hydrogen and methyl, and salt forms thereof.

7. A compound selected from the following:

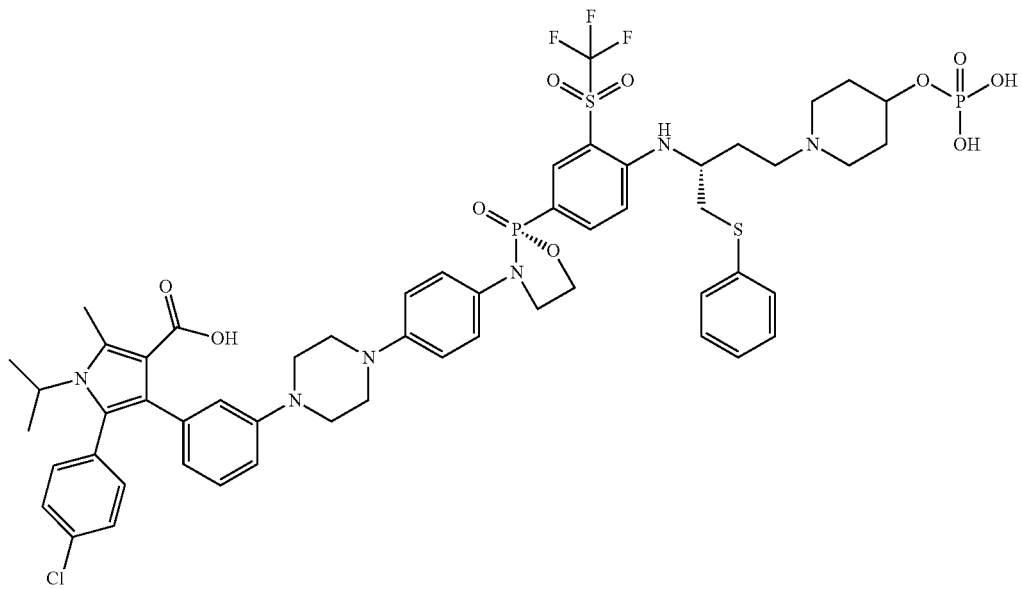

5-(4-chlorophenyl)-1-isopropyl-2-methyl-4-(3-(4-(4-(4-((R)-2-oxido-2-(4-(((R)-1-(phenylthio)-4-(4-(phosphonooxy)piperidin-1-yl)
butan-2-yl)amino)-3-((trifluoromethyl)sulfonyl)phenyl)-1,3,2-oxazaphospholidin-3-yl)phenyl)piperazin-1-yl)
phenyl)-1H-pyrrole-3-carboxylic acid,

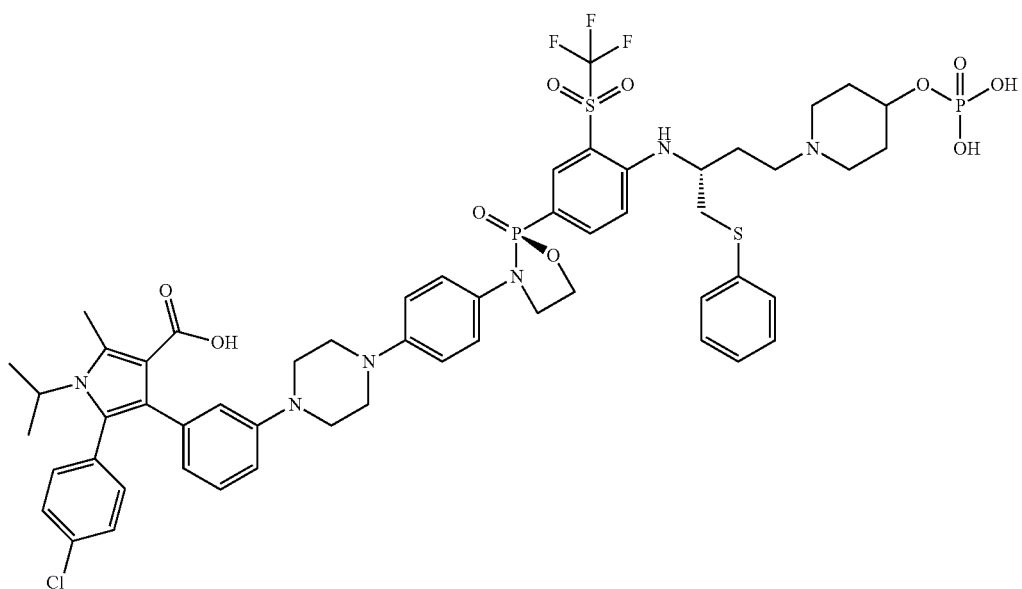

5-(4-chlorophenyl)-1-isopropyl-2-methyl-4-(3-(4-(4-(4-((S)-2-oxido-2-(4-(((R)-1-(phenylthio)-4-(4-(phosphonooxy)piperidin-1-yl)
butan-2-yl)amino)-3-((trifluoromethyl)sulfonyl)phenyl)-1,3,2-oxazaphospholidin-3-yl)phenyl)piperazin-1-yl)
phenyl)-1H-pyrrole-3-carboxylic acid,

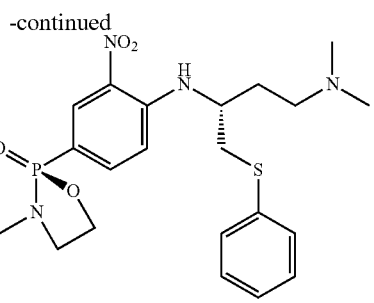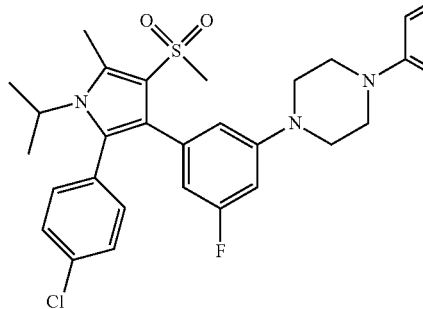

(S)-3-(4-(4-(3-(2-(4-chlorophenyl)-1-isopropyl-5-methyl-4-(methylsulfonyl)-1H-pyrrol-3-yl)-5-fluorophenyl)
piperazin-1-yl)phenyl)-2-(4-(((R)-4-(dimethylamino)-1-(phenylthio)butan-2-yl)amino)-3-nitrophenyl)-
1,3,2-oxazaphospholidine 2-oxide,

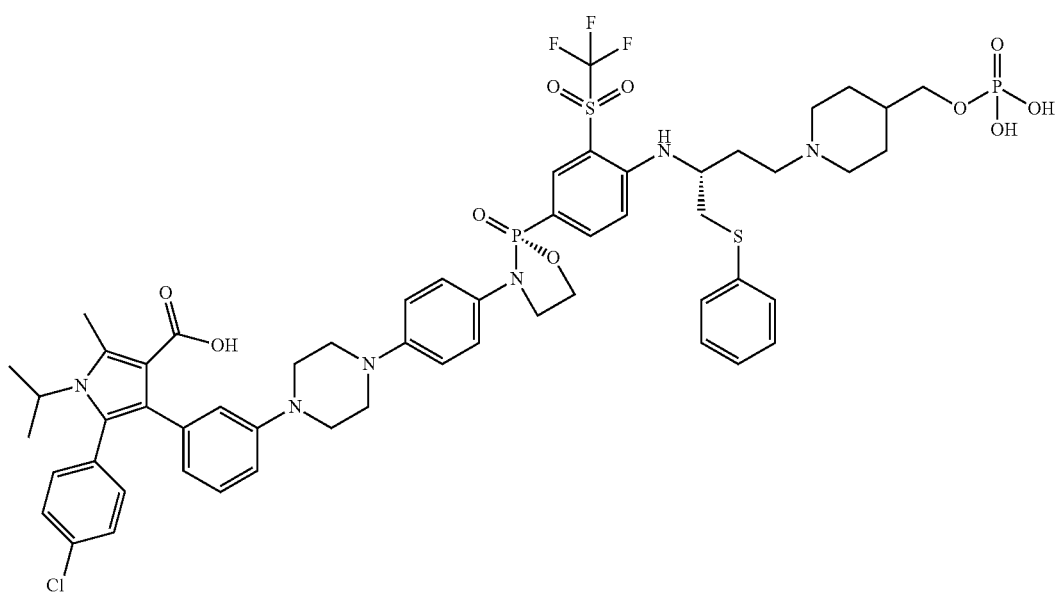

5-(4-chlorophenyl)-1-isopropyl-2-methyl-4-(3-(4-(4-((R)-2-oxido-2-(4-(((R)-1-(phenylthio)-4-(4-((phosphonooxy)methyl)piperidin-1-yl)
butan-2-yl)amino)-3-((trifluoromethyl)sulfonyl)phenyl)-1,3,2-oxazaphospholidin-3-yl)phenyl)piperazin-1-yl)
phenyl)-1H-pyrrole-3-carboxylic acid,

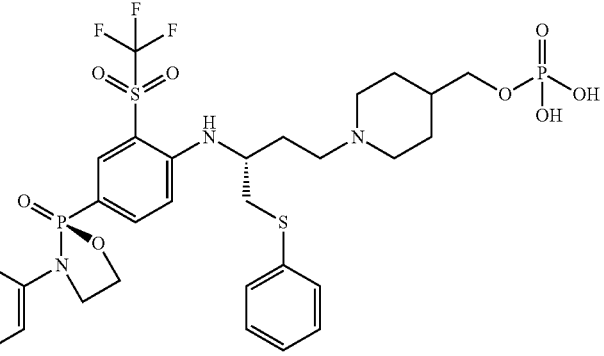
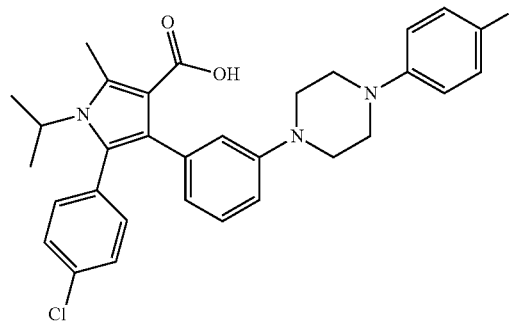

5-(4-chlorophenyl)-1-isopropyl-2-methyl-4-(3-(4-(4-((S)-2-oxido-2-(4-(((R)-1-(phenylthio)-4-(4-((phosphonooxy)
methyl)piperidin-1-yl)butan-2-yl)amino-3-((trifluoromethyl)sulfonyl)phenyl)-1,3,2-oxazaphospholidin-3-yl)phenyl)piperazin-1-yl)
phenyl)-1H-pyrrole-3-carboxylic acid,

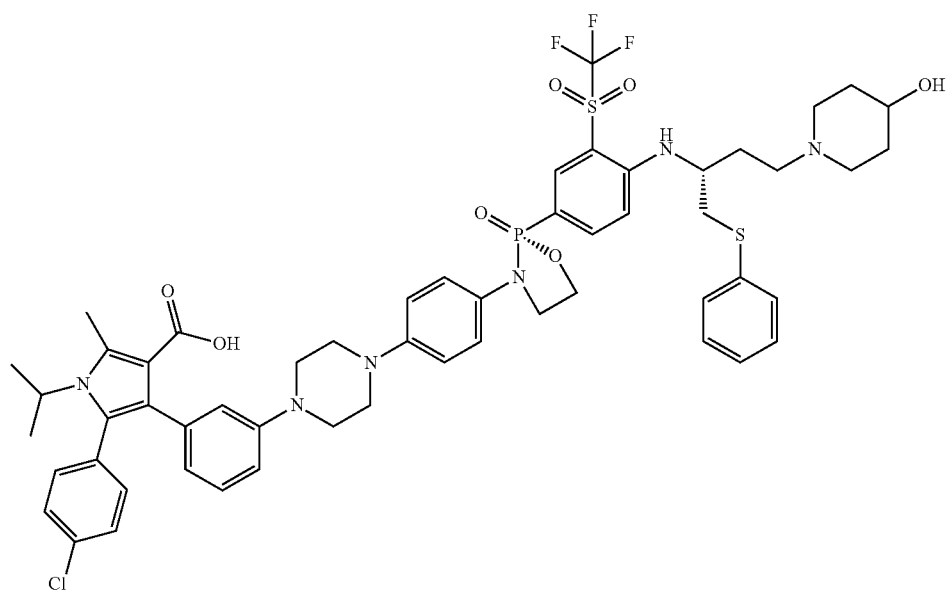

5-(4-chlorophenyl)-4-(3-(4-(4-((R)-2-(4-(((R)-4-(4-hydroxypiperidin-1-yl)-1-(phenylthio)butan-2-yl)amino)-
3-((trifluoromethyl)sulfonyl)phenyl)-2-oxido-1,3,2-oxazaphospholidin-3-yl)phenyl)piperazin-1-yl)
phenyl)-1-isopropyl-2-methyl-1H-pyrrole-3-carboxylic acid, -continued

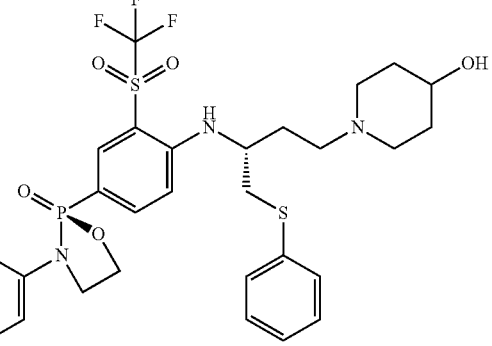
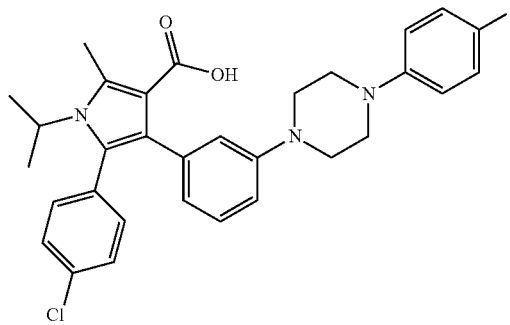

5-(4-chlorophenyl)-4-(3-(4-(4-((S)-2-(4-(((R)-4-(4-hydroxypiperidin-1-yl)-1-(phenylthio)butan-2-yl)amino)-3-((trifluoromethyl)sulfonyl)phenyl)-2-oxido-1,3,2-oxazaphospholidin-3-yl)phenyl)piperazin-1-yl)phenyl)-1-isopropyl-2-methyl-1H-pyrrole-3-carboxylic acid,

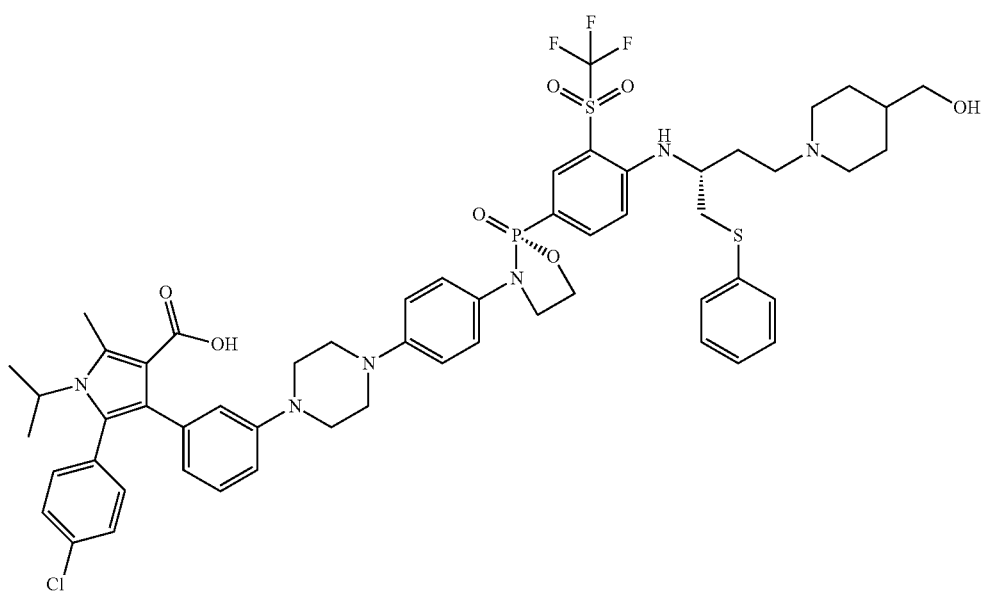

5-(4-chlorophenyl)-4-(3-(4-(4-((R)-2-(4-(((R)-4-(4-hydroxymethyl)piperidin-1-yl)-1-(phenylthio)butan-2-yl)amino)-3-((trifluoromethyl)sulfonyl)phenyl)-2-oxido-1,3,2-oxazaphospholidin-3-yl)phenyl)piperazin-1-yl)phenyl)-1-isopropyl-2-methyl-1H-pyrrole-3-carboxylic acid,

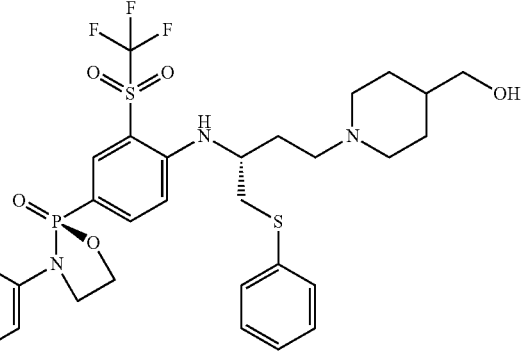
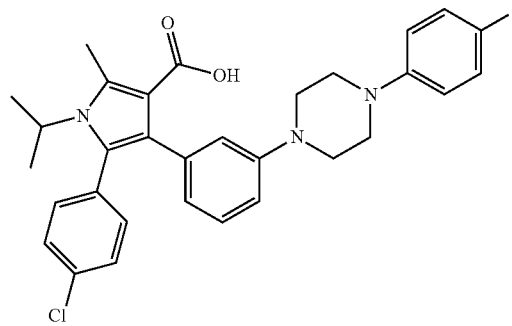

5-(4-chlorophenyl)-4-(3-(4-(4-((S)-2-(4-(((R)-4-(4-(hydroxymethyl)piperidin-1-yl)-1-(phenylthio)butan-2-yl)amino)-3-((trifluoromethyl)sulfonyl)phenyl)-2-oxido-1,3,2-oxazaphospholidin-3-yl)phenyl)piperazin-1-yl)phenyl)-1-isopropyl-2-methyl-1H-pyrrole-3-carboxylic acid,

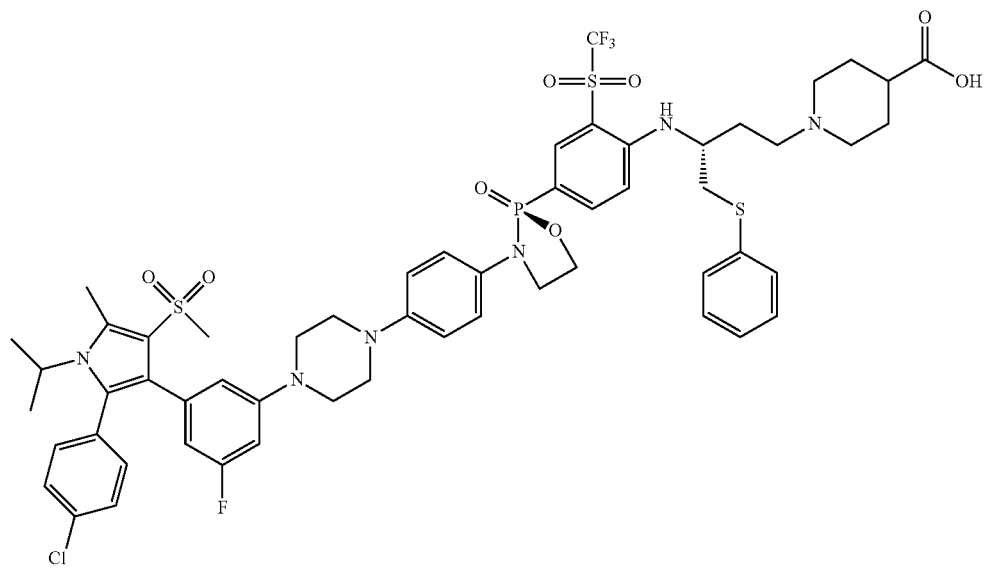

1-((R)-3-((4-((S)-3-(4-(4-(3-(2-(4-chlorophenyl)-1-isopropyl-5-methyl-4-(methylsulfonyl)-1H-pyrrol-3-yl)phenyl)piperazin-1-yl)phenyl)-2-oxido-1,3,2-oxazaphospholidin-2-yl)-2-((trifluoromethyl)sulfonyl)phenyl)amino)-4-(phenylthio)butyl)piperidine-4-carboxylic acid, and -continued

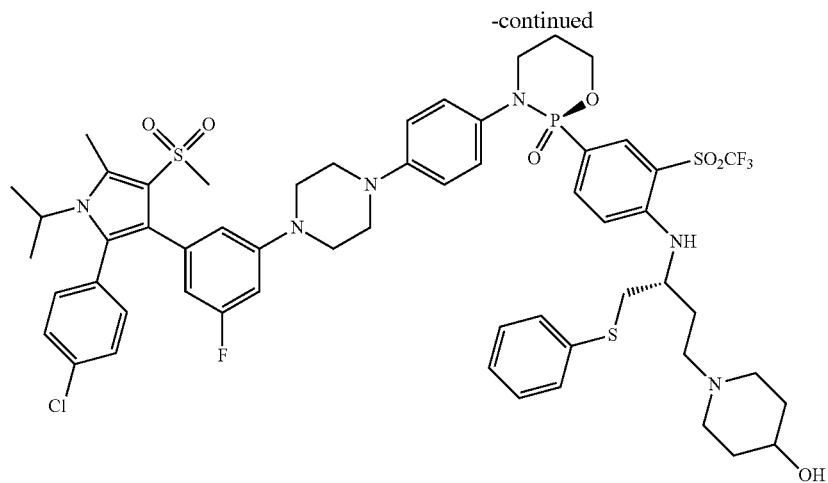

(R)-3-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)-2-(4-(((R)-4-(4-hydroxypiperidin-1-yl)-1-(phenylthio)butan-2-yl)amino-3-((trifluoromethyl)sulfonyl)phenyl)-1,3,2-oxazaphosphinane 2-oxide, and salt forms thereof.

8. The compound of claim 1, wherein $X^2$ is O.
9. The compound of claim 1, wherein $R^{16}$ is Cl and $Z^4$ is N.
10. The compound of claim 1, wherein $Z^{11}—(Z^{12})_n$ is $(CH_2)_2$ or $(CH_2)_3$.
11. The compound of claim 3, wherein $X^2$ is O.
12. The compound of claim 3, wherein $R^{16}$ is Cl and $Z^4$ is N.
13. The compound of claim 3, wherein $Z^{11}—(Z^{12})_n$ is $(CH_2)_2$ or $(CH_2)_3$.
14. The compound of claim 1, wherein:
$R^4$ is selected from $NO_2$, $SO_2CH_3$, and $SO_2CF_3$;
n is 1;
$Z^6$ is selected from O, CHCOOH, CHOH, and CHOPO$(OH)_2$;
$R^{14}$ is selected from H and F;
$R^{16}$ is Cl;
$R^{17}$ is selected from $SO_2R^{52}$ and $CO_2R^{52}$; and
$R^{52}$ is selected from hydrogen and methyl.
15. The compound of claim 6, wherein:
$R^4$ is selected from $NO_2$, $SO_2CH_3$, and $SO_2CF_3$;
n is 1;
$Y^2$ is $N(R^{52})_2$;
$R^{14}$ is selected from H and F;
$R^{16}$ is Cl;
$R^{17}$ is selected from $SO_2R^{52}$ and $CO_2R^{52}$; and
each $R^{52}$ is selected from hydrogen and methyl.

\* \* \* \* \*